United States Patent
Lee

(10) Patent No.: US 8,753,837 B2
(45) Date of Patent: *Jun. 17, 2014

(54) DESIGNER OXYPHOTOBACTERIA AND GREENHOUSE DISTILLATION FOR PHOTOBIOLOGICAL ETHANOL PRODUCTION FROM CARBON DIOXIDE AND WATER

(76) Inventor: James Weifu Lee, Cockeysville, MD (US)

( * ) Notice: Subject to any disclaimer, the term of this patent is extended or adjusted under 35 U.S.C. 154(b) by 456 days.

This patent is subject to a terminal disclaimer.

(21) Appl. No.: 12/918,811

(22) PCT Filed: Feb. 20, 2009

(86) PCT No.: PCT/US2009/034780
§ 371 (c)(1),
(2), (4) Date: Aug. 21, 2010

(87) PCT Pub. No.: WO2009/105714
PCT Pub. Date: Aug. 27, 2009

(65) Prior Publication Data
US 2010/0330639 A1  Dec. 30, 2010

Related U.S. Application Data

(60) Provisional application No. 61/066,770, filed on Feb. 22, 2008, provisional application No. 61/066,771, filed on Feb. 22, 2008, provisional application No. 61/066,832, filed on Feb. 23, 2008.

(51) Int. Cl.
C12P 1/04 (2006.01)
C12P 7/06 (2006.01)
A61K 38/00 (2006.01)

(52) U.S. Cl.
USPC ......... 435/41; 435/6.18; 435/161; 435/292.1; 435/183; 435/257.2; 800/260; 800/276; 800/281; 800/288; 800/295

(58) Field of Classification Search
None
See application file for complete search history.

(56) References Cited

U.S. PATENT DOCUMENTS

| | | | | |
|---|---|---|---|---|
| 2002/0042111 | A1* | 4/2002 | Woods et al. | 435/161 |
| 2005/0106734 | A1* | 5/2005 | Richard et al. | 435/483 |
| 2008/0083045 | A1* | 4/2008 | Norris et al. | 800/305 |
| 2009/0203070 | A1 | 8/2009 | Devroe et al. | |
| 2010/0151545 | A1 | 6/2010 | Roessler et al. | |
| 2010/0291620 | A1* | 11/2010 | Abrams et al. | 435/41 |
| 2012/0322102 | A1* | 12/2012 | Fang et al. | 435/69.1 |

FOREIGN PATENT DOCUMENTS

| | | |
|---|---|---|
| WO | 2007134340 A2 | 11/2007 |
| WO | 2010068821 A1 | 6/2010 |

OTHER PUBLICATIONS (Gfeller and Gibbs (1984) "Fermentative metabolism of *Chlamydomonas reinhardtii*," Plant Physiol. 75:212-218).
(Lee, Blankinship and Greenbaum (1995), "Temperature effect on production of hydrogen and oxygen by *Chlamydomonas* cold strain CCMP1619 and wild type 137c," Applied Biochemistry and Biotechnology 51/52:379-386).
Lee et al., "Discovery of an Alternative Oxygen Sensitivity in Algal Photosynthetic H2 Production", Proceedings of the 2000 U.S. DOE Hydrogen Program Review, NREL/CP-570-28890.
(Lee, Mets, and Greenbaum (2002). "Improvement of photosynthetic efficiency at high light intensity through reduction of chlorophyll antenna size," Applied Biochemistry and Biotechnology, 98-100: 37-48).
(Nakajima, Tsuzuki, and Ueda (1999) "Reduced photoinhibition of a phycocyanin-deficient mutant of *Synechocystis* PCC 6714", Journal of Applied Phycology 10: 447-452).
(Quinn, Barraco, Ericksson and Merchant (2000). "Coordinate copper- and oxygen-responsive Cyc6 and Cpx1 expression in *Chlamydomonas* is mediated by the same element." J Biol Chem 275: 6080-6089).
(Loppes and Radoux (2002) "Two short regions of the promoter are essential for activation and repression of the nitrate reductase gene in *Chlamydomonas reinhardtii*," Mol Genet Genomics 268: 42-48).
(Sjoholm, Oliveira, and Lindblad (2007) "Transcription and regulation of the bidirectional hydrogenase in the *Cyanobacterium nostoc* sp. strain PCC 7120," Applied and Environmental Microbiology, 73(17): 5435-5446).
(Qi, Hao, Ng, Slater, Baszis, Weiss, and Valentin (2005) "Application of the *Synechococcus* nirA promoter to establish an inducible expression system for engineering the Synechocystis tocopherol pathway," Applied and Environmental Microbiology, 71(10): 5678-5684.

(Continued)

*Primary Examiner* — Manjunath Rao
*Assistant Examiner* — Samuel Liu
(74) *Attorney, Agent, or Firm* — August Law, LLC; George Willinghan

(57) ABSTRACT

The present invention provides a photobiological ethanol production and harvesting technology using greenhouse distillation systems with designer photosynthetic organisms, such as designer transgenic oxyphotobacteria. The designer oxyphotobacteria are created such that the endogenous photobiological regulation mechanism is tamed, and the reducing power (NADPH) and energy (ATP) acquired from the photosynthetic process are used for synthesis of ethanol ($CH_3CH_2OH$) directly from carbon dioxide ($CO_2$) and water ($H_2O$). The designer use of a pair of NADPH-dependent vs. NAD-dependent glyceraldehyde-3-phosphate dehydrogenases in the pathway designs offers a special cyclic "transhydrogenase" redox-shuttle function to convert NADPH to NADH for enhanced photobiological ethanol production. Through combined use of a designer photosynthetic organism with a greenhouse distillation system, the waste solar heat associated with the photobiological ethanol-production process is utilized in harvesting the produced ethanol. In addition to production and harvesting of ethanol, use of the technology can also produce intermediate metabolites and freshwater from seawater.

19 Claims, 12 Drawing Sheets

(56) References Cited

OTHER PUBLICATIONS

Maeda, Kawaguchi, Ohe, and Omata (1998) "cis-Acting sequences required for NtcB-dependent, nitrite-responsive positive regulation of the nitrate assimilation operon in the *Cyanobacterium synechococcus* sp. strain PCC 7942," Journal of Bacteriology, 180(16):4080-4088).

[Kojima and Nakamoto (2007) "A novel light- and heat-responsive regulation of the groE transcription in the absence of HrcA or CIRCE in cyanobacteria," FEBS Letters 581:1871-1880).

7942 (Erbe, Adams, Taylor and Hall (1996) "Cyanobacteria carrying an smt-lux transcriptional fusion as biosensors for the detection of heavy metal cations," Journal of Industrial Microbiology, 17:80-83).

(Michel, Pistorius, and Golden (2001) "Unusual regulatory elements for iron deficiency induction of the idiA gene of *Synechococcus elongatus* PCC 7942" Journal of Bacteriology, 183(17):5015-5024).

(Patterson-Fortin, Colvin and Owttrim (2006) "A LexA-related protein regulates redox-sensitive expression of the cyanobacterial RNA helicase, crhR", Nucleic Acids Research, 34(12):3446-3454).

(Fang and Barnum (2004) "Expression of the heat shock gene hsp16.6 and promoter analysis in the *Cyanobacterium, Synechocystis* sp. PCC 6803," Current Microbiology 49:192-198).

(Nakamoto, Suzuki, and Roy (2000) "Constitutive expression of a small heat-shock protein confers cellular thermotolerance and thermal protection to the photosynthetic apparatus in cyanobacteria," FEBS Letters 483:169-174).

(Casey and Grossman (1994) "In vivo and in vitro characterization of the light-regulated cpcB2A2 promoter of Fremyella diplosiphont" Journal of Bacteriology, 176(20):6362-6374).

(Domain, Houot, Chauvat, and Cassier-Chauvat (2004) "Function and regulation of the cyanobacterial genes lexA, recA and ruvB: LexA is critical to the survival of cells facing inorganic carbon starvation," Molecular Microbiology, 53(1):65-80).

(Keppetipola, Coffman, and et al (2003). Rapid detection of in vitro expressed proteins using LumioTM technology, Gene Expression, 25.3: 7-11).

(Griffin, Adams, and Tsien (1998), "Specific covalent labeling of recombinant protein molecules inside live cells", Science, 281:269-272).

(Pattanayak and Chatterjee (1998) "Nicotinamide adenine dinucleotide phosphate phosphatase facilitates dark reduction of nitrate: regulation by nitrate and ammonia," Biologia Plantarium 41(1):75-84).

(Muto, Miyachi, Usuda, Edwards and Bassham (1981) "Light-induced conversion of nicotinamide adenine dinucleotide to nicotinamide adenine dinucleotide phosphate in higher plant leaves," Plant Physiology 68(2):324-328.

Matsumura-Kadota, Muto, Miyachi (1982) "Light-induced conversion of NAD+ to NADP+ in *Chlorella* cells," Biochimica Biophysica Acta 679(2):300-300).

(Liszewski (Jun. 1, 2003) Progress in RNA interference, Genetic Engineering News, vol. 23, No. 11, pp. 1-59).

(Fire, Xu, Montgomery, Kostas, Driver, Mello (1998) "Potent and specific genetic interference by double-stranded RNA in *Caenorhabditis elegans*". Nature 391(6669):806-11.

Dykxhoorn, Novina, Sharp (2003) "Killing the messenger: short RNAs that silence gene expression", Nat Rev Mol Cell Biol. 4(6):457-67).

(Fuhrmann, Stahlberg, Govorunova, Rank and Hegemann (2001) Journal of Cell Science 114:3857-3863).

(Durre, P. 1998 Appl Microbiol Biotechnol 49: 639-648.

Qureshi, Hughes, Maddox, and Cotta 2005 Bioprocess Biosyst Eng 27: 215-222).

(Deng and Coleman (1999) "Ethanol synthesis by genetic engineering in cyanobacteria," Applied and Environmental Microbiology, 65(2):523-528).

(Hirano, Ueda, Hirayama, and Ogushi (1997) "CO2 fixation and ethanol production with microalgal photosynthesis and intracellular anaerobic fermentation" Energy 22(2/3):137-142).

(Hirano, Ueda, Hirayama, and Ogushi (1997) "CO2 fixation and ethanol production with microalgal photosynthesis and intracellular anaerobic fermentation" Energy 22(2/3):137-142.

\* cited by examiner

SEQUENCE LISTING

```
<160> NUMBER OF SEQ ID NOS: 61

<210> SEQ ID NO 1
<211> LENGTH: 1360
<212> TYPE: DNA
<213> ORGANISM: Artificial Sequence
<220> FEATURE:
<223> OTHER INFORMATION: Synthetic Construct-Example 1: a designer
      NAD-dependent Glyceraldehyde-3-Phosphate-Dehydrogenase DNA
      construct

<400> SEQUENCE: 1
agaaaatctg gcaccacacc cttcttgcag aacatgcatg atttacaaaa agttgtagtt      60
```

```
tctgttacca attgcgaatc gagaactgcc taatctgccg agtatatgaa cggatttggc    120
aggataggac gactggtgtt gcgggcggcg gtggagaagg gcacggtgga ggtggtggcg    180
gtgaacgatc cgttcatctt cccggacgcg gcgtacgctg cgtacatgct gcagtacgac    240
tcgacgcacg gggcgttccc gggtgaggtg ggcagcgacg gggagcactt ggtggtgaac    300
gggaagaagc tggcgtgctt tgcgatccgc gatccggcgg agatcccgtg gggctcggtc    360
ggcgccgact acgtcgtgga gtccaccggc gtgttcaccg tgaccgagaa ggcgtcgttg    420
cacgtcaagg gcggcgcgaa gaaggtggtt atatcggcgc cgtcgaagga tgcgcccatg    480
tttgtgatgg gcgtgaacca tgacgcctac accaaggact tgacggtggt gtcgaatgcg    540
tcttgcacca ccaacttgtt tggcgccgct ggccaagatc atcgacgagg cgttcggcat    600
cgggatgggc ctcatgagca ccatccacgc ggtgacggcc acgcaaaaga cggtggatgg    660
gccgagctcc aaagactggc gcggtgtcgc ggcgcgttcc agtcgattat tcccagcagc    720
accggcgctg cgaaagcggt cggcaaggtg tacccgaagc tgaacggcaa gctgaccggc    780
atggcgttcc gcgtgccggt gcccgacgtg tccgtggtag acttgacagt gaccctgaag    840
aaggagacca actacgagga gatcaaaaag gctgtcaagc aggcgtcgca gagcccgcac    900
tacaagggca tcgtggcgta caccgagcac cccatcgtgt cggccgacct ggtgcacaac    960
ccgtactcgt cggtgttcga tgccgaagcc ggtatcatgc tgtcgcccac gtttgtgaaa    1020
ctggtcagct ggtaatagtg atcccggccg ctactaaagc ctgatttgtc ttgatagctg    1080
ctcctgcctt tgggcagggg ctttttttctg tctgccattc ttgaggatgg cggactcttt    1140
cccttttgct ctacgcccat gaatgcgatc gcagtctccc ctgtccagca cgttggagtg    1200
attggtggtg gccagttagc ttggatgctg gcaccagcag cgcaacagtt ggggatgtcg    1260
ctgcacgttc aaacacccaa tgatcacgac ccagcagtag cgatcgcgga tcaaaccgta    1320
ttagcagcag ttgctgacgc ggttctctct tctgccgtta                         1360
```

<210> SEQ ID NO 2  
<211> LENGTH: 1621  
<212> TYPE: DNA  
<213> ORGANISM: Artificial Sequence  
<220> FEATURE:  
<223> OTHER INFORMATION: Synthetic Construct-Example 2: a designer Phosphoglycerate-Kinase DNA construct

<400> SEQUENCE: 2

```
agaaaatctg gcaccacacc cttcttgcag aacatgcatg atttacaaaa agttgtagtt     60
tctgttacca attgcgaatc gagaactgcc taatctgccg agtatatgtc atttgtcttc    120
gagcgcgacg acacccggca gctgttttcc ttccataaac tcgagcgaag cgccgccgcc    180
ggtggagata tgatccattt tgtcggccaa gccgaatttc tcaaccgccg ccgccgaatc    240
cccgccgccg atgaccgaat aggtgtcggg cgcttccgcc agtgcttcgg cgatcgcttt    300
tgtcccatgg gcgaacgctt ccatttcaaa gacgcccatc gggccgttcc agacaacgag    360
cttcgattga cgaatgacat cgcggtacaa ttcgcgcgtt tcgggccgga tgtcaagcgc    420
ctcccaatcg ctcggaatgg cgtcgatggc gacgactttg tgttggcgt cgttcgcaaa    480 ccggtcggcg acgaccacgt ccaccggcat ataaaaacgg acgccttttt ctttcgcctt    540
ttccataaac gatttggcga gttcgatttt gtcctcctca gcagcgact tgccgacgtc    600 atggcgagc gctttgacga acgtatacgc cagtccgccg ccgatgatca agttgtcgac    660
tttttcaagc aaattgtcga tgacgccgat tttgtctttc actttcgcgc cgccgatgat    720
cgccgtaaac gggcggtccg gattcgagag cgctttgccg agcacttcga gttctttttc    780
```

```
catcaaaaac ccggccaccg caggcaagta atgggcgatg ccttccgtcg acgcatgagc    840
gcggtgggcg gcgccgaacg catcgttgac atacagatcc gcgagctccg caaacgcttt    900
ggccagctct ggatcgtttt tctcttcgcc agggtaaaaa cggacgttct caagcaagag    960
cacgtcgcct tcgtttcaaac ggtcgaccgc cgctttcacc tcatcgccga ccgcttcatt   1020
cgttttggcg accggccgtt caagcagctc gccgagccgc ttcgcaacgg catccaaacg   1080
caattcttcg accactttc ctttcgggcg gccgaggtgg ctcgccaaaa tgactttcgc    1140
cccgtgctcg atcaaatagc ggatcgtcgg gagtgcggcg cgaatgcgcg tgtcatcggt   1200
gatggcgcct tgctccatcg gaacgttgaa atcgacgcgg caaaagacgc gctttcccct   1260
cacctcaacg tcgcggatcg tcttcttgtt cattaatagt gatcccggcc gctactaaag   1320
cctgatttgt cttgatagct gctcctgcct ttgggcaggg gcttttttct gtctgccatt   1380
cttgaggatg gcggactctt tccctttgc tctacgccca tgaatgcgat cgcagtctcc    1440
cctgtccagc acgttggagt gattggtggt ggccagttag cttggatgct ggcaccagca   1500
gcgcaacagt tggggatgtc gctgcacgtt caaacaccca atgatcacga cccagcagta   1560
gcgatcgcgg atcaaaccgt attagcagca gttgctgacg cggttctctc ttctgccgtt   1620
a                                                                  1621
```

<210> SEQ ID NO 3
<211> LENGTH: 1990
<212> TYPE: DNA
<213> ORGANISM: Artificial Sequence
<220> FEATURE:
<223> OTHER INFORMATION: Synthetic Construct-Example 3: a designer
      Phosphoglycerate-Mutase DNA construct

<400> SEQUENCE: 3

```
agaaaatctg gcaccacacc cttcttgcag aacatgcatg atttacaaaa agttgtagtt     60
tctgttacca attgcgaatc gagaactgcc taatctgccg agtatatgct cgagcattta    120
tttaataata agcgagcttc ccttcatctc tgaaggtttt tctaaccta agatgtctaa     180 gattgttgga gcaatgtctg ctaagattcc atcatctctt aatttaacat tgccatatcc    240
cacaagatac aaaggcacct tatttgttgt atgagctgta tgaggctcac ctgtctcata    300
atcaatcatc tgttcacagt tgccatggtc agcagtaata ataaccactc caccttttc    360 taaaaccttg ttaacaactt ttccaataca ctcatctaca gcctcaactg cctttattgc    420
agcctctaaa acgcctgtgt gccctaccat gtcaccattt gcatagttac atattatcac    480
atcatattca tctcttttcaa ttctctcaag taaagcttct gttacctcgt atgcactcat    540
ctcaggttta agatcatatg ttgcaacctt tggtgatggt accaataccc tgtcttctcc    600
gacatttggt acttccacac cgccgttgaa gaaaaaggtg acatgagcat acttttctgt    660
ctcagcaatt cgaagttgtt ttaaccctaa cttgctaaaa tactctccca aagtgtttgt    720
caggttctct ggtttgaatg caacatggca atttttatt gtcacatcat actgagtcat    780
gcatacaaag aacacttcga atatcctttt ttccttca aaccgtcaa attcaacatc      840 acaaaacgct cttgtaagct gtcttgctct gtcaggtctg aagttaaaga aaataatact    900
gtcatgttca tttattgttg cgacaggttt tccattttca agcacaacag tcggaattac    960
aaactcatca gtgttaccctt ttttatacga cttttcaacc gcctctaatc ctgagcttgc   1020
atactcgcct tcaccaaaga ccattgcatt atatgccttt tcaactcttt cccatcttt    1080 gtctctgtcc attgcatagt atctgcccat cactgttgca atcttaccac aaccaatttc   1140
```

```
ttttatcttc tgttcaagct cttcaatgta aattttgcg ctcgaaggtg gaacatctcg    1200
cccatccaaa aagcaatgaa catatacttt ttcaagattg tgcctctttg caagttttaa    1260
aagtgcgtaa agatgtgtgt tgtggctgtg aacaccacca tctgataaaa gtcccatcag    1320
atgaagagaa gagttatatt ttttgcaatt ctctattgcc atcaaaaact cttctttttc    1380
aaaaaaatca ccgtctttaa ttgactttgt tattcttgta aattcttggt aaacaattct    1440
tcctgcaccc aggttcagat gtccaacttc agaattcccc atttgtcctt cgggaagacc    1500
aacatccata ccactgctac caatcagggt atatgggtaa ttcttttcgt aatagtcaag    1560
gttaggggtc ttacccaaag caacagcgtt tccctcttgc tttgggttat aaccccaacc    1620
gtccatgata atcaacacaa caggttttt cattaatcta gataatagtg atcccggccg    1680
ctactaaagc ctgatttgtc ttgatagctg ctcctgcctt tgggcagggg ctttttctg    1740 tctgccattc ttgaggatgg cggactcttt cccttttgct ctacgcccat gaatgcgatc    1800
gcagtctccc ctgtccagca cgttggagtg attggtggtg gccagttagc ttggatgctg    1860
gcaccagcag cgcaacagtt ggggatgtcg ctgcacgttc aaacacccaa tgatcacgac    1920
ccagcagtag cgatcgcgga tcaaaccgta ttagcagcag ttgctgacgc ggttctctct    1980
tctgccgtta                                                           1990

<210> SEQ ID NO 4
<211> LENGTH: 1765
<212> TYPE: DNA
<213> ORGANISM: Artificial Sequence
<220> FEATURE:
<223> OTHER INFORMATION: Synthetic Construct-Example 4: a designer
      Enolase DNA construct

<400> SEQUENCE: 4
agaaaatctg gcaccacacc cttcttgcag aacatgcatg atttacaaaa agttgtagtt     60
tctgttacca attgcgaatc gagaactgcc taatctgccg agtatatgct cgagcatatg    120
ctaaataaac ccgtcgtttc cattgaagaa attaccgcta gagaattttt agactctcgt    180
ggccgtccta ccattgaagc agaagtctta ctggaaacag gggctttcgg tattgcccag    240
gttcccagtg gcgcgtcaac tggtagcttc gaggcccacg aattacggga tgatgacccc    300
aaccgctacg gtggtaaagg cgttctcaaa gcggttagta acgttataga cgaaattgcc    360
cctaaaatta tcggaatgga tgggttagat caaactgcga tcgatcacac catgattgag    420
ttagacggtt ctactaataa aaagaattag ggggccaatg ctatccttgc cgtttcctta    480
gccactgcaa aagctgccgc cgatgaatta gcccttcccc tgtaccgtta tttaggggt    540 cccttggcca atgtcttacc cgtccccatg atgaacgtga ttaacggggg ttctcacgcg    600
gataataacg tagacttcca ggagtttatg attatgccag tgggtgcgga ctcttttaaa    660
gaagctttga ggtgggggc cgaagttttt gcttccctca gtaaagttct aaaagagcgt    720
aaattgctct ctggggtagg agacgagggg ggatacgccc cgaacctggg atcgaaccag    780
gaagccttag atttgctcat agaagccatt gaaaaggcgg ggtataagcc agggggaacag    840 gtggctttag cgatggatgt ggcttcaagt gagttttata aggatggcga atatatttat    900
gatggttctc cccattcccc tcaagaattt atcgattatt taggtaaatt agtggatcaa    960
tatcctatta tttccattga agatggctta caagaagata ctgggatag ctggaaaagt   1020 ttgaccgata cgttaggatc tcgcattcag ttagttgggg acgatctttt tgtcacgaac   1080
cccactcgtc tgcaaaaagg cattgatatg ggtgtgggta atagtattct cattaaactc   1140
aatcaaattg gtagtttaac ggaaacgtta gatacgattg ctttagcgac tcgtcatcaa   1200
```

| | |
|---|---|
| tatagttccg ttatttccca tcgttccgga gaaaccgaag acactaccat tgcagactta | 1260 |
| gccgtagcta cacgcgctgg acaaatcaaa accggttctc tgtgtcgtag tgaacgggta | 1320 |
| gccaaatata accgactatt acgtattgaa gaagaattag gcgatcgcgc agtttatgct | 1380 |
| gcaaaagtgg gtttaggccc tcaataaggc tgctgccccg gctgctgcta atctagataa | 1440 |
| tagtgatccc ggccgctact aaagcctgat ttgtcttgat agctgctcct gcctttgggc | 1500 |
| aggggctttt ttctgtctgc cattcttgag gatggcggac tctttccctt ttgctctacg | 1560 |
| cccatgaatg cgatcgcagt ctcccctgtc cagcacgttg gagtgattgg tggtggccag | 1620 |
| ttagcttgga tgctggcacc agcagcgcaa cagttgggga tgtcgctgca cgttcaaaca | 1680 |
| cccaatgatc acgacccagc agtagcgatc gcggatcaaa ccgtattagc agcagttgct | 1740 |
| gacgcggttc tctcttctgc cgtta | 1765 |

<210> SEQ ID NO 5
<211> LENGTH: 1888
<212> TYPE: DNA
<213> ORGANISM: Artificial Sequence
<220> FEATURE:
<223> OTHER INFORMATION: Synthetic Construct-Example 5: a designer
      Pyruvate-Kinase DNA construct

<400> SEQUENCE: 5

| | |
|---|---|
| agaaaatctg gcaccacacc cttcttgcag aacatgcatg atttacaaaa agttgtagtt | 60 |
| tctgttacca attgcgaatc gagaactgcc taatctgccg agtatatgct cgagcatatg | 120 |
| ttaaaaaaga cgaaaatcgt tgcacgcag gtccgtcca cagagaaacc gggcgtaatt | 180 |
| gatgcactga ttgccaatgg catgaactgc gcacgcttca atttctccca tggtgaccac | 240 |
| gaagaacatc ttggccgtat caatatggtt cgtgaagctg ccaagaaggc tggcaaggtt | 300 |
| atctctttaa tcctcgatac caaggtccg gaaatgcgtc tgggcgagtt caaagatggc | 360 |
| aaagttatgc tcgaaaaggg caacaagttc actttgacct atgacgatga accgggtgat | 420 |
| gaaactcatg tttccgtaaa ccacaaaggt ctttacacgg aagttaagcc gggcgacacc | 480 |
| ctgctcctct ccgatggcct cgtagctctc aaagttgatg aaatcaaggg caaggatatc | 540 |
| gttacgacga ttcagaacag cggtaagatg agcacgcgca agcgcgtagc tgctccgggc | 600 |
| gtaccccttg gtctgcctcc tatctccgaa caggatgcta aggacatcat ctttggctgc | 660 |
| gaacaggata tggatttcgt agctgcttcc ttcatccagc gtccggatga tgttatcgcc | 720 |
| atccgcaagc tcatcgaaga gcacaatggc cacatgaaa ttctgccgaa gatcgaaaac | 780 |
| ctcgaaggtg ttaagaactt cgatgcaatc ctggaagttt ccgacggcat catggttgcc | 840 |
| cgtggtgacc tgggcgtaga agttccggca gaagatgtgc cccttattca gaaggaaatc | 900 |
| atccgcaagt gcaacgctgc tggcaagccg gttatcgttg ctacgcagat gctcgactcc | 960 |
| atggaacgca acccgcgtcc gacccgtgca gaagtttctg acgttggtaa cgccatcctc | 1020 |
| gatggtacgg atgccatcat gctgtccggc gaaacggctt ccggtgacta ccggtagaa | 1080 |
| gcagttgcca cgatgaaccg cattgcacag cgcatggaaa gctcccttga atacaaggaa | 1140 |
| ctctatgtag aacgtggtct gcagcacatg gaatcccgta cgcgtgctat cgctcatgct | 1200 |
| acggttcaga tggcttatga gctcgatgct ccggctatta tcacgccgac cgaatccggt | 1260 |
| tacacgacga aggtcgtttc caagtatcgt ccgaaggctg ctatcgtagc ttacacgccg | 1320 |
| agcgaaaaag ttctgcgtca gctgaacctg cgttgggggcg tatatccggt actcggcacc | 1380 |
| cagtggagcg atgtggatga aatgatcagc aatgcaacgg ctgctgctgt taaggaagac | 1440 |

```
ctcgtacagc gcggcgacct caccatcatc acctccggtg tgaagatgga atcccgtacg   1500
cgtgctatcg ctcatgctac ggacatctaa ggctgctgcc ccggctgctg ctaatctaga   1560
taatagtgat cccggccgct actaaagcct gatttgtctt gatagctgct cctgcctttg   1620
ggcaggggct ttttctgtc tgccattctt gaggatggcg gactctttcc cttttgctct    1680
acgcccatga atgcgatcgc agtctcccct gtccagcacg ttggagtgat tggtggtggc   1740
cagttagctt ggatgctggc accagcagcg caacagttgg ggatgtcgct gcacgttcaa   1800
acacccaatg atcacgaccc agcagtagcg atcgcggatc aaaccgtatt agcagcagtt   1860
gctgacgcgg ttctctcttc tgccgtta                                       1888

<210> SEQ ID NO 6
<211> LENGTH: 2188
<212> TYPE: DNA
<213> ORGANISM: Artificial Sequence
<220> FEATURE:
<223> OTHER INFORMATION: Synthetic Construct-Example 6: a designer
      Pyruvate-Decarboxylase DNA construct

<400> SEQUENCE: 6
agaaaatctg gcaccacacc cttcttgcag aacatgcatg atttacaaaa agttgtagtt     60
tctgttacca attgcgaatc gagaactgcc taatctgccg agtatatgct cgagcatatg    120
gtatcaacct acccagaatc agaggttact ctaggaaggt acctctttga gcgactccac    180
caattgaaag tggacaccat tttcggcttg ccgggtgact tcaacctttc cttattggac    240
aaagtgtatg aagttccgga tatgaggtgg gctggaaatg ccaacgaatt gaatgctgcc    300
tatgctgccg atggttactc cagaataaag ggattgtctt gcttggtcac aacttttggt    360
gttggtgaat tgtctgcttt aaacggagtt ggtggtgcct atgctgaaca cgtaggactt    420
ctacatgtcg ttggagttcc atccatatcg tcacaggcta aacagttgtt gctccaccat    480
accttgggta atggtgactt cactgttttt cacagaatgt ccaatagcat ttctcaaact    540
acagcatttc tctcagatat ctctattgca ccaggtcaaa tagatagatg catcagagaa    600
gcatatgttc atcagagacc agtttatgtt ggtttaccgg caaatatggt tgatctcaag    660
gttccttcta gtctcttaga aactccaatt gatttgaaat tgaaacaaaa tgatcctgaa    720
gctcaggaag aagttgttga acagtcctg aagttggtgt cccaagctac aaaccccatt     780
atcttggtag acgcttgtgc cctcagacac aattgcaaag aggaagtcaa acaattggtt    840
gatgccacta attttcaagt ctttacaact ccaatgggta atctggtat ctccgaatct     900 catccaagat ttggcggtgt ctatgtcggg acaatgtcga gtcctcaagt caaaaaagcc    960
gttgaaaatg ccgatcttat actatctgtt ggttcgttgt tatcggactt caatacaggt   1020
tcattttcat actcctacaa gacgaagaat gttgttgaat tccactctga ctatatgaaa   1080
atcagacagg ccaccttccc aggagttcaa atgaaagaag ccttgcaaca gttgataaaa   1140
agggtctctt cttacatcaa tccaagctac attcctactc gagttcctaa aaggaaacag   1200
ccattgaaag ctccatcaga agctcctttg acccaagaat atttgtggtc taaagtatcc   1260
ggctggttta gagagggtga tattatcgta accgaaactg gtacatctgc tttcggaatt   1320
attcaatccc attttcccag caacactatc ggtatatccc aagtcttgtg gggctcaatt   1380
ggtttcacag taggtgcaac agttggtgct gccatggcag cccaggaaat cgaccctagc   1440
aggagagtaa ttttgttcgt cggtgatggt tcattgcagt tgacggttca ggaaatctct   1500
acgttgtgta atgggattg taacaatact tatctttacg tgttgaacaa tgatggttac   1560
actatagaaa ggttgatcca cggcaaaagt gccagctaca acgatataca gccttggaac   1620
```

```
catttatcct tgcttcgctt attcaatgct aagaaatacc aaaatgtcag agtatcgact    1680
gctggagaat tggactcttt gttctctgat aagaaatttg cttctccaga taggataaga    1740
atgattgagg tgatgttatc gagattggat gcaccagcaa atcttgttgc tcaagcaaag    1800
ttgtctgaac gggtaaacct tgaaaattga ggctgctgcc ccggctgctg ctaatctaga    1860
taatagtgat cccggccgct actaaagcct gatttgtctt gatagctgct cctgcctttg    1920
ggcaggggct tttttctgtc tgccattctt gaggatggcg gactctttcc cttttgctct    1980
acgcccatga atgcgatcgc agtctcccct gtccagcacg ttggagtgat tggtggtggc    2040
cagttagctt ggatgctggc accagcagcg caacagttgg ggatgtcgct gcacgttcaa    2100
acacccaatg atcacgaccc agcagtagcg atcgcggatc aaaccgtatt agcagcagtt    2160
gctgacgcgg ttctctcttc tgccgtta                                      2188

<210> SEQ ID NO 7
<211> LENGTH: 1441
<212> TYPE: DNA
<213> ORGANISM: Artificial Sequence
<220> FEATURE:
<223> OTHER INFORMATION: Synthetic Construct-Example 7: a designer
      NAD(P)H-dependent Alcohol-Dehydrogenase DNA construct

<400> SEQUENCE: 7
agaaaatctg gcaccacacc cttcttgcag aacatgcatg atttacaaaa agttgtagtt      60
tctgttacca attgcgaatc gagaactgcc taatctgccg agtatatggt gcagagtttc     120
aataggataa attcaatgaa atatttccct ttgagcaatg gggagcagat tcccgccctg     180
ggtctgggaa catggaaatc gtcccctcag gtagtgggtc aagccgttga gcaagctttg     240
gacttggggt atcgtcacct tgactgtgct gctatctatg gcaatgaagc agaaattgga     300
gctactttag ccaatgcttt caccaagggg gtggtcaagc gagaggaact ctggattacc     360
tccaagctgt ggagtaatgc ccatcatccc gacgcggttt acctgctctc gaaaaaaact     420
ttgcaggatt tgggtctaga ttatttggat ctatatctaa tccattggcc ggtggtcatt     480
caacccgatg ttggatttcc tgaatccggt gatcagttac taccatttac cccggcttcc     540
ctagaaggaa cctggcaagc gttggagaag ccgttgatt tgggactctg tcaccatatt     600
ggggtgtcta atttcagcct gaagaagttg gaaatggtgc tgtccatggc ccgtattccc     660
cccgctgtca atcaggtgga attgcacccc tacctccaac aatcagactt gctaacgttt     720
gctaactcgc aaaacatttt actaacagcc tattctcccc tgggctctgg cgatcgcccg     780
gcggccttcc aacaagcagc agaaccgaaa ttactaactg atccagtgat taatgggatt     840
gcagctgaac aagggtgcag tgcggcccaa gtccttttgg cctgggccat caacggggga     900
accgtgacca ttccgaagtc ggttaatcct gaacgactag aacaaaattt gagggcggca     960
gatatcaccc tcacggatag cgagatgcg aaaattgccc tattagaccg tcattaccgc    1020
tacgtgtcgg agactttttg gaccatgccg ggcagtccct atacgttaca aaacctatgg    1080
gatgaaattt aaggctgctg ccccggctgc tgctaatagt gatcccggcc gctactaaag    1140
cctgatttgt cttgatagct gctcctgcct ttgggcaggg gcttttttct gtctgccatt    1200
cttgaggatg gcggactctt tccctttgc tctacgccca tgaatgcgat cgcagtctcc    1260
cctgtccagc acgttggagt gattggtggt ggccagttag cttggatgct ggcaccagca    1320
gcgcaacagt tggggatgtc gctgcacgtt caaacaccca atgatcacga cccagcagta    1380
gcgatcgcgg atcaaaccgt attagcagca gttgctgacg cggttctctc ttctgccgtt    1440
```

| a | 1441 |

<210> SEQ ID NO 8
<211> LENGTH: 1510
<212> TYPE: DNA
<213> ORGANISM: Artificial Sequence
<220> FEATURE:
<223> OTHER INFORMATION: Synthetic Construct-Example 8: a designer
      NAD(P)H-dependent Alcohol-Dehydrogenase DNA construct

<400> SEQUENCE: 8

| agaaaatctg gcaccacacc cttcttgcag aacatgcatg atttacaaaa agttgtagtt | 60 |
| tctgttacca attgcgaatc gagaactgcc taatctgccg agtatatgtt agctacctct | 120 |
| gtgccagaaa cccaaaaggg tgttattttc tatgagaatg gtgtaaaatt ggaatacaag | 180 |
| gacattccag ttccaaagcc aaagccaaat gaaatcttga tcaacgtcaa gtactccggt | 240 |
| gtgtgtcata ccgatttgca cgcatggaag ggtgactggc cattgccaac caagttgcca | 300 |
| ttggtcggtg gtcacgaagg tgctggtgtc gttgttgcta tgggtgaaaa cgtcaagggc | 360 |
| tggaacattg gtgactttgc gggtatcaaa tggttgaacg gttcttgtat gtcctgtgaa | 420 |
| tactgtgaat tgtccaatga atccaactgt ccagatgctg acttgtctgg ttacacccac | 480 |
| gatggttctt ccaacaata ccgtaccgca gatgctgttc aagctgccag aattccaaag | 540 |
| ggtaccgatt ggctgaagt tgctccaacc ctatgtgccg tgttactgt ttacaaggct | 600 |
| ttgaaaagtg ctaacttgaa ggctggtgac tgggttgcca tctctggtgc tgctggtggt | 660 |
| ctaggttctc tagctgtcca atacgccaag gccatgggtt acagagtcgt tggtatcgac | 720 |
| ggtggtgaag aaaagggtaa gttggtcaag caattgggtg tgaagccttt gttgatttc | 780 |
| accaaaacca aggacatggt tgctgaaatc caagaaatca ccaacggtgg tccacacggt | 840 |
| gtcattaacg tctctgtttc tgaagctgcc atgaacgctt ccactcaatt cgtcagacca | 900 |
| actggtactg tcgtattggt cggttttgcca gctggtgccg tcatcaagtc cgaagtcttc | 960 |
| tcccacgtcg ttaagtctat taacatcaag ggttcttacg tcggtaacag agctgacacc | 1020 |
| agagaagcta tcaacttctt cgctaacggt cacgtccact ctccaatcaa ggttgttggt | 1080 |
| ttgtccgaac taccaaaggt ttacgaattg atggaacaag gtaagatttt gggtagatac | 1140 |
| gttgttgaca cctccaacta gggctgctgc cccggctgct gctaatagtg atccggccg | 1200 |
| ctactaaagc ctgatttgtc ttgatagctg ctcctgcctt tgggcagggg cttttttctg | 1260 |
| tctgccattc ttgaggatgg cggactcttt ccctttgct ctacgcccat gaatgcgatc | 1320 |
| gcagtctccc ctgtccagca cgttggagtg attggtggtg gccagttagc ttggatgctg | 1380 |
| gcaccagcag cgcaacagtt ggggatgtcg ctgcacgttc aaacacccaa tgatcacgac | 1440 |
| ccagcagtag cgatcgcgga tcaaaccgta ttagcagcag ttgctgacgc ggttctctct | 1500 |
| tctgccgtta | 1510 |

<210> SEQ ID NO 9
<211> LENGTH: 1405
<212> TYPE: DNA
<213> ORGANISM: Artificial Sequence
<220> FEATURE:
<223> OTHER INFORMATION: Synthetic Construct-Example 9: a designer
      Phosphofructose-Kinase DNA construct

<400> SEQUENCE: 9

| agaaaatctg gcaccacacc cttcttgcag aacatgcatg atttacaaaa agttgtagtt | 60 |
| tctgttacca attgcgaatc gagaactgcc taatctgccg agtatatgat gccagaagtg | 120 |

-continued

```
aagacaatag gagtgctcac aagtggcgga gatgcacctg gaatgaatgc agctataagg      180
gctgttgtga ggacaggaat ttactatggt tttagagtga tgggtataag gcgcggatat      240
aatgggctaa tagaaggcga tatatttgaa atgaatttaa ggtcagtgtc tgatataatt      300
cagcgtggtg gaacaatact tttgactgcg aggtctccag agtttatgac agaaaacggg      360
ctgaaaaaag cagcttctat gtgcaaaata ttcaagattg atgctcttgt agtaattggt      420
ggagatggat ctttttagagg ggcaagagat ttgagcaaat ttggaataaa tgtagtgggt      480
attcctggta caattgacaa tgacattgca tgtacagatt atacaattgg ttttgacact      540
gctttaaata ctgtacaaga tgcaataaat aagattagag acacagccac ctctcatgag      600
agagtcagca tattagaagt aatgggaaga catgcaggct acattgcact ttatagtggt      660
attgcaggtg gtgctgaatc cattgtaata cctgaaaagg gtttagataa agatgagata      720
ataagaagaa ttattgatgg taagaacaag ggaaagcttc acaatttaat tatcttggca      780
gagggaattg tgggggcaac agaacttgca aaagagattg aagaggcaac aggaattgaa      840
acaagagcaa caattttggg ttatatacaa aggggtggct caccaactgc atatgataga      900
gttatggcaa gccttatggg tgcaagagct gttgaagtaa taaagaagg aaagaagaac       960
aggataattg ccctaaaaga tggaaagatt gttgactatg atattgacga ggcgctttct     1020
atgcaaaaga gcattgacga gtacatgtat gacttggcta caatcttgtc tttataatga     1080
taatagtccc ggccgctact aaagcctgat tgtcttgat agctgctcct gcctttgggc      1140
aggggctttt ttctgtctgc cattcttgag gatggcggac tctttccctt ttgctctacg     1200
cccatgaatg cgatcgcagt ctcccctgtc cagcacgttg gagtgattgg tggtggccag     1260
ttagcttgga tgctggcacc agcagcgcaa cagttgggga tgtcgctgca cgttcaaaca     1320
cccaatgatc acgacccagc agtagcgatc gcggatcaaa ccgtattagc agcagttgct     1380
gacgcggttc tctcttctgc cgtta                                           1405
```

<210> SEQ ID NO 10
<211> LENGTH: 1408
<212> TYPE: DNA
<213> ORGANISM: Artificial Sequence
<220> FEATURE:
<223> OTHER INFORMATION: Synthetic Construct-Example 10: a designer Fructose-Diphosphate-Aldolase DNA construct

<400> SEQUENCE: 10

```
agaaaatctg gcaccacacc cttcttgcag aacatgcatg atttacaaaa agttgtagtt       60
tctgttacca attgcgaatc gagaactgcc taatctgccg agtatatgat gccacttgta      120
acaaccaaag agatgtttaa aaaggccgct gaggggaagt atgctattgg tgccttcaat      180
gtcaacaaca tggagattat ccaggggatt gttgaggcag caaaggagga acaagcacct      240
ttaattttgc aggtctcagc aggagcaaga aaatacgcaa acacgtcta tcttgtaaaa       300
cttgttgagg cagctttaga ggactctggt gatttaccaa ttgcacttca ccttgaccat      360
ggcgaggact tcgagatttg caaggcgtgc atcgatggcg gatttacatc tgttatgatt      420
gatggttcac gtctcccatt tgaagagaac attgcgctta ccaagaaagt tgttgaatat      480
gcgcatgaga ggggagttgt tgttgaggca gagcttggaa agcttgccgg cattgaggac      540
aatgtaaagg ttgcagagca tgaggcagca tttactgacc ctgaccaagc agcagagttt      600
gttgaaagaa caggtgttga ctcattggca gttgcaattg aacaagcca tggggcgtat      660
aagttcaagg gcgagccaag acttgatttt gagagacttc agagaatagt agaaagctt      720
ccaaagggct ttccaattgt tcttcacggt gcgtcgtcag ttttgccaga gtttgttgag      780
```

```
atgtgcaaca agtacggtgg taatatccct ggtgcaaaag gtgtgccaga agatatgcta    840
agaaaggctg ctgagcttgg tgtgagaaag attaacattg acacagattt aagacttgca    900
atgacagcag caataagaaa gcatttggca gaacatcctg accactttga cccaagacag    960
tacctcaaag atggcagaga ggcaattaaa gagatggtta agcacaagct gagaaatgtt   1020
ttgggctgta gtgcaaggc tccagagata cttgaagaga ttaagaagaa cagaggctaa    1080
tgataatagt cccggccgct actaaagcct gatttgtctt gatagctgct cctgcctttg   1140
ggcaggggct tttttctgtc tgccattctt gaggatggcg gactctttcc cttttgctct   1200
acgcccatga atgcgatcgc agtctcccct gtccagcacg ttggagtgat tggtggtggc   1260
cagttagctt ggatgctggc accagcagcg caacagttgg ggatgtcgct gcacgttcaa   1320
acacccaatg atcacgaccc agcagtagcg atcgcggatc aaaccgtatt agcagcagtt   1380
gctgacgcgg ttctctcttc tgccgtta                                     1408
```

<210> SEQ ID NO 11
<211> LENGTH: 1204
<212> TYPE: DNA
<213> ORGANISM: Artificial Sequence
<220> FEATURE:
<223> OTHER INFORMATION: Synthetic Construct-Example 11: a designer Triose-Phosphate-Isomerase DNA construct

<400> SEQUENCE: 11

```
agaaaatctg gcaccacacc cttcttgcag aacatgcatg atttacaaaa agttgtagtt     60
tctgttacca attgcgaatc gagaactgcc taatctgccg agtatatgtc agcctataca    120
agctgctttt attatttcta caaaacttt tacttccagg ctggccccgc ctaccagggc     180
accgtcgatg tccggctggg ccatcagccc cgccgcgttt ccggtttga cgcttccccc    240 gtactggatg cgcatcgccc cggccgcccc ggccccgtac aggtctctta ccaggccgcg    300
gataaagcct atcatctgct gggcgtcctg ctccgaggcg gttttgccgg tgccgatggc    360
ccagaccggc tcgtaggcaa taaccaggcc gccagcctgt tccggggtca ggccagccag    420
cccggactca gcctggcgcc gcaccacctc ttcggtaacg cccgcctccc ttttcttcaag   480 cgtctcgccg acgcacatga tgggcgtaag gccgtgcgcc agcgcggccc ttaccttgcg    540
gttgaccttc tcgtcggtct ccccgaacaa ctgcctccgc tccgaatgcc cgataatgac    600
gtagctgcag ccggcgtcct tgagcattaa aggagagact tccccggtaa aagccccgct    660
ttcctcccag tgcacgtcct gggcgccgac cgcaatgccc gtgccgcgca gggcctccgc    720
caccggaacc agggcggtaa aggggggca aacggctatt tcgacgccgt ccacccccgc    780
cacggccgtt ttcagctcct gcgcaaaggc caccgcttca ggcaccgtct tgaacatctt    840
ccagttacct gcgatgaggg gttttctcgc tgacattgat aatagtcccg gccgctacta    900
aagcctgatt tgtcttgata gctgctcctg cctttgggca gggcttttt tctgtctgcc    960 attcttgagg atggcggact cttttccctt tgctctacgc ccatgaatgc gatcgcagtc   1020
tcccctgtcc agcacgttgg agtgattggt ggtggccagt tagcttggat gctggcacca   1080
gcagcgcaac agttggggat gtcgctgcac gttcaaacac ccaatgatca cgacccagca   1140
gtagcgatcg cggatcaaac cgtattagca gcagttgctg acgcggttct ctcttctgcc   1200
gtta                                                               1204
```

<210> SEQ ID NO 12
<211> LENGTH: 1865
<212> TYPE: DNA

<213> ORGANISM: Artificial Sequence
<220> FEATURE:
<223> OTHER INFORMATION: Synthetic Construct-Example 12: a designer
      hox-promoter-controlled NADP(H)-dependent Alcohol-Dehydrogenase
      DNA construct

<400> SEQUENCE: 12

```
agaaaatctg gcaccacacc gcagaaatat aggggctagg agttgagggt actctggttc      60
gtcaagcatt tgggatgatt tcccctcaca agttcctcaa attattctcc tataaacaat     120
agatataagg tcaaaacttg agttatgagt gctgagtaaa aaattactct ccacgcctca     180
gaggtagata tgatggtgtg ggaatcccac gttccgataa accaggtctt tgagctgagg     240
tgcaaaacaa cagactactt cggcctatgc gccatacaca aatttaacgg cttcgtccgg     300
gagcttaagg ggaaaggcgt ggacagggtt atcctcgtta ctgggagcag ctcctacaag     360
aagtgcggtg catgggacgt tgtcaggcct gcccttgagg aaaacggggt cgagtatgtc     420
cattacgaca aggtggggc caacccaacg gttgacatga tcgatgaagc tgccgagatg     480
gggagagagt tcgggcccca agcggtgata ggcataggtg gtggcagccc catcgatagt     540
gccaagagcg ttgcgattct gctggaatac cctgacaaga ccgccaggga cctctacgag     600
ttcaggttta cccccgtaaa ggccaagcca gtaatagcga taaacacaac ccatggagcc     660
ggaaccgaag ttgacaggtt cgcagtggcg acgattcctg agaaagagta caagccggcc     720
atagcttacg actgcatcta cccgctttac gcaatcgatg acccctcact gacggtaaag     780
ctttccccgg agcagaccct ttacctgacc atcgatgcac tcaatcacgt taccgaagcc     840
gccacaacca agctggccaa tccatattcg atactcctcg ccaaagaggc cgcgaggctg     900
atatttgact acctcccaga ggccctcaaa caccccgaca accttcaggc aaggtacgcc     960
ctgctctacg cctctgccat agccggaata agcttcgaca acggtctgct ccactttacg    1020
cacgcccttg agcacccgct gagtgcggtc aaaccggact tcccccacgg cattggcctc    1080
gcaatgcttc ttccggcggt aatcaggcac atataccctg ccaccgcaaa gatacttgcc    1140
gaggtctaca ggccgctcgt tcccgaggcc aaaggtgttc cgggagaggt ggaactcgtc    1200
gccaggaggg tagaagagtg gctcttcagc atcggcataa ctgaaaagct tgaggacgtc    1260
gggttctctg agacggatgt gaacaggcta acggaacttg ccatgaaaac accaagcctt    1320
aacctgctcc tctccatggc tccgggtgag gccactcggg agagaatagc ggccatatac    1380
cgtgattcgc tttatcccat cagcagaggg tgatgaagta agtaggaagc agggagcagg    1440
ggaaagaaaa ttgacaactg tacaagatta atcgcgtctc tgagcaatga ccaaatacat    1500
ctacctccac ggttttcttc cagcccccta tctgcgaaag cacaagatat tagcaagcgt    1560
ttcgcccaaa ttcacataca gctaacaatc cctgatctca atgctggtga attttctcag    1620
ttaacaatca cgcgccaaat tcaacaagtt gccgcaattt tccctgataa ttctgaacca    1680
ataacgctga taggttctag tttaggcggt ttaactgctg cttatctagg acagcgatat    1740
ttacaagtac aacgcttagt tttattagcg ccagtttggt tttttatccc attggttgcc    1800
caaaatgggt gaagaagctg tcacaagttg gcaacaaacg atataggttc tctcttctgc    1860
cgtta                                                               1865
```

<210> SEQ ID NO 13
<211> LENGTH: 2351
<212> TYPE: DNA
<213> ORGANISM: Artificial Sequence
<220> FEATURE:
<223> OTHER INFORMATION: Synthetic Construct-Example 13: a designer
      hox-promoter-controlled Pyruvate-Decarboxylase DNA construct

```
<220> FEATURE:
<221> NAME/KEY: misc_feature
<222> LOCATION: (814)..(814)
<223> OTHER INFORMATION: n is a, c, g, or t

<400> SEQUENCE: 13
agaaaatctg gcaccacacc gcagaaatat aggggctagg agttgagggt actctggttc      60
gtcaagcatt tgggatgatt tcccctcaca agttcctcaa attattctcc tataaacaat     120
agatataagg tcaaaacttg agttatgagt gctgagtaaa aaattactct ccacgcctca     180
gaggtagata tgatgagtta tactgtcggt acctatttag cggagcggct tgtccagatt     240
ggtctcaagc atcacttcgc agtcgcgggc gactacaacc tcgtccttct tgacaacctg     300
cttttgaaca aaaacatgga gcaggtttat tgctgtaacg aactgaactg cggtttcagt     360
gcagaaggtt atgctcgtgc caaaggcgca gcagcagccg tcgttaccta cagcgtcggt     420 gcgcttccg catttgatgc tatcggtggc gcctatgcag aaaaccttcc ggttatcctg     480
atctccggtg ctccgaacaa caatgaccac gctgctggtc acgtgttgca tcacgctctt     540
ggcaaaaccg actatcacta tcagttggaa atggccaaga acatcacggc cgccgctgaa     600
gcgatttata ccccggaaga agctccggct aaaatcgatc acgtgattaa aactgctctt     660
cgtgagaaga agccggttta tctcgaaatc gcttgcaaca ttgcttccat gccctgcgcc     720
gctcctggac cggcaagcgc attgttcaat gacgaagcca gcgacgaagc ttctttgaat     780
gcagcggttg aagaaaccct gaaattcatc gccnaccgcg acaaagttgc cgtcctcgtc     840
ggcagcaagc tgcgcgcagc tggtgctgaa gaagctgctg tcaaatttgc tgatgctctt     900
ggtggcgcag ttgctaccat ggctgctgca aaaagcttct cccagaaga aaacccgcat      960 tacatcggta cctcatgggg tgaagtcagc tatccgggcg ttgaaaagac gatgaaagaa    1020
gccgatgcgg ttatcgctct ggctcctgtc tttaacgact actccaccac tggttggacg    1080
gatattcctg atcctaagaa actggttctc gctgaaccgc gttctgtcgt cgttaacggc    1140
attcgcttcc ccagcgtcca tctgaaagac tatctgaccc gtttggctca gaaagtttcc    1200
aagaaaaccg gtgctttgga cttcttcaaa tccctcaatg caggtgaact gaagaaagcc    1260
gctccggctg atccgagtgc tccgttggtc aacgcagaaa tcgcccgtca ggtcgaagct    1320
cttctgaccc cgaacacgac ggttattgct gaaccggtg actcttggtt caatgctcag    1380
cgcatgaagc tcccgaacgg tgctcgcgtt gaatatgaaa tgcagtgggg tcacattggt    1440
tggtccgttc ctgccgcctt cggttatgcc gtcggtgctc cggaacgtcg caacatcctc    1500
atggttggtg atggttcctt ccagctgacg gctcaggaag tcgctcagat ggttcgcctg    1560
aaactgccgg ttatcatctt cttgatcaat aactatggtt acaccatcga agttatgatc    1620
catgatggtc cgtacaacaa catcaagaac tgggattatg ccggtctgat ggaagtgttc    1680
aacggtaacg tggttatga cagcggtgct ggtaaaggcc tgaaggctaa accggtggc    1740 gaactggcag aagctatcaa ggttgctctg gcaaacaccg acgcccaac cctgatcgaa    1800 tgcttcatcg gtcgtgaaga ctgcactgaa gaattggtca atggggtaa gcgcgttgct    1860 gccgccaaca gccgtaagcc tgttaacaag ctcctctagt gaagtaagta ggaagcaggg    1920
agcaggggaa agaaaattga caactgtaca agattaatcg cgtctctgag caatgaccaa    1980
atacatctac ctccacggtt ttcttccagc cccctatctg cgaaagcaca agatattagc    2040
aagcgtttcg cccaaattca catacagcta acaatccctg atctcaatgc tggtgaattt    2100
tctcagttaa caatcacgcg ccaaattcaa caagttgccg caattttccc tgataattct    2160
gaaccaataa cgctgatagg ttctagttta ggcggtttaa ctgctgctta tctaggacag    2220
```

```
cgatatttac aagtacaacg cttagtttta ttagcgccag tttggttttt tatcccattg    2280
gttgcccaaa atgggtgaag aagctgtcac aagttggcaa caaacgatat aggttctctc    2340
ttctgccgtt a                                                         2351
```

<210> SEQ ID NO 14
<211> LENGTH: 2414
<212> TYPE: DNA
<213> ORGANISM: Artificial Sequence
<220> FEATURE:
<223> OTHER INFORMATION: Synthetic Construct-Example 14: a designer
      hox-promoter-controlled Pyruvate-Kinase DNA construct

<400> SEQUENCE: 14

```
agaaaatctg gcaccacacc gcagaaatat aggggctagg agttgagggt actctggttc      60
gtcaagcatt tgggatgatt tcccctcaca agttcctcaa attattctcc tataaacaat     120
agatataagg tcaaaacttg agttatgagt gctgagtaaa aaattactct ccacgcctca     180
gaggtagata tgatgcaatt aagagattct gtacgccgga caaaaatcgt cgctacaatt     240
ggccctgcca ctagtagccc cgaaatgctg aaagccatca ttgaagcggg tgcaacaacg     300
ctgcgactca acttttccca cggttcccac gccgaccatc agcgtagtat tcgcctaatt     360
cggcaaaccg cttttgaact aaatcagcca gtggcaattc tccaagattt gcaagggcca     420
aaaattcgct taggaaaatt tgaaaacggg tctatagttt tagctaaagg cgatcgcttc     480
actttaacaa atcgtccagt tgttggtacg caggaaatta gctgtgtcac ctacgattac     540
ttggctgatg aagtccctgt aggtgcaaaa atcctccttg atgatggccg tgtagaaatg     600
gtggtggagg atattaaccg cgacaaaggg gatttacatt gtcgggtgac tgtagcaggt     660
aagttatcta ataacaaagg tgttaacttt cctggcgtat atctctcaat taaagctatg     720
accgacaaag atcgtgagga tctgatgttt ggtctagacc aaggtgttga ttgggtagca     780
cttttccttt g tccgtaatcc ccaagacatc attgaaatta aagagctaat ttccagcact    840
ggtaaacaag tgccagtagt tgccaaaata gaaaagcatg aagcgatcga acaaatggaa     900
gcagttctcg ctttatgtga tggcgtaatg gtggccagag gcgatttagg tgtagaacta     960
ccagcagaag atgtccccgt attacaaaaa cgcttaattg cgacagcaaa ccgcttgggg    1020
attcccatca tcaccgctac ccagatgtta gatagcatgg tgagcaatcc ccgtcccacc    1080
cgcgcggaag tttccgacgt agccaatgcc attcttgatg gtacagatgc ggtaatgctc    1140
tccaatgaaa cggctgtggg tagctaccca gtggaagcgg tggcgacaat ggcaagaatc    1200
gccgaacgca tcgagcagga agaagctatg gctagtaaat tacgccaaat gcgagataac    1260
cgccgttcta tccccaacgc catcagccaa gctgtaggtc aaattgctga acagttggga    1320
gcagcagcaa ttatgactct gacccaaaca ggggcgactg cacgcaacgt tccaagttc     1380 cgcccccaaa caccaatctt agcggtaaca ccccacgtca acgtagctcg tcagctacaa    1440
atggtatggg gtgtaaaacc tttgttggta ttagaattac cttccactgg tcaaacattc    1500
caagccgcca ttaacgtcgc ccaggagcat agtttactgt tgaaggcga tttagtcgtg     1560 atgacagccg ggacactcca agggtatct ggctcaacgg acttgattaa agttgaagtg     1620
gtgacagcag ttctaggtca gggaattggt ctaggacagg gtttgtaag cggttgtgct     1680 agggttgctc acaccggtat ggatgtgggg aactttaact ccggtgatat tttggttgca    1740
ccccgcacag gcgcagattt tgtcgaggcg attcgcaaag caggcgggat tattacagaa    1800
gatgaaagtt taaccagtca tgcggcggtg attggtttac gcctgggtgt accagtaatt    1860
```

```
gtaggtgtga agaaagccac gcaagttatt cgtgatggag caattctgac tctggatttg      1920
caacgaggtt tagtttattc cggtgctgtc ggaactcctt aatgaagtaa gtaggaagca      1980
gggagcaggg gaaagaaaat tgacaactgt acaagattaa tcgcgtctct gagcaatgac      2040
caaatacatc tacctccacg gttttcttcc agcccctat ctgcgaaagc acaagatatt       2100
agcaagcgtt tcgcccaaat tcacatacag ctaacaatcc ctgatctcaa tgctggtgaa      2160
ttttctcagt taacaatcac gcgccaaatt caacaagttg ccgcaatttt ccctgataat      2220
tctgaaccaa taacgctgat aggttctagt ttaggcggtt taactgctgc ttatctagga      2280
cagcgatatt tacaagtaca acgcttagtt ttattagcgc cagtttggtt ttttatccca      2340
ttggttgccc aaaatgggtg aagaagctgt cacaagttgg caacaaacga tataggttct      2400
ctcttctgcc gtta                                                         2414

<210> SEQ ID NO 15
<211> LENGTH: 1934
<212> TYPE: DNA
<213> ORGANISM: Artificial Sequence
<220> FEATURE:
<223> OTHER INFORMATION: Synthetic Construct-Example 15: a designer
      hox-promoter-controlled Enolase DNA construct

<400> SEQUENCE: 15
agaaaatctg gcaccacacc gcagaaatat aggggctagg agttgagggt actctggttc        60
gtcaagcatt tgggatgatt tcccctcaca agttcctcaa attattctcc tataaacaat       120
agatataagg tcaaaacttg agttatgagt gctgagtaaa aaattactct ccacgcctca       180
gaggtagata tgctatttcg gccctaaacc cacagcccca gcataaacag cgcgatcgcc       240
taattcatct tcgatacgta gcaagcggtt gtatttggct acccgttcac tacgacagag       300
ggaaccagtt ttgatttgac ctgcacgggt agcaacggct aaatcagcaa tggtggtgtc       360
ttctgtttca ccagaacgat ggctaatgac tgaacgaaaa ccgttacgag ttcctaagtc       420
gatggtttct agggtttcag tcaaggaacc aatttgattg agtttaatca aatggcgtt        480 acctgctttt tcttggatgc ttttttgtaa gcgggtagcg tttgttacaa acaagtcatc       540
gcccactaac tgcacccgtg aaccgacttt ttgggtgagt aattgccaat tttgccaatc       600
ttcttcgtgt aagccatctt caatggacac aattgggtat tgatcaacca actgccctaa       660
gtaatcgata aactcggttg gtgcatgggg tctaccatca tagacatact gcccttcctt       720
ataaaattca ctagccgcca catctaacgc tagggctact tgttccctg gcttgtatcc        780 tgctttttca atggctgcaa ctagcaattc caaggctacc tgattggatt ccaagttagg       840
tgcaaaacca ccttcatcgc ctacacctgt cagcaagccc ttatcatgca gcacttcact       900
gagggtagca atacctcag cacccccaacg cagggcttcc cggaaggaag ttgcaccaac      960
gggaacgatc ataaattctt ggaaatccac gttattagca gcgtgcgccc cgccgttaat      1020
cacgttcatc aaaggcacag gcaacaaatt cgccaaaggg ccgcctaagt aacgatatag      1080
gggaatcccc aaagatgccg ccccggctct agcagctgcc aaagaaacgg ctaaaatcgc      1140
atttgcaccc aaatttgatt tgttaccaga accatcaagg gcaatcatcg tccggtcgat      1200
gagttcttgg ttaatagcat ccaaatcaat taactttggg gctagtactt cattcacgtt      1260
gtgtacagcc ttgagtaccc cttaccgcc gtaacggctt ttatctttgt ccctgagttc      1320
atgggcttca aatgtgcctg tggaagcgcc gctaggaact tgtgccaagc cgacagcacc      1380
gcttaataaa tgtacttccg cttctattgt tggtctaccg cgtgagtcga gaatttcgcg      1440
ggcgacaatt gcctcaatgg ctgtatcgac aatattactc attgaagtaa gtaggaagca      1500
```

```
gggagcaggg gaaagaaaat tgacaactgt acaagattaa tcgcgtctct gagcaatgac    1560
caaatacatc tacctccacg gtttctcttcc agcccctat ctgcgaaagc acaagatatt    1620
```

```
gggagcaggg gaaagaaaat tgacaactgt acaagattaa tcgcgtctct gagcaatgac    1560
caaatacatc tacctccacg gttttcttcc agcccctat  ctgcgaaagc acaagatatt    1620
agcaagcgtt tcgcccaaat tcacatacag ctaacaatcc ctgatctcaa tgctggtgaa    1680
ttttctcagt taacaatcac gcgccaaatt caacaagttg ccgcaatttt ccctgataat    1740
tctgaaccaa taacgctgat aggttctagt ttaggcggtt taactgctgc ttatctagga    1800
cagcgatatt tacaagtaca acgcttagtt ttattagcgc cagtttggtt ttttatccca    1860
ttggttgccc aaaatgggtg aagaagctgt cacaagttgg caacaaacga tataggttct    1920
ctcttctgcc gtta                                                      1934

<210> SEQ ID NO 16
<211> LENGTH: 2243
<212> TYPE: DNA
<213> ORGANISM: Artificial Sequence
<220> FEATURE:
<223> OTHER INFORMATION: Synthetic Construct-Example 16: a designer
      hox-promoter-controlled Phosphoglycerate-Mutase DNA construct

<400> SEQUENCE: 16
agaaaatctg gcaccacacc gcagaaatat aggggctagg agttgagggt actctggttc      60
gtcaagcatt tgggatgatt tcccctcaca agttcctcaa attattctcc tataaacaat     120
agatataagg tcaaaacttg agttatgagt gctgagtaaa aaattactct ccacgcctca     180
gaggtagata tgatggcaca agcacctgta tctccagtgg tgctggtaat attagacggc     240
tggggttatc gtcctacaga agaggataac gcagttgtaa tggcaaacac tccggtaatg     300
gattgtttgt ggacaaccta tcccagaacc ctaattaaaa catcgggtaa agaagttggc     360
ttacctcaag gtcaaatggg taactcagag gtaggacatc taaaccttgg tgccgggcgc     420
attgttcccc aagagttagt aagaatatcc gatgcagtgg aagagggtgc aatctacgaa     480
aataaagccc tagttagctt gtgtgaagaa gtagcttctc gcaaggggaa actgcacttg     540
atcggtttat gttctgaagg tgggggttcat tcccatttag accacttatt cggacttctc     600
aacctggcgc aaaagcaaaa tctccaggat gtctgcgttc atgctatcac cgatggcaga     660
gataccaaca caacggatgg ggtaaaagcg atcgccagaa ttgaggatca catcgaaaaa     720
ctggggatcg gcgcattgc caccgtcagt gggcgttatt atgccatgga tcgtgatcgc     780
cgttgggatc gggttaaaact ggcctacgat gtaattaccc aagatgggga tggggatgga     840
cgttccgccc ttgaactact aaaagatttt tattctcaag ataaaaccga tgagtttat     900 ccccccactc gtatcgctcc aggagctata gaagcagggg atgggtcat tttcttcaat     960 tttagacctg atcgcgccag acagctttgt tctgccctga ctgtgcctaa ttttgacggc    1020
tttgaacggg agttaatcac tcctctgagt tttgtcacct ttacccaata cgatcctaaa    1080
ctacctgtta aagtagcctt tgaaccccaa aacctcaaca atattttagg ggaagttgtg    1140
gcccgtgaag ggttaaaaca gtttcgtgtg gcagaaacag aaaagtatcc ccacgtcacc    1200 tatttctttta tgggggttt agaagaaccc ttggaagggg aagatcggga gttgattcaa    1260
agtcctatgg tagcgactta tgatctgtct ccagctatgt ctgccgaagc ggtgacaaaa    1320
gctgcttgta atgcagtaga caaagccgtt tattccttgg ttgtgattaa ctatgctaac    1380
cccgatatgg tgggtcatac tgggaatact gaggcggcca tcgaggcgat cgaaaccgtg    1440
gataattgtt tagggaagtt actctctagt gtgagtaaac tggggggaac ggttatcatt    1500
acggcggatc acggtaacgc cgaaaccatg aaagacgaaa atggcaaccc ttggactgca    1560
```

```
cataccacca acccggttcc cttaattttt gtagaagggg aacaacgaaa aattcccggc    1620
cacggtggtt tagtggaact cagagatgac ggcaaactgg ctgatattgc ccccactatc    1680
ctgcaaattt tacagctgga taaaccctca gaaatgacgg gggaatcgct gattaaacca    1740
gcagaaatag aaattcgagc caatcgtaca cctgttcgca tcggtcgtta gtgaagtaag    1800
taggaagcag ggagcagggg aaagaaaatt gacaactgta caagattaat cgcgtctctg    1860
agcaatgacc aaatacatct acctccacgg ttttcttcca gccccctatc tgcgaaagca    1920
caagatatta gcaagcgttt cgcccaaatt cacatacagc taacaatccc tgatctcaat    1980
gctggtgaat ttctcagtt aacaatcacg cgccaaattc aacaagttgc cgcaattttc    2040
cctgataatt ctgaaccaat aacgctgata ggttctagtt taggcggttt aactgctgct    2100
tatctaggac agcgatattt acaagtacaa cgcttagttt tattagcgcc agtttggttt    2160
tttatcccat tggttgccca aatgggtga agaagctgtc acaagttggc aacaaacgat    2220
ataggttctc tcttctgccg tta                                            2243
```

<210> SEQ ID NO 17
<211> LENGTH: 1663
<212> TYPE: DNA
<213> ORGANISM: Artificial Sequence
<220> FEATURE:
<223> OTHER INFORMATION: Synthetic Construct-Example 17: a designer groE-promoter-controlled NADPH-dependent Alcohol-Dehydrogenase DNA construct

<400> SEQUENCE: 17

```
agaaaatctg gcaccacacc tgcttcgcga gcgcgacaac tgtcaggagg gcgattttgc      60
cacagtccag cgtatcaccg aaggctgcac ctttcccgcag caagattccc attcctgcga    120
tcgccgagtt cgggaacccg tactgaggtc gcgttgccct ccgagaaggc ggcccgtaca    180
ttagcactca ggtactggga gtgctaatcc atgcggatca tcccggttgc cctctccccg    240
tgacgacgtt tactcaaaac tatgggttat ccagatactt ttcaagggtt tgccgtaaat    300
gacacctcca aatggagtga agttgagaag atggacttta agccaaagac attcggtcct    360
cttgatatcg acataaagat caaagcatgc ggggtttgtg gttcagatgt ccacactgtc    420
actggaggtt gggaccagcc aagattgcca gtaattgttg gtcacgaaat tgtgggtgaa    480
gtcgtcaaag ttggagacaa tgtttccctg tttaaaatcg gtgatagagt aggaatggga    540
gcccaggctt gggcctgctt agaatgcgat gtctgcaaga atggcgatga aatttattgt    600
ccaaaatggg tcgatacgta taacgacgtt tatccagatg gctcattggc gtatgggggt    660
tactcttcgc atgtcagagt acatgagcac tttgcattcc caattcctga ggcattgtct    720
acagaaggtg tggctccaat gctttgtgct ggtatcacaa catattctcc cttggtaaga    780
aatggagctg gtccaggtaa gaaagttggt gttgttggtg taggcggctt gggccacttt    840
gctataatgt gggcaagagc cttggctgt gaggtctatg tgttctccag gtctttgtct    900
aagaaggatg atgccataaa gcttggagca gatcattata ttgcaactgg agaagaaaat    960
tggaatgagc catataaata caagttggat ttgatattga gtacagctaa ttcgaactcg    1020
ggcttcgata tgggtgcata cctctcaact ttgagagtcc atgggaagta catcgcctta    1080
ggattgccgg aggacgattt caagtttcc ccagaaagtc ttctcaaaaa tggttgtttc    1140
gttggttcat ctcatttggg taatagacaa gaaatgatcg atatgttgaa cttggcagca    1200
gaaaagggga ttgaagcatg gtacgaagct gttccgatag aaagcaagg tatcaaggaa    1260 gccttggaaa gatgtcaatc tggcaaggtg aagtatagat ttaccttgac agattatgag    1320
```

```
aagcaatttg aatagtaata gtgatcccgg ccgctactaa agcctgattt gtcttgatag    1380
ctgctcctgc ctttgggcag gggcttttt ctgtctgcca ttcttgagga tggcggactc    1440
tttccctttt gctctacgcc catgaatgcg atcgcagtct ccctgtcca gcacgttgga    1500 gtgattggtg gtggccagtt agcttggatg ctggcaccag cagcgcaaca gttgggatg    1560 tcgctgcacg ttcaaacacc caatgatcac gacccagcag tagcgatcgc ggatcaaacc    1620
gtattagcag cagttgctga cgcggttctc tcttctgccg tta                     1663

<210> SEQ ID NO 18
<211> LENGTH: 2326
<212> TYPE: DNA
<213> ORGANISM: Artificial Sequence
<220> FEATURE:
<223> OTHER INFORMATION: Synthetic Construct-Example 18: a designer
      groE-promoter-controlled Pyruvate-Decarboxylase DNA construct

<400> SEQUENCE: 18
agaaaatctg gcaccacacc tgcttcgcga gcgcgacaac tgtcaggagg gcgattttgc      60
cacagtccag cgtatcaccg aaggctgcac cttcccgcag caagattccc attcctgcga     120
tcgccgagtt cgggaacccg tactgaggtc gcgttgccct ccgagaaggc ggcccgtaca     180
ttagcactca ggtactggga gtgctaatcc atgcggatca tcccggttgc cctctccccg     240
tgacgacgtt tactcaaaac tatgtccgac gatcaaatca cattaggtca atacttgttt     300
gaaagattga accaaccccc aattaatatc aaaaatgttt ttggtgtgcc tggtgatttc     360
aacttggtat tgttggataa gatcaacgag gttaagggaa tgaaatgggt aggaagtgta     420
aatgaattga acgcagggta cgctaccgac ggatactcaa gagtcaagaa tggatttaca     480
gcagagggtt catcaattgg ttgtttagtg acaactttg gtgttggaga gctactggct     540
gtaaatgcaa ttgcaggagc atattcagaa catgtgggtt tggtccatgt tgttggagtc     600
ccatccactg agtctcaaaa gaaggagttg ttgttgcacc atacattggg taatggtgac     660
ttcaccgttt ttggtaaaat ctcatcatac attagtgcca ctactgcaat tttggatgac     720
ccaagtagag caacaaagga gattgataga gttattgaat ctgctttat taatcaaaga     780 cccacatact tggcgttccc atccaacttt tttaacatga agtgtccaa aagcttgctt     840 gataagccat tgaacttgac accaccacca aataacgaag agatccaaaa tgaagttttg     900
aatgaaatct tgagcatgat ctccaaggct aagaatccag ttgttattat cgatgcttgt     960
tgcggtagac ataattcgac gtacgaggct agtaaattga ttgaattgac caatttaac    1020 tttgcagtca cgccaatggc taaaggatcg agagatattg acgagaatga ccctaggtac    1080
gttggtgttt acttgggaga tttgtcttac cctaaatcca aggagttggt tgagagttcg    1140
gatttggtct tgtcattggg tgctgtgttg tcggatttca ataccggtgc ctttttcttat    1200 tctcttccat cctcaaaagt tgtcgagttc cactcggatt ataccaaaat tagaaatgca    1260 caatacccctg gtattagaat gaaggagttg ttggcaaagt tggttaagtc tccagagttg    1320
aagaagattg tagaaggtta taagccccgt gcatcttctt tggacttgat ccgtcctgtt    1380
gaattaccag atgaccacaa acttactcaa gcatggctct ggtctaattt gggttcttgg    1440
ttgaaagaag gtgatgttat cattaccgaa actggtactt caaattttgg tattgttcaa    1500
accaaattcc ccaaaaatgt tattggaatt tcacaagtct tgtggggctc tatcggttac    1560
tcggttggag cagcatctgg tgctgttatt gcggccgagg aagttgatcc aaacagaaga    1620
gttattttgt ttgttggaga cggctcttta caattgactg tgcaggagat ttcaactatg    1680
gccagacacc ataacaatat ttcattttt gtgttgaaca atagcggttt cacgattgag    1740
```

```
aggttgattc acggtatgga ggccagctac aatgaaattc aagagtggga gtacaccgat     1800
ttgctcaaga catttaaagc tacaaactac gaaaccttct cggttggcaa ggtaggcgag     1860 cttccaaat tgttcaagga caaagatttt gctgttaaca acaaaaccag attggtagaa     1920
```

```
aggttgattc acggtatgga ggccagctac aatgaaattc aagagtggga gtacaccgat     1800
ttgctcaaga catttaaagc tacaaactac gaaaccttct cggttggcaa ggtaggcgag     1860
ctttccaaat tgttcaagga caaagatttt gctgttaaca acaaaaccag attggtagaa     1920
atcaagttgg atacttttga tgctccagag aatttagtga agcaagcaga aatgtcctca     1980
aaaactaacg atgcataata atagtgatcc cggccgctac taaagcctga tttgtcttga     2040
tagctgctcc tgcctttggg caggggcttt tttctgtctg ccattcttga ggatggcgga     2100
ctctttccct tttgctctac gcccatgaat gcgatcgcag tctcccctgt ccagcacgtt     2160
ggagtgattg gtggtggcca gttagcttgg atgctggcac cagcagcgca acagttgggg     2220
atgtcgctgc acgttcaaac acccaatgat cacgacccag cagtagcgat cgcggatcaa     2280
accgtattag cagcagttgc tgacgcggtt ctctcttctg ccgtta                    2326
```

<210> SEQ ID NO 19
<211> LENGTH: 1919
<212> TYPE: DNA
<213> ORGANISM: Artificial Sequence
<220> FEATURE:
<223> OTHER INFORMATION: Synthetic Construct-Example 19: a designer groE-promoter-controlled Pyruvate-Kinase DNA construct

<400> SEQUENCE: 19

```
agaaaatctg gcaccacacc ccgaaggctg caccttcccg cagcaagatt cccattcctg       60
cgatcgccga gttcgggaac ccgtactgag gtcgcgttgc cctccgagaa ggcggcccgt      120
acattagcac tcaggtactg ggagtgctaa tccaatgcgg ctcccaggac agaaaaccaa      180
gataatagcc accctaggtc ctgcgtctct caacgaaaag accataacgg caatggttcg      240
agcggggatg agtgttgcaa ggataaactt cgcccacggt gatctgaaac agcacgagaa      300
gtcgataaaa ctcgtgagaa aggtctctga gaggctcaac aggcccgttg caattctcgg      360
agacctgccc ggagtgaaga tccgcgttgg tgagattgag ggcggctcag tgacgctgag      420
acgctggcag acgtaacccc ttaccacgag ggacgtaatc ggcaacgagg ccgttatacc      480
cgttgagttc aaggactttc caaggctcgt ctcgaagggg gacgtcatct atctcagcga      540
cggtttcata gcgctaaggg ttgaagacgt cagggaccag gatgtcatct gtaaggtgct      600
cgtcggagga actctcttct cccgcaaagg aatcaacatt cccaaggctc gcctggctat      660
cgaagcaata accgagaagg atttagaatt cctggagttc tctctggagc acggagttga      720
cgccgtcggc ataagcttcg tcggttccgc ctacgacgtt ctaaaggcaa ggcgattcgt      780
cgaggaaagg aacggcaagc tgttcctgat agccaaaata gaaaggcccg acgcggtgag      840
aaacttcgac gagattctca gggcggcgga cggggtcatg gtagccaggg gagacctcgg      900
agtggagatg cccatagaaa agctcccgat tctccagaaa aagcttatcc aaaaggcaaa      960
ctgtgcggga agcccgtgaa cagcgac tcagatgcta gagagcatga cccacgagaa     1020
gctcccaacg agggctgagg tcaccgatgt tgcgaacgca atccttgatg gaaccgacgc     1080
cgtgatgctc tccgaggaga cggcggtcgg aaagtacccg gttgagaccg tcaaaatgat     1140
ggccaggata gcgaagacta ccgaggcata cagggactcc aaatgggctg aaagaaccgt     1200
cgaatggaag atgagtgagt tgaggggtac acggccgaca aagggtacca taaggacgc     1260 aataacgagg agtataatag aggccctgaa ctccatagac attaaataca tactaacacc     1320
gaccaggatg ggacaaactg cgaggctaat agcccgtttt aagccaaagc agtgggtact     1380
ggcatttgta actgatgaat gggtcaaaaa cactctgatg ttctcctacg gcgtttatcc     1440
```

```
gttcctcgtt gaggacacca gcgaagagga gatactgcgc gtgataaccg ggctcggact    1500
ggtagatgag ggcgatacgg tacttctgac gaagggaacg cccataggaa agaccgcggg    1560
gacgaacacc atccgcatct tcaacgtttg ataatagtga tcccggccgc tactaaagcc    1620
tgatttgtct tgatagctgc tcctgccttt gggcagggga tttttctgt ctgccattct     1680 tgaggatggc ggactctttc ccttttgctc tacgcccatg aatgcgatcg cagtctcccc    1740
tgtccagcac gttggagtga ttggtggtgg ccagttagct tggatgctgg caccagcagc    1800
gcaacagttg gggatgtcgc tgcacgttca aacacccaat gatcacgacc cagcagtagc    1860
gatcgcggat caaaccgtat tagcagcagt tgctgacgcg gttctctctt ctgccgtta    1919

<210> SEQ ID NO 20
<211> LENGTH: 1778
<212> TYPE: DNA
<213> ORGANISM: Artificial Sequence
<220> FEATURE:
<223> OTHER INFORMATION: Synthetic Construct-Example 20: a designer
      groE-promoter-controlled Enolase DNA construct

<400> SEQUENCE: 20
agaaaatctg gcaccacacc ccgaaggctg caccttcccg cagcaagatt cccattcctg      60
cgatcgccga gttcgggaac ccgtactgag gtcgcgttgc cctccgagaa ggcggcccgt    120
acattagcac tcaggtactg ggagtgctaa tccaagtttc tttttcaaa ttgtaaaacg     180 agcggatgcc ttggtaaatg gccgtgtggc cgagttcatc ttcaatgcgg agcagctggt    240
tgtatttcgc gacgcggtcg gtgcgcgacg gcgcgcccgt tttgatttgg ccggcgttgg    300
tggcgacggc gatgtccgcg atcgtgctgt cttccgtttc gccggaacgg tgcgagacga    360
cggcggtgta gccggcgcgt ttcgccattt cgatggcgtc aaacgtttcg gtgagcgtgc    420
cgatttggtt cactttgatc aaaatcgagt tgccgacgcc tttttcaatg ccttcggcca    480
gttttttcgt gtttgtgaca aacaagtcgt cgccgacaag ctggactttt ttgccgagcc    540
gctcggtcag cagtttatgg ccttcccagt cgttttcatc gagcccgtct tcgatcgaga    600
tgatcggata tttcgataca agctcttcat accaagcgac catttcttcc gacgttttca    660
caacgccttc gccttcaaga tgatatttgc cgtcttcttt gttgtacagc tcggacgagg    720
caacgtccat ggcgagcatc acttgttcgc ccggtttgta gccggctttt tcgatcgctt    780
cgatgatcgt ttgcagcgct tcttcgttcg atttcaagtt cggggcgaag cctccttcat    840
cgccgacggc ggtgttgtag cctttcgctt tcagcaccgc ttttaagctg tggaaaattt    900
ccgcccccat gcgcagcgct tcgcggaagc tttccgcgcc gaccggcatg atcataaatt    960
cttgaatgtc gacgttgttg tccgcatgcg cgccgccgtt taaaatgttc atcatcggca    1020
ccggcagcgt tttggcgtta aagccgccta agtattggta cagcggcagg ccaagctcgt    1080
ccgctgccgc gcgggccacg gcgagcgaga cgcccaaaat ggcgttggcg ccaagcttgc    1140
ttttgttttc cgtgccgtct aattcaatca gcttccggtc gatcgccact tggtcggcga    1200
cctccaggcc gatgatttcc ggcgcgatga tttcgttgac gttttcgacc gcttttaaca    1260
cccctttgcc gaggtagcgg tttttatcgc cgtcgcgcag ttcgaccgct tcatattccc    1320
cggtcgaggc gccgctcggc accaaggcgc ggccgaagcc gccgtcttct gtgtacactt    1380
ccacttccac cgtcgggttg ccgcgcgaat cgagcacttc gcgagcgtag acatcgataa    1440
tggcagacat taatagtgat cccggccgct actaaagcct gatttgtctt gatagctgct    1500
cctgcctttg gcaggggct tttttctgtc tgccattctt gaggatggcg gactctttcc    1560
cttttgctct acgcccatga atgcgatcgc agtctcccct gtccagcacg ttggagtgat    1620
```

```
tggtggtggc cagttagctt ggatgctggc accagcagcg caacagttgg ggatgtcgct    1680
gcacgttcaa acacccaatg atcacgaccc agcagtagcg atcgcggatc aaaccgtatt    1740
agcagcagtt gctgacgcgg ttctctcttc tgccgtta                            1778

<210> SEQ ID NO 21
<211> LENGTH: 1178
<212> TYPE: DNA
<213> ORGANISM: Artificial Sequence
<220> FEATURE:
<223> OTHER INFORMATION: Synthetic Construct-Example 21: a designer
      groE-promoter-controlled Phosphoglycerate-Mutase DNA construct

<400> SEQUENCE: 21
agaaaatctg gcaccacacc ccgaaggctg caccttcccg cagcaagatt cccattcctg      60
cgatcgccga gttcgggaac ccgtactgag gtcgcgttgc cctccgagaa ggcggcccgt     120
acattagcac tcaggtactg ggagtgctaa tccaagtatg gtaaaattgg ttttcgctcg     180
ccacggtgag tctgaatgga acaaagctaa tcttttcaca ggttgggctg acgtagatct     240
ttctgaaaaa ggtactcaac aagctattga cgctggtaaa ttgattaaag aagctggtat     300
tgaatttgac aaagcttaca cttcagtatt gaaacgtgcg atcaaaacaa ctaaccttgc     360
gcttgaagcc tctgaccaac tttgggttcc agttgaaaaa tcatggcgct gaacgaacg      420 tcactacggt ggtttgactg gtaaaaataa agcagaagct gctgaacaat tggtgatga      480 gcaagttcac atctggcgtc gttcatacga tgtattgcct ccaaaaatgg accgtgatga     540
tgagtactca gcacacaaag accgtcgtta cgcttcactt gacgattcag taattccaga     600
tgctgaaaac ttgaaagtaa ctttggaacg tgcccttcca ttctgggaag ataaaattgc     660
tccagctctt aaagatggta aaaacgtatt cgtaggtgca catggtaact caatccgtgc     720
ccttgtaaaa cacatcaaaa aattgtcaga tgacgaaatc atggatgttg aaattccaaa     780
cttcccacca ttggtatttg aatttgacga aaaattgaac gttgtttctg aatattacct     840
cggaaaataa taatagtgat cccggccgct actaaagcct gatttgtctt gatagctgct     900
cctgcctttg ggcaggggct ttttttctgtc tgccattctt gaggatggcg gactctttcc     960 ctttttgctct acgcccatga atgcgatcgc agtctcccct gtccagcacg ttggagtgat    1020
tggtggtggc cagttagctt ggatgctggc accagcagcg caacagttgg ggatgtcgct    1080
gcacgttcaa acacccaatg atcacgaccc agcagtagcg atcgcggatc aaaccgtatt    1140
agcagcagtt gctgacgcgg ttctctcttc tgccgtta                            1178

<210> SEQ ID NO 22
<211> LENGTH: 2361
<212> TYPE: DNA
<213> ORGANISM: Artificial Sequence
<220> FEATURE:
<223> OTHER INFORMATION: Synthetic Construct-Example 22: a designer
      rbcL-promoter-controlled Phosphoglycerate-Mutase DNA construct

<400> SEQUENCE: 22
agaaaatctg gcaccacacc tgccgacggt tccagaatca aaggaatccc tagaatcggg      60
cgaaaaaaca ccagttgtcg ggcaagttta tatcaatcaa ctattaatga cccctattccc    120 tcaccaaaat tctctcaata ccccaaatca accagatgag ccttagcccc acaaaacttt     180
catgattgct tgagtgaaaa ttaaatgttt aaagttctta aaggagattg ttgagaaaca     240
taaatactta attcatctca tttgaacgct ttccctctct aaagatcccg acagaaaacg     300
gttttagccc aatgtctcat taggtagcat ggctgaattc gagcgggatt ttatggcttt     360
```

```
tttaggtatt tttgtaaggg taaaataggc ccatcaaaca gcattagaaa tgctaatcag      420
cccaaaaaac aaaagcaatc ttttttttgtt gctaaaagat aaaaataagt cgaggctgtg     480
gtaacatatc ccacagatta agaaagtca taagacttga atcttcagaa ttttaaaaag      540
cagttttgcc aacgtaagat ttttgaagtt ttcgaccaac aataccgtta ctggtatttg     600
tctgttaaag ataagcattt ttgctggagg aaaaccgcat gatgagtaaa aaaccggttg    660
cgctcatcat tttagacgga tttgcgctgc gcgacgaaac gtacggcaat gcggtcgctc    720
aggcgaacaa accgaacttt gaccgctatt ggaacgaata cccgcacaca acgctcaagg    780
cgtgcggcga ggcggtcggg cttccggaag ggcagatggg caactcggaa gtcggccatc    840
tcaacatcgg cgccgggcgc attgtgtacc aaagcttaac gcgaatcaac attgccattc    900
gcgaaggcga gtttgaccga atgaaacgt ttttggcggc gatgaaccat gtgaaacaac    960
acgggacaag tttgcatttg ttcggcttgc tttccgacgg cggggtgcac agccatattc  1020
accatttgta cgccctcttg cgcttggcgg cgaaagaagg cgtgaagcgc gtgtacatcc  1080
acggcttttt ggacggccgc gacgtcggcc cacaaacagc gccgcaatac attaaagaac  1140
tgcaggaaaa aatcaaggaa tatggcgtcg gcgaaatcgc gacgttatcg ggccgctact  1200
actcgatgga ccgcgacaag cggtgggacc gcgtcgaaaa ggcgtatcgg gcgatggtgt  1260
acggggaagg gccgacgtac cgcgatccgc tcgagtgcat cgaggactcg tacaaacacg  1320
gcatttacga cgaattcgtc ctgccgtcgg tcatcgtccg cgaagacggc cggccggtgg  1380
cgacgattca agacaatgac gcgattatct tctataattt ccgccctgac cgggcgatcc  1440
aaatttcaaa cacgtttacg aacgaagatt tccgcgagtt tgaccgcggc ccgaaacatc  1500
cgaagcattt gttctttgtc tgcttgaccc atttcagcga aacggtgaaa gggtacgtgg  1560
cgttcaagcc gacgaacttg gacaacacga tcggggaagt gctgtcgcag cacggactgc  1620
gccagctgcg catcgccgag accgaaaaat atccgcacgt gacgtttttt atgagcggcg  1680
gccgcgaaga gaaatttcca ggcgaagacc ggattttgat caactcgccg aaagtgccga  1740
cgtatgactt gaagccggaa atgagcgcct atgaagtgac cgatgcgctg ctcaaggaaa  1800
ttgaagccga taagtacgat gcgatcattt tgaactacgc caacccggat atggtcggcc  1860
attcgggcaa gctcgaaccg acgatcaagg cggtggagc agtggacgaa tgcctcggca  1920
aagtcgtcga tgccatttg gccaaaggcg gcatcgccat catcaccgcc gaccacggca  1980
acgccgatga agtattgacg ccggacggca agccgcaaac ggctcatacg acgaatccgg  2040
tgccggtcat cgtgacgaaa aaaggcatca agcttagaga cggcggcatc ttaggcgatt  2100
tggcgccgac gatgctcgat ttgctcggct tgccgcagcc gaaagaaatg acggggaaat  2160
cgttgattgt caaataataa ggttttgttg ttttttgtga cctgaattta atttgaatca  2220
tgcggaatgc gatcgcctta ggacggtcgc attttttgtt tacgtctaaa attagtcgaa  2280
atcccccatc aacgccatgg tagtgatttt gtcttaacgt tattcaccca tcaatttcaa  2340
aggttctctc ttctgccgtt a                                              2361
```

<210> SEQ ID NO 23
<211> LENGTH: 2124
<212> TYPE: DNA
<213> ORGANISM: Artificial Sequence
<220> FEATURE:
<223> OTHER INFORMATION: Synthetic Construct-Example 23: a designer
      rbcL-promoter-controlled Enolase DNA construct

<400> SEQUENCE: 23

```
agaaaatctg gcaccacacc tgccgacggt tccagaatca aaggaatccc tagaatcggg      60
cgaaaaaaca ccagttgtcg ggcaagttta tatcaatcaa ctattaatga ccctattccc     120
tcaccaaaat tctctcaata ccccaaatca accagatgag ccttagcccc acaaaacttt     180
catgattgct tgagtgaaaa ttaaatgttt aaagttctta aaggagattg ttgagaaaca     240
taaatactta attcatctca tttgaacgct ttccctctct aaagatcccg acagaaaacg     300
gttttagccc aatgtctcat taggtagcat ggctgaattc gagcgggatt ttatggcttt     360
tttaggtatt tttgtaaggg taaaataggc ccatcaaaca gcattagaaa tgctaatcag     420
cccaaaaaac aaaagcaatc ttttttttgtt gctaaaagat aaaaataagt cgaggctgtg     480
gtaacatatc ccacagatta aagaaagtca taagacttga atcttcagaa ttttaaaaag     540
cagttttgcc aacgtaagat ttttgaagtt ttcgaccaac aataccgtta ctggtatttg     600
tctgttaaag ataagcattt ttgctggagg aaaaccgcat ggtgggcgtt aatgattttg     660
ctattgagcg cgtttggggc ttacaggtcc tcgatagcag gggcaacccc actgtgaagg     720
cgtatgtcaa gcttgctgga gggagcttgg gctgggggat agcgcccagc ggtgctagca     780
gaggcgagag agaggcggtg gagcttagag acggtggggg taagtggagg ggtaaaggag     840
tttccagggc agtatctctt ttaaacacag tagtagcacc taggctggag ggggtcgacg     900
ccagaagaca agcccaaata gacaggctcc taatagaact agacggcacc ccgaacaaat     960
cgagactcgg cgggaacacg accaccgctc tcagcatagc cgtttcaaga gctgcggcgg    1020
ctcaggcacg cctcgaactc ttccagtatc taggcggcgc cggggctagg agactcccaa    1080
tacctcttct caacgtcata aatggtggtg ttcacgcggg gaacgagcta gactttcagg    1140
agtttatgat aataccttat ggttttgaaa gcttcacaga agctatgagg gctgcggtgg    1200
agacatacgg ggagctcaag agcctgctta aggacaggta tggtgcatct gcagtcaacg    1260
tcggcgacga aggggggtttc gcaccccta tgagaagcgc cgaagaggcc ctcaagactc    1320
tagtggatgc agtggagaaa gcaggctacc agcccgggag cgagatagcc cttggcattg    1380
acgcggctgc gagccagctc tacagtaacg ggcgctacag cgttgaaggg aagagcctgt    1440
ccagagagga gctcctaagc ctctaccagc gcttggtaga gcagtatcca atagtgtatc    1500
ttgaagaccc atttagcgag gacgactatg aaggtttcaa ggccgccgta gacgccctct    1560
cgacagaaac cattatagtg ggggacgatc tcctagttac caatcccag aggggttaagg    1620
aggcttccgc cctcaaagca gtcacaggcc tcctagtaaa ggtgaaccag gtggggactc    1680
tcaccgaagc tctcgaagcc atccaggctg cgagggacga ggggattgtc cacatagtga    1740
gccacaggag cggagacact gaggacacct tcattgccga cctagccgtc gccacagaag    1800
ctttgatgat caaaacggga gccccagccc ggggagagag gacctcgaaa tacaacaggc    1860
tcctagaaat agagaacata ttaggctact cagccgaata tgcaggtcca gaactacgcg    1920
gcgtaatggg caggcgctga taaggttttg ttggttttg tgacctgaat ttaatttgaa    1980
tcatgcggaa tgcgatcgcc ttaggacggt cgcatttttt gtttacgtct aaaattagtc    2040
gaaatccccc atcaacgcca tggtagtgat tttgtcttaa cgttattcac ccatcaattt    2100
caaaggttct ctcttctgcc gtta                                           2124
```

<210> SEQ ID NO 24
<211> LENGTH: 2577
<212> TYPE: DNA
<213> ORGANISM: Artificial Sequence
<220> FEATURE:
<223> OTHER INFORMATION: Synthetic Construct-Example 24: a designer
    rbcL-promoter-controlled Pyruvate-Kinase DNA construct

<400> SEQUENCE: 24

```
agaaaatctg gcaccacacc tgccgacggt tccagaatca aaggaatccc tagaatcggg      60
cgaaaaaaca ccagttgtcg ggcaagttta tatcaatcaa ctattaatga ccctattccc     120
tcaccaaaat tctctcaata ccccaaatca accagatgag ccttagcccc acaaaacttt     180
catgattgct tgagtgaaaa ttaaatgttt aaagttctta aaggagattg ttgagaaaca     240
taaatactta attcatctca tttgaacgct ttccctctct aaagatcccg acagaaaacg     300
gttttagccc aatgtctcat taggtagcat ggctgaattc gagcgggatt ttatggcttt     360
tttaggtatt tttgtaaggg taaaataggc ccatcaaaca gcattagaaa tgctaatcag     420
cccaaaaaac aaaagcaatc tttttttgtt gctaaaagat aaaaataagt cgaggctgtg     480
gtaacatatc ccacagatta aagaaagtca taagacttga atcttcagaa ttttaaaaag     540
cagttttgcc aacgtaagat ttttgaagtt ttcgaccaac aataccgtta ctggtatttg     600
tctgttaaag ataagcattt ttgctggagg aaaaccgcat gttgagaaag acaaagataa     660
tatgtacatt agggccggca accaattcag aagagattat aagaaagctc attgaaaatg     720
gaatggatgt tgcaaggctt aattttttcac atggcaccca cgaagaacat aaaaagaaga     780
ttgatatgat aaaaaagata cgagaagagc ttgataagcc aattccaatt ctgcttgata     840
caaaaggtcc agagattagg attggttttt tcaaagacgg taaggttgag ctaaaagaag     900
gacagagatt cacactcaca accgaagaaa tattaggaaa tgaagagatt gtgagcataa     960
cttacaaaga acttgttaaa gatgttaagc cgggtgataa atattaatt gacgatggac    1020
taattgagct tgttgttgaa gacaagacag acaaaaatat aatctgcaag gtaaaaaatg    1080
gtggtatttt gacaaatcaa aagggagtaa acgtaccagg aataccaata agactacctg    1140
cactgaccca aaaagacaaa gaagacatcc tctttggaat tgaaaacgat gttgactttg    1200
tggcagcttc tttttataaga aaagcaagtg atgtagttga aataagagaa ttttaaata    1260
aacacaatgg caaagacatt ttgataatag caaagataga aactcaagaa ggtgttgcaa    1320
actgtgatga gataataaga gttgctgacg gaattatggt tgcgagagga gatttgggag    1380
ttgaacttcc atttgaggaa gtgccgcttg tgcaaaagat gctcattgaa aaatgttata    1440
aagcaggaaa gccagtaata actgcaaccc aaatgttaga gtcaatgata agaaacccac    1500
gcccaacaag agcagaagtc agcgatattg caaatgcaat ttttgatgga acatctgcaa    1560
taatgctctc tggcgagaca gctatgggca agtatcctgt tgaaagtgtt gctacaatgg    1620
caaagattgc cgaaagggta gaaagtcaaa tagactatgt caaaagattc caatcccaag    1680
tatttgacat gccagtaaat gttacaaatg ctatatctca tgctacctgt acaactgcgc    1740
atgatcttgg agcaaaggca atcatcactg tgacaaagtc aggcaacaca gcaagaatgg    1800
tgtcaaaatt cagacctgcc tgcccaatta tagcaacaac accgtgcgag aaggtaagaa    1860
gacagctcaa tcttcatgg ggtgtttatc cttttttggc agagtataaa gactctacag    1920
atgatatctt tgaccattcg gtggagattg ctgttaaatc aaagattgtt aaaaatggtg    1980
atttggttgt aataacagca ggtgtgccag ttggtgtaag tggcactaca aatattctca    2040
aagttcatgt tgttggtcat gtgcttgttg aaggaagagg ctggggaagt gggaaggtga    2100
cagcaagagt atgtgttgca aaaaatctta atgagctcaa gcaaattttt gaagatggag    2160
atattattgt cacaacgcag acaaccaatg agtttattcc ttatatgaaa agagcagctg    2220
gaataataac agaagaaggc gggcaaaatt ctcatgcggt gattgttggg gcagctttgg    2280
atattcctgt tataaccgat gctaaaaacg ctttagagat acttaaaaat ggtattgttg    2340
```

| | | | | |
|---|---|---|---|---|
| ttacgatgga | tgcacaaaaa | ggacttgtct | ttagtggaga | acttaaaaat taataaggtt | 2400 |
| ttgttggttt | ttgtgacctg | aatttaattt | gaatcatgcg | gaatgcgatc gccttaggac | 2460 |
| ggtcgcattt | tttgtttacg | tctaaaatta | gtcgaaatcc | cccatcaacg ccatggtagt | 2520 |
| gattttgtct | taacgttatt | cacccatcaa | tttcaaaggt | tctctcttct gccgtta | 2577 |

<210> SEQ ID NO 25
<211> LENGTH: 2083
<212> TYPE: DNA
<213> ORGANISM: Artificial Sequence
<220> FEATURE:
<223> OTHER INFORMATION: Synthetic Construct-Example 25: a designer
      nirA-promoter-controlled Pyruvate-Decarboxylase DNA construct

<400> SEQUENCE: 25

| | | | | |
|---|---|---|---|---|
| agaaaatctg | gcaccacacc | ctttatgcag | aaacgtcata | ttatgaaaag ttttgtaaca | 60 |
| acagatacga | atgtcctctg | tgatcccgat | tacctttact | cagtaatgat ggctgaagtc | 120 |
| tcattaggaa | gatatctctt | cgagagattg | taccaattgc | aagtgcagac catcttcggt | 180 |
| gtccctggtg | atttcaactt | gtcgcttttg | gacaagatct | acgaagtgga agatgcccat | 240 |
| ggcaagaatt | cgtttagatg | ggctggtaat | gccaacgaat | tgaatgcatc gtacgctgct | 300 |
| gacggttact | cgagagtcaa | gcgtttaggg | tgtttggtca | ctacctttgg tgtcggtgaa | 360 |
| ttgtctgctt | tgaatggtat | tgccggttct | tatgccgaac | atgttggttt gcttcatgtc | 420 |
| gtaggtgttc | catcgatttc | ctcgcaagct | aagcaattgt | tacttcacca cactttgggt | 480 |
| aatggtgatt | tcactgtttt | ccatagaatg | tccaacaaca | tttctcagac cacagccttt | 540 |
| atctccgata | tcaactcggc | tccagctgaa | attgatagat | gtatcagaga ggcctacgtc | 600 |
| aaacaaagac | cagtttatat | cgggttacca | gctaacttag | ttgatttgaa tgttccggcc | 660 |
| tctttgcttg | agtctccaat | caacttgtcg | ttggaaaaga | acgacccaga ggctcaagat | 720 |
| gaagtcattg | actctgtctt | agacttgatc | aaaaagtcgc | tgaacccaat catcttggtc | 780 |
| gatgcctgtg | cctcgagaca | tgactgtaag | gctgaagtta | ctcagttgat tgaacaaacc | 840 |
| caattcccag | tatttgtcac | tccaatgggt | aaaggtaccg | ttgatgaggg tggtgtagac | 900 |
| ggagaattgt | tagaagatga | tcctcatttg | attgccaagg | tcgctgctag gttgtctgct | 960 |
| ggcaagaacg | ctgcctctag | attcggaggt | gtttatgtcg | gaaccttgtc gaagcccgaa | 1020 |
| gtcaaggacg | ctgtagagag | tgcagatttg | attttgtctg | tcggtgccct tttgtctgat | 1080 |
| ttcaacactg | gttcattttc | ctactcctac | agaaccaaga | catcgtcga attccattct | 1140 |
| gattacacta | agattagaca | agccactttc | ccaggtgtgc | agatgaagga agccttgcaa | 1200 |
| gaattgaaca | agaaagtttc | atctgctgct | agtcactatg | aagtcaagcc tgtgcccaag | 1260 |
| atcaagttgg | ccaatacacc | agccaccaga | gaagtcaagt | taactcagga atggttgtgg | 1320 |
| accagagtgt | cttcgtggtt | cagagaaggt | gatattatta | tcaccgaaac cggtacatcc | 1380 |
| tccttcggta | tagttcaatc | cagattccca | aacaacacca | tcggtatctc ccaagtattg | 1440 |
| tggggttcta | ttggtttctc | tgttggtgcc | actttgggtg | ctgccatggc tgcccaagaa | 1500 |
| ctcgacccta | acaagagaac | catcttgttt | gttggagatg | gttctttgca attgaccgtt | 1560 |
| caggaaatct | ccaccatgat | cagatggggt | accacacctt | accttttcgt gttgaacaat | 1620 |
| gacggttaca | ccatcgagcg | tttgatccac | ggtgtaaatg | cctcatataa tgacatccaa | 1680 |
| ccatggcaaa | acttggaaat | cttgcctact | ttctcggcca | agaactacga cgctgtgaga | 1740 |
| atctccaaca | tcggagaagc | agaagatatc | ttgaaagaca | aggaattcgg aaagaactcc | 1800 |

-continued

```
aagattagat tgatagaagt catgttacca agattggatg caccatctaa ccttgccaaa    1860
caagctgcca ttacagctgc caccaacgcc gaagcttagt aaggttttgt tggttttttgt   1920 gacctgaatt taatttgaat catgcggaat gcgatcgcct taggacggtc gcattttttg    1980
tttacgtcta aaattagtcg aaatccccca tcaacgccat ggtagtgatt ttgtcttaac    2040
gttattcacc catcaatttc aaaggttctc tcttctgccg tta                      2083
```

<210> SEQ ID NO 26
<211> LENGTH: 1950
<212> TYPE: DNA
<213> ORGANISM: Artificial Sequence
<220> FEATURE:
<223> OTHER INFORMATION: Synthetic Construct-Example 26: a designer rbcL-promoter-controlled NAD(P)H-dependent Alcohol-Dehydrogenase DNA construct

<400> SEQUENCE: 26

```
agaaaatctg gcaccacacc tgccgacggt tccagaatca aaggaatccc tagaatcggg     60
cgaaaaaaca ccagttgtcg ggcaagttta tatcaatcaa ctattaatga ccctattccc    120
tcaccaaaat tctctcaata ccccaaatca accagatgag ccttagcccc acaaaacttt    180
catgattgct tgagtgaaaa ttaaatgttt aaagttctta aaggagattg ttgagaaaca    240
taaatactta attcatctca tttgaacgct ttccctctct aaagatcccg acagaaaacg    300
gttttagccc aatgtctcat taggtagcat ggctgaattc gagcgggatt ttatggcttt    360
tttaggtatt tttgtaaggg taaaataggc ccatcaaaca gcattagaaa tgctaatcag    420
cccaaaaaac aaaagcaatc ttttttttgtt gctaaaagat aaaaataagt cgaggctgtg   480
gtaacatatc ccacagatta agaaagtca taagacttga atcttcagaa tttaaaaag     540 cagttttgcc aacgtaagat ttttgaagtt ttcgaccaac aataccgtta ctggtatttg    600
tctgttaaag ataagcattt ttgctggagg aaaaccgcat gatgttgaga ttgacttccg    660
ccagatccat tgttccccca ttgcgtaagg gtgcttttgg ttccatcaga accttagcta    720
cctctgtgcc agaaacccaa aagggtgtta ttttctatga aatggtggt aaattggaat    780 acaaggacat tccagttcca aagccaaagc caaatgaaat cttgatcaac gtcaagtact    840
ccggtgtgtg tcataccgat ttgcacgcat ggaagggtga ctggccattg ccaaccaagt    900
tgccattggt cggtggtcac gaaggtgctg gtgtcgttgt tgctatgggt gaaaacgtca    960
agggctggaa cattggtgac tttgcgggta tcaaatggtt gaacggttct tgtatgtcct   1020
gtgaatactg tgaattgtcc aatgaatcca actgtccaga tgctgacttg tctggttaca   1080
cccacgatgg ttcttttccaa caatacgcta ccgcagatgc tgttcaagct gccagaattc   1140
caaagggtac cgatttggct gaagttgctc aattctatg tgccggtgtt actgtttaca    1200
aggctttgaa aagtgctaac ttgaaggctg gtgactgggt tgccatctct ggtgctgctg   1260
gtggtctagg ttctctagct gtccaatacg ccaaggccat gggttacaga gtcgttggta   1320
tcgacggtgg tgaagaaaag ggtaagttgg tcaagcaatt gggtggtgaa gcctttgttg   1380
atttcaccaa aaccaaggac atggttgctg aaatccaaga aatcaccaac ggtggtccac   1440
acggtgtcat taacgtctct gtttctgaag ctgccatgaa cgcttccact caattcgtca   1500
gaccaactgg tactgtcgta ttggtcggtt gccagctgg tgccgtcatc aagtccgaag   1560
tcttctccca cgtcgttaag tctattaaca tcaagggttc ttacgtcggt aacagagctg   1620
acaccagaga agctatcaac ttcttcgcta acggtcacgt ccactctcca atcaaggttg   1680
ttggtttgtc cgaactacca aaggtttacg aattgatgga acaaggtaag attttgggta   1740
```

```
gatacgttgt tgacacctcc aactagtaag gttttgttgg ttttttgtgac ctgaatttaa    1800 tttgaatcat gcggaatgcg atcgccttag gacggtcgca tttttttgttt acgtctaaaa    1860 ttagtcgaaa tcccccatca acgccatggt agtgattttg tcttaacgtt attcacccat    1920
caatttcaaa ggttctctct tctgccgtta                                      1950

<210> SEQ ID NO 27
<211> LENGTH: 1521
<212> TYPE: DNA
<213> ORGANISM: Artificial Sequence
<220> FEATURE:
<223> OTHER INFORMATION: Synthetic Construct-Example 27: a designer
      Synechocystis sp. PCC 6803 groE-promoter-controlled NAD-dependent
      Glyceraldehyde-3-Phosphate-Dehydrogenase DNA construct

<400> SEQUENCE: 27
agaaaatctg gcaccacacc cgggcaactt tgcagtgaag gatctagtcg gctcccgatt      60
tttgccctga gttcgggaaa ccacactcac cggggtgttg cactgggtca agcaatttag    120
ctaaattagc actcgtgagg tgggagtgct aaacatgaat ggatttgggc ggatcggacg    180
tttagcattc agaagaattc aagatgtaga aggtcttgaa gtagttgcag ttaacgactt    240
aacagatgac gatatgttag ctcatttatt aaaatacgat actatgcaag gtcgtttcac    300
tggagaagtt gaagttatcg aaggtggatt ccgtgttaac gtaaaagaaa ttaaatcatt    360
cgatgaccag atgctgggta aattaccatg gggcgattta gatatcgacg tagtattaga    420
atgtactggt ttctatactg ataaagaaaa agcacaagct cacatcgatg caggtgctaa    480
aaaagtatta atctcagctc cagctaaagg tgatgtaaaa acaatcgtat tcaacactaa    540
ccatgacgca ttagacggtt cagaaacagt tgtttcaggt gcttcttgta ctactaactc    600
attagcacca gttgcaaaag ttttaagtga tgaattcggt ttagttgaag gtttcatgac    660
tacaattcac gcttacactg gtgaccaaaa tacacaagac gcacctcaca gaaaaggtga    720
caaacgtcgt gcacgtgcag cagcagaaaa tattatccct aactcaacag gtgctgctaa    780
agctatcggt aaagttattc cagaaatcga tggtaaatta gacggtggag cacaacgtgt    840
tccagttgct actgggtctt taactgaatt aactgtagta ttagacaaac aagatgtaac    900
tgttgaccaa gttaacagtg ctatgaaaca agcttcagac gaatcattcg gttacactga    960
agacgaaatc gtatcttctg atatcgttgg tatgacttac ggttcattat tcgatgcgac   1020
tcaaactcgt gttatgactg ttggagatcg tcaattagtt aaagttgcag cttggtacga   1080
caaagagtgg ggtagtaatg agttacagtt ttggcaatta ctaaaaaact gacttcaatt   1140
caatgttagc ccgctcccgc gggttttttg ttgcttttc acagtgacta taggtaatca   1200
gcaacacaat acgccctgt tctttggaca gttttttgtat aatgttgacc gcatcctgac   1260 cggattttt atctaagtgg ggaattgtca attgtcaatt aaagctaagt tctactaatg    1320
ttttagaagg cattgtcgat tgaaaataag ggttgaatgg agaaaatttt gagcctttgt   1380
caaagataaa aatttatttc aacagttttt taactagccg aaccagagaa tgacccagtg   1440
gcgctgactt tgctcccgag ttttttgttag aaattaccct caagaagtaa tctaataata   1500
aggttctctc ttctgccgtt a                                             1521

<210> SEQ ID NO 28
<211> LENGTH: 1768
<212> TYPE: DNA
<213> ORGANISM: Artificial Sequence
<220> FEATURE:
<223> OTHER INFORMATION: Synthetic Construct-Example 28: a designer
      Synechocystis sp. PCC 6803 groE-promoter-controlled
```

Phosphoglycerate-Kinase DNA construct

<400> SEQUENCE: 28

| | | | | | |
|---|---|---|---|---|---|
| agaaaatctg | gcaccacacc | cgggcaactt | tgcagtgaag | gatctagtcg | gctcccgatt | 60 |
| tttgccctga | gttcgggaaa | ccacactcac | cggggtgttg | cactgggtca | agcaatttag | 120 |
| ctaaattagc | actcgtgagg | tgggagtgct | aaacatgtta | tttatcgagc | agcgccctta | 180 |
| ctcccggcag | ttgcttccct | tccagaaact | ccagggaagc | gccgccgccg | gttgagatat | 240 |
| gggtcatttt | gccggctacg | ccggccttct | tggccgccgc | cgccgtgtca | ccgccgccga | 300 |
| ttacggtgac | ggcgtttaat | tcggccagcg | tccgggctat | tgcttcggtg | ccctggcaa | 360 |
| aaggatccat | ttcaaaaacg | cccattggtc | cgttccagac | cacggtcctg | gccgccctga | 420 |
| gggcttcggt | gaaaagtctg | atggactcgg | gccctatatc | cagggccatc | cactccgccg | 480 |
| ggatttgatc | gaccggcacc | gtcctttgct | cctggccggg | cgccggcccc | ggcgccacca | 540 |
| ccacatccac | cggcaggagg | agctttactt | ccctgcttct | ggcttctgca | atcagcttcc | 600 |
| tggccaggtc | aatcttgtcg | gcctccagca | gggacttacc | gacgctgtac | ccttgtgcct | 660 |
| tcagaaaggt | attggccatc | cgccgccaa | tgataaccgt | atcgactttg | gtcagcaggt | 720 |
| tgaaaattac | tcccagcttg | tcggaaactt | tcgagccgcc | cacgacggct | gcaaaagggc | 780 |
| gctccgggct | ggtcagcagc | ctgcccagta | tttccagctc | ttttttccatc | agcaggcctg | 840 |
| ccacggccgg | caaaaacccg | gcaacgccct | cggtggaggc | gtgggccgg | tgtgcggttc | 900 |
| caaacgcatc | gtttacaaag | acatctgcca | gctcagccag | ttgccgggca | aacttctcgt | 960 |
| cgttttctc | ctcctccggg | tggaaacgga | cgttttccag | cagcaccacg | tccccgtcct | 1020 |
| gcatctgggc | aacggcggac | ctggcggctt | ctcccacgca | gtcgccggcc | ttaaccaccg | 1080 |
| ttttccccag | cagttcggaa | aggcgcctgg | caacgggatc | catttttgtac | ctctcgtcca | 1140 |
| ccctgcccctt | gggccggccc | agtgcgaaa | ccagaataac | cctggctttt | tgtccgataa | 1200 |
| ggtagtttat | ggtgggcacg | gcctcccttta | ttttaacgtc | atcggccacc | cggccgtttt | 1260 |
| ccatcggcac | gttgaagtcc | acccgcaaca | ggacccgctt | gcccttttaca | tctatatccc | 1320 |
| ttaccgtttt | tttggccact | agtaatgagt | tacagttttg | gcaattacta | aaaaactgac | 1380 |
| ttcaattcaa | tgttagcccg | ctcccgcggg | ttttttgttg | cttttcaca | gtgactatag | 1440 |
| gtaatcagca | acacaatacg | gccctgttct | ttggacagtt | tttgtataat | gttgaccgca | 1500 |
| tcctgaccgg | atttttatc | taagtgggga | attgtcaatt | gtcaattaaa | gctaagttct | 1560 |
| actaatgttt | tagaaggcat | tgtcgattga | aaataagggt | tgaatggaga | aaattttgag | 1620 |
| cctttgtcaa | agataaaat | ttatttcaac | agttttttaa | ctagccgaac | cagagaatga | 1680 |
| cccagtggcg | ctgactttgc | tcccgagttt | tgttagaaa | ttaccctcaa | gaagtaatct | 1740 |
| aataataagg | ttctctcttc | tgccgtta | | | | 1768 |

<210> SEQ ID NO 29
<211> LENGTH: 1225
<212> TYPE: DNA
<213> ORGANISM: Artificial Sequence
<220> FEATURE:
<223> OTHER INFORMATION: Synthetic Construct-Example 29: a designer Synechocystis sp. PCC 6803 groE-promoter-controlled Phosphoglycerate-Mutase DNA construct

<400> SEQUENCE: 29

| | | | | | |
|---|---|---|---|---|---|
| agaaaatctg | gcaccacacc | cgggcaactt | tgcagtgaag | gatctagtcg | gctcccgatt | 60 |
| tttgccctga | gttcgggaaa | ccacactcac | cggggtgttg | cactgggtca | agcaatttag | 120 |

```
ctaaattagc actcgtgagg tgggagtgct aaacatgatg agggaagaca tggcgacaac    180
cttgtatttg accagacatg gggaaacgaa gtggaacgtc gaaaggcgga tgcaaggctg    240
gcaagactcg ccgctcacgg aaaaagggcg gcaagacgcc atgcggcttg aaagcggct    300 tgaagcggtg gaattggccg cgatttacac aagcacaagc ggccgggcgc ttgagacggc    360
ggagattgtc cgcggcgggc ggctcattcc gatctatcaa gacgagcggc tgcgcgagat    420
tcatcttggc gattgggaag gaaagacgca tgacgagatt cggcaaatgg atccgatcgc    480
gttcgaccat ttttggaacg cgccccatct gtacgctcca cagcgaggcg agcggttttg    540
tgacgtgcag cagcgggcgc ttgaagcggt gcagagcatc gttgatcggc acgagggaga    600
aacggtgtta atcgtcactc acggcgtcgt gctgaaaacg ctcatggcgg cgttcaaaga    660
cacgccgctt gaccacctgt ggtcgccgcc gtatatgtac ggcacgagtg tgacgatcat    720
tgaagttgac ggtgggacgt ttcacgtggc cgttgaagga gatgtgtcac atattgagga    780
agtaagggaa gtatagtagt aatgagttac agttttggca attactaaaa aactgacttc    840
aattcaatgt tagcccgctc ccgcgggttt tttgttgctt tttcacagtg actataggta    900
atcagcaaca caatacggcc ctgttctttg gacagttttt gtataatgtt gaccgcatcc    960
tgaccggatt ttttatctaa gtggggaatt gtcaattgtc aattaaagct aagttctact   1020
aatgttttag aaggcattgt cgattgaaaa taagggttga atggagaaaa ttttgagcct   1080
ttgtcaaaga taaaaattta tttcaacagt tttttaacta gccgaaccag agaatgaccc   1140
agtggcgctg actttgctcc cgagttttg ttagaaatta ccctcaagaa gtaatctaat    1200
aataaggttc tctcttctgc cgtta                                          1225
```

<210> SEQ ID NO 30
<211> LENGTH: 1885
<212> TYPE: DNA
<213> ORGANISM: Artificial Sequence
<220> FEATURE:
<223> OTHER INFORMATION: Synthetic Construct-Example 30: a designer
      Synechocystis sp. PCC 6803 groE-promoter-controlled Enolase DNA
      construct

<400> SEQUENCE: 30

```
agaaaatctg gcaccacacc cgggcaactt tgcagtgaag gatctagtcg gctcccgatt     60
tttgccctga gttcgggaaa ccacactcac cggggtgttg cactgggtca agcaatttag    120
ctaaattagc actcgtgagg tgggagtgct aaacatggtg ggcgttaatg attttgctat    180
tgagcgcgtt tggggcttac aggtcctcga tagcagggggc aaccccactg tgaaggcgta    240
tgtcaagctt gctggaggga gcttgggctg ggggatagcg cccagcggtg ctagcagagg    300
cgagagagag gcggtggagc ttagagacgg tgggggtaag tggagggggta aaggagtttc    360 cagggcagta tctcttttaa acacagtagt agcacctagg ctggaggggg tcgacgccag    420
aagacaagcc caaatagaca ggctcctaat agaactagac ggcaccccga acaaatcgag    480
actcggcggg aacacgacca ccgctctcag catagccgtt tcaagagctg cggcggctca    540
ggcacgcctc gaactcttcc agtatctagg cggcgccggg gctaggagac tcccaatacc    600
tcttctcaac gtcataaatg gtggtgttca cgcggggaac gagctagact ttcaggagtt    660
tatgataata ccttatggtt ttgaaagctt cacagaagct atgagggctg cggtggagac    720
atacggggag ctcaagagcc tgcttaagga caggtatggt gcatctgcag tcaacgtcgg    780
cgacgaaggg ggtttcgcac cccctatgag aagcgccgaa gaggccctca agactctagt    840
ggatgcagtg gagaaagcag gctaccagcc cgggagcgag atagcccttg gcattgacgc    900
```

```
ggctgcgagc cagctctaca gtaacgggcg ctacagcgtt gaagggaaga gcctgtccag    960
agaggagctc ctaagcctct accagcgctt ggtagagcag tatccaatag tgtatcttga   1020
agacccattt agcgaggacg actatgaagg tttcaaggcc gccgtagacg ccctctcgac   1080
agaaaccatt atagtggggg acgatctcct agttaccaat ccccagaggg ttaaggaggc   1140
ttccgccctc aaagcagtca caggcctcct agtaaaggtg aaccaggtgg ggactctcac   1200
cgaagctctc gaagccatcc aggctgcgag ggacaggggg attgtccaca tagtgagcca   1260
caggagcgga gacactgagg acaccttcat tgccgaccta gccgtcgcca cagaagcttt   1320
gatgatcaaa acgggagccc cagcccgggg agagaggacc tcgaaataca acaggctcct   1380
agaaatagag aacatattag gctactcagc cgaatatgca ggtccagaac tacgcggcgt   1440
aatgggcagg cgctgatagt aatgagttac agttttggca attactaaaa aactgacttc   1500
aattcaatgt tagcccgctc ccgcgggttt tttgttgctt tttcacagtg actataggta   1560
atcagcaaca caatacggcc ctgttctttg gacagttttt gtataatgtt gaccgcatcc   1620
tgaccggatt ttttatctaa gtggggaatt gtcaattgtc aattaaagct aagttctact   1680
aatgttttag aaggcattgt cgattgaaaa taagggttga atggagaaaa ttttgagcct   1740
ttgtcaaaga taaaaattta tttcaacagt tttttaacta gccgaaccag agaatgaccc   1800
agtggcgctg actttgctcc cgagtttttg ttagaaatta ccctcaagaa gtaatctaat   1860
aataaggttc tctcttctgc cgtta                                         1885
```

<210> SEQ ID NO 31
<211> LENGTH: 2350
<212> TYPE: DNA
<213> ORGANISM: Artificial Sequence
<220> FEATURE:
<223> OTHER INFORMATION: Synthetic Construct-Example 31: a designer
      Synechocystis sp. PCC 6803 groE-promoter-controlled
      Pyruvate-Kinase DNA construct

<400> SEQUENCE: 31

```
agaaaatctg gcaccacacc cgggcaactt tgcagtgaag gatctagtcg gctcccgatt     60
tttgccctga gttcgggaaa ccacactcac cggggtgttg cactgggtca agcaatttag    120
ctaaattagc actcgtgagg tgggagtgct aaacatgtta caacacgctc gcatggccgc    180
ggtagacggc gccaaagccg ccatcgaccg tgatctcttg cccatcttta acaagcttg     240
tggcattttc caccccgacg acgaccggaa tgccaaggct taagccgacg accgccgcat    300
ggctcgtcaa cccgccttcc tcggtgatga tcgccgccgc ttttcgatc gccggcatca    360
tatcggcatc ggtgctgatg gtgactaaaa tgccgccctc taccattttt cggcacgcct    420
cttccgccgt tttggcgacg accgccttgc cgaatgccga cttgcggccg atgccttgcc    480
ctttggcaag caagtcgctg atgacgtgca cttttcattaa gttcgtcgat cccgtttcgc    540
cgaccggcac gccggccgtg atgacgacca agtcgccgtg cttcaccaag ccggagcgca    600
ctgccgcgtc gaccgccaca tcgagcattt catcggttgt attgacatgc ggtgcttctt    660
tcgtatacac gccccaaatg agcgccagcc gccgcgagac cgcttcgttt gatgtcaccg    720
cgatgatcgg ggctttcggg cggtatttcg ccaccatctg cggcgttttt ccgctcaccg    780
tcggcgtcac gatcgccgcg acatccaaat tgagcgctgt gtgggcgacc gattggccga    840
tggcatcggt gatcgtcgtt cggctctctt tcgtgcgctg gacaaaatg tcgcgatgct     900
ccaacgcctg ctcggtgcgg agcgcgattt ggtgcatcgt ccttaccgct tcgaccggat    960
actggccggc tgcggtttct ccggaaagca tgacggcgtc ggtgccgtca aaaatggcgt   1020
```

```
tggcgacatc gctcgcctca gcccgcgtcg ccgcggatt gcgctgcatc gagtcgagca      1080
tttgcgtcgc cgtgatgacc ggcttgccaa gcatgttgca cttttaatg agcattttt       1140 gaatgagagg cacttcctca gccggaatct caacgccaag gtcgccgcgc gccaccatga      1200
ggccatcggc ggcttccaaa atttcatcga tgttggcgac gccttcttca ttttcaattt      1260
tcgcgataat ttggatatgt aaggcgtcat tcgcctcgag cagctcgcgg atttcgagca      1320
catcagacgc ccggcgcaca aacgaggcgg cgatgaagtc gatgccttgg cggatgccaa      1380
ataaaatatc ggctcggtcc ttctcggtga tgcccggcaa attgacacgc acgccgggga      1440
cattgacccc ttttttgttt ttgagcacac cggtgtttag dacggtcgtg gcaatttctc      1500
cagcttgctt gtcgaccgcg ttgacttcaa ggccgatcaa cccgtcgtcc agcaaaattt      1560
tcgaaccaac ggacacatca tcgatcagcc ccggataggt gacagaaatt ttttccggcg      1620
tgccgagcac ttcgctcatc gaaatgatga gctttgcccc ttccttcagt tcgacggcgc      1680
cgttctccat attgtgcgtg cggatttccg ggcctttcgt atcgagcaaa atggcgaccg      1740
tttggcccgt ccgcctcgcc gcctcgcgaa tgttggcgat gcgccgcccg tgttcctcat      1800
gatctccgtg cgaaaagttg aggcgcgcca cgttcatccc cgcttcgatc aattgcacga      1860
gcttgtctac gctctcgctt gccggcccga tcgtacagac gatttccgtt ttccgcttca      1920
ttagtaatga gttacagttt tggcaattac taaaaaactg acttcaattc aatgttagcc      1980
cgctcccgcg gttttttgt tgcttttca cagtgactat aggtaatcag caacacaata       2040
cggccctgtt ctttggacag ttttgtata atgttgaccg catcctgacc ggattttta       2100 tctaagtggg gaattgtcaa ttgtcaatta agctaagtt ctactaatgt tttagaaggc       2160
attgtcgatt gaaaataagg gttgaatgga gaaaattttg agcctttgtc aaagataaaa      2220
atttatttca acagttttt aactagccga accagagaat gacccagtgg cgctgacttt       2280
gctcccgagt ttttgttaga aattaccctc aagaagtaat ctaataataa ggttctctct      2340
tctgccgtta                                                            2350
```

<210> SEQ ID NO 32
<211> LENGTH: 2245
<212> TYPE: DNA
<213> ORGANISM: Artificial Sequence
<220> FEATURE:
<223> OTHER INFORMATION: Synthetic Construct-Example 32: a designer
      Synechocystis sp. PCC 6803 groE-promoter-controlled
      Pyruvate-Decarboxylase DNA construct

<400> SEQUENCE: 32

```
agaaaatctg gcaccacacc cgggcaactt tgcagtgaag gatctagtcg gctcccgatt        60
tttgccctga gttcgggaaa ccacactcac cggggtgttg cactgggtca agcaatttag       120
ctaaattagc actcgtgagg tgggagtgct aaacatgatg aaaataacaa ttgcagaata       180
cttattaaaa agattaaaag aagtaaatgt agagcatatg tttggagttc ctggagatta       240
taacttagga ttttagatt atgttgaaga ttctaaagat attgaatggg ttggaagctg        300
taatgaactt aatgcaggat atgcagcaga tggatatgca agactagag gatttggtgt        360 aatacttaca acttatggag ttggttcact tagtgcaata aatgctacaa caggttcatt       420
tgcagaaaat gttccagtat tacatatatc aggtgtacca tcagctttag ttcaacaaaa       480
cagaaagcta gttcaccatt caactgctag aggagaattc gacacttttg aaagaatgtt       540
tagagaaata acagaatttc aatcaatcat aagcgaaat aatgcagctg aagaaatcga       600
tagagttata gaatcaatat ataaatatca attaccaggt tatatagaat taccagttga      660
```

-continued

```
tatagtttca aaagaaatag aaatcgacga aatgaaaccg ctaaacttaa ctatgagaag      720
caacgagaaa actttagaga aattcgtaaa tgatgtaaaa gaaatggttg caagctcaaa      780
aggacaacat attttagctg attatgaagt attaagagct aaagctgaaa agaattaga      840 aggatttata aatgaagcaa aaatcccagt aaacacttta agtataggaa agacagcagt     900
atcagaaagc aatccatact ttgctggatt attctcagga gaaactagtt cagatttagt     960
taaagaactt tgcaaagctt ctgatatagt tttactattt ggagttaaat tcatagatac    1020
tacaacagct ggatttagat atataaataa agatgttaaa atgatagaaa ttggtttaac    1080
tgattgtaga attggagaaa ctatttatac tggactttac attaaagatg ttataaaagc    1140
tttaacagat gctaaaataa aattccataa cgatgtaaaa gtagaaagag aagcagtaga    1200
aaaatttgtt ccaacagatg ctaaattaac tcaagataga tatttcaaac aaatggaagc    1260
gttcttaaaa cctaatgatg tattagttgg tgaaacagga acatcatata gtggagcatg    1320
taatatgaga ttcccagaag gatcaagctt tgtaggtcaa ggatcttgga tgtcaattgg    1380
atatgctact cctgcagttt taggaactca tttagctgat aagagcagaa gaaacattct    1440
tttaagtggt gatggttcat tccaattaac agttcaagaa gtttcaacaa tgataagaca    1500
aaaattaaat acagtattat ttgtagttaa caatgatgga tatacaattg aaagattaat    1560
ccacggacct gaaagagaat ataaccatat tcaaatgtgg caatatgcag aacttgtaaa    1620
aacattagct actgaaagag atatacaacc aacttgtttc aaagttacaa ctgaaaaaga    1680
attagcagct gcaatggaag aaataaacaa aggaacagaa ggtattgctt ttgttgaagt    1740
agtaatggat aaaatggatg ctccaaaatc attaagacaa gaagcaagtc tatttagttc    1800
tcaaaataac tactaatagt aatgagttac agttttggca attactaaaa aactgacttc    1860
aattcaatgt tagcccgctc ccgcgggttt tttgttgctt tttcacagtg actataggta    1920
atcagcaaca caatacggcc ctgttctttg gacagttttt gtataatgtt gaccgcatcc    1980
tgaccggatt ttttatctaa gtggggaatt gtcaattgtc aattaaagct aagttctact    2040
aatgttttag aaggcattgt cgattgaaaa taagggttga atggagaaaa ttttgagcct    2100
ttgtcaaaga taaaaattta tttcaacagt tttttaacta gccgaaccag agaatgaccc    2160
agtggcgctg actttgctcc cgagtttttg ttagaaatta ccctcaagaa gtaatctaat    2220
aataaggttc tctcttctgc cgtta                                          2245
```

<210> SEQ ID NO 33
<211> LENGTH: 1594
<212> TYPE: DNA
<213> ORGANISM: Artificial Sequence
<220> FEATURE:
<223> OTHER INFORMATION: Synthetic Construct-Example 33: a designer
Synechocystis sp. PCC 6803 nirA-promoter-controlled
NAD(P)H-dependent Alcohol-Dehydrogenase DNA construct

<400> SEQUENCE: 33

```
agaaaatctg gcaccacacc ctaaatgcgt aaactgcata tgccttggct gagtgtaatt      60
tacgttacaa attttaacga aacgggaacc ctatattgat ctctacatga actcttcttt     120
cgctatccca gaaactcaaa agggtgttat cttctacgaa aatggtggta agttggaata     180
caaggatttg ccagttccaa agccaaaggc taacgaaatt ttgattaacg ttaagtactc     240
cggtgtttgt cacaccgatt tgcacgcctg gaagggtgac tggccattgc cagttaaatt     300
gccattagtc ggtggtcacg aaggtgctgg tatcgttgtt gccaagggtg aaaacgttaa     360
gaacttcgaa attggtgatt acgctggtat caagtggttg aacggttctt gtatgtcttg     420
```

```
tgaattgtgt gaacaaggtt acgaatctaa ctgtttgcaa gctgacttgt ctggttacac      480
ccatgacggt tctttccaac aataccgtac cgctgatgcc gttcaagctg ctcaaattcc      540
aaagggtacc gatttggctg aaatcgcccc aatcttgtgt gccggtgtta ccgtttacaa      600
ggctttgaag accgctgact tgaaaccagg ccaatgggtt gctatctccg gtgctgccgg      660
tggtttaggt tcccttgctg tgcaataccg caaggccatg ggtttgagag tcctaggtat      720
tgacggtggt gatggtaagg aagaattgtt caagcaatgt ggtggtgaag tcttcatcga      780
cttcagaaag tctaaggaca tggtcgccga tatccaagaa gctaccaacg tggtcctca       840 cggtgtcatt aacgtctccg tctccgaggc tgctgtctcc atgtctaccg aataccttag      900
accaaccggt cttgttgtct tggtcggttt gccagctgac gcttacgtca gtccgaagt       960 cttctcccac gtcgttaagt ccatctccat caagggttct tacgtcggta acagagctga     1020
caccagagaa gccaccgacc tcttcaccag aggtttggtc aagtctccaa tcaagatcat     1080
cggtctatct gaattgccag aagcttatgc cctaatggaa caaggtaaga tcttgggtag     1140
attcgtcgtt gacacttaca ataatagta atgagttaca gttttggcaa ttactaaaaa      1200
actgacttca attcaatgtt agcccgctcc cgcgggtttt tgttgctttt tcacagtga      1260 ctataggtaa tcagcaacac aatacggccc tgttctttgg acagttttg tataatgttg      1320 accgcatcct gaccggattt tttatctaag tggggaattg tcaattgtca attaaagcta     1380
agttctacta atgttttaga aggcattgtc gattgaaaat aagggttgaa tggagaaaat     1440
tttgagcctt tgtcaaagat aaaaatttat ttcaacagtt ttttaactag ccgaaccaga    1500
gaatgaccca gtggcgctga ctttgctccc gagttttgt tagaaattac cctcaagaag     1560
taatctaata ataaggttct ctcttctgcc gtta                                1594

<210> SEQ ID NO 34
<211> LENGTH: 2212
<212> TYPE: DNA
<213> ORGANISM: Artificial Sequence
<220> FEATURE:
<223> OTHER INFORMATION: Synthetic Construct-Example 34: a designer
      Thermosynechococcus elongatus BP-1 groE-promoter-controlled
      thermotolerant Phosphoglycerate-Mutase DNA construct

<400> SEQUENCE: 34
agaaaatctg gcaccacacc tttaatggaa agcttgctaa accattactc cctactcccc       60
aatcattcta gttcggaaaa ccgtactgca acaggagttg cgatcgccaa ccgtctctcg      120
ctacattagc actcgaaggg tgagagtgct aagcctacgc cggcgcctgc ttctcctcct      180
gccggcagca cttctccaaa gggtgcacgt tcgcttctct tgtaatcagg gtctggccgg      240
tcatctcggc cggtttcggg atgcccagca ggtgcaggat ggtgggggcc acatcccgca      300
ggctgccgtc ccgcagcgca atgccggcgg tatcccgccc gatcaggatg aacggcaccg      360
ggctggtggt gtgggccgta tgaggctgtc cctcttcgtc caccatctca tccgcattgc      420
cgtggtctgc cgttatcagg agcgtgccgt ccttttccag gacggcccgc gccacctttc      480
caaggcagcg gtcgattgtt tctatggcct ttaccgttgc cttcatgtcg ccggtatgcc      540
cgaccatgtc gggattggcg taattcatta tgattacgtc gtacttgccc gaggccagcc      600
gctccagaaa ggtgccggtg acctcgttgg cgctcatttc gggcttcagg tcgtaggtgg      660
ccacccgcgg ggagggcacc aggatcctgt cttcgccggg gtatggcttt tctaagccgc      720
cgttgaagaa gaaggtcaca tgggcgtact tttccgtttc ggccaggcgg agctgggtca      780
tgccgtgcct gcttaaaacc tcgcccaggg tattgcgcag ctcctgcggc tgaaacgcca      840
```

```
ccggcgcctt aatggtcttg tcgtaaaggg tcatgcaggt aaaatgcacg gcagggtagc      900
cctgctttct ggcaaacccg gtgaaatcct cgtccacaaa ggccctggta atctggcggg      960
cccggtccgg ccggaagtta agaaaataa cggcgtcgcc cttcattatt ttggcggccg     1020
gcccacccga cccgtttacc acgacggtgg gctggataaa ctcgtcggtt tcatcccttc     1080
cgtaccccag gtcaaccgcc tccagcgggc ttgttgcctg aatgccctcg cctaaaacca     1140
ttgcgttgta cgcccgctcg gtgcggtccc agcggcggtc tctgtccatg gcgtaatagc     1200
gccccattac cgttgccacc gccccaaagc ccagttcgcc cagcttcttc cttaactgct     1260
cgaagtattc ttttgcgttg gccggcggca cgtcgcgccc gtccaggaag gcatggacaa     1320
agacgttgcg catgttctcg cgggcggcca ggtccaggag ggcgaaaagg tggctgatat     1380
ggctgtgcac tccgccgtcc gataaaagcc ccatcaggtg aagggcctta ttattctccc     1440
tggcgtatct caccgcctcc agcaggactt cgttcttgaa aaaggtcccg tccttgatgg     1500
cgcggcttat tctggtaagc tcctggtaca ccaccctgcc ggcgcctatg ttcaagtgtc     1560
ccacctcgga attgcccatc tggccctcgg gaagcccac gtcctcgccg gaacagctca     1620
gggcacagtg ggggtaaccg gccagaaagc tcttgaaatt cggtgtgctg gcagggcta     1680 tggcattgcc ccggacattg gaactgaggc cccagccgtc cagaaccacc agcaccaggg     1740
gcctgccgcc ggcataccgg ccgcaggcg ttgcagctac gtcttccttc aataatagtg     1800
aggctgagat cttcttcagt gcattgtagt tgaatgaagg gttagggggg aaatgccccc     1860
ctattttttg tctagccatc ctgccacgtt tgacaggta gcaatttcga cacgatagcg     1920
tgctgtactg ttttttgctc gtcagggttg ggttttgtca tcgacaccca aggattggag     1980
tcggtgctca ataatcgcca gttgctgttg ggcagccgcc aattgcgcct gagccgcagc     2040
gaccacctct ggttgggctt tgttgacaaa attagggttg ttgaggcgag cggttaaaga     2100
ttgaatctct ttcctcaggc gatcgccttc cttctggagc ttgcttacca aggcctccag     2160
atctacgacc cccgctaggg gaatgagtac ctggttctct cttctgccgt ta              2212
```

<210> SEQ ID NO 35
<211> LENGTH: 1882
<212> TYPE: DNA
<213> ORGANISM: Artificial Sequence
<220> FEATURE:
<223> OTHER INFORMATION: Synthetic Construct-Example 35: a designer
      Thermosynechococcus elongatus BP-1 groE-promoter-controlled
      Enolase DNA construct

<400> SEQUENCE: 35

```
agaaaatctg gcaccacacc tttaatggaa agcttgctaa accattactc cctactcccc       60
aatcattcta gttcggaaaa ccgtactgca acaggagttg cgatcgccaa ccgtctctcg      120
ctacattagc actcgaaggg tgagagtgct aagcatgtta ttttttcttc aagttaaaga      180
atgcgttcat tccaggataa acggcaatgc tgccaagctc ttcttcaatt ctcaagagct      240
gattgtattt tgctactctg tctgttcttg acggtgcacc tgtctttatc tgaccagcat      300
ttactgcaac aacaaggtca gcaattgttg tatcttcagt ctcacctgat ctgtgggata      360
caactgcagt gtagcctgct ctatttgcca tttcaatagc ttctaaagtt tctgtaagtg      420
ttcctatctg attaagctta atcaatattg agtttgcaac gccaagttct attcccttttg     480 caagcctctt tgtgtttgta acaaacaaat catcacccac aagctgaatc ttcttgccaa      540
gtgcttcagt tagcatcttc cagccttccc agtcctcttc tgcaacaccg tcttcaattg      600
atacaattgg gtacttttca acaagtttta cccagaattc taccatttct tcttttgttc      660
```

```
taactttacc ttctctttcg aaatgatact ttccatcttc ttcattgtag agctcagatg    720
ttgcagggtc aagcgcaatt gcaatatcct taccaggagt ataaccagct ttttcaattg    780
cttcgacaat tacttccaat ggctcttcgt tagacttcaa gtttggtgca aatccacctt    840 catcaccac tgttgtgttg tatcctcttg ccttcaatac atttcttaat tgatggaatg    900
tctcagcaca catcctgagt gcttcgctaa aagattttgc accaactggc attatcataa    960
actcttgtag gtcaacagag ttgtcagcat gcttttccacc gttcaaaata ttcatcattg   1020
gcacaggtaa atactttgca ttgacaccac caatgtattg gtacagtgga agaccaagtg   1080
cgtttgccgc tgccttcgca actgccaaag atacacccaa aattgcattt gcaccaagct   1140
tgctcttgtt ctctgtccca tcaagctcaa tcataagcct gtcaatctca acttggttaa   1200
gagcgttcat tccaattatt tctggcgcaa taacctcgtt tacattttcg actgctttga   1260
gaaccccttt tcccatatat ctttttttat caccgtctct gagttcaaca gcctcgaaca   1320
tacctgttga cgcacctgat ggaacagcag ctctacctac aaattcatca tttacaacaa   1380
cttctacttc aacagttggg tttcctcttg aatccagaat ttctcttgct tttacagctg   1440
taattgaaag atcaaccttc attaatagtg aggctgagat cttcttcagt gcattgtagt   1500
tgaatgaagg gttagggggg aaatgccccc ctatttttttg tctagccatc ctgccacgtt   1560
tgacagggta gcaatttcga cacgatagcg tgctgtactg ttttttgctc gtcagggttg   1620
ggttttgtca tcgacaccca aggattggag tcggtgctca ataatcgcca gttgctgttg   1680
ggcagccgcc aattgcgcct gagccgcagc gaccacctct ggtttgggctt tgttgacaaa   1740 attagggttg ttgaggcgag cggttaaaga ttgaatctct ttcctcaggc gatcgccttc   1800
cttctggagc ttgcttacca aggcctccag atctacgacc cccgctaggg gaatgagtac   1860
ctggttctct cttctgccgt ta                                              1882

<210> SEQ ID NO 36
<211> LENGTH: 1918
<212> TYPE: DNA
<213> ORGANISM: Artificial Sequence
<220> FEATURE:
<223> OTHER INFORMATION: Synthetic Construct-Example 36: a designer
      Thermosynechococcus elongatus BP-1 groE-promoter-controlled
      thermotolerant Pyruvate-Kinase DNA construct

<400> SEQUENCE: 36
agaaaatctg gcaccacacc tttaatggaa agcttgctaa accattactc cctactcccc     60
aatcattcta gttcggaaaa ccgtactgca acaggagttg cgatcgccaa ccgtctctcg    120
ctacattagc actcgaaggg tgagagtgct aagcatggtg ttcactaaaa ttgtagctac    180 attgggggcct tcgactgata gactgccgga tataacggcc ctgttgagca aggttcacgg    240
cgtgcggata aatatgtctc acgcatcgcc atcggaggta gaggcccgcg tgaacgccgt    300
gaggaagtat gaggagacca gcggaggta tatagccatt atagcggatc taaggggccc    360
cagcgtcagg accggcctta tgcgccctct acagataacg gcgggcgccc gcgtctcctt    420
taaattagcc gagaaggggg acggcttcgt acctgtgccg cggcgtgagt tcttcgaagt    480
aatcgaggag ggagacgagg ttcttatgtt agacggaaaa ctcgtcttga ggataatcag    540
cgcagcgcag acctcggccg aggccgagtc gttatcctcc ggcgtcatat ccagcaataa    600
ggcaatagtg gtcaaaggca aggaatatca tatagagcag cctgtggagg aagacataag    660
ggcgcttcag acgctctctc ggttcagaga cgacgtagac tacgtggccc tcagccttgt    720
gagagacgga gcagacgtga ggaaaatgag gagcgtcgtc gaggaggctg ggctcacctc    780
```

```
cggcataatg gccaaaatag agacgaagag cgcagtagat aaaatcgagg agataatcaa    840
tgcggccgac tacatagtta tagcgagagg cgatctggcg ctgcactacg gactggagta    900
cattcctaaa gtacagaggc tcttggtgga gagatctctc tcggcaggaa ggcccgtggc    960
ggtggccacg cagcttttgg actctatgca gaccaacacg acgcccacta gggcggaggt   1020
caacgacgtg tacacaacgg cgagtctcgg agtggactct ctgtggctga ccaacgagac   1080
tgcgagcgga gagcacccgt tagaggcagt ggattggctg aggaggatag tgtcgcaggt   1140
cgagttcggg agacttaagg ctgcgtcgcc ggccgacgca cgcgataggt tcgccaaagc   1200
cgtggtagat atggccgagg acatgggagg ggaaatcgca gtatactcaa tgacgggaac   1260
tctggcgaag agaatagcta aatttaggcc gatgacgaca gtctacgtcg gagtcaacga   1320
gaggaggctc gcgaggatgt tggagctccg cgaggatgtt ggagctcata tggggcctag   1380
agcctgtggt cgtgccggcg catacttacg aggagggcct cgagaggctc ctctccagat   1440
tctccgacaa agtcttgata gccacgtatg ggctcagagg cggcacacat actattaata   1500
atagtgaggc tgagatcttc ttcagtgcat tgtagttgaa tgaagggtta gggggaaat    1560 gccccctat tttttgtcta gccatcctgc cacgtttgac agggtagcaa tttcgacacg    1620
atagcgtgct gtactgtttt ttgctcgtca gggttgggtt ttgtcatcga cacccaagga   1680
ttggagtcgg tgctcaataa tcgccagttg ctgttgggca gccgccaatt gcgcctgagc   1740
cgcagcgacc acctctggtt gggctttgtt gacaaaatta gggttgttga ggcgagcggt   1800
taaagattga atctctttcc tcaggcgatc gccttcctcc tggagcttgc ttaccaaggc   1860
ctccagatct acgaccccg ctagggaat gagtacctgg ttctctcttc tgccgtta      1918
```

<210> SEQ ID NO 37
<211> LENGTH: 2281
<212> TYPE: DNA
<213> ORGANISM: Artificial Sequence
<220> FEATURE:
<223> OTHER INFORMATION: Synthetic Construct-Example 37: a designer
      Thermosynechococcus elongatus BP-1 groE-promoter-controlled
      thermotolerant Pyruvate-Decarboxylase DNA construct
<220> FEATURE:
<221> NAME/KEY: misc_feature
<222> LOCATION: (776)..(776)
<223> OTHER INFORMATION: n is a, c, g, or t

<400> SEQUENCE: 37

```
agaaaatctg gcaccacacc tttaatggaa agcttgctaa accattactc cctactcccc     60
aatcattcta gttcggaaaa ccgtactgca acaggagttg cgatcgccaa ccgtctctcg    120
ctacattagc actcgaaggg tgagagtgct aagcatgagt tatactgtcg gtacctattt    180
agcggagcgg cttgtccaga ttggtctcaa gcatcacttc gcagtcgcgg gcgactacaa    240
cctcgtcctt cttgacaacc tgcttttgaa caaaaacatg gagcaggttt attgctgtaa    300
cgaactgaac tgcggtttca gtgcagaagg ttatgctcgt gccaaaggcg cagcagcagc    360
cgtcgttacc tacagcgtcg gtgcgctttc gcatttgat gctatcggtg cgcctatgc     420 agaaaacctt ccggttatcc tgatctccgg tgctccgaac aacaatgacc acgctgctgg    480
tcacgtgttg catcacgctc ttggcaaaac cgactatcac tatcagttgg aaatggccaa    540
gaacatcacg gccgccgctg aagcgattta taccccggaa gaagctccgg ctaaaatcga    600
tcacgtgatt aaaactgctc ttcgtgagaa gaagccggtt tatctcgaaa tcgcttgcaa    660
cattgcttcc atgccctgcg ccgctcctgg accggcaagc gcattgttca atgacgaagc    720
cagcgacgaa gcttctttga atgcagcggt tgaagaaacc ctgaaattca tcgccnaccg    780
```

-continued

```
cgacaaagtt gccgtcctcg tcggcagcaa gctgcgcgca gctggtgctg aagaagctgc      840
tgtcaaattt gctgatgctc ttggtggcgc agttgctacc atggctgctg caaaaagctt      900
cttcccagaa gaaaacccgc attacatcgg tacctcatgg ggtgaagtca gctatccggg      960
cgttgaaaag acgatgaaag aagccgatgc ggttatcgct ctggctcctg tctttaacga     1020
ctactccacc actggttgga cggatattcc tgatcctaag aaactggttc tcgctgaacc     1080
gcgttctgtc gtcgttaacg gcattcgctt ccccagcgtc catctgaaag actatctgac     1140
ccgtttggct cagaaagttt ccaagaaaac cggtgctttg gacttcttca atccctcaa      1200
tgcaggtgaa ctgaagaaag ccgctccggc tgatccgagt gctccgttgg tcaacgcaga     1260
aatcgcccgt caggtcgaag ctcttctgac cccgaacacg acggttattg ctgaaaccgg     1320
tgactcttgg ttcaatgctc agcgcatgaa gctcccgaac ggtgctcgcg ttgaatatga     1380
aatgcagtgg ggtcacattg gttggtccgt tcctgccgcc ttcggttatg ccgtcggtgc     1440
tccggaacgt cgcaacatcc tcatggttgg tgatggttcc ttccagctga cggctcagga     1500
agtcgctcag atggttcgcc tgaaactgcc ggttatcatc ttcttgatca ataactatgg     1560
ttacaccatc gaagttatga tccatgatgg tccgtacaac aacatcaaga actgggatta     1620
tgccggtctg atggaagtgt tcaacggtaa cggtggttat gacagcggtg ctggtaaagg     1680
cctgaaggct aaaaccggtg cgaactggca gaagctatc aaggttgctc tggcaaacac      1740
cgacggccca accctgatcg aatgcttcat cggtcgtgaa gactgcactg aagaattggt     1800
caaatggggt aagcgcgttg ctgccgccaa cagccgtaag cctgttaaca agctcctcta     1860
gtaatagtga ggctgagatc ttcttcagtg cattgtagtt gaatgaaggg ttagggggga     1920
aatgccccc tatttttgt ctagccatcc tgccacgttt gacagggtag caatttcgac       1980
acgatagcgt gctgtactgt ttttgctcg tcagggttgg gttttgtcat cgacacccaa      2040
ggattggagt cggtgctcaa taatcgccag ttgctgttgg gcagccgcca attgcgcctg     2100
agccgcagcg accacctctg gttgggcttt gttgacaaaa ttagggttgt tgaggcgagc     2160
ggttaaagat tgaatctctt tcctcaggcg atcgccttcc ttctggagct tgcttaccaa     2220
ggcctccaga tctacgaccc ccgctagggg aatgagtacc tggttctctc ttctgccgtt     2280
a                                                                     2281
```

<210> SEQ ID NO 38
<211> LENGTH: 1795
<212> TYPE: DNA
<213> ORGANISM: Artificial Sequence
<220> FEATURE:
<223> OTHER INFORMATION: Synthetic Construct-Example 38: a designer
     Thermosynechococcus elongatus BP-1 groE-promoter-controlled
     thermotolerant and NADP(H)-dependent Alcohol-Dehydrogenase DNA
     construct

<400> SEQUENCE: 38

```
agaaaatctg gcaccacacc tttaatggaa agcttgctaa accattactc cctactcccc       60
aatcattcta gttcggaaaa ccgtactgca acaggagttg cgatcgccaa ccgtctctcg      120
ctacattagc actcgaaggg tgagagtgct aagcatggtg tgggaatccc acgttccgat      180
aaaccaggtc tttgagctga ggtgcaaaac aacagactac ttcggcctat gcgccataca      240
caaatttaac ggcttcgtcc gggagcttaa ggggaaaggc gtggacaggg ttatcctcgt      300
tactgggagc agctcctaca agaagtgcgg tgcatgggac gttgtcaggc ctgcccttga      360
ggaaaacggg gtcgagtatg tccattacga caaggtgggg gccaacccaa cggttgacat      420
gatcgatgaa gctgccgaga tggggagaga gttcggggcc caagcggtga taggcatagg      480
```

```
tggtggcagc cccatcgata gtgccaagag cgttgcgatt ctgctggaat accctgacaa      540
gaccgccagg gacctctacg agttcaggtt tacccccgta aaggccaagc cagtaatagc      600
gataaacaca acccatggag ccggaaccga agttgacagg ttcgcagtgg cgacgattcc      660
tgagaaagag tacaagccgg ccatagctta cgactgcatc tacccgcttt acgcaatcga      720
tgacccctca ctgacggtaa agctttcccc ggagcagacc ctttacctga ccatcgatgc      780
actcaatcac gttaccgaag ccgccacaac caagctggcc aatccatatt cgatactcct      840
cgccaaagag gccgcgaggc tgatatttga ctacctccca gaggccctca aacaccccga      900
caaccttcag gcaaggtacg ccctgctcta cgcctctgcc atagccggaa taagcttcga      960
caacggtctg ctccacttta cgcacgccct tgagcacccg ctgagtgcgg tcaaaccgga     1020
cttcccccac ggcattggcc tcgcaatgct tcttccggcg gtaatcaggc acatataccc     1080
tgccaccgca aagatacttg ccgaggtcta caggccgctc gttcccgagg ccaaaggtgt     1140
tccgggagag gtggaactcg tcgccaggag ggtagaagag tggctcttca gcatcggcat     1200
aactgaaaag cttgaggacg tcgggttctc tgagacggat gtgaacaggc taacggaact     1260
tgccatgaaa acaccaagcc ttaacctgct cctctccatg gctccgggtg aggccactcg     1320
ggagagaata gcggccatat accgtgattc gctttatccc atcagcagag ggtgataata     1380
gtgaggctga gatcttcttc agtgcattgt agttgaatga agggttaggg gggaaatgcc     1440
cccctatttt ttgtctagcc atcctgccac gtttgacagg gtagcaattt cgacacgata     1500
gcgtgctgta ctgtttttg ctcgtcaggg ttgggttttg tcatcgacac ccaaggattg     1560
gagtcggtgc tcaataatcg ccagttgctg ttgggcagcc gccaattgcg cctgagccgc     1620
agcgaccacc tctggttggg cttttgttgac aaaattaggg ttgttgaggc gagcggttaa     1680
agattgaatc tctttcctca ggcgatcgcc ttccttctgg agcttgctta ccaaggcctc     1740
cagatctacg acccccgcta ggggaatgag tacctggttc tctcttctgc cgtta         1795
```

<210> SEQ ID NO 39
<211> LENGTH: 1983
<212> TYPE: DNA
<213> ORGANISM: Artificial Sequence
<220> FEATURE:
<223> OTHER INFORMATION: Synthetic Construct-Example 39: a designer
      Thermosynechococcus elongatus BP-1 nirA-promoter-controlled
      NADP-dependent Glyceraldehyde-3-Phosphate-Dehydrogenase DNA
      construct

<400> SEQUENCE: 39

```
agaaaatctg gcaccacacc actcgccacc cgcaaaccaa tggcatggcc gagcgctgca       60
acggtcgcat tgccaagatt ctgcgtgctg agcgctttgt ctccgctgct gatctgcaag      120
agacgctcac gcgataccts tgggcgtgca atcaccgcat tccccaacgc gctttgggcc      180
acatgacccc catcgagaga ctccgaacgt ggcaaatgga gggaccagag ttgttcagtt      240
cacaggtaga taatgtcgcg ggtcttgata gttagcaata aatacagttt cagaatatct      300
gtaatacaaa aactgtatcg agacaagaaa aaagtagcaa aatttacaaa tgttcatgat      360
tcatctggct aaattggatg ttcaactgac ccattgaaga caagggcaac aaccgtgatg      420
gtgacgattc gagttgcgat caatggcttt ggccgtattg gccggaattt ctccgttgc      480 tggtttggac ggcagaacac cgatctagag gttgtggcca ttaacaacac ctcggatgca      540
cggacggctg ctcacctgct ggagtacgac tctgttctcg gccggttcaa cgccgacatc      600
agctacgacg agaattcgat caccgtcaac ggcaagacga tgaaaatcgt ctgcgatcgc      660
```

```
aaccccctca acctgccttg gaaagagtgg gatatcgatc tcgtcattga atctacaggt      720
gtgttcgtca ccgctgaagg cgcatccaag cacatccaag ccggggccaa gaaagttctg      780
atcacggctc ctggtaaagc cgaaggtgtc ggcacctacg tcatcggtgt caacgattcg      840
gaataccgcc acgaagactt cgcagtcatc agcaatgcaa gctgcaccac caactgctta      900
gcaccggtcg ccaaagttct gcatgacaac tttggcatca tcaaaggcac gatgaccacc      960
acccacagct acacgctgga ccagcgcatc ttggacgcca gccaccgtga tctacgtcgg     1020
gctcgggctg cagccgttaa catcgttccc accacgaccg gcgctgctaa agccgttgct     1080
ttggtgatcc ccgagctgaa aggcaaacta acgggattgc gctgcgcgtt cctacgcca      1140 aacgtgtctg tcgttgactt ggtggttcaa gtcgagaaac cgacgatcac tgagcaggtc     1200
aatgaagtcc tgcaaaaagc ttctcaaacg acgatgaagg gcatcatcaa gtactcggat     1260
ctgcccttgg tctcttccga cttccggggt actgacgagt cttcgatcgt tgactccagc     1320
ctgaccttgg taatggatgg cgatctcgtc aaagtaattg cttggtacga caacgagtgg     1380
ggctacagcc aacgagttgt cgacttggct gaactggccg ctcgcaaatc gggccgctta     1440
ggacttgttc aaaccctctt aatttctagt caagatagcc tcccattaac gggaggcttt     1500
tttgtggcca agagagaaca ccccaggagc caagattcga tcaatccatc aggccccgat     1560
tagtaatagt gaggctgaga tcttcttcag tgcattgtag ttgaatgaag ggttaggggg     1620
gaaatgcccc cctatttttt gtctagccat cctgccacgt tgacagggt agcaatttcg      1680 acacgatagc gtgctgtact gttttttgct cgtcagggtt gggttttgtc atcgacaccc     1740
aaggattgga gtcggtgctc aataatcgcc agttgctgtt gggcagccgc caattgcgcc     1800
tgagccgcag cgaccacctc tggttgggct ttgttgacaa aattagggtt gttgaggcga     1860
gcggttaaag attgaatctc tttcctcagg cgatcgcctt ccttctggag cttgcttacc     1920
aaggcctcca gatctacgac ccccgctagg ggaatgagta cctggttctc tcttctgccg     1980
tta                                                                  1983
```

<210> SEQ ID NO 40
<211> LENGTH: 1793
<212> TYPE: DNA
<213> ORGANISM: Artificial Sequence
<220> FEATURE:
<223> OTHER INFORMATION: Synthetic Construct-Example 40: a designer Thermosynechococcus elongatus BP-1 nirA-promoter-controlled NAD-dependent Glyceraldehyde-3-Phosphate Dehydrogenase DNA construct

<400> SEQUENCE: 40

```
agaaaatctg gcaccacacc actcgccacc cgcaaaccaa tggcatggcc gagcgctgca       60
acggtcgcat tgccaagatt ctgcgtgctg agcgctttgt ctccgctgct gatctgcaag      120
agacgctcac gcgataccte tgggcgtgca atcaccgcat tccccaacgc gctttgggcc      180
acatgacccc catcgagaga ctccgaacgt ggcaaatgga gggaccagag ttgttcagtt      240
cacaggtaga taatgtcgcg ggtcttgata gttagcaata aatacagttt cagaatatct      300
gtaatacaaa aactgtatcg agacaagaaa aaagtagcaa aatttacaaa tgttcatgat      360
tcatctggct aaattggatg ttcaactgac ccattgaaga caagggcaac aaccgtgatg      420
aatggatttg gacgaatcgg tcgccagagc ttcaaggcaa tgctggagta ttaccccgaa      480
gagttcgaga tcgtcgctat caacgacctg accgacgcgc aaacgctggc ccatcttctg      540
cgctacgatt cgacctatgg tgccttcgat ggcgaagtaa cggtgaccga aaggcgatt      600 gtggtagagc aggacgatat tcgctacgag ttgttgacgc tggccgagcg cgacccggca      660
```

```
gcattgccct ggaaggagct ggggggttgac atcgtgatcg agtcgaccgg ccgtttcacc        720
gatgcggaaa aggccaaggc tcacctcgcg gcgggtgcga agaaagtgat cattacggca        780
ccggcgaaag gtgaggacat caccatctgt ctgggtgtga acgacgcgaa atacgatcac        840
gagaagcatc acatcatctc gaatgcatcc tgcacaacca actgtctggc accggtagcg        900
aaggtgctca atgatcgctt cgggatcgag cgtggtctga tgacgaccat ccactcgtac        960
acgatggatc aaaacttgca ggataacgta cacaaggatt gcgccgggc gcgggctgcg       1020 gctatcaaca tggtgccaac gaccactggt gccgcgaagg cggtggcgct ggttattccc       1080
gaattgaaag gcaagttcca cggttatgcc gtgcgcgtgc cgacgccgac ggtgtcgatg       1140
gttgacttct cggtgctgct gagcaccaag acctcggtcg aggagattaa ccaggccttc       1200
atcgaagcca gcgagagcga agagcttgag ggcattctcg gcgtgagcca cgatccgctg       1260
gttagcaccg acttcatcgg taccacctac agcagtgtag tcgatttacc gctcacaatg       1320
agcatgggcg acgatttctt caagatcgtg gcctggtacg ataatgagtg gggtaatagt       1380
gaggctgaga tcttcttcag tgcattgtag ttgaatgaag ggttaggggg gaaatgcccc       1440 cctattttt gtctagccat cctgccacgt ttgacagggt agcaatttcg acacgatagc       1500
gtgctgtact gttttttgct cgtcagggtt gggttttgtc atcgacaccc aaggattgga       1560
gtcggtgctc aataatcgcc agttgctgtt gggcagccgc caattgcgcc tgagccgcag       1620
cgaccacctc tggttgggct tgttgacaa aattagggtt gttgaggcga gcggttaaag       1680
attgaatctc tttcctcagg cgatcgcctt ccttctggag cttgcttacc aaggcctcca       1740
gatctacgac ccccgctagg ggaatgagta cctggttctc tcttctgccg tta            1793

<210> SEQ ID NO 41
<211> LENGTH: 1992
<212> TYPE: DNA
<213> ORGANISM: Artificial Sequence
<220> FEATURE:
<223> OTHER INFORMATION: Synthetic Construct-Example 41: a designer
      Thermosynechococcus elongatus BP-1 nirA-promoter-controlled
      thermotolerant and NADH-dependent Alcohol-Dehydrogenase DNA
      construct

<400> SEQUENCE: 41
agaaaatctg gcaccacacc actcgccacc cgcaaaccaa tggcatggcc gagcgctgca         60
acggtcgcat tgccaagatt ctgcgtgctg agcgctttgt ctccgctgct gatctgcaag        120
agacgctcac gcgataccto tgggcgtgca atcaccgcat tccccaacgc gctttgggcc        180
acatgacccc catcgagaga ctccgaacgt ggcaaatgga gggaccagag ttgttcagtt        240
cacaggtaga taatgtcgcg ggtcttgata gttagcaata aatacagttt cagaatatct        300
gtaatacaaa aactgtatcg agacaagaaa aaagtagcaa aatttacaaa tgttcatgat        360
tcatctggct aaattggatg ttcaactgac ccattgaaga caaggcaac aaccgtgatg        420 atggcttctt caacttttta tattcctttc gtcaacgaaa tgggcgaagg ttcgcttgaa        480
aaagcaatca aggatcttaa cggcagcggc tttaaaaatg cgctgatcgt ttctgatgct        540
ttcatgaaca aatccggtgt tgtgaagcag gttgctgacc tgttgaaagc acagggtatt        600
aattctgctg tttatgatgg cgttatgccg aacccgactg ttaccgcagt tctggaaggc        660
cttaagatcc tgaaggataa caattcagac ttcgtcatct ccctcggtgg tggttctccc        720
catgactgcg ccaaagccat cgctctggtc gcaaccaatg gtggtgaagt caaagactac        780
gaaggtatcg acaaatctaa gaaacctgcc ctgcctttga tgtcaatcaa cacgacggct        840
```

```
ggtacggctt ctgaaatgac gcgtttctgc atcatcactg atgaagtccg tcacgttaag      900
atggccattg ttgaccgtca cgttaccccg atggtttccg tcaacgatcc tctgttgatg      960
gttggtatgc caaaaggcct gaccgccgcc accggtatgg atgctctgac ccacgcattt     1020
gaagcttatt cttcaacggc agctactccg atcaccgatg cttgcgcctt gaaggctgcg     1080
tccatgatcg ctaagaatct gaagaccgct tgcgacaacg gtaaggatat gccagctcgt     1140
gaagctatgc cttatgccca attcctcgct ggtatggcct tcaacaacgc ttcgcttggt     1200
tatgtccatg ctatggctca ccagttgggc ggctactaca acctgccgca tggtgtctgc     1260
aacgctgttc tgcttccgca tgttctggct tataacgcct ctgtcgttgc tggtcgtctg     1320
aaagacgttg gtgttgctat gggtctcgat atcgccaatc tcggtgataa agaaggcgca     1380
gaagccacca ttcaggctgt tcgcgatctg gctgcttcca ttggtattcc agcaaatctg     1440
accgagctgg gtgctaagaa agaagatgtg ccgcttcttg ctgaccacgc tctgaaagat     1500
gcttgtgctc tgaccaaccc gcgtcagggt gatcagaaag aagttgaaga actcttcctg     1560
agcgctttct aataatagtg aggctgagat cttcttcagt gcattgtagt tgaatgaagg     1620
gttaggggg aaatgccccc ctattttttg tctagccatc ctgccacgtt tgacagggta      1680
gcaatttcga cacgatagcg tgctgtactg ttttttgctc gtcagggttg ggttttgtca     1740
tcgacaccca aggattggag tcggtgctca ataatcgcca gttgctgttg ggcagccgcc     1800
aattgcgcct gagccgcagc gaccacctct ggttgggctt tgttgacaaa attagggttg     1860
ttgaggcgag cggttaaaga ttgaatctct ttcctcaggc gatcgccttc cttctggagc     1920
ttgcttacca aggcctccag atctacgacc cccgctaggg gaatgagtac ctggttctct     1980
cttctgccgt ta                                                         1992

<210> SEQ ID NO 42
<211> LENGTH: 1265
<212> TYPE: DNA
<213> ORGANISM: Artificial Sequence
<220> FEATURE:
<223> OTHER INFORMATION: Synthetic Construct-Example 42: a designer
      Prochlorococcus marinus MED4 groE-promoter-controlled
      Phosphoglycerate-Mutase DNA construct

<400> SEQUENCE: 42
agaaaatctg gcaccacacc cagctcataa tgcgaaatat taccatcccg agggtatatt       60
cgttaactgg gttcggccaa ccgcacagtt aaagagtggt ttaattgctg cttaacagat      120
tatgttattt accatacggt ttgagtaata ctctcatgat gcccacgctc gttttgtccc      180
gtcacggaca gtccgaatgg aaccttgaaa accgtttcac cggttggtgg gacgttaacc      240
tgactgaaca gggtgttcag gaagcaacgg ccggtggtaa agctctggct gaaaagggtt      300
ttgaattcga tatcgctttc accagcgttc tgacccgcgc catcaaaacc accaatctta      360
ttctcgaagc cggtaaaacc ctttgggttc cgaccgaaaa agattggcgt ttgaatgaac      420
gtcactatgg tggtctgacc ggtctgaaca aggctgaaac cgccgctaaa catggtgaag      480
aacaggttca tatttggcgc cgttcttatg acgttccgcc gccccgatg gaaaaggca       540
gcaagttcga tctgtctggc gatcgtcgtt atgatggtgt caagattcct gaaacggaaa      600
gcctgaaaga caccgttgct cgcgtgctgc cttattggga agaacgcatt gcccctgaac      660
tgaaggctgg caagcgcgtc ctgatcggtg cgcatggtaa ctcattgcgc gctctcgtta      720
agcatctgtc gaaattgtcg gacgaagaaa tcgtcaaatt cgaattgccc accggtcagc      780
cgttggtcta cgaattgaat gatgatctga ccccgaaaga tcgttacttc cttaacgaac      840
```

```
gttaataaat ttttatttaa cagtcaatat ctttctcctt tcaaaactac aattttatt      900 ggagaaagtt ttttttaaga gttactaatt tgaagattat gtcaacaaaa acaagtagag      960
agattgcact agaaagaaga aaggctatga gtgatggcgg gaaaaaagct gccttacatt     1020
cttcttctac taaagatagg gttagatcat ctcaagatat aaattcaact ggagcaactt     1080
cttcaaataa aaaagtttta acatcaccaa gtaaatctaa tatacctgcc aataaaattg     1140
ctagaaaatc tacttcatca aaattatcga gtaaagaact tggtatagaa agaagaaaag     1200
caatgtctac acatggtaaa tcagctatta attcttcaga tagaaggttc tctcttctgc     1260
cgtta                                                                 1265

<210> SEQ ID NO 43
<211> LENGTH: 1877
<212> TYPE: DNA
<213> ORGANISM: Artificial Sequence
<220> FEATURE:
<223> OTHER INFORMATION: Synthetic Construct-Example 43: a designer
      Prochlorococcus marinus MED4 groE-promoter-controlled Enolase DNA
      construct

<400> SEQUENCE: 43
agaaaatctg gcaccacacc cagctcataa tgcgaaatat taccatcccg agggtatatt       60
cgttaactgg gttcggccaa ccgcacagtt aaagagtggt ttaattgctg cttaacagat      120
tatgttattt accatacggt ttgagtaata ctctcatggt gggcgttaat gatttttgcta     180 ttgagcgcgt ttggggctta caggtcctcg atagcagggg caaccccact gtgaaggcgt      240
atgtcaagct tgctggaggg agcttgggct ggggggatagc gcccagcggt gctagcagag     300
gcgagagaga ggcggtggag cttagagacg gtgggggtaa gtggagggggt aaaggagttt    360 ccagggcagt atctctttta aacacagtag tagcacctag gctggagggg gtcgacgcca     420
gaagacaagc ccaaatagac aggctcctaa tagaactaga cggcacccccg aacaaatcga    480 gactcggcgg gaacacgacc accgctctca gcatagccgt ttcaagagct gcggcggctc     540
aggcacgcct cgaactcttc cagtatctag gcggcgccgg ggctaggaga ctcccaatac     600
ctcttctcaa cgtcataaat ggtggtgttc acgcggggaa cgagctagac tttcaggagt     660
ttatgataat accttatggt tttgaaagct tcacagaagc tatgagggct gcggtggaga     720
catacgggga gctcaagagc ctgcttaagg acaggtatgg tgcatctgca gtcaacgtcg     780
gcgacgaagg gggtttcgca ccccctatga gaagcgccga agaggccctc aagactctag     840
tggatgcagt ggagaaagca ggctaccagc ccgggagcga gatagccctt ggcattgacg     900
cggctgcgag ccagctctac agtaacgggc gctacagcgt tgaagggaag agcctgtcca     960
gagaggagct cctaagcctc taccagcgct tggtagagca gtatccaata gtgtatcttg    1020
aagacccatt tagcgaggac gactatgaag gtttcaaggc cgccgtagac gccctctcga    1080
cagaaaccat tatagtgggg gacgatctcc tagttaccaa tccccagagg gttaaggagg    1140
cttccgccct caaagcagtc acaggcctcc tagtaaaggt gaaccaggtg gggactctca    1200
ccgaagctct cgaagccatc caggctgcga gggacagggg gattgtccac atagtgagcc    1260
acaggagcgg agacactgag gacaccttca ttgccgacct agccgtcgcc acagaagctt    1320
tgatgatcaa aacgggagcc ccagcccggg gagagaggac ctcgaaatac aacaggctcc    1380
tagaaataga gaacatatta ggctactcag ccgaatatgc aggtccagaa ctacgcggcg    1440
taatgggcag gcgctgataa atttttattt aacagtcaat atctttctcc tttcaaaact    1500 acaatttta ttggagaaag ttttttttaa gagttactaa tttgaagatt atgtcaacaa     1560
```

-continued

```
aaacaagtag agagattgca ctagaaagaa gaaaggctat gagtgatggc gggaaaaaag    1620
ctgccttaca ttcttcttct actaaagata gggttagatc atctcaagat ataaattcaa    1680
ctggagcaac ttcttcaaat aaaaaagttt taacatcacc aagtaaatct aatatacctg    1740
ccaataaaat tgctagaaaa tctacttcat caaaattatc gagtaaagaa cttggtatag    1800
aaagaagaaa agcaatgtct acacatggta aatcagctat taattcttca gatagaaggt    1860
tctctcttct gccgtta                                                   1877
```

<210> SEQ ID NO 44
<211> LENGTH: 2093
<212> TYPE: DNA
<213> ORGANISM: Artificial Sequence
<220> FEATURE:
<223> OTHER INFORMATION: Synthetic Construct-Example 44: a designer
      Prochlorococcus marinus MED4 groE-promoter-controlled
      Pyruvate-Kinase DNA construct

<400> SEQUENCE: 44

```
agaaaatctg gcaccacacc cagctcataa tgcgaaatat taccatcccg agggtatatt     60
cgttaactgg gttcggccaa ccgcacagtt aaagagtggt ttaattgctg cttaacagat    120
tatgttattt accatacggt ttgagtaata ctctcatgat gtcgtcttct tctctcgcct    180
ggttgtccca attgaacacc accgacaccc ccgacaaggt gctccgtcgt tcctccatca    240
tcggaaccat tggcccaaag accaactctg tcgaagtctt ggtcaagttg agaaaggccg    300
gtcttaacat cgtgagaatg aacttctccc acggctcgta cgagtaccac cagtcggtca    360
tcgacaacgc taagaagtcc gaagaagtgt atgttggccg tccactcgct attgccttgg    420
acaccaaggg cccagaaatt agaaccggta ctaccgtgga taatgtcgac tatccaattc    480
cacctaacca cgaaatgatc ttcaccaccg acgacgccta caagaccaag tctgacgaca    540
agatcatgta catcgactac gccaacatca caaaggtcat tgaagtcggc agaatcatct    600
acgttgatga tggtgttctt tccttcgaag tgttggaaat cgttgacgaa aagaccttga    660
aggtcaagtc catcaacgct ggtaaggtct gctcgcacaa gggtgtcaac ttgccaggta    720
ctgacgtcga cttgccagct ttgtctgaaa ggacaaggc cgacatccgt tttggtgtca    780
agaacggtgt acacatgatc tttgcttcgt tcatcagaac cggggacgat atcaaggaaa    840
tcagaagagt acttggtgaa gacggtaagc aaattcaaat cattgctaag atcgaaaacc    900
aacagggtgt caacaacttc gacgacatct tggctgaaac cgacggtgtc atggttgcta    960
gaggtgactt gggtattgaa attccagctc ctcaagtttt tgttgtgcaa aagcagttga    1020
ttgctaagtg taacttggct gctaagccag tcatctgtgc cacccagatg ttggagtcta    1080
tgacttacaa cccaagacca accagagccg aagtctccga tgtcggtaac gccatcttgg    1140
atggtgctga ctgtgtcatg ttgtctggag aaaccgctaa gggtgactac ccattcgaag    1200
ctgtttccat gatgcacaac actgccatca ttgctgaaaa ggctatctct taccagtcgt    1260
tgcacaacga actcagagtc ttggccaaaa agccaactcc tacttccgaa acctgtgctg    1320
tagctgccgt ttctgctgcc tacgaacagg acgctaaggc tatcgttgtc ttgtccactt    1380
ctggtttgag tgccagactc gtgtccaagt acaagccaaa cgtgccaatc atgatggtta    1440
ccagaaacga aacatccgcc agatactccc acttgtacag aggtgtgtat cctttcatct    1500
acaccaagga aaaggttgct aactggcaag aagacgtcga aaacagattg agatgggctg    1560
tttccgaagc cattgagttg ggtatcatcc acaagggtga ctctattgtc actgtgcagg    1620
gttggactag aggttcaggt cactccaaca ctgtcagaat cgttcaagct tagtaaattt    1680
```

```
ttatttaaca gtcaatatct ttctcctttc aaaactacaa ttttattgg agaaagtttt      1740 ttttaagagt tactaatttg aagattatgt caacaaaaac aagtagagag attgcactag     1800
aaagaagaaa ggctatgagt gatggcggga aaaaagctgc cttacattct tcttctacta    1860
aagatagggt tagatcatct caagatataa attcaactgg agcaacttct tcaaataaaa     1920 aagtttaac atcaccaagt aaatctaata tacctgccaa taaaattgct agaaaatcta      1980
cttcatcaaa attatcgagt aaagaacttg gtatagaaag aagaaaagca atgtctacac    2040
atggtaaatc agctattaat tcttcagata gaaggttctc tcttctgccg tta           2093

<210> SEQ ID NO 45
<211> LENGTH: 2369
<212> TYPE: DNA
<213> ORGANISM: Artificial Sequence
<220> FEATURE:
<223> OTHER INFORMATION: Synthetic Construct-Example 45: a designer
      Prochlorococcus marinus MED4 groE-promoter-controlled
      Pyruvate-Decarboxylase DNA construct

<400> SEQUENCE: 45
agaaaatctg gcaccacacc cagctcataa tgcgaaatat taccatcccg agggtatatt      60
cgttaactgg gttcggccaa ccgcacagtt aaagagtggt ttaattgctg cttaacagat     120
tatgttattt accatacggt ttgagtaata ctctcatgat ggctgaagtc tcattaggaa     180
gatatctctt cgagagattg taccaattgc aagtgcagac catcttcggt gtccctggtg     240
atttcaactt gtcgcttttg gacaagatct acgaagtgga agatgcccat ggcaagaatt     300
cgtttagatg ggctggtaat gccaacgaat tgaatgcatc gtacgctgct gacggttact     360
cgagagtcaa gcgtttaggg tgtttggtca ctacctttgg tgtcggtgaa ttgtctgctt     420
tgaatggtat tgccggttct tatgccgaac atgttggttt gcttcatgtc gtaggtgttc     480
catcgatttc ctcgcaagct aagcaattgt tacttcacca cactttgggt aatggtgatt     540
tcactgtttt ccatagaatg tccaacaaca tttctcagac cacagccttt atctccgata     600
tcaactcggc tccagctgaa attgatagat gtatcagaga ggcctacgtc aaacaaagac     660
cagtttatat cgggttacca gctaacttag ttgattgaa tgttccggcc tctttgcttg     720
agtctccaat caacttgtcg ttggaaaaga acgacccaga ggctcaagat gaagtcattg     780
actctgtctt agacttgatc aaaaagtcgc tgaacccaat catcttggtc gatgcctgtg     840
cctcgagaca tgactgtaag gctgaagtta ctcagttgat tgaacaaacc caattcccag     900
tatttgtcac tccaatgggt aaaggtaccg ttgatgaggg tggtgtagac ggagaattgt     960
tagaagatga tcctcatttg attgccaagg tcgctgctag gttgtctgct ggcaagaacg    1020
ctgcctctag attcggaggt gtttatgtcg gaaccttgtc gaagcccgaa gtcaaggacg    1080
ctgtagagag tgcagatttg attttgtctg tcggtgccct tttgtctgat tcaacactg     1140 gttcattttc ctactcctac agaaccaaga acatcgtcga attccattct gattacacta    1200
agattagaca agccactttc ccaggtgtgc agatgaagga agccttgcaa gaattgaaca    1260
agaaagtttc atctgctgct agtcactatg aagtcaagcc tgtgcccaag atcaagttgg    1320
ccaatacacc agccaccaga gaagtcaagt taactcagga atggttgtgg accagagtgt    1380
cttcgtggtt cagagaaggt gatattata tcaccgaaac cggtacatcc tccttcggta    1440
tagttcaatc cagattccca aacaacacca tcggtatctc ccaagtattg tggggttcta    1500
ttggtttctc tgttggtgcc actttgggtg ctgccatggc tgcccaagaa ctcgacccta    1560
acaagagaac catcttgttt gttggagatg gttcttgca attgaccgtt caggaaatct    1620
```

```
ccaccataat cagatggggt accacacctt accttttcgt gttgaacaat gacggttaca    1680
ccatcgagcg tttgatccac ggtgtaaatg cctcatataa tgacatccaa ccatggcaaa    1740
acttggaaat cttgcctact ttctcggcca agaactacga cgctgtgaga atctccaaca    1800
tcggagaagc agaagatatc ttgaaagaca aggaattcgg aaagaactcc aagattagat    1860
tgatagaagt catgttacca agattggatg caccatctaa ccttgccaaa caagctgcca    1920
ttacagctgc caccaacgcc gaagcttagt aaattttat ttaacagtca atatctttct     1980
cctttcaaaa ctacaatttt tattggagaa agtttttttt aagagttact aatttgaaga    2040
ttatgtcaac aaaaacaagt agagagattg cactagaaag aagaaaggct atgagtgatg    2100
gcgggaaaaa agctgcctta cattcttctt ctactaaaga tagggttaga tcatctcaag    2160
atataaattc aactggagca acttcttcaa ataaaaagt tttaacatca ccaagtaaat      2220
ctaatatacc tgccaataaa attgctagaa aatctacttc atcaaaatta tcgagtaaag    2280
aacttggtat agaaagaaga aaagcaatgt ctacacatgg taaatcagct attaattctt    2340
cagatagaag gttctctctt ctgccgtta                                       2369

<210> SEQ ID NO 46
<211> LENGTH: 1586
<212> TYPE: DNA
<213> ORGANISM: Artificial Sequence
<220> FEATURE:
<223> OTHER INFORMATION: Synthetic Construct-Example 46: a designer
      Prochlorococcus marinus MED4 groE-promoter-controlled
      NAD-dependent Glyceraldehyde-3-Phosphate-Dehydrogenase DNA
      construct

<400> SEQUENCE: 46
agaaaatctg gcaccacacc cagctcataa tgcgaaatat taccatcccg agggtatatt      60
cgttaactgg gttcggccaa ccgcacagtt aaagagtggt ttaattgctg cttaacagat     120
tatgttattt accatacggt ttgagtaata ctctcatgaa gataggaata aatggatttg     180
gtcgtattgg gaggctggtt ttgcgtgttg cattgagcaa ggaagatatc gaagtagttg     240
caatcaatga cccttttcatt gatgccaaat acatggctta catgtttaag tatgattcaa    300
ctcatggggt atacaaaggg agcttgaaga ttgttgatga tacgactctt gaaattgatg    360
gtcacagaat tactgtcaat tctaaaaggg atccttcaga gattccctgg ggtaactatg    420
gagctgagta tgttgtagaa tcatctggag ctttacaac aaccgagaag gcttctgcac     480
atcttaaggg tggagcgaag aaggttgtaa tttctgctcc atcagcggat gcacccatgt    540
ttgtggttgg agtaaacgaa ggatcatata agcctgaaat gtctattgtt tcaaatgcaa    600
gctgcacaac taattgcctt gctcctcttg caaaggtggt gaatgaagaa tttggtattg    660
ctgaggccct catgaccact gttcatgcaa caacagctac acagaagaca gtagatggtc    720
catctatgaa ggattggcgt ggaggtcgtg gtgctggaca aaatatcatt ccaagctcaa    780
ctggtgctgc aaaggcagtt gggaaggtcc ttccagagtt gaatggaaag cttactggaa    840
tggctttccg tgtaccaaca cccaatgtct cagttgtgga tctgacatgt cgccttgaga    900
aaccagcatc ttacgatgat ataaaagcag caatgaaggc cgcatctgaa gggtcactaa    960
aaggcatcct tggatacact gatgaagatg tcgtttcgaa tgattttgta ggcgatgcaa   1020
gatcgagtat ctttgatgct aaggctggta tagccttgag ttctacattt gtgaaacttg   1080
tttcttggta tgacaatgag tggggataca gcaaccgagt ggtggacttg atctcacaca   1140
tggctttagt tgcttcacgc aaatagtaaa tttttattta acagtcaata tctttctcct   1200
ttcaaaacta caattttat tggagaaagt ttttttaag agttactaat ttgaagatta     1260
```

```
tgtcaacaaa aacaagtaga gagattgcac tagaaagaag aaaggctatg agtgatggcg   1320
ggaaaaaagc tgccttacat tcttcttcta ctaaagatag ggttagatca tctcaagata   1380
taaattcaac tggagcaact tcttcaaata aaaaagtttt aacatcacca agtaaatcta   1440
atatacctgc caataaaatt gctagaaaat ctacttcatc aaaattatcg agtaaagaac   1500
ttggtataga aagaagaaaa gcaatgtcta cacatggtaa atcagctatt aattcttcag   1560
atagaaggtt ctctcttctg ccgtta                                        1586
```

<210> SEQ ID NO 47
<211> LENGTH: 1730
<212> TYPE: DNA
<213> ORGANISM: Artificial Sequence
<220> FEATURE:
<223> OTHER INFORMATION: Synthetic Construct-Example 47: a designer
      Prochlorococcus marinus MED4 groE-promoter-controlled
      NADH-dependent Alcohol-Dehydrogenase DNA construct

<400> SEQUENCE: 47

```
agaaaatctg gcaccacacc cagctcataa tgcgaaatat taccatcccg agggtatatt    60
cgttaactgg gttcggccaa ccgcacagtt aaagagtggg ttaattgctg cttaacagat   120
tatgttattt accatacggt ttgagtaata ctctcatgat ggcttcttca acttttttata  180 ttcctttcgt caacgaaatg ggcgaaggtt cgcttgaaaa agcaatcaag gatcttaacg   240
gcagcggctt taaaaatgcg ctgatcgttt ctgatgcttt catgaacaaa tccggtgttg   300
tgaagcaggt tgctgacctg ttgaaagcac agggtattaa ttctgctgtt tatgatggcg   360
ttatgccgaa cccgactgtt accgcagttc tggaaggcct taagatcctg aaggataaca   420
attcagactt cgtcatctcc ctcggtggtg gttctcccca tgactgcgcc aaagccatcg   480
ctctggtcgc aaccaatggt ggtgaagtca agactacga aggtatcgac aaatctaaga   540
aacctgccct gcctttgatg tcaatcaaca cgacggctgg tacggcttct gaaatgacgc   600
gtttctgcat catcactgat gaagtccgtc acgttaagat ggccattgtt gaccgtcacg   660
ttaccccgat ggtttccgtc aacgatcctc tgttgatggt tggtatgcca aaaggcctga   720
ccgccgccac cggtatggat gctctgaccc acgcatttga agcttattct caacggcag   780 ctactccgat caccgatgct tgcgccttga aggctgcgtc catgatcgct aagaatctga   840
agaccgcttg cgacaacggt aaggatatgc cagctcgtga agctatggct tatgcccaat   900
tcctcgctgg tatggccttc aacaacgctt cgcttggtta tgtccatgct atggctcacc   960
agttgggcgg ctactacaac ctgccgcatg gtgtctgcaa cgctgttctg cttccgcatg   1020
ttctggctta taacgcctct gtcgttgctg gtcgtctgaa agacgttggt gttgctatgg   1080
gtctcgatat cgccaatctc ggtgataaag aaggcgcaga gccaccatt caggctgttc   1140 gcgatctggc tgcttccatt ggtattccag caaatctgac cgagctgggt gctaagaaag   1200
aagatgtgcc gcttcttgct gaccacgctc tgaaagatgc ttgtgctctg accaacccgc   1260
gtcagggtga tcagaaagaa gttgaagaac tcttcctgag cgctttctaa taaattttta   1320
tttaacagtc aatatctttc tccttcaaa actacaattt ttattggaga agttttttt     1380 taagagttac taattttgaag attatgtcaa caaaaacaag tagagagatt gcactagaaa   1440
gaagaaaggc tatgagtgat ggcgggaaaa agctgccctt acattcttct tctactaaag   1500
atagggttag atcatctcaa gatataaatt caactggagc aacttcttca aataaaaaag   1560
ttttaacatc accaagtaaa tctaatatac ctgccaataa aattgctaga aaatctactt   1620
catcaaaatt atcgagtaaa gaacttggta tagaaagaag aaaagcaatg tctacacatg   1680
```
gtaaatcagc tattaattct tcagatagaa ggttctctct tctgccgtta      1730

<210> SEQ ID NO 48
<211> LENGTH: 1630
<212> TYPE: DNA
<213> ORGANISM: Artificial Sequence
<220> FEATURE:
<223> OTHER INFORMATION: Synthetic Construct-Example 48: a designer
      Prochlorococcus marinus MIT9313 groE-promoter-controlled
      NADH-dependent Alcohol-Dehydrogenase DNA construct

<400> SEQUENCE: 48
agaaaatctg gcaccacacc ccctttcaga gcggcgcaac attaccactg catggcgaga        60
tcttctcagg gttcggtgac ccgcacaggt atccactagt cggcacagca tcaacacaca       120
tagggttggc actcaatggc cacgagtgct actcatgtta gctacctctg tgccagaaac       180
ccaaaagggt gttatttttct atgagaatgg tggtaaattg aatacaagg acattccagt       240 tccaaagcca aagccaaatg aaatcttgat caacgtcaag tactccggtg tgtgtcatac       300
cgatttgcac gcatggaagg gtgactggcc attgccaacc aagttgccat tggtcggtgg       360
tcacgaaggt gctggtgtcg ttgttgctat gggtgaaaac gtcaagggct ggaacattgg       420
tgactttgcg ggtatcaaat ggttgaacgg ttcttgtatg tcctgtgaat actgtgaatt       480
gtccaatgaa tccaactgtc cagatgctga cttgtctggt tacacccacg atggttcttt       540
ccaacaatac cgtaccgcag atgctgttca agctgccaga attccaaagg gtaccgattt       600
ggctgaagtt gctccaaccc tatgtgccgg tgttactgtt tacaaggctt tgaaaagtgc       660
taacttgaag gctggtgact gggttgccat ctctggtgct gctggtggtc taggttctct       720
agctgtccaa tacgccaagg ccatgggtta cagagtcgtt ggtatcgacg gtggtgaaga       780
aaagggtaag ttggtcaagc aattgggtgg tgaagccttt gttgatttca ccaaaaccaa       840
ggacatggtt gctgaaatcc aagaaatcac caacggtggt ccacacgtg tcattaacgt       900 ctctgtttct gaagctgcca tgaacgcttc cactcaattc gtcagaccaa ctggtactgt       960
cgtattggtc ggtttgccag ctggtgccgt catcaagtcc gaagtcttct cccacgtcgt      1020
taagtctatt aacatcaagg gttcttacgt cggtaacaga gctgacacca gagaagctat      1080
caacttcttc gctaacggtc acgtccactc tccaatcaag gttgttggtt tgtccgaact      1140
accaaaggtt tacgaattga tggaacaagg taagattttg ggtagatacg ttgttgacac      1200
ctccaactag tgatttagtt tcggtgtcta tctcttaata gcctcgatttt attttcgggg      1260 ctattaatca actctcagag gcgacaagct tcttcttccc ttacgacgtt tttattggtt      1320
ggacatggca aaacaatcca gtcgagagct agcgcttgaa cgccgtaagg ccctgagtaa      1380
ttcaggtaag aaatcaacca cattaaatgg atcaagtcct aatcgcatcc gtactgcctc      1440
tgatgcacgt ctaaccagga ctgatcaatc tttcgttaag gctgggaaag aatctgtgca      1500
gctaaccgct cctaagagag agcaactaga tacgtctttt gttgcttcta gagaatcatc      1560
cggagcttcg cgccgtcaag tgaaaacgat ccgaaattca agcagagaat ggttctctct      1620
tctgccgtta                                                              1630

<210> SEQ ID NO 49
<211> LENGTH: 2272
<212> TYPE: DNA
<213> ORGANISM: Artificial Sequence
<220> FEATURE:
<223> OTHER INFORMATION: Synthetic Construct-Example 49: a designer
      Prochlorococcus marinus MIT9313 groE-promoter-controlled
      Pyruvate-Decarboxylase DNA construct

<400> SEQUENCE: 49

```
agaaaatctg gcaccacacc ccctttcaga gcggcgcaac attaccactg catggcgaga        60
tcttctcagg gttcggtgac ccgcacaggt atccactagt cggcacagca tcaacacaca       120
tagggttggc actcaatggc cacgagtgct actcatgatg tcggaaatta cattaggtcg       180
ttacttgttt gaaaggttaa agcaggtgca ggttcagacg atcttcggat taccgggtga       240
ctttaatttg tctttgttgg acaagattta cgaggttccg ggtttgaggt gggcgggtaa       300
tgcaaatgag ttgaatgcgg cttatgcagc agatggttac gctagagtca aaggtatgtc       360
ttgtattgtt actacctttg gtgtcggtga gttgtctgcg ctgaacggta ttgcgggttc       420
gtatgcagaa cacgtcgggg tcttgcacgt tgtcggcgtt ccatcagtct cgtcccaagc       480
ccaacagttg ctattgcatc acacgttagg caacggtgac tttaccgtgt ttcatagaat       540
gtcctccgaa atctccgaaa ctactgcagt gatcactgat atcaaagatg ctccaaagga       600
aattgacagg tgtattaagg tcacttactc taagcagaga cccgtgtatt tgggtctccc       660
agctaacttg gttgatttga aggtttccgc atctttgttg gacactccga tcgatttgtc       720
catgaccccc aatgatgccg atgccgaaga tgaagttgtt gaaacggtct tggcaatggt       780
ctccaaggca agaaaccctg tcattctagc agacgcatgt tgtactagac acgacgtcaa       840
acgggaaacc aagaagttga tcgatttgac ccagttcccc gcttttgtga caccaatggg       900
caagggctcc atcgacgagg atcatccaag gtttggcggt gtttacgtgg gcactttgtc       960
tgatcctgaa gtaaaggaag ccgttgagtc tgcggacttg gtcttatccg tcggcgccct      1020
gctatctgat ttcaacaccg gttcttttttc ttactcctac aagaccaaga atattgtgga      1080
attccactct gactacacca agtcagaaa tgccactttc cccggtgtgc agatgaaact       1140
cgtgttgcaa aaactgttat ccaaggtgtc cgatgcagca agcggttata aaccagttcc      1200
agttcccaag ggtacaagat ctaacccagg agtcgaatct tctactcctt tgaaacagga      1260
atggatttgg aaccacatta gcgactggtt ggaagaaggc gatgttgtca ttacagagac      1320
cggcacttct gcgttcggta tcaaccagtc ccgtttccct aacagcacct acggtatttc      1380
tcaagtcttg tgggggtcta ttggctattc tgtcggctct tgtttaggtg ctgcttttgc      1440
cgcagaagag ttgacaagag atagaagggt catcttgttc gttggggatg gttctttaca      1500
actaaccgtc caagagattt ccacaatggt cagatggggt ctcaagccat atttgtttgt      1560
gttgaacaac gatggttata caatcgaaag gttaattcat ggtgagactg ctcagtataa      1620
cgacgttcaa ccgtggttac atttgaacct gctaccaact tttggtgcca aggattacga      1680
ttcgattaga atttccacta caggcgaatt tctcaagttg actgaggatc aggctttcag      1740
taggaattcc aagattaggt tgattgaagt aatgttaccc gttatggatg ctccttcgac      1800
gttggttaag caagcccaat tgactgccgc tacaaatgct aagcagggct aatgatttag      1860
tttcggtgtc tatctcttaa tagcctcgat ttattttcgg ggctattaat caactctcag      1920
aggcgacaag cttcttcttc ccttacgacg tttttattgg ttggacatgg caaaacaatc      1980
cagtcgagag ctagcgcttg aacgccgtaa ggccctgagt aattcaggta agaaatcaac      2040
cacattaaat ggatcaagtc ctaatcgcat ccgtactgcc tctgatgcac gtctaaccag      2100
gactgatcaa tctttcgtta aggctgggaa agaatctgtg cagctaaccg ctcctaagag      2160
agagcaacta gatacgtctt ttgttgcttc tagagaatca tccggagctt cgcgccgtca      2220
agtgaaaacg atccgaaatt caagcagaga atggttctct cttctgccgt ta              2272
```

<210> SEQ ID NO 50
<211> LENGTH: 2092
<212> TYPE: DNA
<213> ORGANISM: Artificial Sequence
<220> FEATURE:
<223> OTHER INFORMATION: Synthetic Construct-Example 50: a designer
Prochlorococcus marinus MIT9313 groE-promoter-controlled
Pyruvate-Kinase DNA construct

<400> SEQUENCE: 50

| | | | | | |
|---|---|---|---|---|---|
| agaaaatctg | gcaccacacc | cccttcaga | gcggcgcaac | attaccactg | catggcgaga | 60 |
| tcttctcagg | gttcggtgac | ccgcacaggt | atccactagt | cggcacagca | tcaacacaca | 120 |
| tagggttggc | actcaatggc | cacgagtgct | actcatgatg | tcacactctt | cattaacatg | 180 |
| gttgtccaac | ttgaaccttg | agcagactcc | tcacaaatac | ttgagaagat | cctccatcat | 240 |
| tggtactatt | ggaccaaaaa | ccaacaatgt | tgatgtcttg | gtcaagttga | gaaaagctgg | 300 |
| tttgaacatt | gtcagaatga | acttttccca | cggttcttat | gaataccacc | aatctgtcat | 360 |
| tgacaatgct | agaaaatccg | aagaggttta | caaaggtaga | ccattggcca | ttgccttgga | 420 |
| caccaagggt | ccagaaatta | gaactggtac | cacaattgat | gaaaaagact | acccaatccc | 480 |
| accaaaccac | caaatgatct | tcaccactga | tgacgcctac | aaactcaaat | gtaacgatga | 540 |
| gattatgtac | attgactaca | aaaacattac | aaaggttatc | tcccctggta | aaatcatcta | 600 |
| cgttgatgac | ggtgtcttgt | cctttgaagt | tgaatccgtc | gaagatgaca | cactttgaa | 660 |
| ggttagatcc | atcaatggtg | gtaagatttc | atcccacaag | ggtgtcaact | tgccaggaac | 720 |
| tgatgtcgac | ttgcctccat | tatccgaaaa | ggataaggcc | gatatcagat | tcggtgttaa | 780 |
| gaacaaggtc | cacatgatct | ttgcttcatt | tatcagatca | gcagatgaca | ttagacacat | 840 |
| tagagaagtt | tgggtgagg | atggaaaaga | aatccaaatc | attgccaaga | ttgaaaacca | 900 |
| acaaggtgtc | aacaactttg | acgagatttt | ggaagtcacc | gatggtgtta | tggttgccag | 960 |
| aggagacttg | ggtatcgaga | tcccagctcc | tcaagtgttt | atcgtgcaaa | agaaattgat | 1020 |
| tgctaaatgt | aacttggctg | ctaaaccagt | tgtctgtgct | actcaaatgt | tggagtcaat | 1080 |
| gacctacaac | ccaagaccaa | caagagctga | agtttcagat | gttggtaacg | ccatcttaga | 1140 |
| cggtgctgat | tgtgtgatgt | tgtctggtga | aacagccaaa | ggtgactacc | cattcgaagc | 1200 |
| cgtgtcaatg | atgcacaaca | cctgtcttat | tgcagaaaag | gcaattgcat | acccacaatt | 1260 |
| attcaacgaa | ttgagatcat | tggccgtcaa | gccaacctca | accaccgaaa | cctgtgcaat | 1320 |
| ggctgccgtt | gccgctgcat | acgaccaaga | cgccaaggcc | attgtcgttc | tttcaacttc | 1380 |
| aggtcactca | gcaagatacg | tctccaagta | caagccagat | gttccaatct | tgatggtcac | 1440 |
| tagaaacgaa | aacagtgcca | aatactcaca | cttgtataga | ggtgtctacc | cattcgtgta | 1500 |
| caagaaggac | agattaccaa | actggcaaga | ggatgtcgag | agcagattga | gatgggctgt | 1560 |
| ctccgaagca | gttgacttgg | gaattatcgc | caagggtgac | tccattgtca | ctgtgcaagg | 1620 |
| atggaccaga | ggttctggac | actccaacac | tgtgagaatc | gtccaagctt | aatgatttag | 1680 |
| tttcggtgtc | tatctcttaa | tagcctcgat | ttattttcgg | ggctattaat | caactctcag | 1740 |
| aggcgacaag | cttcttcttc | ccttacgacg | tttttattgg | ttggacatgg | caaaacaatc | 1800 |
| cagtcgagag | ctagcgcttg | aacgccgtaa | ggccctgagt | aattcaggta | agaaatcaac | 1860 |
| cacattaaat | ggatcaagtc | ctaatcgcat | ccgtactgcc | tctgatgcac | gtctaaccag | 1920 |
| gactgatcaa | tctttcgtta | aggctgggaa | agaatctgtg | cagctaaccg | ctcctaagag | 1980 |
| agagcaacta | gatacgtctt | ttgttgcttc | tagagaatca | tccggagctt | cgcgccgtca | 2040 |
| agtgaaaacg | atccgaaatt | caagcagaga | atggttctct | cttctgccgt | ta | 2092 |

<210> SEQ ID NO 51
<211> LENGTH: 1897
<212> TYPE: DNA
<213> ORGANISM: Artificial Sequence
<220> FEATURE:
<223> OTHER INFORMATION: Synthetic Construct-Example 51: a designer
Prochlorococcus marinus MIT9313 groE-promoter-controlled Enolase
DNA construct

<400> SEQUENCE: 51

```
agaaaatctg gcaccacacc cccttctcaga gcggcgcaac attaccactg catggcgaga      60
tcttctcagg gttcggtgac ccgcacaggt atccactagt cggcacagca tcaacacaca     120
tagggttggc actcaatggc cacgagtgct actcatgatg gctatttcaa agatccactc     180
cagatacgtc tacgactcca gaggaaaccc aactgttgag gttgaattga ccactgaaaa     240
gggtactttt agatcaattg tcccatccgg tgcttccact ggtgtccacg aagccttgga     300
attgagagac ggtgacaaat caaaatggtt gggtaaaggt gtcttgaagg ctgttgccaa     360
cgttaacgac acaattgccc cagccttgat tgaggccaac attgatgttg ctgaccaagc     420
caagattgac gaattcttgt tgaaattgga cggtactcca aacaaggcca agttgggtgc     480
caacgccatc ttgggtgtct cattggctgc cgctaaagcc ggtgccgctc aaaaagatgt     540
cccattgtac aagcacattg ctgacatttc aaaggccaag gaaggtaaat tgttttgcc      600
agttcctttc caaaacgtct tgaacggtgg ttcccacgct ggtggtgact ggctttcca      660
agaatttatg attgtcccat ccggtgctcc atcattctct gaaggtttga gaatcggttc     720
agaagtttac caccacttga aatcattgac caagaagaag tatggtcaat ccgctggtaa     780
cgttggtgac gaaggtggtg ttgctccaga tatcaaaacc gctaaggaag ctttggactt     840
gatcgtttca gctattgaag ctgctggtta caccggtcaa gttgacattg ccatggatgt     900
tgcatcatcc gaattctaca aggatggatt gtacgacttg gactttaaaa atccaaactc     960
tgacaagtcc aaatggatca ctggtccaca attggctgaa ttgtacgagc aattgttgaa    1020
tgaatacccca attgtctcca ttgaagaccc attcgctgag gatgactggg aagcttggag    1080
ccacttttc tccaaggttg aaggtaagac tcaaattgtt ggtgatgact tgaccgttac    1140
caacccaatc agaatcaaga aggccatcga gaccaaggct gctgacgcct tgttgttgaa    1200
ggttaaccaa atcggtactt tgaccgaatc aatccaagct gccaatgact catacgctgc    1260
cggttggggt gttatggtct cccacagatc aggtgagacc gaagacacct ttatcgctga    1320
cttgtccgtc ggtattagat caggtcaaat caagactggt gctccagcta gatccgagag    1380
attggccaaa ttgaaccaaa tcttgagaat cgaggaagag ttgggtgaca aggccatcta    1440
cgccggtaag gacttccaca agcccactc tttataatga tttagtttcg gtgtctatct    1500
cttaatagcc tcgatttatt ttcgggggcta ttaatcaact ctcagaggcg acaagcttct    1560
tcttccctta cgacgttttt attggttgga catggcaaaa caatccagtc gagagctagc    1620
gcttgaacgc cgtaaggccc tgagtaattc aggtaagaaa tcaaccacat taaatggatc    1680
aagtcctaat cgcatccgta ctgcctctga tgcacgtcta accaggactg atcaatcttt    1740
cgttaaggct gggaaagaat ctgtgcagct aaccgctcct aagagagagc aactagatac    1800
gtctttttgtt gcttctagag aatcatccgg agcttcgcgc cgtcaagtga aacgatccg    1860
aaattcaagc agagaatggt tctctcttct gccgtta                             1897
```

<210> SEQ ID NO 52
<211> LENGTH: 2113

<212> TYPE: DNA
<213> ORGANISM: Artificial Sequence
<220> FEATURE:
<223> OTHER INFORMATION: Synthetic Construct-Example 52: a designer
    Prochlorococcus marinus MIT9313 groE-promoter-controlled
    Phosphoglycerate-Mutase DNA construct

<400> SEQUENCE: 52

| | | | | | |
|---|---|---|---|---|---|
| agaaaatctg | gcaccacacc | cccttttcaga | gcggcgcaac | attaccactg | catggcgaga | 60 |
| tcttctcagg | gttcggtgac | ccgcacaggt | atccactagt | cggcacagca | tcaacacaca | 120 |
| tagggttggc | actcaatggc | cacgagtgct | actcatgatg | agtaaaaagc | cagtagcatt | 180 |
| aatcatctta | gatggttttg | cattacgcga | tgaagataaa | ggtaatgcgg | taacacatgc | 240 |
| aaaaaaacca | aacttcgacc | gtttctggaa | cgagtatcct | catgctacac | ttcaggcgtc | 300 |
| tggagaagct | gtaggcttac | cagaaggcca | aatgggtaac | tctgaagtag | gtcacttaaa | 360 |
| catcggcgca | ggccgaattg | tgtaccaaag | cttaactcgt | gtaaacgtag | caattcgtga | 420 |
| aggcgagttt | gaacaaaacg | aaacgcttct | agcagctgta | aagcacgcaa | agaaaaggg | 480 |
| tacaaacctt | catcttttcg | ggcttttatc | tgatggcggt | gtacacagtc | atatcgaaca | 540 |
| tctatatgca | ttattgcgtc | tagctaagag | tgaaggctta | gaaaaagtct | acattcatgg | 600 |
| cttcttagat | ggtcgtgacg | tagcacctca | atctgctgaa | acgtatttaa | agaacttaa | 660 |
| tgaaaaaatt | gaagagtacg | gcgttggtga | aattgcaaca | ctttcaggac | gttactactc | 720 |
| aatggaccgc | gacaaacgct | gggagcgcgt | agagaaatca | tatcgcgcaa | tggtgtacgg | 780 |
| cgaaggtcca | tcatatacaa | gcgctgaaga | gtgcgtaaaa | gattcgtatg | acaatggaat | 840 |
| ctatgacgaa | ttcgttttac | cttctgttat | tacaaaagaa | gacggatcgc | cagttgcgac | 900 |
| aattcaagac | gaagatgcag | ttattttcta | caacttccgt | ccggatcgcg | caattcaaat | 960 |
| ttcaaatacg | ttcgcaaacg | aagatttccg | ttcatttgat | cgcggtgaaa | aacatccaaa | 1020 |
| acacttacat | tttgtatgtt | taactcactt | cagcgaaaca | gttgacggat | atgtagcctt | 1080 |
| taagccaatt | aacttggata | cacgcttgg | tgaagtatta | tctcaaaata | acttaaagca | 1140 |
| gcttcgtatt | gccgagacag | aaaaatatcc | tcacgtaacg | ttctttatga | gcggtggacg | 1200 |
| tgaagcagag | tttcctggtg | aaacacgtat | cttaatcgat | tcaccaaaag | tagcaacata | 1260 |
| tgacttgaaa | cctgagatga | gtgcttatga | agtgacggac | gcgttgcttg | cagaaatcga | 1320 |
| aggcgataag | caagacgcta | ttttattaaa | ctttgcaaat | cctgatatgg | taggccattc | 1380 |
| aggtatgtta | gaaccaactg | taaaagcgat | tgaaacagta | gatgagtgct | taggcaaaat | 1440 |
| tgtagatgca | atttagcta | aaggcggtac | agcaatcatc | acagcagacc | atggtaatgc | 1500 |
| tgatgaagtg | attacgcttg | aaggtaatcc | aatgacggct | catacaacga | atcctgttcc | 1560 |
| agtaatcgta | accaaacaag | gcttagagct | tcgtgaagac | ggtattctag | agatctagc | 1620 |
| tcctacgatg | cttactcttt | ttctagacgt | agcgcagcca | aaagaaatga | caggtaaaac | 1680 |
| attaattaaa | taatgattta | gtttcggtgt | ctatctctta | atagcctcga | tttattttcg | 1740 |
| gggctattaa | tcaactctca | gaggcgacaa | gcttcttctt | cccttacgac | gtttttattg | 1800 |
| gttggacatg | gcaaaacaat | ccagtcgaga | gctagcgctt | gaacgccgta | aggccctgag | 1860 |
| taattcaggt | aagaaatcaa | ccacattaaa | tggatcaagt | cctaatcgca | tccgtactgc | 1920 |
| ctctgatgca | cgtctaacca | ggactgatca | atctttcgtt | aaggctggga | agaatctgt | 1980 |
| gcagctaacc | gctcctaaga | gagagcaact | agatacgtct | tttgttgctt | ctagagaatc | 2040 |
| atccggagct | tcgcgccgtc | aagtgaaaac | gatccgaaat | tcaagcagag | aatggttctc | 2100 |
| tcttctgccg | tta | | | | | 2113 |

<210> SEQ ID NO 53
<211> LENGTH: 1776
<212> TYPE: DNA
<213> ORGANISM: Artificial Sequence
<220> FEATURE:
<223> OTHER INFORMATION: Synthetic Construct-Example 53: a designer Prochlorococcus marinus MIT9313 nirA-promoter-controlled NAD-dependent Glyceraldehyde-3-Phosphate-Dehydrogenase DNA construct

<400> SEQUENCE: 53

| | | | | | |
|---|---|---|---|---|---|
| agaaaatctg | gcaccacacc | tgccaacatc | agccgggttc | agaatgtaca | caaagacacc | 60 |
| aattcttgaa | tttcacacaa | atgctcagtt | ttgttcaatc | tgataccgcc | aatacCctct | 120 |
| tccatcaggc | ttaatgactc | cattcgcagc | ctggcctcac | tcctcaacac | ctctagttgc | 180 |
| caacatcagc | cgggttcaga | atgtacacaa | agacaccaat | tcttgaattt | cacacaaatg | 240 |
| ctcagttttg | ttcaatctga | taccgccaat | accctcttcc | atcaggctta | atgactccat | 300 |
| tcgcaactta | cccttgcttc | aataatggca | gggcctaaaa | accatggcta | tcgaatgcgc | 360 |
| gaataaaatt | taaacaacat | gatcacttct | tttcaagttt | aatttcaaca | aaatttcatg | 420 |
| aacggattcg | ggaggatagg | tagcctggta | ctgagggcca | ccctcgaccg | caaggatgtg | 480 |
| aaggttgttg | ccatcaacga | ccccttcatt | gagggcgagt | acatggcata | catgttcaag | 540 |
| tatgacagcg | tgcacggccg | ctatgaggga | gatgtgcagg | gggacaagca | cggtatcacc | 600 |
| atcaatgggg | agcagatcaa | gaccttggca | atgatggacc | ccacacagat | tccctggggc | 660 |
| gaggttggtg | ctgactatgt | tgtcgagtca | actggtgtat | tcacaacagt | ggacaagtgc | 720 |
| caggcccatt | tgaagggagg | tgccaagaag | gttgtcatct | ctgctccctc | agcagatgca | 780 |
| cccatgtttg | tgatgggtgt | caacgcagac | aagtacgacc | caagcagca | cacagtcgtc | 840 |
| tccaacgcat | cctgcacaac | caactgcctg | gctccactgg | ctaaggttgt | gaatgacaca | 900 |
| tttggcatca | aggaggctct | gatgaccacc | gtgcacgcca | ccactgccac | ccagaagaca | 960 |
| gtagatggcc | catcaaagaa | ggactggcgt | ggtggtcgtg | gtgccagcgc | caacatcatc | 1020 |
| ccttcaagca | ctggtgctgc | caaggctgtc | ggcaaggtca | tccctgagct | caacggcaag | 1080 |
| ttgaccggca | tggcattccg | tgtcccaact | caggatgtgt | cagttgtgga | cctgacctgc | 1140 |
| atacttgaga | agccggctaa | gtatgaggac | atcatggctg | cactcaaggc | tgccagtgag | 1200 |
| ggaccaatga | agggcatcct | ggggtacact | gaggatgatg | ttgtgtcctc | tgactttgtg | 1260 |
| tccgaccccg | cctcctcaac | tgttgatgcc | aaggccggca | ttatgctcag | cccaacattt | 1320 |
| gtgaagctgg | tcagctggta | cgataacgag | tggggctgat | ttagtttcgg | tgtctatctc | 1380 |
| ttaatagcct | cgatttattt | tcggggctat | taatcaactc | tcagaggcga | caagcttctt | 1440 |
| cttcccttac | gacgttttta | ttggttggac | atggcaaaac | aatccagtcg | agagctagcg | 1500 |
| cttgaacgcc | gtaaggccct | gagtaattca | ggtaagaaat | caaccacatt | aaatggatca | 1560 |
| agtcctaatc | gcatccgtac | tgcctctgat | gcacgtctaa | ccaggactga | tcaatctttc | 1620 |
| gttaaggctg | ggaaagaatc | tgtgcagcta | accgctccta | agagagagca | actagatacg | 1680 |
| tcttttgttg | cttctagaga | atcatccgga | gcttcgcgcc | gtcaagtgaa | aacgatccga | 1740 |
| aattcaagca | gagaatggtt | ctctcttctg | ccgtta | | | 1776 |

<210> SEQ ID NO 54
<211> LENGTH: 934
<212> TYPE: DNA
<213> ORGANISM: Artificial Sequence
<220> FEATURE:

<223> OTHER INFORMATION: Synthetic Construct-Example 54: a designer
      nirA-promoter-controlled Glycogen-Synthase-iRNA DNA construct

<400> SEQUENCE: 54

| | | | | | |
|---|---|---|---|---|---|
| agaaaatctg | gcaccacacc | cttcttgcag | aacatgcatg | atttacaaaa | agttgtagtt | 60 |
| tctgttacca | attgcgaatc | gagaactgcc | taatctgccg | agtatatgat | gcggattctg | 120 |
| ttcgtggctg | ccgaatgtgc | tcccttcgcc | aaagtgggag | gcatgggaga | tgtggttggt | 180 |
| tccctgccca | aagtgctgaa | agctctgggc | catgatgtcc | gaatcttcat | gccgtactac | 240 |
| ggctttctga | acagtaagct | cgatattccc | gctgaaccga | tctggtgggg | ctacgcgatg | 300 |
| tttaatgcac | tgcgctacgg | cagtgtgccg | attgtgcgcc | gtacgggggg | gttggtcgat | 360 |
| acggtcttcc | accacgatcc | gcgtcatgcc | gagggcaatg | gctattgctt | cgatcgctac | 420 |
| gagccgctgg | acctctatac | ctgtctggtg | cgggcttggg | agagttacca | gtaccagccc | 480 |
| caatggcaaa | agctacagca | acggggtatg | gccgttgatc | tgagctggaa | acaatcggcg | 540 |
| atcgcctacg | aacagctcta | cgctgaagcg | attgggctac | cgatcgatgt | cttacaggag | 600 |
| gcctagtaat | agtgatcccg | gccgctacta | aagcctgatt | tgtcttgata | gctgctcctg | 660 |
| cctttgggca | ggggcttttt | tctgtctgcc | attcttgagg | atggcggact | cttccccttt | 720 |
| tgctctacgc | ccatgaatgc | gatcgcagtc | tcccctgtcc | agcacgttgg | agtgattggt | 780 |
| ggtggccagt | tagcttggat | gctggcacca | gcagcgcaac | agttgggat | gtcgctgcac | 840 |
| gttcaaacac | ccaatgatca | cgacccagca | gtagcgatcg | cggatcaaac | cgtattagca | 900 |
| gcagttgctg | acgcggttct | ctcttctgcc | gtta | | | 934 |

<210> SEQ ID NO 55
<211> LENGTH: 1408
<212> TYPE: DNA
<213> ORGANISM: Artificial Sequence
<220> FEATURE:
<223> OTHER INFORMATION: Synthetic Construct-Example 55: a designer
      groE-promoter-controlled Glycogen-Synthase-iRNA DNA construct

<400> SEQUENCE: 55

| | | | | | |
|---|---|---|---|---|---|
| agaaaatctg | gcaccacacc | tttaatggaa | agcttgctaa | accattactc | cctactcccc | 60 |
| aatcattcta | gttcggaaaa | ccgtactgca | acaggagttg | cgatcgccaa | ccgtctctcg | 120 |
| ctacattagc | actcgaaggg | tgagagtgct | aagcatgcta | ggtcactgcc | ggtaccagcg | 180 |
| ttggactagg | attgggcatg | gtttccggcg | gcaagccata | gatggaatta | taaagagcat | 240 |
| tgtaggcgag | tgccgatttt | gtccagctaa | agtcctcgcg | cataccccgc | tgctggaggg | 300 |
| catgccactc | ccgtttgtag | cgatacccctt | cccatgcccg | cactagacag | gtgtaaaagt | 360 |
| caagggctc | atagcggtca | aagcagtagc | ccgttccggt | ttgctgctca | gggttgtggt | 420 |
| gggagacggt | atccacaagg | ccaccggtgc | ggcggactga | gtgacctgat | aagtaaccta | 480 |
| ataggtagcc | tagcggtgag | cagcatgcaa | tattttagcg | tcgatactcg | gaaactatag | 540 |
| gagcgcatca | gccgaccgat | gttcgcgttg | ctgtcgcagg | cccaaccgtg | ccaccgccgt | 600 |
| ggtgtgcaag | gcgcagaagg | cggccaggcc | gccgctgccg | ctgctctggc | catgagtgac | 660 |
| ctgataagta | acctaatagg | tagcctaggt | ccgccgcacc | ggtggccttg | tggataccgt | 720 |
| ctcccaccac | aaccctgagc | agcaaaccgg | aacgggctac | tgctttgacc | gctatgagcc | 780 |
| ccttgacttt | tacacctgtc | tagtgcgggc | atgggaaggg | tatcgctaca | aacgggagtg | 840 |
| gcatgccctc | cagcagcggg | gtatgcgcga | ggacttagc | tggacaaaat | cggcactcgc | 900 |
| ctacaatgct | ctttataatt | ccatctatgg | cttgccgccg | gaaaccatgc | ccaatcctag | 960 |

```
tccaacgctg gtaccggcag tgacctagta atagtgaggc tgagatcttc ttcagtgcat    1020
tgtagttgaa tgaagggtta gggggaaat gcccccctat ttttgtcta gccatcctgc      1080 cacgtttgac agggtagcaa tttcgacacg atagcgtgct gtactgtttt ttgctcgtca    1140
gggttgggtt ttgtcatcga cacccaagga ttggagtcgg tgctcaataa tcgccagttg    1200
ctgttgggca gccgccaatt gcgcctgagc cgcagcgacc acctctggtt gggctttgtt    1260
gacaaaatta gggttgttga ggcgagcggt taaagattga atctctttcc tcaggcgatc    1320
gccttccttc tggagcttgc ttaccaaggc ctccagatct acgaccccg ctaggggaat     1380 gagtacctgg ttctctcttc tgccgtta                                       1408
```

<210> SEQ ID NO 56
<211> LENGTH: 2470
<212> TYPE: DNA
<213> ORGANISM: Artificial Sequence
<220> FEATURE:
<223> OTHER INFORMATION: Synthetic Construct-Example 56: a designer
      Amylase DNA construct

<400> SEQUENCE: 56

```
agaaatctg gcaccacacc cttcttgcag aacatgcatg atttacaaaa agttgtagtt      60
tctgttacca attgcgaatc gagaactgcc taatctgccg agtatatggt gattcatctc    120
aataaaggta aaccatttcc tttagggagt tctctaactt cacaaggggt aaattttttcc   180 ttaatagcca caaatgctga atatgtagaa atattattgt ttgagagaga agactctatt    240
ttcccaaaaa gcatattcaa attagatcag actcacaata aaggtcctta ctggcatgcg    300
gaaataaaaa atctaaatga aggttgcatt tatgctttta gagtgaaaca aaaaaataat    360
ggaattaata ataactatga aaaaaaagta ttacttgatc catgttcaag gggtataacc    420
ggatggggga gttataaaag agaaaattca ttaaaaacgc atgaaaatac taattcttgt    480
cttaaaagcg ttgtttgcga taggaaatta ttttaatttta aggattatcc aagaccaaaa    540
cattcttggg aagaaacaat tatttatgaa cttcacatca aagctttac tgaatcaact    600 gatagagatg aaagttgttt taagaaattt ttaaaaaaaa ttccgtatct caaagaactt    660
ggtattacaa caattgaatt acttccaatt ttttgtttg atcctactga tgccccaaac    720
ggtctaaaaa attttggggg ttatagtcca attaattggt ttactccgca ttttgaatat    780
ctttcgaatg aatccgccga agagaataga gaggagttta gaagatttgt agaggaatgt    840
cacaaagcag acattgaggt catcttagat gttgtgtata atcacacctc cgaaggtgat    900 tccaaggtc cagcaatatc ttggaaaggt atagatgaaa tctttatta ctttattgga    960 aaagataaaa attatcagga cgtctcggga tgtggtaata ctattgcagc aaacagagga    1020
ttagttagaa aactaataat tgaatcatta aaatgttggg cgagtgaatt aggagttgat    1080
ggttttagat ttgatttagg gattgcccta tcaagaggcg aaaatctctc accacttgat    1140
aatcctccga ttttgaaga tatagaatgt gaaccagaac ttattgatat aaaatttata    1200
agtgagccat gggattgtgg tggtttatat aaattagggg attttccatc taagaatact    1260
ttcacttgga atggtcattt tagagatgat ttgcgaagat tttggaaggg ggataaagat    1320
acagcttgga atatgagcga taaaatcaaa ggctctccat cgatttataa agaagataat    1380
attttcccaa aatcaataaa ctttattact tcgcatgatg gattactct gaaagattta    1440 gtaactttca atagaaaaca taattttgcc aacagagagc aaaacagaga tggtgataac    1500
cataacaatt cttggaatca tggggaggag ggaccaacta caaacttatt aattaatgat    1560
ttaagaaaaa gacaacaaaa aaatcttatt cttagttac ttatctctag aggtgttcca    1620
```

```
atgatactta tgggtgatga gataggaaga tcacaaggcg gcaacaataa ttcttggtgt    1680
caaaataatt tattgggctg gatgaattgg gaacatggtc atcaagattt ggaattatta    1740
gaatatttta aatacgttat aaaaatcaga aagaactaa taaacatttt taatccacca    1800
ttcttcccta agaataaaac taatgaaaat attccaacat atcattggca tggaacaaaa    1860
ttagataatc ccgattggag tagttggtct cacacagttg cttttagcat taacaaagga    1920
attactaatc cactggtctg gatcggttta aatgcatatt caaaaagtat caatttcccc    1980
ttgccgaaat gtaaatataa ttggttaaaa gttattgaca ctagcatgtc taaaattttt    2040
gaacccttaa ctattgatga aaatttgtt tcaataaaga gtagaagctc tttattaata    2100
atttcagaag aagtatttgg ggcaaaaaat aatttattct aatgataata gtcccggccg    2160
ctactaaagc ctgatttgtc ttgatagctg ctcctgcctt tgggcagggg ctttttttctg    2220 tctgccattc ttgaggatgg cggactcttt ccctttttgct ctacgcccat gaatgcgatc    2280
gcagtctccc ctgtccagca cgttggagtg attggtggtg gccagttagc ttggatgctg    2340
gcaccagcag cgcaacagtt ggggatgtcg ctgcacgttc aaacacccaa tgatcacgac    2400
ccagcagtag cgatcgcgga tcaaaccgta ttagcagcag ttgctgacgc ggttctctct    2460
tctgccgtta                                                            2470
```

<210> SEQ ID NO 57
<211> LENGTH: 1993
<212> TYPE: DNA
<213> ORGANISM: Artificial Sequence
<220> FEATURE:
<223> OTHER INFORMATION: Synthetic Construct-Example 57: a designer
     4-alpha-Glucanotransferase DNA construct

<400> SEQUENCE: 57

```
agaaaatctg gcaccacacc cttcttgcag aacatgcatg atttacaaaa agttgtagtt     60
tctgttacca attgcgaatc gagaactgcc taatctgccg agtatatgat gcactttccc    120
cgctcctgtg gtttactgct ccatcccacc tcccttcccg gcggtcacgg cattggtgag    180
ttgggtaccg ctgcccgtga gttcttggaa tttttagtgg ccagtgatca gcagtactgg    240
caggtgctgc ccctaggccc caccggcttt ggcaattccc cctatatgtg ctattcggct    300
atggcgggta acccactgct gattagcttg gaggaagtcg caaaagcggg ttggttaacg    360
gaggcggatc tagggcagat tacccttgag aatcgcgatc gcgtggattt cgacgctgtg    420
attagccaga agctgccgct cctacgcctg gcggcgcaac gttccagag tcaggctacc    480 ccaggagact ggcaggcctt ccgggacttc caagcccttg cccactactg gctgcccaac    540
tatgccctct ttatgcaat taaggaccac caccaggga agccgtggta tgaatggccc    600
gctcctttgc gcgatcgcga gcccaccgcc cttgccgcta ccaagtggt tctcaaagac    660 cgcattttttg agtacgaatt tcagcaattt ctctttttacc agcagtggca cgccctcaag    720
gaggccgcca accaacaggg gattcaaatt atcggtgata ttcccattta cgttgcccac    780
gacagtgtag atgtttgggc ctttccccaa tttttttgagc tgaatccaga aaccggtgcc    840
gctgccctga tggccggtgt gccccccgat tacttcagtg ctacaggaca actctggggc    900
aatcccattt acaactggaa agccttgcg gccgatggcc actctggtg gattgagcgc    960 ttccgtgccc tcctcgccta tgtggacatt atccgtgtcg atcactttcg tggctttcag   1020
gcctactggc aagtgccgga aggggagaaa acagctgtca acggccaatg gcaaccaggt   1080
cctggtgctg ccttcttcga agctttgcaa gcggccttgg gacgactgcc tattctagcg   1140
```

-continued

```
gaggatttgg gggatattac ccccgatgtc attgccctgc gggatcagtt tcagtttccg    1200
gggatgaaaa ttctccagtt tgcctttggc ggtggttcgg ataatccgtt tttgcccttt    1260
aatcaagagc gcaactgtgt ggtgtatacc ggcacccacg acaacgacac aactgtgggc    1320
tggtatcgta acctcagtaa ctgggaacgg cagcgtttta ttgactattt gggctatacc    1380
cccagcgagc cccactgggc cttgattcgc atggccttgg gaaccgttgc caaccaagcc    1440
attattcccg ttcaagacct gctcggcctc gatagccatg cccgcatgaa ttttcccggt    1500
actgaccaag gcaactgggc gtggcggctg actcctgggc aactcacccc tgaacttgcc    1560
gctcatttga ggcacctggt gcacctcttt ggccgtcaag cgcccccccag acctcagcct    1620
ggtgaagccg aggcaggaac cctcggaatg gagaagcagc cctaatgata atagtcccgg    1680
ccgctactaa agcctgattt gtcttgatag ctgctcctgc ctttgggcag ggcttttt      1740
ctgtctgcca ttcttgagga tggcggactc tttcccttt gctctacgcc catgaatgcg     1800
atcgcagtct cccctgtcca gcacgttgga gtgattggtg gtggccagtt agcttggatg    1860
ctggcaccag cagcgcaaca gttggggatg tcgctgcacg ttcaaacacc caatgatcac    1920
gacccagcag tagcgatcgc ggatcaaacc gtattagcag cagttgctga cgcggttctc    1980
tcttctgccg tta                                                      1993
```

<210> SEQ ID NO 58
<211> LENGTH: 2965
<212> TYPE: DNA
<213> ORGANISM: Artificial Sequence
<220> FEATURE:
<223> OTHER INFORMATION: Synthetic Construct-Example 58: a designer Glycogen-Phosphorylase DNA construct

<400> SEQUENCE: 58

```
agaaaatctg gcaccacacc cttcttgcag aacatgcatg atttacaaaa agttgtagtt      60
tctgttacca attgcgaatc gagaactgcc taatctgccg agtatatgct actgccctgg     120
ggaggtcatg taggcggttg ccggtaggac aattttcacc ggttgaacgt gccagatgtc     180
ttggcagtac tcgcgaatgg cgcgatcgct agaaaatttg cccatccgtg ccacattgag     240
aatcgacatt tttgcccatt gggcttgatc ttgataggacc tgaagcaccc gttggtaaca    300
atctacatag cttggtagt ctgccaagag gcaatagcga tcgtcttgcc agaggtgctc      360
aaccagggt cgaaagagtt ccgtatcccc atgggaaaag taaccagagc tgatgaggtc      420
aaggacccgc tttagcattg gatgaccatt ggcaaactcc cacggacggt agccgttgca     480
ccgtaattcc tgcaactgct ctactgtatg gccaaagagg aagaagtttt ccgcccccac     540
cgcttcgcga atctccacgt tggcaccatc gagggtgcca atcgttagcg ccccattgag    600
ggcaaatttc atattcccctg tgcctgaggc ttcgtagccg gctgttgaaa tttgctggga    660
aagatccgct gctggataga cccgctgccc cagcgttacg ttgtagttgg gcaaaaagac    720
gaccctcagg cgatcgcgca ccactggatc acgattgatc acatccgcca ctgagttaat    780
aaacttgatg atcaacttgg ccatatagta gcccggggct gccttaccac caaaaataaa    840
tgtttgcggc accatctcca ggtgcggctg atccctcaac atctgataaa gcgtgatgac    900
cttgagaaca cacaggtgct gccgtttgta ttcgtggatg cgcttcacca agatggagaa    960
aagggaatgg ggatccaccg ttaccccgat gcgatcgcga atgtattgcg caaggcgttc   1020
cttgttccca tgcttgaccg atcgccactg ggctgcaaac tcggcatccg ctgccaaggg   1080
ttccaattgc cgcagttgat ctaagtgctt caccccaatct tcgccaatgc gttcagtgat   1140
caggcgggtc aatcctggat tgctgagcac catccaccgc cgagggtgaa cgccattggt   1200
```

-continued

```
tttattggag aatttctctg gtgtcagttc gtagaaatcc ctgagtactg tttgtttcaa    1260
gagttctgag tgcagcaccg ccaccccgtt gatggcatga ctgcccaccg ctgccaagtg    1320
ggccatgcgg acatagcgac agccactttc atcaataatc gacagccgcc gcaggcgatc    1380
gttgtccccc gggtattgca ggcgcacctc atctaggaaa cggcggttga tttcatagat    1440
aatttgcaag tggcggggca agagtgagcc aaagagatct aggggccatt tttcgagcgc    1500
ctcgggcagg agggtgtgat tggtgtaggc aaaggtttgg cgggtaatgt cccatgcctg    1560
ctcccaaggc atgagatgct catcgaccaa caggcgcatg agttctgcga ccgagattgc    1620
agggtgagta tcgttcaact gcacagtgaa cttttcatgg aagcgactca gatcctgttt    1680
gcccgattgc ttgtagaggc ggatcatatc ctgaagggca caggaacaaa agaaatattc    1740
ctgcatcagc cgcagttctt tgccctgcaa ttgctcgtca ttgggataga ggaccttagt    1800
gatgttttct gaagcaattt tttggttaac agcaccgtag taatcgcccg tgttaaaggc    1860
ttgaaagtca aaggactcca ccgcctctgc ccgccataga cgcagaagat tggctgtatt    1920
caccttgtag cccaagatgg gggtgtcata agcaacccc tgaaccactt gatgggttc     1980 ccaaatgacc cggtagcggc cctgatcatc ggtgtagcta taggtatggc cgccaaactt    2040
cactggcaaa attaactctg gtcgcggaat ttcccaaggg ttgccatagc gtaaccactt    2100
atccgtaatc tcgacttgcc aaccatcgcg aatctcctgg tcaaagatac cgtactcata    2160
gcgaatgcca tagccaatgg cgggaatttc cagtgtggcg agagaatcca tgtagcaggc    2220
tgccaagcga cccaagccgc cattacccaa gcccggctct tcctcctgat cgaggagttc    2280
tttgaggttt aaacccgttt gccgcatggc ttcttcaacg gcctcataga gtccgaggtt    2340
aatcaggtta ttgccaaggt gtggccctag caaaaattcg gcggagagat agcaaacggt    2400
gcggctttct tgatctcgat aggttttgc cgaattgagc cagcgcaaca gcaggcgatc     2460
gcgcacggtg taggccaagg ccaagtagta atcattttc gtcgccactt cggggaatcg    2520
cccttggata agaaaagat tatccataaa ggcgcggcgc agggtttcaa tactggtgcc     2580
ggtgcgatcg tcttccgtga ggactgtagg acaaccgggc ggaatcagac tggtcattga    2640
taatagtccc ggccgctact aaagcctgat ttgtcttgat agctgctcct gcctttgggc    2700
aggggctttt ttctgtctgc cattcttgag gatggcggac tctttccctt ttgctctacg    2760
cccatgaatg cgatcgcagt ctcccctgtc cagcacgttg gagtgattgg tggtggccag    2820
ttagcttgga tgctggcacc agcagcgcaa cagttgggga tgtcgctgca cgttcaaaca    2880
cccaatgatc acgacccagc agtagcgatc gcggatcaaa ccgtattagc agcagttgct    2940
gacgcggttc tctcttctgc cgtta                                          2965
```

<210> SEQ ID NO 59
<211> LENGTH: 2119
<212> TYPE: DNA
<213> ORGANISM: Artificial Sequence
<220> FEATURE:
<223> OTHER INFORMATION: Synthetic Construct-Example 59: a designer
      Phosphoglucomutase DNA construct

<400> SEQUENCE: 59

```
agaaaatctg gcaccacacc cttcttgcag aacatgcatg atttacaaaa agttgtagtg      60
tctgttacca attgcgaatc gagaactgcc taatctgccg agtatatgat gtccgatttc     120
tccgtccaga ccattgccac cacggccttc acagaccaaa agcctggaac ctctggtctc     180
agaaagaaag ttactgtgtt tcaacagcct cactacactg aaaacttcat tcaggctatt     240
```

```
ctcgatgcca ttccggaagg tgcccaaggt gccactcttg ttgtaggagg tgatggccgt      300
ttctacaacg acaaggtcat caacttgatc gccaaaatcg cctcggccaa cggagtttcc      360
aagttgattt tgggtcaaga cgggattctt ccactccag caacttcgca tgtaatcagg      420
atcaggggtg caactggagg aattattctc actgcttcac acaaccccgg aggccccaaa      480
aacgatttgg gtattaagta caacttggga acggtgcac cagctccaga atcggttacc      540
aacaagatct atgatgtctc caaggaattg acttcgtaca agctcattga tttacccgac      600
attgatttgt ccaaaaccca gaccgtgcaa ttgggccctc ttgaagtgga aatcattgac      660
tccacctctg attacgtagc catgttgaag gatatctttg acttcccctt gatcaagtcg      720
ttcctcgaga ctgccactaa ggagcaggga ttcaaggttt tatttgattc gctcaatggt      780
gtcactggcc cctacggcta caagatcttc gttgaagaat taggattgcc tcttaactca      840
atccaaaatt accacccatt gcctgacttt ggtggtttac acccagatcc aaacttgacc      900
tatgctcata ctttggtcga gagggtcgat aaggagaata ttgcctttgg tgctgcatct      960
gatggtgacg gtgacagaaa catgatctac ggtgctggta cctttgtttc gcctggtgac     1020
tctgtagcca tcatctcgga atacgccgat tccatccctt acttcaagaa gcaaggtgtc     1080
tacggtttgg ccagatccat gcctacctct ggagccatcg atttggtagc aaaggctaaa     1140
ggattgaatg tttacgaagt gccaaccggt tggaagttct tctgcaacct tttcgacgct     1200
gacaagttga gtatctgtgg tgaagagtcg tttggaacag gctccaacca catcagagaa     1260
aaggacggcc tttgggctgt agttgcctgg ttgaacgtgc tagcagatta caacgtcaag     1320
aatccagaat ccaagacatc tatttctgta gtgcagaact cgttttggaa gaaatacgga     1380
agaactttct tcactagata tgactacgaa aacgtatcgt ctgaaggtgc tgccgagctc     1440
atcaacttgt tgtcttctat tgttgactct aagaaaccag gaagtagctt agctgatggc     1500
tacgtcgtca aggaagctgc taacttctcg tacaccgatt tggacggctc tgtttcgtcc     1560
aaccaaggtt tgttcatcaa gtttgaaagc ggcttgagat tcatagtaag attgtctggt     1620
actggatcat ccggtgctac agtcagatta tatctcgaaa agcactctgc cgacgaatcc     1680
acctatggct taggcgtaga ccagtactta gttgatgaca tcaagtttgt cttggacttg     1740
ttgaagttca agcagttctt gggaaaggat gaaccagatg ttcgtaccta gtgataatag     1800 tccccggccgc tactaaagcc tgatttgtct tgatagctgc cctgccttt gggcaggggc     1860 ttttttctgt ctgccattct tgaggatggc ggactcttc cctttgctc tacgcccatg     1920 aatgcgatcg cagtctcccc tgtccagcac gttggagtga ttggtggtgg ccagttagct     1980
tggatgctgg caccagcagc gcaacagttg gggatgtcgc tgcacgttca aacacccaat     2040
gatcacgacc cagcagtagc gatcgcggat caaaccgtat tagcagcagt tgctgacgcg     2100
gttctctctt ctgccgtta                                                  2119
```

<210> SEQ ID NO 60  
<211> LENGTH: 1852  
<212> TYPE: DNA  
<213> ORGANISM: Artificial Sequence  
<220> FEATURE:  
<223> OTHER INFORMATION: Synthetic Construct-Example 60: a designer Glucokinase DNA construct

<400> SEQUENCE: 60

```
agaaaatctg gcaccacacc cttcttgcag aacatgcatg atttacaaaa agttgtagtt       60
tctgttacca attgcgaatc gagaactgcc taatctgccg agtatatgat gaatattgaa      120
ttagaagctg ctgttgagga aattgtcaag caattcgcta ttgacaagga tttccttgtc      180
```

```
gaagcaacta acatttca cgaatccatg agcgctggtt tagcaacttc taccccaact      240
agagattaca tgcctatgat ccaacttat gtaactggaa ttccaacagg aaaagaaaag      300
ggattgtact tggccgcaga cttgggtggt accaacttta gagtatgctc catccacttg     360
ggtggtgacc acacatttga aatgaagcag tccaagtaca agattcctgt ggatttgatg    420
caaggtgaag atgccactgc cgatggtttg ttcaactatt tggcagaaaa ggtaaaaact    480
ttcttggacc agcatcacaa tgaacatgct gaacagttga aattgggctt taccttttct   540
ttcccagtga accaaactgc cttgaataga ggaacattga ttcgttggac caagggtttt   600
gatttgcctg attgtgtaga caaggatgtc gtcgaattat tgcagaagca tatggaattg   660
ttaggtgtca aggttcatgt tgctgctttg gcaaatgata ctgttggtac cttattgtct   720
agagcatact ctaatgatat ttccaagaca aattccaata ccgttgttgg tgccatcttt   780
ggcacaggaa cgaacggagc ttactttgaa actttgaaaa acattccaaa gttgaagaag   840
gaagatatac tgaaggagc caagggtatg gtgattaaca ctgagtgggg ttcgttcgac   900
aatacattga agattttgcc ttgtaccaag tacgataaac ttgttgacga tgagactgca   960
aacgtcggct atcacttatt tgaaaagaga atcagcggta tgttttttggg tgaattgttg  1020 agagttgcct taatggattt attcgaccgt ggcttgatct tccaggaatt gtacaaggct  1080
agaggtggta ccttgcccca cagaattttc gaaccatggc ttatttctgc agaggtgtta  1140
tcttatttac aaattgatga ttccactgac ttgaagatgt cagaattggt cttggaaaac  1200
cacttgagat tgccaaccaa caagaagaa aggcttgtta ttcagaaatt gactcagtca  1260
atttcacata gggctgcata tcttcagct attccattgg catcaattgt tgctcgtgtt  1320
caggatcaat ataaggatga cgatagagat ttcgaattg gttgcgatgg ttccgttgtt  1380
gagttctatc ctggcttcag atcaaagatt ttggaagcag ttgctttgat tgacccattg  1440
aaaggttctt cgaaaaagat ccacctcaga attgccaagg atggaagtgg agtcggagca  1500
gcattgtgtg caagtgtctc ctaatgataa tagtcccggc cgctactaaa gcctgatttg  1560
tcttgatagc tgctcctgcc tttgggcagg ggctttttc tgtctgccat tcttgaggat  1620
ggcggactct ttcccttttg ctctacgccc atgaatgcga tcgcagtctc ccctgtccag  1680
cacgttggag tgattggtgg tggccagtta gcttggatgc tggcaccagc agcgcaacag  1740
ttggggatgt cgctgcacgt tcaaacaccc aatgatcacg acccagcagt agcgatcgcg  1800
gatcaaaccg tattagcagc agttgctgac gcggttctct cttctgccgt ta            1852

<210> SEQ ID NO 61
<211> LENGTH: 2101
<212> TYPE: DNA
<213> ORGANISM: Artificial Sequence
<220> FEATURE:
<223> OTHER INFORMATION: Synthetic Construct-Example 61: a designer
      Glucose-6-Phosphate-Isomerase DNA construct

<400> SEQUENCE: 61
agaaaatctg gcaccacacc cttcttgcag aacatgcatg atttacaaaa agttgtagtt      60
tctgttacca attgcgaatc gagaactgcc taatctgccg agtatatgat gtccaataac     120
tcattcacta acttcaaact ggccactgaa ttgccagcct ggtctaagtt gcaaaaaatt    180
tatgaatctc aaggtaagac tttgtctgtc aagcaagaat tccaaaaaga tgccaagcgt   240
tttgaaaaat tgaacaagac tttcaccaac tatgatggtt ccaaaatctt gttcgactac   300
tcaaagaact tggtcaacga tgaaatcatt gctgcattga ttgaactggc caaggaggct  360
```

```
aacgtcaccg gtttgagaga tgctatgttc aaaggtgaac acatcaactc cactgaagat    420
cgtgctgtct accacgtcgc attgagaaac agagctaaca agccaatgta cgttgatggt    480
gtcaacgttg ctccagaagt cgactctgtc ttgaagcaca tgaaggagtt ctctgaacaa    540
gttcgttctg gtgaatggaa gggttatacc ggtaagaaga tcaccgatgt tgttaacatc    600
ggtattggtg gttccgattt gggtccagtc atggtcactg aggctttgaa gcactacgct    660
ggtgtcttgg atgtccactt cgtttccaac attgacggta ctcacattgc tgaaaccttg    720
aaggttgttg acccagaaac tactttgttt ttgattgctt ccaagacttt cactaccgct    780
gaaactatca ctaacgctaa cactgccaag aactggttct tgtcgaagac aggtaatgat    840
ccatctcaca ttgctaagca tttcgctgct ttgtccacta acgaaaccga agttgccaag    900
ttcggtattg acaccaaaaa catgtttggt ttcgaaagtt gggtcggtgg tcgttactct    960
gtctggtcgg ctattggttt gtctgttgcc ttgtacattg gctatgacaa ctttgaggct   1020
ttcttgaagg gtgctgaagc cgtcgacaac cacttcaccc aaacccccatt ggaagacaac   1080 attccattgt tgggtggttt gttgtctgtc tggtacaaca acttctttgg tgctcaaacc   1140
catttggttg ctccattcga ccaatacttg cacagattcc cagcctactt gcaacaattg   1200
tcaatggaat ctaacggtaa gtctgttacc agaggtaacg tgtttactga ctactctact   1260
ggttctatct tgtttggtga accagctacc aacgctcaac actctttctt ccaattggtt   1320
caccaaggta ccaagttgat tccatctgat ttcatcttag ctgctcaatc tcataaccca   1380
attgagaaca aattacatca aaagatgttg gcttcaaact tctttgctca agctgaagct   1440
ttaatggttg gtaaggatga agaacaagtt aaggctgaag gtgccactgg tggtttggtc   1500
ccacacaagg tcttctcagg taacagacca actacctcta tcttggctca aaagattact   1560
ccagctactt tgggtgcttt gattgcctac tacgaacatg ttactttcac tgaaggtgcc   1620
atttggaata tcaactcttt cgaccaatgg ggtgttgaat tgggtaaagt cttggctaaa   1680
gtcatcggca aggaattgga caactcctcc accatttcta cccacgatgc ttctaccaac   1740
ggtttaatca atcaattcaa ggaatggatg tgatgataat agtcccggcc gctactaaag   1800
cctgatttgt cttgatagct gctcctgcct ttgggcaggg gctttttttct gtctgccatt   1860 cttgaggatg gcggactctt tcccttttgc tctacgccca tgaatgcgat cgcagtctcc   1920
cctgtccagc acgttggagt gattggtggt ggccagttag cttggatgct ggcaccagca   1980
gcgcaacagt tggggatgtc gctgcacgtt caaacaccca atgatcacga cccagcagta   2040
gcgatcgcgg atcaaaccgt attagcagca gttgctgacg cggttctctc ttctgccgtt   2100
a                                                                  2101
```

DESIGNER OXYPHOTOBACTERIA AND GREENHOUSE DISTILLATION FOR PHOTOBIOLOGICAL ETHANOL PRODUCTION FROM CARBON DIOXIDE AND WATER

CROSS-REFERENCE TO RELATED APPLICATIONS

This Application claims the benefit of U.S. Provisional Application No. U.S. 61/066,832 filed on Feb. 23, 2008, U.S. 61/066,770 and U.S. 61/066,771 filed on Feb. 22, 2008. The entire disclosures of the three applications are incorporated herein by reference.

FIELD OF THE INVENTION

The present invention generally relates to biofuels-production technology. More specifically, the present invention provides a photobiological ethanol production and harvesting methodology with greenhouse distillation systems and designer transgenic oxyphotobacteria that are created to use the reducing power (NADPH) and energy (ATP) acquired from the photosynthetic process for synthesis of ethanol ($CH_3CH_2OH$) directly from carbon dioxide ($CO_2$) and water ($H_2O$).

BACKGROUND OF THE INVENTION

Ethanol ($CH_3CH_2OH$) can be used as a liquid fuel to run engines such as cars. A significant market for ethanol as a liquid fuel already exists in the current transportation and energy systems. In the United States, currently, ethanol is generated primarily from corn starch using a yeast-fermentation process. Therefore, the "cornstarch ethanol production" process requires a number of energy-consuming steps including agricultural corn-crop cultivation, corn-grain harvesting, corn-grain starch processing, and starch-to-sugar-to-ethanol fermentation. Independent studies have recently shown that the net energy gain of the "cornstarch ethanol production" process is very limited. That is, the "cornstarch ethanol production" process costs nearly as much energy as the energy value of its product ethanol. This is not surprising, understandably because the cornstarch that the current technology can use represents only a small fraction of the corn crop biomass that includes the corn stalks, leaves and roots. The cornstovers are commonly discarded in the agricultural fields where they slowly decompose back to $CO_2$, because they represent largely lignocellulosic biomass materials that the current biorefinery industry cannot efficiently use for ethanol production. There are research efforts in trying to make ethanol from lignocellulosic plant biomass materials—a concept called "cellulosic ethanol". However, plant biomass has evolved effective mechanisms for resisting assault on its cell-wall structural sugars from the microbial and animal kingdoms. This property underlies a natural recalcitrance, creating roadblocks to the cost-effective transformation of lignocellulosic biomass to fermentable sugars. Therefore, one of its problems known as the "lignocellulosic recalcitrance" represents a formidable technical barrier to the cost-effective conversion of plant biomass to fermentable sugars. That is, because of the recalcitrance problem, lignocellulosic biomasses (such as cornstover, switchgrass, and woody plant materials) could not be readily converted to fermentable sugars to make ethanol without certain pretreatment, which is often associated with high processing cost. Despite more than 50 years of R&D efforts in lignocellulosic biomass pretreatment and fermentative ethanol-production processing, the problem of recalcitrant lignocellulosics still remains as a formidable technical barrier that has not yet been eliminated so far. Furthermore, the steps of lignocellulosic biomass cultivation, harvesting, pretreatment processing, and cellulose-to-sugar-to-ethanol fermentation all cost energy. Therefore, any new technology that could bypass these bottleneck problems of the biomass technology would be useful.

Oxyphotobacteria are prokaryotic organisms that are capable of performing oxygenic autotrophic photosynthesis using water as the source of electrons and carbon dioxide as the source of carbon. In nature, there are two orders of oxygenic photosynthetic prokaryotes within the class of the Oxyphotobacteria: Cyanobacteria (such as, *Synechococcus elongatus*, *Anabaena* sp., *Synechocystis* sp., *Nostoc punctiforme*, *Spirulina platensis*, and *Thermosynechococcus elongatus*) and Oxychlorobacteria (such as *Prochlorococcus marinus*, *Prochloron didemni*, and *Prochlorothrix hollandica*). Cyanobacteria are commonly also known as "blue-green algae"; and Oxychlorobacteria are sometimes regarded as "the 'other' Cyanobacteria" or more scientifically classified as Prochlorophytes since they contain both chlorophyll-a (Chl-a) and chlorophyll-b (Chl-b). For example, *Prochlorococcus marinus* MED4 (oxychlorobacterium) possesses an unorthodox pigment composition of divinyl derivatives of Chl-a and Chl-b, a-carotene, zeaxanthin, and a type of phycoerythrin. By contrast, the highly related *Synechococcus* (cyanobacterium) contains Chl-a and phycobilins that are more typical of cyanobacteria. However, both Cyanobacteria and Oxychlorobacteria can perform photosynthetic assimilation of $CO_2$ with 0, evolution from water in a liquid culture medium with a maximal theoretical solar-to-biomass energy conversion of about 10%; these oxygenic photosynthetic prokaryotes have tremendous potential to be a clean and renewable energy resource. However, the wild-type oxygenic photosynthetic organisms, such as the wild-type cyanobacteria, do not possess the ability to produce ethanol directly from $CO_2$ and $H_2O$. The wild-type photosynthesis uses the reducing power (NADPH) and energy (ATP) from the photosynthetic water splitting and proton gradient-coupled electron transport process through the thylakoid membrane system to reduce $CO_2$ into carbohydrates $(CH_2O)_n$ with a series of enzymes collectively called the "Calvin cycle" at the cytoplasm stroma region in Cyanobacteria. The net result of the wild-type photosynthetic process is the conversion of $CO_2$ and $H_2O$ into carbohydrates $(CH_2O)_n$ and $O_2$ using sunlight energy according to the following process reaction:

$$nCO_2 + nH_2O \rightarrow (CH_2O)_n + nO_2 \quad [1]$$

The carbohydrates $(CH_2O)n$ are then further converted to all kinds of complicated cellular (biomass) materials including proteins, lipids, glycogen, and cellulose and other cell-structural materials during cell metabolism and growth.

Based on the current scientific knowledge, wild-type oxyphotobacteria including cyanobacteria (such as *Synechococcus* sp. PCC 7942, *Nostoc* sp. PCC 7120, *Synechomtis* sp. PCC 6803, and *Thermosynechococcus elongatus* BP-1) and oxychlorobacteria (such as *Prochlorococcus marinus* MIT 9313, *Prochlorococcus marinus* SS120, and *Prochlorococcus marinus* MED4) are not capable of photosynthetic ethanol production directly from $CO_2$ and $H_2O$. The fundamental properties of oxygenic photosynthesis in oxyphotobacteria are quite similar to those in eukaryotic algae and higher plants. However, there are also some significant differences between the prokaryotes (oxyphotobacteria) and the eukaryotes (algae and higher plants). The Calvin-cycle activity (the photosynthetic $CO_2$-fixation process) in eukaryotic algae (and higher plants) occurs inside a chloroplast, which is a well-organized photosynthetic organelle. On the other hand, the Calvin-cycle activity in oxyphotobacteria occurs in the cytoplasm since the prokaryotic organisms do not have a chloroplast organelle. In addition, oxyphotobacteria as prokaryotes do not have a nucleus organelle; and their molecular genetic organization and machineries are also somewhat different from those of the eukaryotes. The present application discloses a more-specific method in creating prokaryotic designer oxyphotobacteria for photosynthetic ethanol production directly from $CO_2$ and $H_2O$.

The present invention provides a photobiological ethanol production and harvesting methodology with greenhouse distillation systems and designer transgenic oxyphotobacteria that are capable of synthesizing ethanol directly from $CO_2$ and $H_2O$.

The integrated photobiological ethanol production and harvesting technology provided by the present invention could bypass all the bottleneck problems of the biomass industry mentioned above.

SUMMARY OF THE INVENTION

The present invention provides photobiological ethanol production and harvesting methods based on designer transgenic oxyphotobacteria and greenhouse distillations. The designer oxyphotobacteria are created through genetic engineering such that the endogenous photosynthesis regulation mechanism is tamed, and the reducing power (NADPH) and energy (ATP) acquired from the photosynthetic water splitting and proton gradient-coupled electron transport process are used for immediate synthesis of ethanol ($CH_3CH_2OH$) directly from carbon dioxide ($CO_2$) and water ($H_2O$). The designer use of a special pair of NADPH-dependent vs. NAD-dependent glyceraldehyde-3-phosphate dehydrogenases in the oxyphotobacterial pathway designs offers a cyclic "transhydrogenase" redox-shuttle function to convert NADPH to NADH for enhanced photobiological ethanol production. The photosynthetic ethanol-production technology of the present invention is expected to have a much higher solar-to-ethanol energy-conversion efficiency than the current technology.

A fundamental feature of the present photosynthetic ethanol production methodology is to create designer oxyphotobacteria that contain transgenes coding for a set of enzymes that can act on an intermediate product of the Calvin cycle and convert the intermediate product immediately into ethanol, instead of making glycogen and other complex biomass materials. Accordingly, the present invention provides, inter alia, methods for producing ethanol based on a designer oxyphotobacterium, DNA constructs encoding genes of a designer oxyphotobacterial ethanol-production pathway, as well as the designer oxyphotobacteria created.

In one aspect, the present invention provides a method for photobiological production of ethanol by growing a designer oxyphotobacterium (such as a designer cyanobacterium) in a liquid culture medium, wherein the oxyphotobacterial cells are genetically engineered to express a set of enzymes in the cytoplasm that act on an intermediate product of the Calvin cycle and convert the intermediate product into ethanol.

According to the present invention, a designer oxyphotobacterium for use in the photobiological ethanol production can be created utilizing essentially any oxyphotobacteria as host organisms that have a photosynthetic capability and can be cultured in a liquid medium. Preferred species of oxyphotobacteria for use in the present invention include (but not limited to): *Thermosynechococcus elongatus*, *Nostoc* sp. PCC 7120, *Synechococcus elongatus* PCC 6301, *Syncechococcus* sp. strain PCC 7942, *Syncechococcus* sp. strain PCC 7002, *Syncechocystis* sp. strain PCC 6803, *Spirulina platensis* (*Arthrospira platensis*), *Spirulina pacifica*, *Lyngbya majuscule*, *Anabaena* sp., *Synechocystis* sp., *Synechococcus elongatus*, *Nostoc punctiforme*, *Syncechococcus* sp. strain PCC 7943, *Synechocyitis* PCC 6714 phycocyanin-deficient mutant PD-1, *Cyanothece* strain 51142, *Oscillatoria limosa*, *Gloeobacter violaceus*, *Prochlorococcus marinus*, *Prochlorococcus marinus* MIT 9313, and *Prochlorococcus marinus* MED4.

Higher ethanol tolerance can be translated to a more robust and efficient ethanol-production technology. In one of the various embodiments, various photosynthetic organisms are screened for higher ethanol tolerance by characterizing their rates of photosynthesis under anaerobic conditions in the presence of ethanol using a specially designed dual- and/or multi-reactor-flow detection system that can be used for simultaneous measurement of $CO_2$ fixation, ethanol production, pH, $O_2$ and $H_2$ evolution, cells density, and actinic intensity. The screening process comprises the following steps: a) Measuring the rates of photosynthesis in the organisms in the presence of ethanol at a concentration range from 0% to about 20% and/or under certain environmental conditions of special interest including (but not limited to) heat, cold, and salinity stresses; b) Plotting measured photosynthesis rates as a function of ethanol concentration for each strain of photosynthetic organisms; and c) Identifying ethanol-tolerant photosynthetic organisms by comparing their photosynthesis rate vs. ethanol concentration curves.

The selection of the enzymes appropriate for use to create a designer oxyphotobacterial ethanol-production pathway in a host depends on from which intermediate product of the Calvin cycle the designer pathway branches off from the Calvin cycle. In one embodiment, the designer pathway branches off from the point of glyceraldehydes-3-phosphate and converts it into ethanol by using, for example, the set of enzymes consisting of NAD-dependent glyceraldehyde-3-phosphate dehydrogenase, phosphoglycerate kinase, phosphoglycerate mutase, enolase, pyruvate kinase, pyruvate decarboxylase, and alcohol dehydrogenase. In this designer pathway, for conversion of one molecule of glyceraldehyde-3-phosphate to ethanol, an NADH molecule is generated from $NAD^+$ at the step from glyceraldehyde-3-phosphate to 1,3-diphosphoglycerate catalyzed by NAD-dependent glyceraldehyde-3-phosphate dehydrogenase while an NADH molecule is converted to $NAD^+$ at the terminal step from acetaldehyde to ethanol catalyzed by alcohol dehydrogenase. That is, the number of NADH molecules consumed is balanced with the number of NADH molecules generated. Therefore, this designer ethanol-production pathway can operate continuously.

In another embodiment, the designer oxyphotobacterial pathway branches off from the point of 3-phosphoglycerate of the Calvin cycle, and is composed of a set of enzymes including, for example, phosphoglycerate mutase, enolase, pyruvate kinase, pyruvate decarboxylase, and alcohol dehydrogenase. In order for this ethanol-production pathway to operate, the alcohol dehydrogenase has to be able to use NADPH that can be generated by the photo-driven electron-transport process. Therefore, it is a preferred practice to use an alcohol dehydrogenase that can use NADPH or both NADPH and NADH (i.e., NAD(P)H) for this particular designer ethanol-production pathway. Alternatively, when an alcohol dehydrogenase that can only use NADH is employed, it is preferably here to use an additional embodiment for an NADPH/NADH conversion mechanism in the designer organism's cytoplasm to facilitate photosynthetic production of ethanol through this designer pathway.

In still another embodiment, the designer oxyphotobacterial pathway branches off from the point of fructose-1,6-diphosphate and converts it into ethanol by a set of enzymes including, for example, fructose-diphosphate aldolase, triose-phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase.

In yet another embodiment, the designer oxyphotobacterial pathway branches off from the point of fructose-6-phosphate and is composed of a set of enzymes including, for example, phosphofructose kinase, fructose-diphosphate aldolase, triose-phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase. It can be noted that certain sets of designer enzymes may permit two or more designer pathways, i.e., pathways that branches off from two or more points of the Calvin cycle for the production of ethanol.

Further in accordance with a number of the various embodiments, the expression of the designer oxyphotobacterial ethanol-producing pathway is controlled through the use of an externally inducible promoter so that the designer transgenes are inducibly expressed under certain specific conditions. In one embodiment, the inducible promoter used to control the expression of designer oxyphotobacterial genes is a promoter that is inducible by anaerobiosis, including, for example, the promoters of the bidirectional hydrogenase hox operon. Additional inducible promoters suitable for use in the present invention include the nitrite reductase (nirA) promoters, the heat- and light-responsive groE promoters, the zinc-inducible smt promoter, the iron-responsive idiA promoter, the redox-responsive crhR promoter, the $CO_2$-responsive promoters of carbonic-anhydrase genes, the small-heat-shock protein promoters including the hsp16.6 promoter and hspA promoter, the red/green-light-responsive cpcB2A2 promoter, the UV-light responsive lexA, recA and ruvB promoters, and the Rubisco-operon promoters including the rbcL promoter.

In another aspect of the present invention, designer oxyphotobacterial DNA constructs are provided, which contain one or more nucleotide sequences encoding one or more designer ethanol-production-pathway enzymes, each of which is placed in an operable linkage to an inducible promoter. The constructs may contain additional appropriate sequences, such as a selection marker gene to facilitate the screening and identification of transformants. Nucleic acid constructs carrying designer genes can be delivered into a host oxyphotobacteria using the available gene-transformation techniques, such as electroporation, ballistic delivery of DNA, polyethylene glycol (PEG) induced uptake, and conjugation and natural transformation.

The designer oxyphotobacteria including designer cyanobacteria and designer oxychlorobacteria that have been created to contain one or more designer construct, form another embodiment of the present invention. In a further aspect, the present invention provides additional methods for enhanced photosynthetic ethanol production, the related designer constructs and designer oxyphotobacteria.

In a specific embodiment, a photosynthetic ethanol-producing designer oxyphotobacterium, as described above, has been further modified to contain additional designer transgenes to inducibly express one or more enzymes to facilitate the NADPH/NADH conversion, such as the NADPH phosphatase and NAD kinase, and more importantly the designer use of a pair of NADPH-dependent and NAD-dependent glyceraldehyde-3-phosphate dehydrogenases in the pathway designs conferring a cyclic "transhydrogenase" function to covert NADPH to NADH for enhanced photobiological ethanol production. Alternatively, the alcohol dehydrogenase can be selected and modified so that it can directly use NADPH as well.

In another embodiment, a photosynthetic ethanol-producing designer oxyphotobacterium has been further modified to inactivate glycogen-synthesis activity. In a specific embodiment, such further modification includes introduction of a designer DNA construct that encodes and inducibly expresses an interfering RNA (iRNA) molecule that specifically inhibits the synthesis of a glycogen-synthesis-pathway enzyme, for example, glycogen synthase, glucose-1-phosphate adenylyltransferase, and/or phosphoglucomutase for enhanced photobiological production of ethanol.

In still another embodiment, a photosynthetic ethanol-producing oxyphotobacterium has been further modified to contain an additional set of designer genes that facilitate glycogen (starch) degradation and glycolysis in the cytoplasm. Such additional designer genes include, for example, genes coding for amylase, 4-alpha-glucanotransferase, glycogen phosphorylase, glucokinase, phosphoglucomutase, and glucose-6-phosphate isomerase.

The present invention also provides a process of using a designer oxyphotobacterium, in combination with a photobiological reactor system and an ethanol separation/harvesting process for photosynthetic production of ethanol and $O_2$ directly from $CO_2$ and $H_2O$ using sunlight. Both industrial $CO_2$ sources and/or atmospheric $CO_2$ from the environment may be used in the designer-oxyphotobacteria photobiological ethanol-production process.

The present invention further provides a combined photobiological ethanol production and harvesting technology using a special solar-greenhouse-distillation system with designer photosynthetic organisms, such as transgenic oxyphotobacteria, designer transgenic algae, or transgenic plant cells that can use the reducing power (NADPH) and energy (ATP) acquired from the photosynthetic process for immediate synthesis of ethanol ($CH_3CH_2OH$) directly from carbon dioxide ($CO_2$) and water ($H_2O$). The integrated solar-greenhouse-distillation system comprises typically a series of distillation greenhouses working together in series and/or in parallel for photobiological culture growth, ethanol production and harvesting with efficient utilization of sunlight energy. In various embodiments, sunlight is used to drive photobiological ethanol production and, at the same time, generate heat in the culture medium. The solar heat associated with the photobiological process is utilized in vaporizing the product ethanol (and water) for harvesting by fractional greenhouse distillation. Consequently, a fundamental feature of the present photobiological ethanol production and harvesting methodology is to use solar energy to drive both photosynthesis and ethanol harvesting through greenhouse distillation with high sunlight utilization efficiency and minimal cost.

In one of the various embodiments, a distillation greenhouse comprises a photobiological ethanol-production culture reactor in a sealed greenhouse with a tilted vapor-condensing transparent ceiling, condensate-collecting ducts around the greenhouse walls below the ceiling level, and a tail-gas condensing and venting unit. As the use of sunlight driving photosynthesis and generating heat in the photobiological ethanol-production liquid culture medium, the associated solar heat vaporizes the product ethanol (with water)

from the reactor medium. The ethanol-richer vapor condenses onto the vapor-condensing transparent tilted ceiling that is cooled by air, winds, and thermo infra-red radiation to the outer space. The vapor-condensing transparent ceiling can also be cooled flexibly by running cold water through a water-chamber system over the ceiling. Depending on the surface property of the ceiling material, the tilted-ceiling angle α should be at least above 5 degrees, preferably 15-30 degrees, and more preferably 30-70 degrees at all inner surface areas of the ceiling to prevent condensate droplets from free falling from the ceiling surface back into the culture medium below. In this way, as the vapor condenses, the condensate droplets can slide downwards along the inner surface of the tilted ceiling and finally flow into the collecting ducts around the greenhouse walls by use of the surface tension (interaction) and the Earth gravity pulling force. The collected condensate which is richer in ethanol content is then transported through a condensate-transferring tube by use of gravity to a storage tank or into the next distillation greenhouse for re-distillation until achieving the desired ethanol concentration in the final distillate(s).

According to one of the various embodiments, a tail-gas condensing and venting unit comprises a cold-water-bath chamber, a tail-gas condensing tube coil, a gas-condensate chamber, and a vertical venting tube. During the operation, the tail-gas condensing tube coil, gas-condensate chamber, and vertical venting tube are all cooled by running cold water through the cold-water-bath chamber so that the vapor in the tail gas will condense along the condensing tube coil which is connected with gas-condensate chamber before venting through the vertical venting tube.

In another embodiment, the condensate (containing ethanol and water) from a tail-gas condensing and venting system is collected for harvesting. Therefore, product ethanol and fresh water can also be harvested from the tail gas through use of a tail-gas condensing and venting unit or a number of tail-gas condensing and venting units in series and/or in parallel.

In another embodiment, a distillation greenhouse comprises a photobiological reactor with a series of tubes, adjustable inlets, adjustable outlets, and/or baffles to guide the flow of the liquid culture medium for enhanced photobiological ethanol production and harvesting.

In another embodiment, a distillation greenhouse comprises a photobiological reactor with a water-chamber transparent tilted ceiling that can be cooled by running cold water through the chamber over the ceiling to enhance the distillation process. The use of a water-cooled ceiling system can also moderate the greenhouse temperature so that not only thermophilic but also mesophilic designer organisms can be used with the greenhouse distillation system for photobiological ethanol production and harvesting.

In yet another embodiment, a distillation greenhouse comprises a lower bioreactor chamber for photobiological culture growth and an upper chamber for beer distillation. The upper distillation chamber and lower bioreactor chamber are separated by a transparent impermeable plate and/or film (or membrane) that allows only sunlight to go through. Sunlight drives photosynthesis and generates heat in the photosynthetic cell culture at the lower bioreactor chamber. The solar waste heat is used for evaporation of the ethanol-containing liquid at the upper distillation chamber above the photobiological culture reactor. The vapor is then condensed onto the inner surface of the ceiling as mentioned previously. The distillation chamber is preferably compartmentalized so that the vapor in one compartment is separated from those of other compartments while only the beer liquid can gradually flow from one compartment to the next in series through the guiding baffles, adjustable inlets and outlets, tubes, and/or a channel or hole at the lower part (immersed in the beer liquid) of an inter compartment wall. As the beer passes through the compartments in series, its ethanol content is removed by distillation. Depending on the need and processing conditions, any number of distillation compartments (such as 2, 3, 4, 5, 6, 7, 8, 9, 10, 11, 12, and etc) can be used in series. Therefore, as a beer liquid passes through the distillation compartments in series, the ethanol content in the beer liquid can be reduced to a minimal level so that the residual liquid exiting from the last re-distillation compartment is essentially freshwater that may be recycled for making culture media and/or for other use as a byproduct.

In still another embodiment, a photobiological ethanol-production and solar-heat-driven greenhouse distillation system comprises a bioreactor (for photobiological culture with headspace), distillation chambers above the bioreactor, and an oxygen-gas harvesting system. The headspace in the bioreactor allows convenient gas exchange for $CO_2$ feeding and flexible $O_2$ harvesting. Both industrial $CO_2$ and/or atmospheric $CO_2$ from the environment can be fed through a pipeline into the bioreactor for use in the oxygenic photobiological ethanol-production process. The oxygen-gas harvesting system comprises an $O_2$-separation membrane system, an oxygen-gas pump, and an $O_2$ storage tank. Use of this oxygen-gas harvesting system connected through a pipeline can flexibly harvest the photosynthetically produced $O_2$ from the headspace of the bioreactor.

According to one of the various embodiments, any number of distillation greenhouses (such as 1, 2, 3, 4, 5, 6, 7, 8, 9, 10, 11, 12, and etc) can be used in series and/or in parallel. As the number of re-distillations increase, the resulting ethanol concentration in the condensates (distillates) increases. The maximum achievable ethanol concentration through this type of fractional greenhouse distillation is 96% ethanol, which is sufficiently high in quality that can be used directly as a fuel to run ethanol-powered and/or flexible-fuel vehicles. Therefore, this process technology is designed to efficiently and maximally utilize solar (both its visible and infra-red radiation) energy for both photobiological production of ethanol from $CO_2$ and $H_2O$ and harvesting of the product ethanol through a series of greenhouse distillations with minimal cost. In addition to the photobiological production and harvesting of ethanol, use of the technology can also produce freshwater, oxygen gas, and used biomass culture as byproducts. The photobiological ethanol production and harvesting technology of the present invention is expected to have a much higher solar-to-ethanol energy-conversion efficiency than the current technology and could also help protect the Earth's environment from the dangerous accumulation of $CO_2$ in the atmosphere.

DETAILED DESCRIPTION OF THE INVENTION

The present invention is directed to a photobiological ethanol production and harvesting technology based on designer transgenic oxyphotobacteria and greenhouse distillations. The designer oxyphotobacteria are created using genetic engineering techniques such that the endogenous photosynthesis regulation mechanism is tamed, and the reducing power (NADPH) and energy (ATP) acquired from the photosynthetic water splitting and proton gradient-coupled electron transport process can be used for immediate synthesis of ethanol ($CH_3CH_2OH$) directly from carbon dioxide ($CO_2$) and water ($H_2O$) according to the following process reaction:

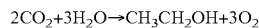
[2]

Figure 1:
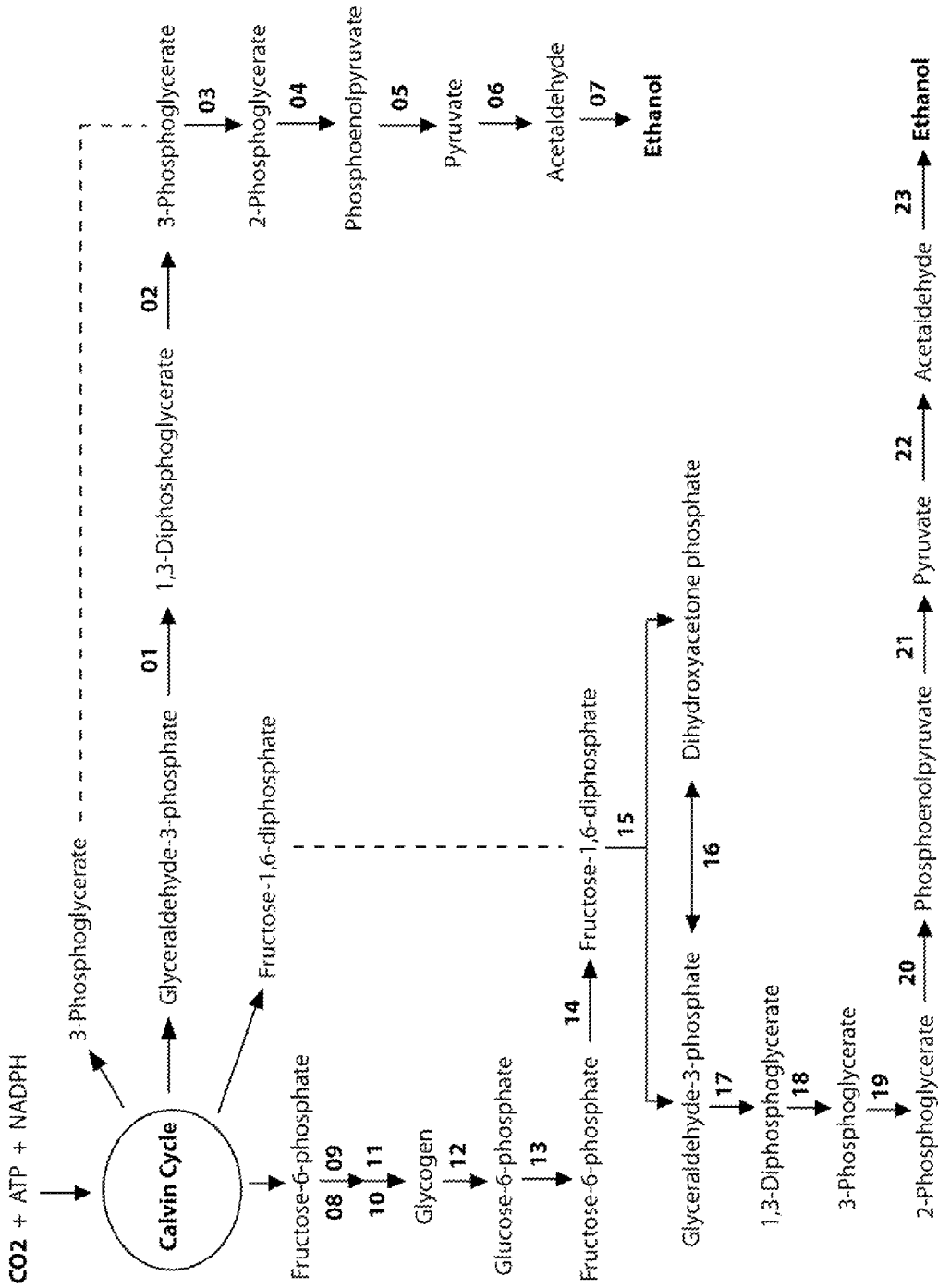
FIG. 1 presents designer oxyphotobacterial ethanol-production pathways that work with the Calvin cycle in using the reducing power (NADPH) and energy (ATP) from the photosynthetic water splitting and proton gradient-coupled electron transport process to reduce carbon dioxide ($CO_2$) into ethanol ($CH_3CH_2OH$) in the cytoplasm (stroma region) of oxyphotobacteria such as cyanobacteria.

The oxyphotobacterial ethanol-production methods of the present invention completely eliminate the problem of recalcitrant lignocellulosics by bypassing the bottleneck problem of the biomass technology. As shown in FIG. 1, the photobiological process in a designer oxyphotobacterium such as designer cyanobacterium effectively uses the reducing power (NADPH) and energy (ATP) from the photosynthetic water splitting and proton gradient-coupled electron transport process for immediate synthesis of ethanol ($CH_3CH_2OH$) directly from carbon dioxide ($CO_2$) and water ($H_2O$) without being drained into the other pathway for synthesis of the undesirable lignocellulosic materials that are very hard and often inefficient for the biorefinery industry to use. This approach is also different from the existing "cornstarch ethanol production" process. In accordance with one of the various embodiments, ethanol will be produced directly from carbon dioxide ($CO_2$) and water ($H_2O$) without having to go through many of the energy consuming steps that the cornstarch ethanol-production process has to go through, including corn crop cultivation, corn-grain harvesting, corn-grain cornstarch processing, and starch-to-sugar-to-ethanol fermentation. Furthermore, through the combined use of designer photosynthetic organisms and greenhouse distillation systems, the waste solar heat associated with the photobiological ethanol-production process is now also utilized in harvesting the produced ethanol. As a result, the photobiological ethanol production and harvesting technology of the present invention is expected to have a much (more than 10-times) higher solar-to-ethanol energy-conversion efficiency than the current technology. Assuming a 10% solar energy conversion efficiency for the photobiological ethanol-production process, the maximal theoretical productivity (yield) could be about 88,700 kg of ethanol per acre per year, which could support about 140 cars (per year per acre). Therefore, this invention could bring a significant capability to the society in helping to ensure energy security. It could also help protect the Earth's environment from the dangerous accumulation of $CO_2$ in the atmosphere, because the present methods convert $CO_2$ directly into clean ethanol energy and use the associated solar waste heat for harvesting through greenhouse distillations.

Another fundamental feature of the present methodology is utilizing a oxyphotobacterium (such as a cyanobacterium) as a host organism, introducing into the oxyphotobacterium nucleic acid molecules coding for a set of enzymes that can act on an intermediate product of the Calvin cycle and convert the intermediate product into ethanol as illustrated in FIG. 1, instead of making glycogen and other complicated cellular (biomass) materials as the end products by the wild-type photosynthetic pathway.

Accordingly, the present invention provides, inter alia, methods for producing ethanol based on a designer oxyphotobacterium, DNA constructs encoding genes of a designer oxyphotobacterial ethanol-production pathway, as well as the designer oxyphotobacteria created. The various aspects of the present invention are described in further detail hereinbelow.

Host Oxyphotobacterium

According to the present invention, a designer oxyphotobacterium for the photobiological ethanol production of the invention can be created utilizing as host, any oxyphotobacteria including Cyanobacteria (Cyanophyta) and Oxychlorobacteria (Prochlorophytes) that have an oxygenic photosynthetic capability, i.e., an active photosynthetic apparatus and enzymatic pathway that captures light energy through photosynthesis, using this energy to convert inorganic substances (water and $CO_2$) into organic matter.

Suitable genera of Cyanophyta include (but not limited to) *Phoridium, Synechocystis, Syncechococcus, Oscillatoria,* and *Anabaena.* Suitable genera of Prochlorophytes include (but not limited to) *Prochloron, Prochlorothrix,* and *Prochlorococcus.* Preferred species of oxyphotobacteria for use in the present invention include (but not limited to): *Thermosynechococcus elongatus* BP-1, *Nostoc* sp. PCC 7120, *Synechococcus elongatus* PCC 6301, *Syncechococcus* sp. strain PCC 7942, *Syncechococcus* sp. strain PCC 7002, *Syncechocystis* sp. strain PCC 6803, *Prochlorococcus marinus* MED4, *Prochlorococcus marinus* MIT 9313. *Prochlorococcus marinus* NATL1A, *Prochlorococcus* SS120, *Spirulina platensis* (*Arthrospira platensis*), *Spirulina Pacifica, Lyngbya Majuscule, Anabaena* sp., *Synechocystis* sp., *Synechococcus elongates, Synechococcus* (MC-A), *Trichodesmium* sp., *Richelia intracellularis, Synechococcus* WH7803, *Synechococcus* WH8102, *Nostoc punctiforme, Syncechococcus* sp. strain PCC 7943, *Synechocyitis* PCC 6714 phycocyanin-deficient mutant PD-1, *Cyanothece* strain 51142, *Cyanothece* sp. CCY0110, *Oscillatoria limosa, Lyngbya majuscula, Symploca muscorum, Gloeobacter violaceus, Prochloron didemni, Prochlorothrix hollandica, Synechococcus* (MC-A), *Trichodesmium* sp., *Richelia intracellularis, Prochlorococcus marinus, Prochlorococcus* SS120, *Synechococcus* WH8102, *Lyngbya majuscula, Symploca muscorum, Synechococcus bigranulatus,* cryophilic *Oscillatoria* sp., *Phormidium* sp., *Nostoc* sp.-1, *Calothrix parietina,* thermophilic *Synechococcus bigranulatus, Synechococcus lividus,* thermophilic *Mastigocladus laminosus, Chlorogloeopsis fritschii* PCC 6912, *Synechococcus vulcanus, Synechococcus* sp. strain MA4, *Synechococcus* sp. strain MA19, and *Thermosynechococcus elongates.*

Oxyphotobacteria can be cultured in a liquid medium. Ethanol produced from an aquatic oxyphotobacterium can diffuse into water, permitting normal cell growth and more robust production of ethanol from the designer organism. Liquid cultures of oxyphotobacterial cells are highly preferred for use, since the ethanol molecules produced from a designer oxyphotobacterial ethanol-production pathway can readily diffuse out of the cells into the liquid water medium, which can serve as a large pool to store the product ethanol that can be subsequently harvested by filtration and/or distillation techniques.

By "liquid medium" is meant liquid water plus relatively small amounts of inorganic nutrients (e.g., N, P, K etc, commonly in their salt forms) for photoautotrophic cultures; and sometimes also including certain organic substrates (e.g., sucrose, glucose, or acetate) for photomixotrophic and/or photoheterotrophic cultures. The use of oxyphotobacteria has several advantages. They can be grown in an open pond at large amounts and low costs. Harvest and purification of ethanol from the water phase is also easily accomplished by distillation or membrane separation.

Ethanol-tolerant photosynthetic organisms are highly desirable in photobiological ethanol production, because a higher ethanol tolerance can be translated to a more robust and efficient ethanol-production technology. Therefore, in one of the various embodiments, various photosynthetic organisms are screened for higher ethanol tolerance by characterizing their rates of photosynthesis in the presence of ethanol and under various environmental conditions (such as heat, cold, and salinity stresses) using a specially designed dual- and/or multi-reactor-flow detection system that can be used for simultaneous measurement of $CO_2$ fixation, ethanol production, pH, $O_2$ and $H_2$ evolution, cells density, and actinic intensity. The screening process comprises the following steps: a) Measuring the rates of photosynthesis in the organisms in the presence of ethanol at a concentration range from 0% to about 20% and/or under certain environmental conditions of special interest including (but not limited to) heat, cold, and salinity stresses; b) Plotting measured photosynthesis rates as a function of ethanol concentration for each strain of photosynthetic organisms; and c) Identifying ethanol-tolerant photosynthetic organisms by comparing their photosynthesis rate vs. ethanol concentration curves.

In accordance with one of the various embodiments, any of the components a) through c) of this screening process are adjusted to suit for certain specific conditions. In practice, any of the components a) through c) of this screening process are applied in full or in part, and/or in any adjusted combination to achieve more desirable results. For example, in one of the various embodiments, the step a) of measuring the rates of photosynthesis in the organisms is performed preferably under anaerobic conditions to avoid pseudo tolerance to ethanol because of oxidative consumption of ethanol through respiratory pathway(s). Under anaerobic conditions, oxidative consumption of ethanol by the organism under screening is minimized. This will help avoid the selection of "pseudo ethanol-tolerance" phenotype that is due to the respiratory consumption (removal) of ethanol from the culture medium; it will enhance the selection of true ethanol tolerance that is useful to photobiological ethanol-production technology development.

According to one of various embodiments, an ethanol tolerant and environmental stress (such as heat, cold, salinity) tolerant photosynthetic organism for can be selected from many photosynthetic organisms including Cyanobacteria (Cyanophyta) and Oxychlorobacteria (Prochlorophytes) that have an oxygenic photosynthetic capability, i.e., an active photosynthetic apparatus and enzymatic pathway that captures light energy through photosynthesis, using this energy to convert inorganic substances (water and $CO_2$) into organic matter. Preferably, the photosynthetic organisms should have an adequate photosynthetic $CO_2$ fixation rate, for example, to support photosynthetic ethanol production from $CO_2$ and $H_2O$ at least about 1,780 kg ethanol per acre per year, more preferably, 8,870 kg ethanol per acre per year, or even more preferably, 88,700 kg ethanol per acre per year.

Many photosynthetic organisms such as oxyphotobacteria can be cultured in a liquid medium, which typically is liquid water plus relatively small amounts of inorganic nutrients (e.g., N, P, K etc, commonly in their salt forms) for photoautotrophic cultures. According to one of the various embodiments, their ethanol tolerance and other stress (including but not limited to heat, cold, and salinity) tolerance can be measured by measuring their rates of photosynthesis such as $CO_2$ fixation and/or $O_2$ evolution in the presence of ethanol at certain concentrations in the liquid culture medium and/or at various temperature and salinity conditions. Use of a dual- and/or multi-reactor-flow detection system can facilitate the measurements that include simultaneous measurement of $CO_2$ fixation, ethanol production, pH, $O_2$ and $H_2$ evolution, cells density, and actinic intensity. The advantage of a dual- (or multi)-reactor-flow detection system is that it allows assay of two or multiple different samples simultaneously and at virtually identical conditions. Any systematic error of the dual-reactor system can be eliminated by interchanging two samples between the two reactors for each replication of assays. Therefore, use of this type of dual-reactor-flow systems can provide reliable measurements for screening of ethanol tolerance and/or other environmental stress tolerance. Typically, the $O_2$ concentration in the reactor medium or in the carrier gas stream is below 100 ppmv so that no significant respiratory consumption of ethanol by the organism could occur. Therefore, the photosynthesis rates measured under anaerobic conditions in the presence of ethanol will reflect the true ethanol tolerance of a given organism that is relevant to the potential capability for robust photobiological ethanol production. The tolerance of other environmental stresses (such as heat, cold, and salinity stresses) can be similarly measured and screened.

According to another embodiment, an ethanol-tolerant photosynthetic organism can be developed through a mutagenesis and screening process that comprises the following steps: a) Mutagenizing photosynthetic organisms; b) Selecting mutagenized photosynthetic organisms in the presence of a critical ethanol concentration; c) Growing selected photosynthetic organisms into colonies for isolation and further selection; d) Growing a selected colony into a liquid culture; e) Further screening for ethanol-tolerant photosynthetic organisms by measuring photosynthesis rate in the presence of ethanol at a concentration range from 1% to about 20% and/or under certain environmental conditions including (but not limited to) heat, cold, and salinity stresses; and f) repeating steps a) through e) for a plurality of operational cycles to achieve more desirable results.

In practice, any of the steps a) through f) of this ethanol-tolerance developing process are applied in full or in part, and/or in any adjusted combination to achieve more desirable results. In one of the various embodiments, for example, the step of mutagenizing photosynthetic organisms is carried out by a series of mutagenesis techniques such as radiation induced mutagenesis, insertional mutagenesis, and chemical-induced mutagenesis that are known to those skilled in the art. The step b) of selecting mutagenized photosynthetic organisms in the presence of a critical ethanol concentration is performed preferably under anaerobic conditions to avoid pseudo tolerance to ethanol because of oxidative consumption of ethanol through respiratory pathway(s).

Screening for ethanol-tolerant photosynthetic organisms in combination with proper selection for their genetic backgrounds and certain special features is also beneficial. For example, a photosynthetic-ethanol-producing designer oxyphotobacterium created from cryophilic oxyphotobacteria (psychrophiles) such as the cryophilic *Oscillatoria* sp., *Phormidium* sp., *Nostoc* sp.-1, and *Calothrix parietina* that can grow in snow and ice, permits ethanol production even in cold seasons or regions such as Canada. Meanwhile, a designer oxyphotobacterium created from thermophilic oxyphotobacteria such as the thermophilic *Synechococcus bigranulatus*, and *Synechococcus lividus* (which can grow in hot springs, intense sunlight, high temperature), thermophilic *Mastigocladus laminosus*, *Chlorogloeopsis fritschii* PCC 6912, *Synechococcus vulcanus*, *Synechococcus* sp. strain MA4, *Synechococcus* sp. strain MA19, and *Thermosynechococcus elongatus* BP-1, may permit the practice of this invention to be well extended into the hot seasons or areas such as Mexico and the Southwestern region of the United States including Nevada, California, Arizona, New Mexico and Texas, where the weather can often be hot. Furthermore, a photosynthetic-ethanol-producing designer oxyphotobacterium created from a marine oxyphotobacterium, such as the phycoerythrin-containing marine *Synechococcus* sp. strains (also known as *Synechococcus* (MC-A)), the non-heterosystous nitrogen-fixing *Trichodesmium* sp., the heterocyst-containing *Richelia intracellularis*, *Prochlorococcus marinus*, *Prochlorococcus* SS120, *Synechococcus* WH8102, *Lyngbya majuscula*, and *Symploca muscorum*, permits the practice of this invention using seawater, while the designer oxyphotobacterium created from a freshwater oxyphotobacterium such as the freshwater *Synechococcus* sp. strain PCC 6301, the freshwater *Synechococcus elongatus*, *Synechocystis* sp. strain PCC 6803, *Nodularia spumigena*, *Anabaena flosaquae* and *Microcystis aeruginosa*, can use freshwater. Additional optional features of a photosynthetic ethanol-producing designer oxyphotobacterium include the benefits of reduced chlorophyll-antenna size, which has been demonstrated to provide higher photosynthetic productivity (Lee, Mets, and Greenbaum (2002). "Improvement of photosynthetic efficiency at high light intensity through reduction of chlorophyll antenna size," *Applied Biochemistry and Biotechnology*, 98-100: 37-48) and ethanol-tolerance that allows for more robust and efficient photobiological production of ethanol from $CO_2$ and $H_2O$. By use of a phycocyanin-deficient mutant of *Synechocystis* PCC 6714, it has been experimentally demonstrated that photoinhibition can be reduced also by reducing the content of light-harvesting pigments (Nakajima, Tsuzuki, and Ueda (1999). "Reduced photoinhibition of a phycocyanin-deficient mutant of *Synechocystis* PCC 6714", *Journal of Applied Phycology* 10: 447-452). These optional features can be incorporated into a designer oxyphotobacterium, for example, by use of an ethanol-tolerant and/or light-harvesting-pigment-antenna-deficient mutant (e.g., *Synechocystis* PCC 6714 phycocyanin-deficient mutant PD-1) as a host organism, for gene transformation with the designer oxyphotobacterial ethanol-production-pathway genes. Therefore, in one of the various embodiments, a host oxyphotobacterium is selected from the group consisting of marine oxyphotobacteria, freshwater oxyphotobacteria, unicellular oxyphotobacteria, multicellular oxyphotoobacteria, cold-tolerant oxyphotobacterial strains, heat-tolerant oxyphotobacterial strains, ethanol-tolerant oxyphotobacterial strains, light-harvesting-pigment-antenna-deficient mutants, and combinations thereof.

Creating a Designer Oxyphotobacterial Ethanol-Production Pathway in a Host

Selecting Appropriate Designer Enzymes

One of the key features in the present invention is the creation of a designer oxyphotobacterial ethanol-production pathway to tame and work with the natural photosynthetic mechanisms to achieve the desirable synthesis of ethanol directly from $CO_2$ and $H_2O$. The natural photosynthetic mechanisms include (1) the process of photosynthetic water splitting and proton gradient-coupled electron transport through the oxyphotobacterial thylakoid membrane, which produces the reducing power (NADPH) and energy (ATP), and (2) the Calvin cycle, which reduces $CO_2$ by consumption of the reducing power (NADPH) and energy (ATP) in the cytoplasm.

In accordance with the present invention, a series of enzymes are used to create a designer oxyphotobacterial ethanol-production pathway that takes an intermediate product of the Calvin cycle and converts the intermediate product into ethanol. A "designer ethanol-production-pathway enzyme" is hereby defined as an enzyme that serves as a catalyst for at least one of the steps in a designer oxyphotobacterial ethanol-production pathway. According to the present invention, a number of intermediate products of the Calvin cycle can be utilized to create designer oxyphotobacterial ethanol-production pathway(s); and the enzymes required for a designer oxyphotobacterial ethanol-production pathway are selected depending upon from which intermediate product of the Calvin cycle the designer ethanol-production pathway branches off from the Calvin cycle.

In one example, a designer oxyphotobacterial pathway is created that takes glyceraldehydes-3-phosphate and converts it into ethanol by using, for example as shown with numerical labels 01-07 in FIG. 1, a set of enzymes consisting of preferably NAD-dependent glyceraldehyde-3-phosphate dehydrogenase 01, phosphoglycerate kinase 02, phosphoglycerate mutase 03, enolase 04, pyruvate kinase 05, pyruvate decarboxylase 06, and alcohol dehydrogenase 07. In this glyceraldehyde-3-phosphate-branched designer pathway, for conversion of one molecule of glyceraldehyde-3-phosphate to ethanol, an NADH molecule is generated from $NAD^+$ at the step from glyceraldehyde-3-phosphate to 1,3-diphosphoglycerate catalyzed by NAD-dependent glyceraldehyde-3-phosphate dehydrogenase; meanwhile an NADH molecule is converted to $NAD^+$ at the terminal step catalyzed by alcohol dehydrogenase in reducing acetaldehyde to ethanol. Consequently, in this designer pathway, the number of NADH molecules consumed is balanced with the number of NADH molecules generated. Therefore, the glyceraldehyde-3-phosphate-branched designer ethanol-production pathway (01-07) can operate continuously.

In another example, a designer oxyphotobacterial pathway (03-07 as labeled in FIG. 1) can also be created that takes the intermediate product, 3-phosphoglycerate, and converts it into ethanol by using, for example, a set of enzymes consisting of phosphoglycerate mutase 03, enolase 04, pyruvate kinase 05, pyruvate decarboxylase 06, and alcohol dehydrogenase 07. It can be seen that the last five enzymes (03-07) of the glyceraldehyde-3-phosphate-branched ethanol-production pathway (01-07) are identical with those utilized in the designer 3-phosphoglycerate-branched ethanol-production pathway (03-07) as shown in FIG. 1. In other words, the designer enzymes (01-07) of the glyceraldehyde-3-phosphate-branched designer pathway permits ethanol production from both the point of 3-phosphoglycerate and the point of glyceraldehydes 3-phosphate in the Calvin cycle. These two pathways, however, have different characteristics. Unlike the glyceraldehyde-3-phosphate-branched ethanol-production pathway, the 3-phosphoglycerate-branched pathway which consists of the activities of only five enzymes (03-07) could not itself generate any NADH for use in the terminal step to reduce acetaldehyde to ethanol. That is, if (or when) an alcohol dehydrogenase that can strictly use only NADH but not NADPH is employed, it would require a supply of NADH for the 3-phosphoglycerate-branched pathway to operate. Consequently, in order for the 3-phosphoglycerate-branched ethanol-production pathway to operate, it is important to use an alcohol dehydrogenase that can use NADPH which can be supplied by the photo-driven electron transport process. Therefore, it is a preferred practice to use an alcohol dehydrogenase that can use NADPH or both NADPH and NADH (i.e., NAD(P)H) for the 3-phosphoglycerate-branched ethanol-production pathway (03-07 as labeled in FIG. 1). Alternatively, when an alcohol dehydrogenase that can use only NADH is employed, it is preferably here to use an additional embodiment that can confer an NADPH/NADH conversion mechanism (to supply NADH by converting NADPH to NADH, see more detail later in the text) in the designer oxyphotobacterial cytoplasm to facilitate photosynthetic production of ethanol through the 3-phosphoglycerate-branched designer pathway.

In still another example, a designer oxyphotobacterial pathway (15-23) is created that takes fructose-1,6-diphosphate and converts it into ethanol by using, for example, a set of enzymes consisting of aldolase 15, triose phosphate isomerase 16, NAD-dependent glyceraldehyde-3-phosphate dehydrogenase 17, phosphoglyccrate kinase 18, phosphoglycerate mutase 19, enolase 20, pyruvate kinase 21, pyruvate decarboxylase 22, and alcohol dehydrogenase 23, as shown in FIG. 1, with aldolase 15 and triose phosphate isomerase 16 being the only two additional enzymes relative to the designer glyceraldehyde-3-phosphate-branched pathway (01-07). The addition of yet one more enzyme in the designer organism, phosphofructose kinase 14, permits the creation of another designer pathway which branches off from the point of fructose-6-phosphate for the production of ethanol. Like the glyceraldehyde-3-phosphate-branched ethanol-production pathway (01-07), both the fructose-1,6-diphosphate-branched pathway (15-23) and the fructose-6-phosphate-branched pathway (14-23) can themselves generate NADH for use in their terminal step to reduce acetaldehyde to ethanol. In each of these designer ethanol-production pathways, the numbers of NADH molecules consumed are balanced with the numbers of NADH molecules generated. Therefore, these designer oxyphotobacterial ethanol-production pathways can operate continuously.

Table 1 lists examples of the enzymes including those identified above for construction of the designer oxyphotobacterial ethanol-production pathways. Throughout this specification, when reference is made to an enzyme, such as, for example, any of the enzymes listed in Table 1, it includes their isozymes, functional analogs, and designer modified enzymes and combinations thereof. These enzymes can be selected for use in construction of the designer oxyphotobacterial ethanol-production pathways. The "isozymes or functional analogs" refer to certain enzymes that have the same catalytic function but may or may not have exactly the same protein structures. For example, in *Saccharomyces bayanus*, there are four different genes (accession numbers: AY216992, AY216993, AY216994, and AY216995) encoding four alcohol dehydrogenases. These alcohol dehydrogenases essentially have the same function as an alcohol dehydrogenase, although there are some variations in their protein sequences. Therefore, the isozymes or functional analogs can also be selected and/or modified for use in construction of the designer ethanol-production pathway(s). The most essential feature of an enzyme is its active site that catalyzes the enzymatic reaction. Therefore, certain enzyme-protein fragment(s) or subunit(s) that contains such an active catalytic site may also be selected for use in this invention. For various reasons, some of the natural enzymes contain not only the essential catalytic structure but also other structure components that may or may not be desirable for a given application. With techniques of bioinformatics-assisted molecular design, it is possible to select the essential catalytic structure(s) for use in construction of a designer DNA construct encoding a desirable designer enzyme. Therefore, in one of the various embodiments, a designer enzyme gene is created by artificial synthesis of a DNA construct according to bioinformatics-assisted molecular sequence design. With the computer-assisted synthetic biology approach, any DNA sequence (thus its protein structure) of a designer enzyme may be selectively modified to achieve more desirable results by design. Therefore, the terms "designer modified sequences" and "designer modified enzymes" are hereby defined as the DNA sequences and the enzyme proteins that are modified with bioinformatics-assisted molecular design. For example, when a DNA construct for a designer enzyme is designed from the sequence of a mitochondrial enzyme, it is a preferred practice to modify some of the protein structures, for example, by selectively cutting out certain structure component(s) such as its mitochondrial transit-peptide sequence that is not suitable for the given application. Therefore, one of the various embodiments flexibly employs the enzymes, their isozymes, functional analogs, designer modified enzymes, and/or the combinations thereof in construction of the designer ethanol-production pathway(s).

Figure 2A:
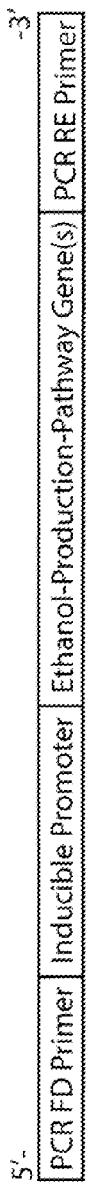
FIG. 2A presents a DNA construct for designer oxyphotobacterial ethanol-production-pathway gene(s).

As shown in Table 1, many genes of the enzymes identified above have been cloned and/or sequenced from various organisms. Both genomic DNA and/or mRNA sequence data can be used in designing and synthesizing the designer DNA constructs for transformation of host oxyphotobacterial cells to create a designer oxyphotobacterium for photobiological ethanol production (FIG. 1). However, because of possible variations often associated with various source organisms and cellular compartments with respect to a specific host oxyphotobacterium where the ethanol-production pathway(s) is designed to work with the Calvin cycle, certain molecular engineering art work in DNA construct design including codon-usage optimization and sequence modification is often necessary for a designer DNA construct (FIG. 2) to work well. For example, to provide the switchability for a designer ethanol-production pathway, it is important to include a functional inducible promoter sequence such as the promoter of a nitrite reductase (nirA) or nitrate reductase (narB) gene in certain designer DNA construct(s) as illustrated in FIG. 2A to control the expression of the designer gene(s). In addition, as mentioned before, certain functional derivatives or fragments of these enzymes (sequences), and inducible promoter sequences can also be selected for use in full, in part or in combinations thereof, to create the designer oxyphotobacteria according to various embodiments of this invention. The arts in creating and using the designer oxyphotobacteria are further described hereinbelow.

Table 1 lists examples of enzymes for construction of designer oxyphotobacterial ethanol-production pathways.

TABLE 1 lists examples of enzymes for construction of designer oxyphotobacterial ethanol-production pathways.

| Enzyme | Source (Organism) | NCBI/GenBank Accession Number, or Other Citation |
|---|---|---|
| Alcohol dehydrogenase | Pichia slipitis CBS 6054 NADPH-dependent alcohol dehydrogenase; | XM_001384263 [NADPH], ABN66271 [NADPI I], EAZ62840 [NADP], XM_001386628[NADP(H)]; |
| | Thermococcus sp. NADP(H)-dependent; | U72646 [NADP(H), thermophilic]; |
| | Entamoeba histolytica NADP-dependent; | M88600 [NADP]; |
| | Kluyveromyces lactis mitochondrial Alcohol dehydrogenase III [NAD(P)H]; | XM_451932 [NAD(P)H], X62766 [NAD(P)H], X62767 [NAD(P)H]; |
| | Saccharomyces cerevisiae [NADP-adh 6, 7]; | Q04894 [NADP], P25377 [NADP]; |
| | Trichomonas vaginalis G3 [NADP-]; | XM_001315996 [NADP]; |
| | Leishmania braziliensis [NADP-]; | XM_001565062 [NADP]: |
| | Botryotinia fitckeliana B05.10 [NADP-]; | XM_001559311 [NADP]; |
| | Aspergillu.vfittnigatus A1293 [NADP-]; | XM_726411 [NADP]; |
| | Chlatnydomonas reinhardtii mitochondrial; Saccharomyces bayanus; | AJ620190, XM_001703533; AY216992, AY216993, AY216994, AY216995; |
| | Kluyveromyces marxianus thermotolerant; | X60224 [thermotolerant]; |
| | Caldicelhdosiruptor saccharolyticus DSM 8903 [NAD, thermophilic]: | ABP66046 [NAD, thermophilic]; |
| | Aeropyrum pemix K1 [NAD, thermophilic]; | NP_148480 [NAD, thermophilic]; |
| | Pelotonzaculum thermopropionicum SI thermophilic]; | YP_001213191, YP_001213446 thermophilic]; |
| | Geobacillus kaustophilus HTA26; | BAD76237 [thermophilic]; |
| | Geobacillus thermoleovorans; | BAA94092 [thennophilic]; |
| | Pyrococcus horikoshii OT3; | NP_142684 [thermophilic]; |
| | Thermoanaerobacter brockii [NADP-] | P14941 [NADP, thermophilic]; |
| | Saccharomyces cerevisiae [NADII-dependent ADH1]; | CAA99098 [NADII], 2007 Biosci Biotechnol Biochem, 71(5):1170-1182; |
| | Entamoeba histolytica NADH-dependent; | D49910 [NADII]; |
| | Zymomonas mobilis alcohol dehydrogenase II (AdhB); | M15394 [NADH]; |
| | Dianthus caryophyllus: | AY263389; |
| | Saccharomyces pastorianus: | AY217000, AY21700I, AY217002, AY217003; |
| | Lachancea kluyveri: | AY216997, AY216998, AY216999, AY216996, AF218309; |
| | Lotus corniculatus; | AY227202; |
| | Giardia lamblia ATCC 50803; | XM_001710186; |
| | Chlorobittmlerrooxidans DSM 13031; | ZP_01385742; |
| | Prosthecochloris aestuarii DSM 271; | ZP_00592015; |
| | Prochlorococcus marinus sir. AS9601; | YP_001009842; |
| | Thermosynechococcus elongatus BP-1; | CyanoBase: tlr0227 |
| | Synechocystis sp. PCC 6803; | CyanoBase: slr0942 [NADP]; |
| | Gloeobacter violaceus PCC 7421; | CyanoBase: gll2836, gll4111; |
| | Microcystis aeruginosa NIES-843; | MAE58620, MAE49340; |
| | Prochlorococcus Marinas MED4; | CyanoBase: PMM1234; |
| | Synechococcus sp. CC9311; | sync 0822, sync_ 2669; |
| | Synechococcus sp. PCC 7002; | SYNPCC7002 A0868, A2590; |
| | Acatyochloris marina MB1C 11017; | AM1_0442, 1335, 4548, D0148; |
| | Synechococcus sp. JA-2-3Ba's (2-13); | CYB_0241, CYB 0338; |
| | Synechococcus sp. JA-3-3Ab; | CYA 0473, CYA 0992; |
| | Prochlorococcus Marinus sir. AS9601 | A9601_14521; |
| | Synechococcus sp. WH 7803; | SynWH7803_0815, 0871; |

TABLE 1-continued lists examples of enzymes for construction of designer oxyphotobacterial ethanol-production pathways.

| Enzyme | Source (Organism) | NCBI/GenBank Accession Number, or Other Citation |
|---|---|---|
| | Cyanothece sp. ATCC 51142; | cce_0002, 0206, 4888; |
| | Nostoc Punctiforme ATCC 21933; | Npun_AR200, DF037, F1458; |
| | Chlorobium tepidum TLS; | CT0951, CT 1152, CT1275: |
| | Rhodopseudomonas palustris CGA009 | RPA2018, RPA3188 RPA0586; |
| | Anabaena sp. PCC 7120 | CyanoBase: all0879, all0879; all5334; alr0895; alr0897: |
| | Clostridium beikrinckii [NADP-]; | P25984 [NADP]; |
| | Thermoanaerobacter brockii [NADP-]; | P14941 [NADP]; |
| | Clavibacter michiganensis subsp. michiganensis NCPPB 382 [NADP-]; | YP_001221402 [NADP]; |
| | Bacillus subtilis subsp. subtilis str. 168 [NADP-dependent]; | NP_390579 [NADP]; |
| | Bacillus licheniformis ATCC 14580 [NADP-dependent]; | AAU23621 [NADP]; |
| | Sphingomonas wittichii RW1 [NADPH-]; | YP_001263332 [NADPH]; |
| | Polaromonas naphthalenivorans CJ2 [NADPH-dependent]; | ABM38530 [NADPH]; |
| | Halorhodospira halophila SLI [NADPH]; | ABM62958 [NADPH]; |
| | Nitrobacter hamburgensis X14 [NADPH-]; | ABE62842 [NADPH]; |
| Pyruvate decarboxylase | Pichia stipitis; | U75310, U75311, XM_001387668, XM_001387532, XM_001385859; |
| | Lodderomyces elongisporus; | XM_001526215, XM_001523117; |
| | Zymomonas mobilis; | BAF76067, AB359063, DD 161475, M20667, M15368, M15393, X59558 AAA27696, CAA42157; |
| | Zymobacter palmae; | AF474145, DD161472, AAM49566; |
| | Lachancea kluyveri; | AF193853; |
| | Acetobacter pasteurianus; | AAM21208; |
| | Planctomyces maris DSM 8797; | ZP_01856731; |
| | Sarcina ventriculi; | AAL18557; |
| | Psychrobacter cryohalolentis K5; | ABE74745; |
| | Legionella pneumophila str. Corby; | YP_001249946; |
| | Pelobacter carbinolicus DSM 2380; | YP_358263; |
| | Arabidopsis thaliana; | NM_121744, NM_124878; |
| | Lycoris aurea; | DQ996286, DQ996285; |
| | Chaetomium glohosum; | XM_001219657; |
| | Citrus sinensis; | DQ001726; |
| | Petunia x hybrida; | AY928611; |
| | Candida glabrata; | AF545432; |
| | Saccharomyces kluyveri; | AY245517, AY245516, AY302469; |
| | Zea mays; | AF370006; |
| | Rhizopus oryzae; | AF282846; |
| | Lotus corniculatus; | AY227204; |
| | Oryza sativa; | U38199: |
| | Ajellotnyces capsulants NAm1; | XM_001542350, XM_001536406; |
| | Lodderomyces elongisporus; | XM_001526215, XM_001523117; |
| | Alicrocystis aeruginosa NIES-843, | CyanoBase: MAE36750; |
| | Cyanothece sp. ATCC 51142 | CyanoBase: cce_3766; cce_4913; |
| | Dianthus caryophyllus; | AY263388; |
| | Chlamyclomonas reinhardiii cytoplasm; | E15259; |
| | Aspergillus fumigants Af293; | XM_749419; |
| | Aspergillus clavatus NRRL 1; | XM_001271109, XM_001270420; |
| | Aspergillus terreus N1H2624; | XM_001209567; |
| | Aspergillus oryzae; | AF098293; |
| | Aspergillus parasiticus; | 000967; |
| | Neosartotyalischeri NRRL 181; | XM_001263351: |
| | Paracoccidioides brasiliensis; | AF443183; |
| | Rhizopus oryzae; | AF282846; |
| | Sarcina ventriculi; | AF354297; |
| | Candida albicans SC5314; | XM_717733, XM_710496; |
| | Chaetomium glohosum CBS 148.51; | XM_001219657; |
| | Emericella nidulans; | U13635, L26109; |
| | Hanseniaspora uvarum; | U73I94; |
| | Neurospora crassa; | U65927, L09125; |
| | Kluyveromyces marxianus; | L09727; |
| | Saccharomyces cerevisiae; | X77316, X66843, X773I5 (mutant), X15668, X04675, X65608; |

TABLE 1-continued lists examples of enzymes for construction of designer oxyphotobacterial ethanol-production pathways.

| Enzyme | Source (Organism) | NCBI/GenBank Accession Number, or Other Citation |
|---|---|---|
| Glyceraldehyde-3-phosphate dehydrogenase | *Pinus sylvestris* [NAD-dependent]; | GenBank: L32561 [NAD], L32560 [NAD], AJ001706 [NAD]; |
| | *Fischerella muscicola* UTEX 1829 [NAD]; | AJ252113 [NAD]; |
| | *Nostoc sp.* PCC 7120 [NAD-]; | CAC41000 [NAD]; |
| | *Stanieria cyanosphaera* PCC 7437 [NAD]; | CAC80994 [NAD]; |
| | *Lynghya aestuarii* PCC 7419 [NAD-]; | CAC81002 [NAD]; |
| | *Scenedesmus vacuolatus* [NAD-]; | CAC81012 [NAD]; |
| | *Cyanidium caldarium* [cytosolic, NAD-]; | CAC85917 [NAD]; |
| | *Cycmidium sp.* 3-8 CR [NAD-dependent]; | CAC85918 [NAD]; |
| | *Cyanophora paradoxa* [NAD-dependent]; | CAC85919 [NAD]; |
| | *Euglena sp.* CRRdV [NAD-dependent]; | CAC85128 [NAD]; |
| | *Bacillus subtilis* [NAD-dependent]; | P09124 [NAD]; |
| | *Sardina pilchardus* [cytosolic, NAD-]; | EF621524 [NAD]; |
| | *Blastochloris viridis* [NAD-dependent]; | CAC80993 [NAD]; |
| | *Heliobacterium chlorum* [NAD-dependent]; | AJ252110 [NAD], CAC80992 [NAD]; |
| | *Rhodospirillum rubrum* [NAD-dependent]; | CAC80991 [NAD]; |
| | *Ambidopsis thaliana* [NADP-]: | NM_001084060 [NADP]; |
| | *Synec.hococcus elongates* PCC 7942 [NADP]; | BAA09602 [NADP]; |
| | *Synechocystis sp.* PCC 6803 [NAD(P)-]; | X83564 [NAD(P)], P80505 [NAD(P)]; |
| | *Anabaena variabilis* ATCC 29413; | NC_007413, YP_322831, P34916: |
| | *Nodularia spumigena* CCY9414; | ZP_01630710; |
| | *Anabaena sp.* PCC 7120; | NP_486606, P58559; |
| | *Cyanothece sp.* CCY0110; | ZP_01729953; |
| | *Prochlorococcus marinus str.* MIT 9313; | NP_893861; |
| | *Prochlorococcus marinus str.* NATL1A; | YP_001014980: |
| | *Synechococcus sp.* CC9605; | YP_382146; |
| | *Synechococcus sp.* CC9902; | YP_377816, YP_376044; |
| | *Mesostigma viride cytosol*; | DQ873404; |
| | *Triticum aestivum cytosol*; | EF592180; |
| | *Chlamydomonas reinhardtii chloroplast*; | L27668: |
| | *Bonyotinia fuckeliana*; | XM_001549497: |
| | *Saccharomyces cerevisiae*; | J01324; |
| | *Zymomonas mobilis*; | M18802; |
| | *Karenia brevis*; | EU078558; |
| | *Ajellomyces capsulatus*; | XM_001539393; |
| | *Pichia stipitis*; | XM_001386423, XM_001386568; |
| | *Pichia guilhermondii*; | XM_001485596; |
| | *Kluyveromyces marxianus*; | DQ681075; |
| | *Triticum aestivum*; | EF592180; |
| | *Arabidopsis thaliana*; | NM_101214; |
| | *Bradyrhizobium japonicum* USDA 110; | NP_768163; |
| | *Synechococcus elongatus* PCC 7942 [NADP-dependent; NAD(P)-dependent]; | D61379 [NADP], YP_400759 [NAD(P)]; |
| | *Xanthobacterflavus* [NAD-dependent]; | P51009 [NAD]; |
| Phosphoglycerate kinase | *Thermosynechococcus elongatus* BP-1; | BAC09820, NP_683058; |
| | *Geobacillus kaustophilus* HTA426 (thermo); | YP 148910, BAD77342; |
| | *Bacillus megaterium*; | AAA73203, P35167; |
| | *Pelotomaculum thermopropionicum* SI; | YP_001213272, BAF60903; |
| | *Chlorobium limicola* DSM 245. | ZP00512205; |
| | *Thermoanaerobacter tengcongensis*; | Q8R965; |
| | *Bradyrhizobium japonicum* USDA 110; | NP_768162; |
| | *Synechococcus elongatus* PCC 7942; | YP_400133; |
| | *Synechococcus sp.* BL107; | ZP_01469266; |
| | *Synechocystis sp.* PCC 6803; | P74421, P74421; |
| | *Anabaena variabilis* ATCC 29413; | YP 321291; |
| | *Thermosynechococcus elongatus*; | Q8DGP7; |
| | *Nostoc punctiforme* PCC 73102; | ZP_00111277; |
| | *Nostoc sp.* PCC 7120; | NP_488171, Q8YPR1; |
| | *Prochlorococcus marinus str.* MIT 9211; | Z11_01006089; |
| | *Prochlorococcus marinus str.* MIT 9313; | Q7V461; |
| | *Prochlorococcus marinus str.* MIT 9515; | YP_001010540; |
| | *Synechococcus sp.* WH 8102; | Q7U3VO; |
| | *Prochlorococcus marinus str.* MIT 9303; | YP_001018792; |
| | *Synechococcus sp.* WH7805; | ZP_01125319; |
| | *Chlamydonionas reinhardtii* chloroplast; | U14912, AF244144; |
| | *Plasmodium vivax*; | XM_001614707; |
| | *Babesia bovis*; | XM_001610679; |
| | *Botryotinia fickeliana*; | XM_001548271; |
| | *Monocercomonoides sp.*; | DQ665858; |
| | *Lodderomyces elongisporus*; | XM_001523843; |
| | *Pichia guilliermondii*; | XM_001484377; |

TABLE 1-continued lists examples of enzymes for construction of designer oxyphotobacterial ethanol-production pathways.

| Enzyme | Source (Organism) | NCBI/GenBank Accession Number, or Other Citation |
|---|---|---|
| | *Arabidopsis thaliana*; | NM_179576; |
| | *Ilelianthus annuus*; | DQ835564; |
| | *Otyza saliva*; | EF122488; |
| | *Dictvostelium discoideum*; | AF316577; |
| | *Euglena gracilis*; | AY647236; |
| | *Chondrus crispus*; | AY029776; |
| | *Phaeodactylum tricornutum*; | AF108452; |
| | *Solanum tuherosum*; | AF073473; |
| | *Brucella melitensis*; | Q8YIYO; |
| Phosphoglycerate mutase | *Thermosynechococcus elongatus* BP-1; | GenBank: NP_682018, BAC09084, BA000039; |
| | *Pelotomaculum thermopropionicum* SI; | YP_001213270, BAF60901; |
| | *Caldicellulosiruptor saccharolyticus* DSM 8903; | ABP67536; |
| | *Geobacillus kaustophilus* HTA426; | BAD75751; |
| | *Streptococcus thermophilus* LMG 18311; | AF442555; |
| | *Geobacillus stearothermophilus*; | AF120091; |
| | *Bacillus megaterium*; | AF120090; |
| | *Bacillus subtilis*; | L29475; |
| | *Zymomonas mobilis*; | L09651; |
| | *Streptomyces coelicolor*; | M83661; |
| | *Pseudomonas entomophila*; | CT573326; |
| | *Clavibacter michiganensis* subsp. *michiganensis* NCPPB 382; | NC_009480; |
| | *Methylobacillus flagellants* KT; | ABE50455; |
| | *Psychromonas ingrahamii* 37; | ABM04898; |
| | *Bartonella henselae* sir. Houston-1; | AY074773; |
| | *Synechococcus elongatus* PCC 7942; | YP_399504, YP_401095; |
| | *Synechocystis sp.* PCC 6803; | NP_439971; |
| | *Crocosphaera watsonii* WH 8501; | |
| | *Nostoc sp.* PCC 7120; | Q8YPL2, M80912; |
| | *Anabaena variabilis* ATCC 29413; | YP_322692, YP_321242; |
| | *Synechococcus elongatus* PCC 6301; | YP_173211, YP_171759, Q5N381; |
| | *Cyanothece sp.* CCY0110; | ZP_01731261; |
| | *Chlamydomonas reinharthii* cytoplasm; | AF268078, M001702169; |
| | *Aspergillus fumigatus*; | XM_747847; |
| | *Coccidioides immilis*; | XM_749597; |
| | *Leishmania bruziliensis*; | XM_001248115; |
| | *Ajellomyces capsulatus*; | XM_001569263; |
| | *Monocercomonoides sp.*; | XM_001539892; |
| | *Aspergillus clavatu.s*; | DQ665859; |
| | *Arahidopsis thaliana*; | XM_001270940; |
| | *Zea mays*; | NM_117020; |
| | *Synechococcus sp.* JA-3-3A b; | NP_488222; |
| | *Prochlorococcus marinus str.* MIT 9515; | YP_475082; |
| | *Prochlorococcus marinus*; | YP_001011927; |
| | *Prochlorococcus marinus str.* MIT 9211; | Q7VA78; |
| | *Prochlorococcus marlin's sir.* MIT 9303; | ZP_01005784; |
| | *Synechococcus sp.* WH 8102; | YP_001016525; |
| | *Synechococcus sp.* CC9902; | Q7U8U2; |
| | *Synechococcus sp.* RS9917; | YP_376525; |
| | *Chlorobium ferrooxidans* DSM 13031; | ZP_01079480; |
| | *Chlorobium chlorochromatii* CaD3; | ZP_01386058, Q3AU60; |
| Enolase | *Thermosynechocomis elongatus* BP-1; | GenBank: BAC08209, Q8DL40; |
| | *Caldicellulosiruptor saccharolyticus* DSM 8903; | ABP67535; |
| | *Geo bacillus kaustophilus*; | BAD77339, Q5KVE7; |
| | *Aeropyrum pernix K1* thermophilic; | BAA8I473, NP_148623; |
| | *Pyrococcus horikoshii* thermophilic; | O59605; |
| | *Cvanothece sp.* CCY0110; | ZP_01727912; |
| | *Anabaena variabilis* ATCC 29413; | YP_324019; |
| | *Nodularia spumigena* CCY9414; | ZP_01629547; |
| | *Prochlorococcus marinus str.* MIT 9211; | ZP_01006075; |
| | *Prochlorococcus marinus str.* MIT 9515; | NC_008817; |
| | *Prochlorococcus marinus sir.* MIT 9303; | NC_008820; |
| | *Pmchlorococcus marinus str.* MIT 9312; | Q3AVW5, YP378I62; |
| | *Synechococcus sp.* CC9902; | Q31CX3; |
| | *Synechococcus sp.* CC9311; | Q016K2; |
| | *Trichodesmium erythraeum* IMS101; | Q110V4; |
| | *Anabaena variabilis* ATCC 29413; | Q3M7B2; |
| | *Chlamydomonas reinhardiii*; | X66412, P31683; |
| | *Arabidopsis thalami*; | AK222035; |
| | *Leishmania Mexicana*; | DQ221745; |
| | *Lodderomyces elongisporus*; | XM_001528071; |
| | *Babesia hovis*; | XM_001611873; |

TABLE 1-continued lists examples of enzymes for construction of designer oxyphotobacterial ethanol-production pathways.

| Enzyme | Source (Organism) | NCBI/GenBank Accession Number, or Other Citation |
|---|---|---|
| | *SelerOfinia sclerotiorum*; | XM_001594215; |
| | *Pichia guilliermondii*; | XM_001483612; |
| | *Spirotrichonympha leidvi*; | AB221057; |
| | *Oryza saliva*; | EF122486, U09450; |
| | *Trimastix pyrifOrmis*; | DQ845796; |
| | *Leuconostoc mesenteroides*; | AB088633; |
| | *Davidiella iassiana*; | U82438; |
| | *Aspergillus wyzae*; | D64113; |
| | *Schizosaccharomyces pombe*; | U13799; |
| | *Brassica napus*; | AY307449; |
| | *Zea mays*; | U17973; |
| | *Prochlorococcus marinus sir.* MIT 9313; | Q7V483; |
| Pyruvate kinase | *Thermosynechococcus elongatus.* BP-1; | GenBank: BAC09827, BAC08068. NP_683065, NP_681306; |
| | *Pelotomaculum thermopropionicum* SI; | YP_001212764, BAF60395;- |
| | *Geobacillus kaustophilus* HTA426; YP_148592; | BAD77024, YP_148872, |
| | *Caldicellulosiruptor saccharolyticus* DSM 8903; | ABP67416, YP_001180607; |
| | *Thermococcus kodakarensis*; | AB098541 ; |
| | *Selenomonas ruminantium*; | AB037182; |
| | *Microbispora rosea subsp. Aerata*; | AB003928; |
| | *Thermopmieus tenax*; | AF065890; |
| | *Pichia stipitis* CBS 6054; | XM_001384591; |
| | *Pichia guilliermondii*; | XM_001487289; |
| | *Pichia supitis*; | XM_001384591; |
| | *Lodderomyces elongisporus*; | XM_001528210; |
| | *Saccharomyces cerevisiae*; | AY949876, AY949890, AY949888; |
| | *Yarroivia lipolytica*; | M86863; |
| | *Hypocrea jecorina* (*Trichoderma reesei*); | L07060; |
| | *Synechococcus elongatus* PCC 6301; | YP_172116; |
| | *Anabaena variabilis* ATCC 29413; | YP_321013, YP_322211; |
| | *Cyanwhece sp.* CCY0110; | ZP_01726446; |
| | *Lyngbya sp.* PCC 8106; | ZP_01620033; |
| | *Synechocystis sp.* PCC 6803; | P73534, Q55863; |
| | *Nostoc punctiforme* PCC 73102; | ZP_00106833; |
| | *Prochlorococcus marinus str.* MIT 9211; | ZP_01005438; |
| | *Prochlorococcus marinus str.* MIT 9515; | YP001011309; |
| | *Giardia lamblia* ATCC 50803; | XM_001709477; |
| | *Sclerotinia sclerotiorum* 1980; | XM_001594710; |
| | *Escherichia coli*; | M24636; |
| | *Chlamydomonas reinhardtii* cytoplasm; | XM_001700585, XM_001695686; |
| | *Arabidopsis thaliana*; | AK229638; |
| | *Lactobacillus renter*; | DQ466585; |
| | *Nitrosovibrio .vp.* FJI82; | AY858982; |
| | *Nitrosospira sp.* TYM9; | AY858979; |
| | *Nitrosomonas sp.* CNS332; | AY858967; |
| | *Phaeodactylum tricornutum*; | AY608680; |
| | *Bacillus licheniformis*; | DQ665860; |
| | *Corynebacterium glutamicum*; | XM_745543; |
| | *Monocercomonoides sp.* PA203; | XM_001267896; |
| | *Aspergillus fumigants* Af293; | XM_001468786; |
| | *Aspergillus clavatus* NRRL 1; | XM_362480; |
| | *Leishmania infantum* JPCM5; | XM_001257861; |
| | *Magnaporthe grisea* 70-15; | D31955; |
| | *Neosartotya fischeri* NRRL 181; | L27126; |
| | *Babesia bovis*; | XM_001612087; |
| | *Sclerotinia sclerotiorum*; | XM_001594710; |
| | *Trichomonas vaginalis*; | XM_001329865; |
| | *Trimastix pyriformis*; | DQ845797; |
| | *Coccidioides immitis*; | XM_001240868; |
| | *Glycine max* (soybean); | L08632; |
| | *Synechococcus sp.* WI! 7805; | ZP_01124109; |
| | *Synechococcus ,vp.* CC9605: | YR_381745; |
| | *Prochlorococcus marinus str.* MIT 9303; | YP001017552; |
| Phosphofructose kinase | *Thermosynechococcus elongatus* BP-1; | GenBank: BAC08868, NP_682106, Q8DJB1; |
| | *Pelotomaculum thermopropionicum* SI; BAF60396, BAF59567; | YP_001212765, YP_001211936, |
| | *Geobacillus kaustophilus* HTA426; | YP_148593, BAD77025; |
| | *Caldicellulosiruptor saccharolyticus* DSM 8903; | ABP67415, YP_001180606, ABP67944; |
| | *Synechococcus elongatus* PCC 7942; | YP_399611; |
| | *Nostoc sp.* PCC 7120;; | NP_485953, Q8YVR1, Q8YKG3; |

TABLE 1-continued lists examples of enzymes for construction of designer oxyphotobacterial ethanol-production pathways.

| Enzyme | Source (Organism) | NCBI/GenBank Accession Number, or Other Citation |
|---|---|---|
| | *Cyanothece sp.* CCY0110; | ZP_01726216; |
| | *Nostoc punctiforme* PCC 73102; | ZP_00111935; |
| | *Synechocystis sp.* PCC 6803; | P72830; |
| | *Anabaena variabilis* ATCC 2941; | YP_323549; |
| | *Synechococcus elongatus*; | Q8DJB1; |
| | *Chlamydomonas reinhardtii*; | JG1 Chlre2 protein ID 159495; |
| | *Arabidopsis thaliana*; | GenBank: NM_001037043; |
| | *Ajellomyces capsulatus*; | XM_001537193; |
| | *Yarrowia lipolytica*; | AY142710; |
| | *Pichia stipitis*; | XM_001382359, XM_001383014; |
| | *Dictyostelium discoideum*; | XM_639070; |
| | *Tetrahymena thermophila*; | XM_001017610; |
| | *Trypanosoma hrucei*; | XM_838827; |
| | *Plasmodium falciparum*; | XM_001347929; |
| | *Spinacia oleracea*; | DQ437575; |
| | *Prosthecochloris aestuarii* DSM 271; | ZP_00593042; |
| | *Streptomyces coelicolor*; | O08333; |
| | *Chlorobium phaeobacteroides* DSM 266; | YP_911069; |
| Fructose-diphosphate aldolase | *Thermosynechococcus elongatus* BP-1; | NP_681166, NP_681166; |
| | *Caldicellulosiruptor saccharolyticus* DSM 8903; | ABP66792, YP_001179983; |
| | *Geobacillus kaustophilus* HTA426; | BAD76171, YP_1 47739, BAD77671; |
| | *Aeropyrum pernix* K1; | BAA78920, NP_146901; |
| | *Synechococcus sp.* RS9917; | ZP_01080195; |
| | *Synechocystis sp.* PCC 6803; | Q55664; |
| | *Synechococcus sp.* CC9902; | YP_376807; |
| | *Synechococcus sp.* BL107; | ZP_01468246; |
| | *Cyanothece sp.* CCY0110; | ZP_01729481; |
| | *Nostoc commune*; | Q9XDP3; |
| | *Anabaena variabilis* ATCC 29413; | YP_322108, YP_323002; |
| | *Chlamydomonas reinhardtii* chloroplast; | X69969; |
| | *Fragaria x ananassa* cytoplasm; | AF308587; |
| | *Homo sapiens*; | NM_005165; |
| | *Babesia hovis*; | XM_001609195; |
| | *Trichomonas vaginalis*; | XM_001312327, |
| | *Pichia stipitis*; | |
| | *Arabidopsis thaliana*; | NM_120057, NM_001036644; |
| | *Blastopirellula marina* DSM 3645; | ZP_01094015; |
| | *Porphyromonas gingival*1s; | P60053; |
| | *Escherichia coil* K12; | P0A991: |
| | *Prochlorococcus marinus str.* NATL IA; | YP_001014643; |
| | *Chlorobium limicola* DSM 245; | ZP_00511285; |
| | *Treponema pallidum*; | O83668; |
| | *Bradyrhizobium japonicum* USDA 110; | NP_768160, NP_769224; |
| | *Rhodobacter sphaeroides*; | P29271; |
| | *Nostoc punctiforme* PCC 73102; | ZP_00110670; |
| Triose phosphate isomerase | *Thermosynechococcus elongatus* BP-1; | GenBank: NP_681756, BAC08518, Q8DKA0: |
| | *Pelotomaculum thermopropionicum* SI; | YP_001213271, BAF60902; |
| | *Geobacillus stearothermophilus*; | CAA46920, P00943: |
| | *Moraxella sp.*; | CAA46921, Q01893; |
| | *Bacillus megalerium*; | AAA73207, P35144: |
| | *Synechococcus elongatus* PCC 7942; | YP_400278; |
| | *Synechococcus sp.* BL107; | ZP_01468206; |
| | *Synechococcus sp.* RS9917; | ZP_01081528; |
| | *Cyanothece sp.* CCY0110; | ZP_01728915; |
| | *Nostoc sp.* PCC 7120; | Q8YP17; |
| | *Anabaena variabilis* ATCC 29413; | YP_323793: |
| | *Synechocystis sp.* PCC 6803 | Q59994; |
| | *Arabidopsis thaliana*; | NM_127687, AF247559; |
| | *Chlamydomonas reinhardtii*; | AY742323; |
| | *Sclerolinia sclerotiorum*; | XM_001587391; |
| | *Chlorella pyrenoidosa*; | AB240149; |
| | *Pichia gitilliermondii*; | XM_001485684; |
| | *Euglena intermedia*; | DQ459379; |
| | *Euglena Tonga*; | AY742325; |
| | *Spinacia oleracea*; | L36387; |
| | *Solanum chacoense*; | AY438596; |
| | *Hordeum vulgare*; | U83414; |
| | *Oryza saliva*; | EF575877; |

TABLE 1-continued lists examples of enzymes for construction of designer oxyphotobacterial ethanol-production pathways.

| Enzyme | Source (Organism) | NCBI/GenBank Accession Number, or Other Citation |
|---|---|---|
| | *Prochlorococcus marinus* str. MIT 9313; | NP_894649, Q7V7D2; |
| | *Prochlorococcus marinus* str. MIT 9515; | YP_001011218; |
| | *Prochlorococcus marinus* str. MIT 9303; | YP_001017403; |
| | *Prosthecochloris aestuarii* DSM 271; | ZP_00593096; |
| | *Clostridium tetania* | Q898R2; |
| Glucose-1-phosphate adenylyltransferase | *Thermosynechococcus elongates* BP-1; | BAC08839, NP_682077; |
| | *Caldicellulosiruptor saccharolyticus* DSM 8903; | YP_001179593, ABP66402; |
| | *Anabaena variabilis* ATCC 29413; | YP_322537; |
| | *Nostoc sp.* PCC 7120; | P30521, NP_488685; |
| | *Anabaena variabilis* ATCC 29413; | Q3MBJ4; |
| | *Synechocystis sp.*; | AAA27275; |
| | *Nostoc punctiforme* PCC 73102; | Q31QN4; |
| | *Synechococcus elongatus* PCC 7942; | ZP_00108334; |
| | *Prochlorococcus marinus* str. MIT 9211; | ZP_01005291; |
| | *Synechococcus sp.* WH 7805; | ZP_01124028; |
| | *Arabidopsis thaliana*; | NM_127730, AY059862; |
| | *Zea mays*; | EF694839, EF694838; |
| | *Chlamydia trachomatis*; | AF087165; |
| | *Solomon tuherosum* (potato); | P55242; |
| | *Shigella flexneri*; | NP_709206; |
| | *Lycopersicon esculentum*; | T07674; |
| | *Agrobacterium tumefacieas* str. C58; | Q8U8L5; |
| | *Bradyrhizobium japonicum* USDA 110; | NP_773098; |
| | *Synechocystis sp.* PCC 6803; | P52415; |
| Glycogen/starch synthase | *Thermosynechococcus elongatus* BP-1; | GenBank: BAC08314, NP_681552, Q8DKU2; |
| | *Pelotomaculum thermopropionicum* SI; | YP_001211882, BAF59513; |
| | *Caldicellulosiruptor saccharolyticus* DSM 8903; | ABP66400, YP_001179591; |
| | *Synechococcus elongatus* PCC 7942; | NC_007604, YP_401535, Q935Y7; |
| | *Nostoc punctilbrme* PCC 73102; | ZP_00106629; |
| | *Anabaena variabilis* ATCC 29413; | YP_325267, Q3M3R4; |
| | *Prochlorococcus marinus* str. MIT 9211; | ZP_01005242; |
| | *Prochlorococcus marinus* str. MIT 9313; | Q7V8F0; |
| | *Chlantydomonas reinhardtii*; | AF026422, DQ019314, AF433156; |
| | *Phaseolus vulgaris*; | AB293998; |
| | *Oryza sativa*; | D16202, AB115917, AY299404; |
| | *Arabidopsis thaliana*; | AK226881, NM_101044; |
| | *Colocasia esculenta*; | AY225862, AY142712; |
| | *Amaranthus cruentus*; | DQ178026; |
| | *Parachlorella kessleri*; | AB232549; |
| | *Triticum aestivum*; | Y16340; |
| | *Sorghum bicolor*; | AF168786; |
| | *Astragalus membranaceus*; | AF097922; |
| | *Perilla fruteseens*; | AF210699; |
| | *Zea mays*; | AF019297; |
| | *Ipomoea batatas*; | AF068834; |
| | *Synechococcus sp.* CC9605; | YP_381436, Q3AKK1; |
| | *Synechococcus sp.* RS9917; | ZP_01080052; |
| | *Synechococcus sp.* WH 8102; | Q7U712; |
| | *Chlorobium ferrooxidans* DSM 13031; | ZP_01386406; |
| | *Pelodicivon luteolum* DSM 273; | Q3B6C3; |
| | *Bradyrhizobium japonicum* USDA 110; | NP_773099; |
| | *Mesorhizohium loci*; | Q985P2; |
| Isoamylase/alpha-amylase | *Bacillus sp.* WPD616; | GenBank: AAX85453; |
| | *Caldicellulosiruptor saccharolvticus* DSM 8903; | ABP68005, ABP66065, YP001181196, ABP66047; |
| | *Geobacillus stearothermophilus*; | 1107236A, P06279; |
| | *Geobacillus kaustophilus* HTA426; | BAD74992, YP_146560; |
| | *Bacillus licheniformis*; | P06278; |
| | *Halothermothrix orenii*; | AAN52525; |
| | *Streptomyces sp.*; | CAA73775; |
| | *Synechococcus elongatus* PCC 6301; | BAD79608, YP_172128; |
| | *Prochlorococcus marinus* str. MIT 9301; | YP_001091732, AB018131; |
| | *Prochlorococcus marinus* str. NATL1A; | YP_001015569, ABM76305; |
| | *Synechococcus sp.* WH 5701; | ZP_01085914, EAQ74243; |
| | *Synechococcus sp.* RS9917; | ZP_01079541, EAQ69517; |
| | *Trichodesmium erythroeum* IMS101; | |
| | *Anabaena variabilis* ATCC 29413; | YP_321946; |
| | *Lyngbya sp.* PCC 8106; | ZP_01623987; |
| | *Hordeum vulgare* aleurone cells; | J04202; |
| | *Trichomonas vaginalis*; | XM_001319100; |

TABLE 1-continued lists examples of enzymes for construction of designer oxyphotobacterial ethanol-production pathways.

| Enzyme | Source (Organism) | NCBI/GenBank Accession Number, or Other Citation |
|---|---|---|
| | *Phanerochaete cluysosporium*; | EF143986; |
| | *Chlamydomonas reinhardtii*; | AY324649; |
| | *Arabidopsis thaliana*; | NM_129551; |
| | *Nodularia spumigena* CCY9414; | ZP_01628466; |
| | *Streptomyces hvidans*; | Q05884; |
| | *Nostoc punctilbrme* PCC 73102; | ZP_00112373; |
| | *Mycobacterium tuberculosis*; | P0A4Y4; |
| | *Prochlorococcus marinus str.* MIT 9515; | YP_001011797; |
| | *Prochlorococcus marinus str.* MIT 9303; | YP_001016586; |
| | *Chlorobium limicola* DSM 245; | ZP_00511777, ZP_00511189; |
| | *Pelodictyon phaeoclathratiforme* BU-1; | ZP_00588326; |
| | *Prosthecochloris vibrioformis* DSM 265; | ZP_00660626; |
| | *Chlorohium phaeobactemides* BSI; | ZP_00530772; |
| 1,4-Alpha-glucan branching enzyme/ glycogen branching enzyme | *Thermosynechococcus clangours* BP-1; | BAC08130, NP 681368; |
| | *Pelotomaculum thermopropionicum* SI; | YP_001212136, BAF59767; |
| | *Caldicellulosiruptor saccharolyticus* DSM 8903; | ABP66403, YP_001179594; |
| | *Sullblobus acidocaldarius*; | BAA11864; |
| | *Sulfolobus shibatae*; | AAM81590; |
| | *Synechococcus elongatus* PCC 6301; | Y13_171174; |
| | *Nodularia spumigena* CCY9414; | ZP01631468, BAD78654; |
| | *Anabaena variahilis* ATCC 29413; | YP_325108; |
| | *Synechococcus sp.* WH 5701; | ZP_01086077; |
| | *Nostoc sp.* PCC 7120; | NP_484756; |
| | *Cyanothece sp.* CCY0110; | ZP_01730776, ZP_01728659, EAZ91920, EAZ89831; |
| | *Synechococcus sp.* RS99/6; | ZP_01472691: |
| | *Synechococcus sp.* BL107; | ZP_01468109; |
| | *Synechocystis sp.* PCC 6803; | NP_442003, BAA10073; |
| | *Nostoc sp.* PCC 7120; | BAB72670; |
| | *Nostoc punctiforme* PCC 73102; | ZP_00110833; |
| 4-Alpha-glucanotransferase | *Thermosynechococcus elongatus* BP-1; | BAC08259, NP_681497; |
| | *Pelotomaculum thermopropionicum* SI; | YP_001212135, BAF59766; |
| | *Lyngbya sp.* PCC 8106; | ZP_01620509; |
| | *Crocosphaera watsonii* WH 8501; | ZP_00514038; |
| | *Anabaena variahilis* ATCC 29413; | YP_322339; |
| | *Synechocystis sp.* PCC 6803; | P72785; |
| | *Nostoc punctiforme* PCC 73102; | ZP_00107363; |
| | *Therms thermophiles*; | 087172; |
| | *Prochlorococcus marinus str.* MIT 9211; | ZP_01005176; |
| | *Prochlorococcus marinas str.* MIT 9515; | YP_001011485; |
| | *Prochlorococcus marinas str.* MIT 9303; | YP_001016993; |
| | *Synechococcus sp.* CC9605; | YP_381918; |
| | *Synechococcus sp.* WH 7805; | Z1301124435; |
| | *Haemophihrs influenzae*; | P45176; |
| | *Bradyrhizobium japonicum* USDA 110: | NP_773405; |
| Beta-amylase | *Thermoanaerobacterium thermosulfurigenes*; | GenBank: AAA23204, P19584; |
| | *Arahidopsis thaliana*; | NM_113297; |
| | *Hordeum vulgare*; | D21349; |
| | *Musa acuminate* | DQ166026; |
| Glycogen/starch phosphorylase | *Thermosynechococcus clangours* BP-1; | BAC09631, BAC08804, BAC08333, NP_682869, NP_682042; |
| | *Caldicellulosiruptor saccharolyticus* DSM 8903; | ABP66399, YP_001179590; |
| | *Synechocystis sp.* PCC 6803; | NP_440871, P73511; |
| | *Synechococcus elongatus* PCC 7942; | AAL26558; |
| | *Lynghya sp.* PCC 8106; | ZP_01621571,ZP_01624055; |
| | *Crocosphaera waisonii* WH 8501; | ZP_00515288; |
| | *Citrus hybrid cultivar* root; | AY098895; |
| | *Solanum tuberosum* chloroplast; | P53535; |
| | *Arahidopsis thaliana*; | NM_113857, NM_114564; |
| | *Triticum aestivum*; | AF275551; |
| | *Ipomoea batalas*; | M64362; |
| | *Anabaena variahilis* ATCC 29413; | YP_323501; |
| | *Thermosivnechococcus elongatus* BP-1; | NP_681571; |
| | *Chlorobium phaeobacteroides* DSM 266; | YP_911074; |
| | *Bradyrhizobium japonicum* USDA 110; | NP_774779; |
| Alpha-glucan phosphorylase | *Caldicellulosiruptor saccharolylicus* DSM 8903; | ABP66068,YP_001179259; |
| | *Anabaena variahilis* ATCC 29413 (*Anabaena flos-aquac* UTEX 1444); | ABA20708, YP_321603, ABA22606, YP_323501; |
| | *Synechococcus sp.* JA-3-3A b; | YP_475530, AB1300267; |
| | *Nodularia .spumigena* CCY9414: | ZP_01631306, EAW44063; |

TABLE 1-continued lists examples of enzymes for construction of designer oxyphotobacterial ethanol-production pathways.

| Enzyme | Source (Organism) | NCBI/GenBank Accession Number, or Other Citation |
| --- | --- | --- |
| Phospho-glucomutase | *Thermosynechococcus elongatus* BP-1; | BAC09528, NP_682766; |
| | *Caldicellulosiruptor saccharolyticus* DSM 8903; | ABP67873, YP_001181064; |
| | *Geo bacillus kaustophilus* HTA426; | BAD74439, YP_146007; |
| | *Cyanothece sp.* CCY0110; | ZP_01730000; |
| | *Trichodesmium erythraeum* IMS101; | YP_720925; |
| | *Prochlorococcus marinus str.* MIT 9211; | ZP_001006218; |
| | *Prochlorococcus marinus str.* MIT 9515; | YP_001010402; |
| | *Prochlorococcus marinus str.* MIT 9303; | YP_001016289; |
| | *Synechococcus sp.* RS9917; | ZP_01081115; |
| | *Oryza sativa* plastid; | AC105932, AF455812; |
| | *Ajellomyces capsulatus*; | XM_001536436; XM_001383281; |
| | *Pichia stipitis*; | XM_001527445; |
| | *Lodderomyces elongisporus*; | XM_749345; |
| | *Aspergillus fumigatus*; | NM_124561, NM_180508, |
| | *Arahidopsis thaliana*; | AY128901; |
| | *Populus tomentosa*; | AY479974; |
| | *Oryza saliva*; | AF455812; |
| | *Zea mays*; | U89342, U89341; |
| | *Gluconacetobacter xylinus*; | P38569; |
| | *Myxococcus xanthus* DK 1622; | YP_633045; |
| | *Anabaena variabilis* ATCC 29413; | YP_322254; |
| | *Agrobacterium tumcfaciens*; | P39671; |
| | *Lyngbya sp.* PCC 8106; | ZP_01621593; |
| | *Synechococcus sp.* RS9917; | ZP_01078899; |
| | *Synechococcus sp.* WH 7805; | ZP_01122702; |
| | *Pelodictyon luteolum* DSM 273; | YP_375637; |
| | *Bradyrhizobium japonicum* USDA 110; | NP_769029, NP_774048; |
| | *Synechococcus sp.* JA-3-3Ab; | YP_473505; |
| | *Synechococcus sp.* CC9605; | YP_380559; |
| Glucokinase | *Thermosynechococcus elongatus* BP-1; | BAC09047, NP_682285, BAC09907, NP_683145; |
| | *Geobacillus kaustophilus* HTA426; | BAD76727, YP_148295; |
| | *Caldicellulostruptor saccharolvlicus* DSM 8903; | ABP66397; |
| | *Synechococcus elongatus* PCC 7942; | ABB56253; |
| | *Anahaena variabilis* ATCC 29413; | YP_322778, YP_321452; |
| | *Crocosphaera watsonii* WH 8501; | ZP_00516463; |
| | *Nostoc sp.* PCC 7120; | NP_487013, P58616; |
| | *Anabaena variahilis* ATCC 29413; | Q3MEM9; |
| | *Ajellomyces capsulatus*; | XM_001541513; |
| | *Pichia stipitis*; | XM_001386652, AY278027; |
| | *Pichia stipitis* CBS 6054; | XM_001386035; |
| | *Thermosynechococcus elongatus*; | NC_004113; |
| | *Babesia Bovis*; | XM_001608698; |
| | *Solanum chacoense*; | DQ177440; |
| | *Oryza saliva*; | DQ116383; |
| | *Arabidopsis thaliana* ; | NM_112895; |
| | *Bacillus halodurans*; | Q9KCZ4; |
| | *Nitrococcus mobilis* Nb-231; | ZP_01128348; |
| | *Prochlorococcus marinus str.* MIT 9211; | ZP_01005229; |
| | *Prochlorococcus marinus str.* MIT 9312; | YP_397093; |
| | *Synechocyslis sp.* PCC 6803; | Q55855; |
| | *Prochlorococcus marinus str.* MIT 9303; | YP_001017866; |
| | *Synechococcus sp.* CC9605; | YP_381345; |
| | *Synechococcus sp.* WH 7805; | ZP_01125095; |
| | *Streptomyces lividans* ; | P0A4E2; |
| Hexose phosphate (glucose-6-phosphate) isomerase | *Thermosynechococcus elongatus* BP-1; | BAC08268, NP_681506; |
| | *Photobacterium profundum* 3TCK; | ZP_01220283, EAS43162; |
| | *Sinorhizobium medicae* WSM419; | YP_001328130, ABR61295; |
| | *Verminephrobacter eiseniae* EF01-2; | YP_996849, ABM57831; |
| | *Acidobacteria bacterium* Ellin345; | ABF39658, YP_589732; |
| | *Vibrio shilonii* AK1; | ZP_01865585, EDL55762; |
| | *Sagiuula stellata* E-37; | ZP_01748199, EBA06106; |
| | *Sinorhizobium meliloti* 1021; | NP_437690 NP_386660; |
| | *Geobacillus kaustophilus* HTA426; | YP_148777; |
| | *Burkhokleria dolosa* AUO158; | EAY70672; |
| | *Burkholderia sp.* 383; | ABB11370, YP_372014, YP_372014; |
| | *Synechococcus elongatus*; | Q8DKY2; |
| | *Prochlorococcus marinus str.* MIT 9515; | YP_001011286; |
| | *Prochlorococcus marinus str.* MIT 9312; | Q31AX5; |
| | *Prochlorococcus marinus str.* MIT 9303; | YP_001017516; |
| | *Synechococcus sp.* CC9605; | Q3AJU7; |
| | *Chlamydomonas reinhardtii*; | JGI Chlre3 protein ID 135202; |

TABLE 1-continued lists examples of enzymes for construction of designer oxyphotobacterial ethanol-production pathways.

| Enzyme | Source (Organism) | NCBI/GenBank Accession Number, or Other Citation |
|---|---|---|
| NADP(H) phosphatase | Saccharomyces cerevisiae; Pichia stipitis; Ajellomyces capsulatus; Spinacia oleracea cytosol; Otyza saliva cytoplasm; Arabidopsis thaliana; Zea mays; Methanococcus jannaschii; | GenBank: M21696: XM_001385873; XM_001537043; T09154; P42862; NM_123638, NM_118595; U17225; The Journal of Biological Chemistry 280 (47): 39200-39207 (2005); |
| NAD kinase | Arthrobacter sp. KM; Arthrobacter sp.; Crocosphaera watsonii WH 8501; Nodularia spumigena CCY9414; Bahesia bovis; Trichomonas vaginalis | P83576, P83575; A59480; GenBank: ZP_00519346, EAM47569; ZP_01632610; XM_001609395; XM_001324239 |

Expression of the Designer Oxyphotobacterial Ethanol-Producing Pathway(s).

Figure 3:
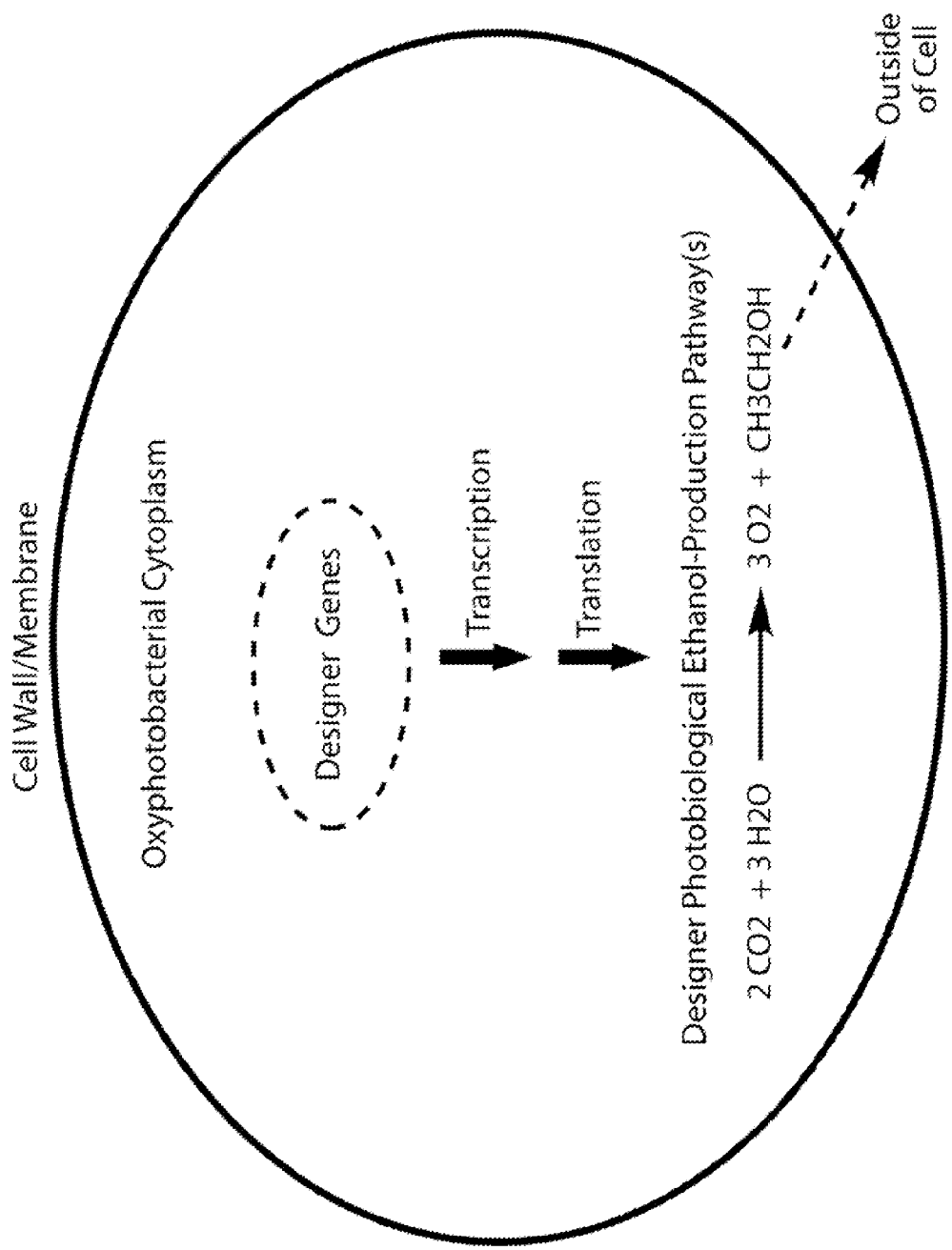
FIG. 3 illustrates a designer oxyphotobacterial cell expressing the designer ethanol-production-pathway genes for photobiological production of ethanol (CH3CH2OH) from carbon dioxide (CO2) and water (H2O).

Some of the designer enzymes discussed above, such as the alcohol dehydrogenase, pyruvate decarboxylase, pyruvate kinase, enolase, phosphoglycerate mutase, and NAD-dependent glyceraldehyde-3-phosphate dehydrogenase, are known to function in the glycolytic pathway, but generally do not function with the Calvin cycle for photosynthetic ethanol production. Therefore, nucleic acids encoding for these enzymes need to be genetically engineered such that the enzymes are properly expressed to directly interact with the Calvin cycle in creating a desirable designer organism of the present invention. Depending on the genetic background of a particular host oxyphotobacterium, some of the enzymes discussed above may exist at some background levels in its native form in a wild-type host oxyphotobacterium. For various reasons including often the lack of their controllability, however, some of the background enzymes may or may not be sufficient to serve as a significant part of the designer ethanol-production pathway(s). Consequently, nucleic acids encoding for these enzymes also need to be genetically engineered with proper sequence modification such that the enzymes are controllably expressed to create a designer ethanol-production pathway. FIG. 3 illustrates how the use of designer genes including their transcription and translation can form the designer enzymes conferring the function of the ethanol-production pathway(s) for photobiological production of ethanol ($CH_3CH_2OH$) from carbon dioxide ($CO_2$) and water ($H_2O$) in a designer oxyphotobacterium.

Use of a Genetic Switch to Control the Expression of Designer Oxyphotobacterial Ethanol-Producing Pathway Another key feature of the invention is the application of a genetic switch to control the expression of designer oxyphotobacterial ethanol-producing pathway(s), as illustrated in FIGS. 1 and 3. This switchability is accomplished through the use of an externally inducible promoter so that the designer oxyphotobacterial transgenes are inducibly expressed under certain specific inducing conditions (FIG. 2A). Preferably, the promoter employed to control the expression of designer oxyphotobacterial genes in a host is originated from the host itself or a closely related organism. The activities and inducibility of a promoter in a host cell can be tested by placing the promoter in front of a reporting gene, introducing this reporter construct into the host cells by any of the known DNA delivery techniques, and assessing the expression of the reporter gene.

With a controllable designer-enzyme expression mechanism, the cells will not only be able to produce ethanol but also to grow and regenerate themselves when they are returned to conditions under which the designer pathway is turned off, such as under aerobic conditions when designer oxygen-sensitive bidirectional hydrogenase (hox) promoter-controlled ethanol-production-pathway genes are used. Designer oxyphotobacteria that contain normal respiratory mechanisms should be able to use the reducing power (NADH) from organic reserves (and/or some exogenous organic substrate such as glucose or acetate) to power the cells immediately after returning to aerobic conditions. Consequently, when the designer oxyphotobacteria cells are returned to aerobic conditions after use under anaerobic conditions for photosynthetic ethanol production, the cells will stop making the ethanol-producing enzymes and start to restore the normal photoautotrophic capability by synthesizing new and functional Calvin-cycle enzymes and producing new cells. Therefore, it is possible to use such genetically engineered designer oxyphotobacteria for repeated cycles of photoautotrophic growth under normal aerobic conditions and efficient production of ethanol directly from $CO_2$ and $H_2O$ under certain specific designer ethanol-producing conditions such as under anaerobic conditions.

Therefore, in one of the various preferred embodiments, the inducible promoter used to control the expression of designer oxyphotobacterial genes is a promoter that is inducible by anaerobiosis, i.e., active under anaerobic conditions but inactive under aerobic conditions. A designer oxyphotobacterium such as a designer cyanobacterium can perform autotrophic photosynthesis using $CO_2$ as the carbon source under aerobic conditions, and when the designer oxyphotobacterium culture is grown and ready for photosynthetic ethanol production, anaerobic conditions will be applied to turn on the promoter and the designer genes to perform photobiological ethanol production.

A number of promoters that become active under anaerobic conditions are suitable for use in the present invention. For example, the promoters of the anaerobic-responsive bidirectional hydrogenase hox genes of *Nostoc* sp. PCC 7120 (GenBank: BA000019), *Prochlorothrix hollandica* (GenBank: U88400; hoxUYH operon promoter), *Synechocystis* sp. strain PCC 6803 (CyanoBase: sll1220 and sll1223), *Synechococcus elongatus* PCC 6301 (CyanoBase: syc1235_c), *Arthrospira platensis* (GenBank: ABC26906), *Cyanothece* sp. CCY0110 (GenBank: ZP_01727419) and *Synechococcus* sp. PCC 7002 (GenBank: AAN03566), which are active under anaerobic conditions but inactive under aerobic conditions (Sjoholm, Oliveira, and Lindblad (2007) "Transcription and regulation of the bidirectional hydrogenase in the Cyanobacterium *Nostoc* sp. strain PCC 7120," *Applied and Environmental Microbiology*, 73(17): 5435-5446), can be used as an effective genetic switch to control the expression of the designer genes in a host oxyphotobacterium, such as *Nostoc* sp. PCC 7120, *Synechocystis* sp. strain PCC 6803, *Synechococcus elongatus* PCC 6301, *Cyanothece* sp. CCY0110, *Arthrospira platensis*, or *Synechococcus* sp. PCC 7002.

In another embodiment, the inducible promoter used in the present invention is a nitrite reductase (nirA) promoter, which is inducible by growth in a medium containing nitrate and repressed in a nitrate-deficient but ammonium-containing medium (Qi, Hao, Ng, Slater, Baszis, Weiss, and Valentin (2005) "Application of the *Synechococcus* nirA promoter to establish an inducible expression system for engineering the *Synechocystis* tocopherol pathway," *Applied and Environmental Microbiology*, 71(10): 5678-5684; Maeda, Kawaguchi, Ohe, and Omata (1998) "cis-Acting sequences required for NtcB-dependent, nitrite-responsive positive regulation of the nitrate assimilation operon in the Cyanobacterium *Synechococcus* sp. strain PCC 7942," *Journal of Bacteriology*, 180(16):4080-4088). Therefore, the nirA promoter sequences can be selected for use to control the expression of the designer genes in a number of oxyphotobacteria according to the concentration levels of nitrate in a culture medium. The nirA promoter sequences that can be selected and modified for use include (but not limited to) the nirA promoters of the following oxyphotobacteria: *Synechococcus elongatus* PCC 6301 (GenBank: AP008231, region 355890-255950), *Synechococcus* sp. (GenBank: X67680.1, D16303.1, D12723.1, and D00677), *Synechocystis* sp. PCC 6803 (GenBank: NP_442378, BA000022, AB001339, D63999-D64006, D90899-D90917), *Anabaena* sp. (GenBank: X99708.1), *Nostoc* sp. PCC 7120 (GenBank: BA000019.2 and AJ319648), *Plectonema boryanum* (GenBank: D31732.1), *Synechococcus elongatus* PCC 7942 (GenBank: P39661, CP000100.1), *Thermosynechococcus elongatus* BP-1 (GenBank: BAC08901, NP_682139), *Phormidium laminosum* (GenBank: CAA79655, Q51879), *Mastigocladus laminosus* (GenBank: ABD49353, ABD49351, ABD49349, ABD49347), *Anabaena variabilis* ATCC 29413 (GenBank: YP_325032), *Prochlorococcus marinus* str. MIT 9303 (GenBank: YP_001018981), *Synechococcus* sp. WH 8103 (GenBank: AAC17122), *Synechococcus* sp. WH 7805 (GenBank: ZP_01124915), and *Cyanothece* sp. CCY0110 (GenBank: ZP_01727861).

In yet another embodiment, an inducible promoter selected for use is the light- and heat-responsive chaperone gene groE promoter, which can be induced by heat and/or light [Kojima and Nakamoto (2007) "A novel light- and heat-responsive regulation of the groE transcription in the absence of Heat shock Regulation at Controlling Inverted Repeat of Chaperone Expression (CIRCE) elements (HrcA) or CIRCE in cyanobacteria," FEBS Letters 581:1871-1880). A number of groE promoters such as the groES and groEL (chaperones) promoters are available for use as an inducible promoter in controlling the expression of the designer ethanol-production-pathway enzyme(s). The groE promoter sequences that can be selected and modified for use in one of the various embodiments include (but not limited to) the groES and/or groEL promoters of the following oxyphotobacteria: *Synechocystis* sp. (GenBank: D12677.1), *Synechocystis* sp. PCC 6803 (GenBank: BA000022.2), *Synechococcus elongatus* PCC 6301 (GenBank: AP008231.1), *Synechococcus* sp (GenBank: M58751.1), *Synechococcus elongatus* PCC 7942 (GenBank: CP000100.1), *Nostoc* sp. PCC 7120 (GenBank: BA000019.2), *Anabaena variabilis* ATCC 29413 (GenBank: CP000117.1), *Anabaena* sp. L-31 (GenBank: AF324500); *Thermosynechococcus elongatus* BP-1 (CyanoBase: tll0185, tll0186), *Synechococcus vulcanus* (GenBank: D78139), *Oscillatoria* sp. NKBG091600 (GenBank: AF054630), *Prochlorococcus marinus* MIT9313 (GenBank: BX572099), *Prochlorococcus marinus* str. MIT 9303 (GenBank: CP000554), *Prochlorococcus marinus* str. MIT 9211 (GenBank: ZP_01006613), *Synechococcus* sp. WH8102 (GenBank: BX569690), *Synechococcus* sp. CC9605 (GenBank: CP000110), *Prochlorococcus marinus* subsp. *marinus* str. CCMP1375 (GenBank: AE017126), and *Prochlorococcus marinus* MED4 (GenBank: BX548174).

Additional inducible promoters that can also be selected for use in the present invention include: for example, the metal (zinc)-inducible smt promoter of *Synechococcus* PCC 7942 (Erbe, Adams, Taylor and Hall (1996) "Cyanobacteria carrying an smt-lux transcriptional fusion as biosensors for the detection of heavy metal cations," *Journal of Industrial Microbiology*, 17:80-83); the iron-responsive idiA promoter of *Synechococcus elongatus* PCC 7942 (Michel, Pistorius, and Golden (2001) "Unusual regulatory elements for iron deficiency induction of the idiA gene of *Synechococcus elongatus* PCC 7942" *Journal of Bacteriology*, 183(17):5015-5024); the redox-responsive cyanobacterial crhR promoter (Patterson-Fortin, Colvin and Owttrim (2006) "A LexA-related protein regulates redox-sensitive expression of the cyanobacterial RNA helicase, crhR", *Nucleic Acids Research*, 34(12):3446-3454); the heat-shock gene hsp16.6 promoter of *Synechocystis* sp. PCC 6803 (Fang and Barnum (2004) "Expression of the heat shock gene hsp16.6 and promoter analysis in the Cyanobacterium, *Synechocystis* sp. PCC 6803," *Current Microbiology* 49:192-198); the small heat-shock protein (Hsp) promoter such as *Synechococcus vulcanus* gene hspA promoter (Nakamoto, Suzuki, and Roy (2000) "Constitutive expression of a small heat-shock protein confers cellular thermotolerance and thermal protection to the photosynthetic apparatus in cyanobacteria," FEBS Letters 483:169-174); the $CO_2$-responsive promoters of oxyphotobacterial carbonic-anhydrase genes (GenBank: EAZ90903, EAZ90685, ZP_01624337, EAW33650, ABB17341, AAT41924, CAO89711, ZP_00111671, YP_400464, AAC44830; and CyanoBase: all2929, PMT1568 slr0051, slr1347, and syc0167_c); the nitrate-reductase-gene (narB) promoters (such as GenBank accession numbers: BAC08907, NP_682145, AAO25121; ABI46326, YP_732075, BAB72570, NP_484656); the green/red light-responsive promoters such as the light-regulated cpcB2A2 promoter of *Fremyella diplosiphon* (Casey and Grossman (1994) "In vivo and in vitro characterization of the light-regulated cpcB2A2 promoter of *Fremyella diplosiphont*" *Journal of Bacteriology*, 176(20):6362-6374); and the UV-light responsive promoters of cyanobacterial genes lexA, recA and ruvB (Domain, Houot, Chauvat, and Cassier-Chauvat (2004) "Function and regulation of the cyanobacterial genes lexA, recA and ruvB: LexA is critical to the survival of cells facing inorganic carbon starvation," *Molecular Microbiology*, 53(1):65-80).

Throughout this specification, when reference is made to inducible promoter, such as, for example, any of the inducible promoters described above, it includes their analogs, functional derivatives, designer sequences, and combinations thereof. A "functional analog" or "modified designer sequence" in this context refers to a promoter sequence derived or modified (by, e.g., substitution, moderate deletion or addition or modification of nucleotides) based on a native promoter sequence, such as those identified hereinabove, that retains the function of the native promoter sequence.

Furthermore, in one of the various embodiments, certain "semi-inducible" or constitutive promoters can also be selected for use in combination of an inducible promoter(s) for construction of a designer oxyphotobacterial ethanol-production pathway(s) as well. For example, the promoters of oxyphotobactcrial Rubisco operon such as the rbcL genes (GenBank: X65960, ZP_01728542, Q3M674, BAF48766, NP_895035, 0907262A; CyanoBase: PMT1205, PMM0550, Pro0551, tll1506, SYNW1718, glr2156, alr1524, slr0009), which have certain light-dependence but could be regarded almost as constitutive promoters, can also be selected for use in combination of an inducible promoter(s) such as the nirA, hox, and/or groE promoters for construction of the designer ethanol-production pathway(s).

DNA Constructs and Transformation into Oxyphotobacterial Cells

DNA constructs are generated in order to introduce designer ethanol-production-pathway genes into a host oxyphotobacterial cell(s). That is, a nucleotide sequence encoding a designer ethanol-production-pathway enzyme is placed in a vector, in an operable linkage to a promoter, preferably an inducible promoter. In a preferred embodiment, nucleic acid constructs are made to have the elements placed in the following 5' (upstream) to 3' (downstream) orientation: an externally inducible promoter, a nucleic acid encoding a designer ethanol-production-pathway enzyme(s), and preferably an appropriate transcription termination sequence. One or more designer genes (DNA constructs) can be placed into one genetic vector. An example of such a construct is depicted in FIG. 2A. As shown in the embodiment illustrated in FIG. 2A, a designer ethanol-production-pathway transgene is a nucleic acid construct comprising: a) a PCR forward primer; b) an externally inducible promoter; c) a designer ethanol-production-pathway-enzyme-encoding sequence with an appropriate transcription termination sequence; and d) a PCR reverse primer.

In accordance with various embodiments, any of the components a) through d) of this DNA construct are adjusted to suit for certain specific conditions. In practice, any of the components a) through d) of this DNA construct are applied in full or in part, and/or in any adjusted combination to achieve more desirable results. For example, when a redox-responsive bidirectional hydrogenase hox promoter is used as an inducible promoter in the designer ethanol-production-pathway DNA construct, a transgenic designer oxyphotobacterium that contains this DNA construct will be able to perform autotrophic photosynthesis using ambient-air $CO_2$ as the carbon source and grows normally under aerobic conditions, such as in an open pond. When the oxyphotobacterial culture is grown and ready for ethanol production, the designer transgene(s) can then be expressed by induction under anaerobic conditions because of the use of the hox promoter. The expression of the designer gene(s) produces a set of designer ethanol-production-pathway enzymes to work with the Calvin cycle in the designer prokaryote's cytoplasm for photobiological ethanol production (FIG. 3).

The two PCR primers are a PCR forward primer (PCR FD primer) located at the beginning (the 5' end) of the DNA construct and a PCR reverse primer (PCR RE primer) located at the other end (the 3' end) as shown in FIG. 2A. This pair of PCR primers is designed to provide certain convenience when needed for relatively easy PCR amplification of the designer DNA construct, which is helpful not only during and after the designer DNA construct is synthesized in preparation for gene transformation, but also after the designer DNA construct is delivered into the genome of a host oxyphotobacterium for verification of the designer gene in the transformants. For example, after the transformation of the designer gene is accomplished in a *Synechococcus elongatus* PCC 7942 host cell using the techniques of electroporation and selection-marker screening, the resulted transformants can be then analyzed by a PCR DNA assay of their DNA using this pair of PCR primers to verify whether the entire designer ethanol-production-pathway gene (the DNA construct) is successfully incorporated into the genome of a given transformant. When the DNA PCR assay of a transformant can generate a PCR product that matches with the predicted DNA size and sequence according to the designer DNA construct, the successful incorporation of the designer gene into the genome of the transformant is verified.

Therefore, the various embodiments also teach the associated method to effectively create the designer transgenic oxyphotobacteria for photobiological ethanol production. This method, in one embodiment, includes the following steps: a) Selecting an appropriate host oxyphotobacterial cells with respect to their genetic backgrounds and special features in relation to photobiological ethanol production; b) Introducing the nucleic acid constructs of the designer genes into the genome of said host oxyphotobacterial cells; c) Verifying the incorporation of the designer genes in the transformed oxyphotobacterial cells with DNA PCR assays using the said PCR primers of the designer DNA construct; d) Measuring and verifying the designer oxyphotobacterium features such as the inducible expression of the designer ethanol-pathway genes for photobiological ethanol production from carbon dioxide and water by assays of mRNA, protein, and ethanol-production characteristics according to the specific designer features of the DNA construct(s) (FIG. 2A).

The above embodiment of the method for creating the designer transgenic oxyphotobacterium for photobiological ethanol production can also be repeatedly applied for a plurality of operational cycles to achieve more desirable results. In various embodiments, any of the steps a) through d) of this method described above are adjusted to suit for certain specific conditions. In various embodiments, any of the steps a) through d) of the method are applied in full or in part, and/or in any adjusted combination.

Examples of designer ethanol-production-pathway genes (DNA constructs) are shown in the sequence listings. SEQ ID NO: 1 presents example 1 for a detailed DNA construct (1360 base pairs (bp)) of a designer NAD-dependent Glyceraldehyde-3-Phosphate-Dehydrogenase gene including: a PCR FD primer (sequence by 1-20), a 88-bp nirA promoter (21-108) selected from the *Synechococcus* sp. strain PCC 7942 (freshwater cyanobacterium) nitrite-reductase-gene promoter sequence, an enzyme-encoding sequence (109-1032) selected and modified from a *Cyanidium caldarium* cytosolic NAD-dependent glyceraldehyde-3-phosphate-dehydrogenase sequence (GenBank accession number: CAC85917), a 308-bp *Synechococcus* sp. strain PCC 7942 rbcS terminator (1033-1340), and a PCR RE primer (1341-1360) at the 3' end. The 88-bp nirA promoter (21-108) is used as an example of an inducible promoter to control the expression of a designer ethanol-production-pathway Glyceraldehyde-3-Phosphate-Dehydrogenase gene (DNA sequence 109-1032). The rbcS terminator (DNA sequence 1033-1340) is employed so that the transcription and translation of the designer gene is properly terminated to produce the designer pathway enzyme (NAD-dependent Glyceraldehyde-3-Phosphate Dehydrogenase) as desired. The resulting Glyceraldehyde-3-Phosphate Dehydrogenase then resumes its function as an enzyme for the designer ethanol-production pathway to work with the oxyphotobacterial Calvin-cycle enzymatic activities in the cytoplasm. The two PCR primers (sequences 1-20 and 1341-1360) are selected and modified from the sequence of a Human actin gene and can be paired with each other. Blasting the sequences against oxyphotobacterial genome databases using the CyanoBase and NCBI/BLAST tools found no homologous sequences of them. Therefore, they can be used as appropriate PCR primers in DNA PCR assays for verification of the designer gene in the transformed oxyphotobacteria.

SEQ ID NO: 2 presents example 2 for a designer Phosphoglycerate Kinase DNA construct (1621 bp) that includes a PCR FD primer (sequence 1-20), a 88-bp Synechococcus sp. strain PCC 7942 nitrite-reductase nirA promoter (21-108), a phosphoglycerate-kinase-encoding sequence (109-1293) selected from a Geobacillus kaustophilus HTA426 phosphoglycerate-kinase sequence (GenBank: BAD77342), a 308-bp Synechococcus sp. strain PCC 7942 rbcS terminator (1294-1601), and a PCR RE primer (1602-1621). This designer DNA construct is quite similar to example 1, SEQ ID NO: 1, except that a phosphoglycerate-kinase-encoding sequence (109-1293) selected from a Geobacillus kaustophilus HTA426 phosphoglyccrate-kinase sequence (GenBank: BAD77342) is used. Therefore, this is also an example where the sequence of an exogenous enzyme such as the thermophilic Geobacillus kaustophilus phosphoglycerate kinase can also be used in construction of a designer ethanol-production pathway gene when appropriate with a proper inducible promoter such as the nirA promoter (DNA sequence 21-108).

SEQ ID NO: 3 presents example 3 for a designer Phosphoglycerate-Mutase DNA construct (1990 bp) that includes a PCR FD primer (sequence 1-20), a 88-bp Synechococcus sp. strain PCC 7942 nitrite-reductase nirA promoter (21-108), a 9-bp Xho I NdeI site (109-117), a phosphoglycerate-mutase encoding sequence (118-1653) selected from the sequences of a Caldicellulosiruptor saccharolyticus DSM 8903 phosphoglycerate mutase (GenBank: ABP67536), a 9-bp XbaI site (1654-1662), a 308-bp Synechococcus sp. strain PCC 7942 rbcS terminator (1663-1970), and a PCR RE primer (1971-1990). This designer DNA construct is also similar to example 1, SEQ ID NO: 1, except that a phosphoglycerate-mutase encoding sequence (118-1653) selected from the sequences of a Caldicellulosiruptor saccharolyticus phosphoglycerate mutase (GenBank: ABP67536) is used and restriction sites of Xho I NdeI and XbaI are added to make the key components such as the designer enzyme sequence (118-1653) as a modular unit that can be flexible replaced when necessary to save the cost of gene synthesis and enhance work productivity. Please note, the enzyme does not have to a Caldicellulosiruptor saccharolyticus phosphoglycerate mutase; a number of phosphoglycerate mutase enzymes (such as those listed in Table 1) including their isozymes, designer modified enzymes, and functional analogs from other sources, such as Pelotomaculum thermopropionicum, Geobacillus kaustophilus, Streptococcus thermophilus, Geobacillus stearothermophilus, Bacillus megaterium, Bacillus subtilis, Zymomonas mobilis, Streptomyces coelicolor, Pseudomonas entomophila, Clavibacter michiganensis, Aspergillus fumigatus, Coccidioides immitis, Leishmania braziliensis, Ajellomyces capsulatus, Monocercomonoides sp., Crocosphaera watsonii, and Aspergillus clavatus, can also be selected for use.

SEQ ID NO: 4 presents example 4 for a designer Enolase DNA construct (1765 bp) that includes a PCR FD primer (sequence 1-20), a 88-bp Synechococcus sp. strain PCC 7942 nitrite reductase nirA promoter (21-108), a 9-bp Xho I NdeI site (109-117), an enolase-encoding sequence (118-1407) selected from the sequence of a Cyanothece sp. CCY0110 enolase (GenBank: ZP_01727912), a 21-bp Lumio-tag-encoding sequence (1408-1428), a 9-bp XbaI site (1429-1437) containing a stop codon, a 308-bp Synechococcus sp. strain PCC 7942 rbcS terminator (1438-1745), and a PCR RE primer (1746-1765) at the 3' end. This DNA construct is similar to example 3, SEQ ID NO: 3, except that an enolase-encoding sequence (118-1407) selected from the sequence of a Cyanothece sp. CCY0110 enolase (GenBank: ZP_01727912) is used and a 21-bp Lumio tag (corresponding to DNA sequence 1408-1428) is added at the C-terminal end of the enolase sequence. The 21-bp Lumio-tag sequence (1408-1428) is employed here to encode a Lumio peptide sequence Gly-Cys-Cys-Pro-Gly-Cys-Cys (SEQ ID NO: 58), which can become fluorescent when treated with a Lumio reagent that is now commercially available from Invitrogen [https://catalog.invitrogen.com]. The Lumio molecular tagging technology is based on an EDT (1,2-ethanedithiol) coupled biarsenical derivative (the Lumio reagent) of fluorescein that binds to an engineered tetracysteine sequence (Keppetipola, Coffman, and et al (2003). Rapid detection of in vitro expressed proteins using Lumio™ technology, Gene Expression, 25.3: 7-11). The tetracysteine sequence consists of Cys-Cys-Xaa-Xaa-Cys-Cys (SEQ ID NO: 59), where Xaa is any non-cysteine amino acid such as Pro or Gly in this example. The EDT-linked Lumio reagent allows free rotation of the arsenic atoms that quenches the fluorescence of fluorescein. Covalent bond formation between the thiols of the Lumio's arsenic groups and the tetracysteines prevents free rotation of arsenic atoms that releases the fluorescence of fluorescein (Griffin, Adams, and Tsien (1998), "Specific covalent labeling of recombinant protein molecules inside live cells", Science, 281:269-272). This also permits the visualization of the tetracysteine-tagged proteins by fluorescent molecular imaging. Therefore, use of the Lumio tag in this manner enables monitoring and/or tracking of the designer Enolase when expressed to verify whether the designer ethanol-production pathway enzyme is indeed expressed in a host organism as designed. The Lumio tag (a short 7 amino acid peptide) that is linked to the C-terminal end of the Enolase protein in this example should have minimal effect on the function of the designer enzyme, but enable the designer enzyme molecule to be visualized when treated with the Lumio reagent. Use of the Lumio tag is entirely optional. If the Lumio tag somehow affects the designer enzyme function, this tag can be deleted in the DNA sequence design.

SEQ ID NO: 5 presents example 5 for a designer Pyruvate Kinase DNA construct (1888 bp) that includes a PCR FD primer (sequence 1-20), a 88-bp Synechococcus sp. strain PCC 7942 nitrite reductase nirA promoter (21-108), a 9-bp Xho I NdeI site (109-117), a Pyruvate-Kinase-encoding sequence (118-1530) selected from a Selenomonas ruminantium Pyruvate Kinase sequence (GenBank: AB037182), a 21-bp Lumio-tag sequence (1531-1551), a 9-bp XbaI site (1552-1560), a 308-bp Synechococcus sp. strain PCC 7942 rbcS terminator (1561-1868), and a PCR RE primer (1869-1888). This DNA construct is similar to example 4, SEQ ID NO: 4, except that a Pyruvate-Kinase-encoding sequence (118-1530) selected from a Selenomonas ruminantium pyruvate-kinase sequence (GenBank: AB037182) is used; this is also another example where a fluorescent molecular Lumio tag (a short 7 amino acid peptide) is used to monitor the expression of a designer enzyme.

SEQ ID NO: 6 presents example 6 for a designer Pyruvate Decarboxylase DNA construct (2188 bp) that includes a PCR FD primer (sequence 1-20), a 88-bp *Synechococcus* sp. strain PCC 7942 nitrite reductase nirA promoter (21-108), a 9-bp Xho I NdeI site (109-117), a Pyruvate-Decarboxylase-encoding sequence (118-1830) selected from the sequences of a *Pichia stipitis* pyruvate-decarboxylase sequence (GenBank: XM_001387668), a 21-bp Lumio-tag sequence (1831-1851), a 9-bp XbaI site (1852-1860), a 308-bp *Synechococcus* sp. strain PCC 7942 rbcS terminator (1861-2168), and a PCR RE primer (2169-2188) at the 3' end. This DNA construct is also similar to example 4, SEQ ID NO: 4, except that a Pyruvate-Decarboxylase-encoding sequence (118-1830) selected from the sequences of a *Pichia stipitis* pyruvate-decarboxylase sequence (GenBank: XM_001387668) is used.

SEQ ID NO: 7 presents example 7 for a designer NAD(P)H-dependent Alcohol-Dehydrogenase DNA construct (1441 bp) that includes a PCR FD primer (sequence 1-20), a 88-bp *Synechococcus* sp. strain PCC 7942 nitrite reductase nirA promoter (21-108), a NAD(P)H dependent Alcohol-Dehydrogenase-encoding sequence (109-1092) selected/modified from the sequence of a NADP-dependent alcohol dehydrogenase from *Synechocystis* sp. PCC 6803 (CyanoBase: slr0942), a 21-bp Lumio-tag sequence (1093-1113), a 308-bp *Synechococcus* sp. strain PCC 7942 rbcS terminator (1114-1421), and a PCR RE primer (1422-1441) at the 3' end.

SEQ ID NO: 8 presents example 8 for a designer NAD(P)H-dependent Alcohol Dehydrogenase DNA construct (1510 bp) that includes a PCR FD primer (sequence 1-20), a 88-bp *Synechococcus* sp. strain PCC 7942 nitrite-reductase nirA promoter (21-108), a NAD(P)H dependent Alcohol-Dehydrogenase-encoding sequence (109-1161) selected/modified (its mitochondrial signal peptide sequence removed) from the sequence of a *Kluyveromyces lactis* alcohol dehydrogenase (ADH3) gene (GenBank: X62766), a 21-bp Lumio-tag sequence (1162-1182), a 308-bp *Synechococcus* sp. strain PCC 7942 rhcS terminator (1183-1490), and a PCR RE primer (1491-1510) at the 3' end. This DNA construct is also similar to example 4, SEQ ID NO: 4, except an NAD(P)H dependent Alcohol-Dehydrogenase-encoding sequence (109-1161) selected/modified (its mitochondrial signal peptide sequence removed) from the sequence of a *Kluyveromyces lactis* alcohol dehydrogenase (ADH3) gene (GenBank: X62766) is used. An NAD(P)H-dependent alcohol-dehydrogenase is capable of using both NADH and/or NADPH in reduction of acetaldehyde to ethanol.

SEQ ID NO: 9 presents example 9 for a designer Phosphofructose-Kinase DNA construct (1405 bp) that includes a PCR FD primer (sequence 1-20), a 88-bp *Synechococcus elongatus* PCC 6301 nirA promoter (21-108), a Phosphofructose-Kinase-encoding sequence (109-1077) selected from a *Caldicellulosiruptor saccharolyticus* DSM 8903 phosphofructose-kinase sequence (GenBank: YP_001180606), a 308-bp *Synechococcus elongatus* PCC 6301 rbcS terminator (1078-1385), and a PCR RE primer (1386-1405).

SEQ ID NO: 10 presents example 10 for a designer Fructose-Diphosphate-Aldolase DNA construct (1408 bp) that includes a PCR FD primer (sequence 1-20), a 88-bp *Synechococcus elongatus* PCC 6301 nirA promoter (21-108), a Fructose-Diphosphate-Aldolase-encoding sequence (109-1080) selected from a *Caldicellulosiruptor saccharolyticus* DSM 8903 fructose-diphosphate-aldolase sequence (GenBank: ABP66792), a 308-bp *Synechococcus elongatus* PCC 6301 rbcS terminator (1081-1388), and a PCR RE primer (1389-1408).

SEQ ID NO: 11 presents example 11 for a designer Triose-Phosphate-Isomerase DNA construct (1204 bp) that includes a PCR FD primer (sequence 1-20), a 88-bp *Synechococcus elongatus* PCC 6301 nirA promoter (21-108), a Triose-Phosphate-Isomerase-encoding sequence (109-876) selected from a *Pelotomaculum thermopropionicum* SI triose-phosphate-isomerase sequence (GenBank: YP_001213271), a 308-bp *Synechococcus elongatus* PCC 6301 rbcS terminator (877-1184), and a PCR RE primer (1185-1204).

Note, SEQ ID NOs: 1-8 represent a set of *Synechococcus* sp. PCC 7942 nirA-promoter-controlled designer ethanol-production-pathway genes that can be used in an oxyphotobacterial host such as *Synechococcus* sp. PCC 7942. Consequently, they together constitute an example of a designer ethanol-production pathway(s) such as the glyceraldehyde-3-phosphate-branched pathway (01-07 as labeled in FIG. 1) in a designer oxyphotobacterium such as a photosynthetic ethanol-producing designer *Synechococcus*. Both SEQ ID NO: 7 and/or 8 encodes a designer NAD(P)H-dependent Alcohol-Dehydrogenase. Therefore, the designer DNA constructs of SEQ ID NO: 3-7 (or 3-6 and 8) can be selected for construction of the 3-phosphoglycerate-branched ethanol-production pathway (03-07 as labeled in FIG. 1) as well. Similarly, the designer DNA constructs of SEQ ID NO: 1-10 can be selected for construction of the fructose-1,6-diphosphate-branched ethanol-production pathway (15-23 in FIG. 1); and the designer DNA constructs of SEQ ID NO: 1-11 can be selected for construction of the fructose-6-phosphate-branched ethanol-production pathway (14-23 in FIG. 1).

SEQ ID NO: 12 presents example 12 for a designer hox-promoter-controlled NADP(H)-dependent Alcohol-Dehydrogenase DNA construct (1865 bp) that includes a PCR FD primer (sequence 1-20), a 172-bp *Nostoc* sp. strain PCC 7120 (*Anabaena* PCC 7120) hox promoter (21-192), an NADP(H)-dependent Alcohol-Dehydrogenase-encoding sequence (193-1413) selected/modified from the sequence of a *Thermococcus* sp. NADP(H)-dependent alcohol dehydrogenase (GenBank: U72646), a 432-bp *Nostoc* sp. strain PCC 7120 gor terminator (1414-1845), and a PCR RE primer (1846-1865) at the 3' end. This designer DNA construct is quite similar to example 1, SEQ ID NO:1, except that a 172-bp *Nostoc* sp. strain PCC 7120 hox promoter (21-192) and an NADP(H)-dependent Alcohol-Dehydrogenase-encoding sequence (193-1413) selected/modified from the sequence of a *Thermococcus* sp. NADP(H)-dependent alcohol dehydrogenase (GenBank: U72646) are used. The designer NADP(H)-dependent alcohol dehydrogenase (GenBank: U72646) is capable of using NADPH in reduction of acetaldehyde to ethanol. Use of the hox promoter (21-192) enables activation of designer enzyme expression by using anaerobic conditions.

With the same principle of using an inducible hox promoter as that shown in SEQ ID NO: 12 (example 12), SEQ ID NOs: 13-16 show designer-gene examples 13-16. Briefly, SEQ ID NO: 13 presents example 13 for a designer hox-promoter-controlled Pyruvate-Decarboxylase DNA construct (2351 bp) that includes a PCR FD primer (sequence 1-20), a 172-bp *Nostoc* sp. strain PCC 7120 hox promoter (21-192), a pyruvate-decarboxylase-encoding sequence (193-1899) selected/modified from the sequence of a *Zymomonas mobilis* pyruvate decarboxylase (GenBank: AB359063), a 432-bp *Nostoc* sp. strain PCC 7120 gor terminator (1900-2331), and a PCR RE primer (2332-2351) at the 3' end.

SEQ ID NO: 14 presents example 14 for a designer hox-promoter-controlled Pyruvate-Kinase DNA construct (2414 bp) that includes a PCR FD primer (sequence 1-20), a 172-bp *Nostoc* sp. strain PCC 7120 hox promoter (21-192), a pyruvate-kinase-encoding sequence (193-1962) selected/modified from the sequence of a *Anabaena variabilis* ATCC 29413 pyruvate kinase (GenBank: YP_322211), a 432-bp *Nostoc* sp. strain PCC 7120 gor terminator (1963-2394), and a PCR RE primer (2395-2414) at the 3' end.

SEQ ID NO: 15 presents example 15 for a designer hox-promoter-controlled Enolase DNA construct (1934 bp) that includes a PCR FD primer (sequence 1-20), a 172-bp *Nostoc* sp. strain PCC 7120 hox promoter (21-192), a pyruvate-kinase-encoding sequence (193-1482) selected/modified from the sequence of an *Anabaena variabilis* ATCC 29413 enolase (GenBank: YP_322211), a 432-bp *Nostoc* sp. strain PCC 7120 gor terminator (1483-1914), and a PCR RE primer (1915-1934) at the 3' end.

SEQ ID NO: 16 presents example 16 for a designer hox-promoter-controlled Phosphoglycerate-Mutase DNA construct (2243 bp) that includes a PCR FD primer (sequence 1-20), a 172-bp *Nostoc* sp. strain PCC 7120 hox promoter (21-192), a phosphoglycerate-mutase-encoding sequence (193-1791) selected/modified from the sequence of a *Crocosphaera watsonii* WH 8501 (*Synechocystis* sp. WH 8501) phosphoglycerate mutase (GenBank: ZP_00518183), a 432-bp *Nostoc* sp. strain PCC 7120 gor terminator (1792-2223), and a PCR RE primer (2224-2243) at the 3' end.

Note, SEQ ID NOs: 12-16 represent a set of hox-promoter-controlled designer ethanol-production-pathway genes that can be used in an oxyphotobacterial host such as *Nostoc* sp. strain PCC 7120. They together constitute another example of a designer ethanol-production pathway such as the 3-phosphoglycerate-branched pathway (03-07 as labeled in FIG. 1) in a designer oxyphotobacterium created from a host cyanobacterium such as *Nostoc* sp. strain PCC 7120.

SEQ ID NO: 17 presents example 17 for a designer groE-promoter-controlled NADPH-dependent Alcohol-Dehydrogenase DNA construct (1663 bp) that includes a PCR FD primer (sequence 1-20), a 241-bp *Synechococcus* sp. strain PCC 7942 light- and heat-responsive groE promoter (21-261), an NADPH-dependent Alcohol-Dehydrogenase-encoding sequence (262-1335) selected/modified from the sequence of a *Pichia stipitis* CBS 6054 NADPH-dependent alcohol dehydrogenase (GenBank: XM_001384263), a 308-bp *Synechococcus* sp. strain PCC 7942 rbcS terminator (1336-1643), and a PCR RE primer (1644-1663) at the 3' end. This designer DNA construct is quite similar to example 1, SEQ ID NO:1, except that a 241-bp light- and heat-responsive groE promoter (21-261) and an NADPH-dependent Alcohol-Dehydrogenase-encoding sequence (262-1335) selected/modified from the sequence of a *Pichia stipitis* CBS 6054 NADPH-dependent alcohol dehydrogenase (GenBank: XM_001384263) are used. The designer NADPH-dependent alcohol dehydrogenase (GenBank: XM_001384263) is capable of using NADPH in reduction of acetaldehyde to ethanol. Use of the groE promoter (21-261) enables activation of designer enzyme expression by using light and/or heat in a culture medium.

With the same principle of using an inducible groE promoter as that shown in SEQ ID NO: 17 (example 17), SEQ ID NOs: 18-21 show designer-gene examples 18-21. Briefly, SEQ ID NO: 18 presents example 18 for a designer groE-promoter-controlled Pyruvate-Decarboxylase DNA construct (2326 bp) that includes a PCR FD primer (sequence 1-20), a 241-bp *Synechococcus* sp. strain PCC 7942 light- and heat-responsive groE promoter (21-261), a pyruvate-decarboxylase-encoding sequence (262-1998) selected/modified from the sequence of a *Lodderomyces elongisporus* NRRL YB-4239 pyruvate decarboxylase (GenBank: XM_001526215), a 308-bp *Synechococcus* sp. strain PCC 7942 rbcS terminator (1999-2306), and a PCR RE primer (2307-2326) at the 3' end.

SEQ ID NO: 19 presents example 19 for a designer groE-promoter-controlled Pyruvate-Kinase DNA construct that includes a PCR FD primer (sequence 1-20), a 134-bp *Synechococcus* sp. strain PCC 7942 light- and heat-responsive groE promoter (21-154), a pyruvate-kinase-encoding sequence (155-1591) selected/modified from the sequence of a *Thermococcus kodakarensis* pyruvate kinase (GenBank: AB098541), a 308-bp *Synechococcus* sp. strain PCC 7942 rbcS terminator (1592-1899), and a PCR RE primer (1900-1919).

SEQ ID NO:20 presents example 20 for a designer groE-promoter-controlled Enolase DNA construct (1778 bp) that includes a PCR FD primer (sequence 1-20), a 134-bp *Synechococcus* sp. strain PCC 7942 light- and heat-responsive groE promoter (21-154), an enolase-encoding sequence (155-1450) selected/modified from the sequence of a thermophilic *Geobacillus kaustophilus* HTA426 enolase (GenBank: BAD77339), a 308-bp *Synechococcus* sp. strain PCC 7942 rbcS terminator (1451-1758), and a PCR RE primer (1759-1778) at the 3' end.

SEQ ID NO:21 presents example 21 for a designer groE-promoter-controlled Phosphoglycerate-Mutase DNA construct (1178 bp) that includes a PCR FD primer (sequence 1-20), a 134-bp *Synechococcus* sp. strain PCC 7942 light- and heat-responsive groE promoter (21-154), a phosphoglycerate-mutase-encoding sequence (155-850) selected/modified from the sequence of a *Streptococcus thermophilus* LMG 18311 phosphoglycerate mutase (GenBank: AF442555), a 308-bp *Synechococcus* sp. strain PCC 7942 rbcS terminator (851-1158), and a PCR RE primer (1159-1178) at the 3' end.

Note, SEQ ID NOs: 17-21 represent a set of groE-promoter-controlled designer ethanol-production-pathway genes that can be used in an oxyphotobacterial host cell such as *Synechococcus* sp. strain PCC 7942; they together constitute another example of a designer ethanol-production pathway such as the 3-phosphoglycerate-branched pathway (03-07 as labeled in FIG. 1) in a designer oxyphotobacterium created from a host cyanobacterium such as *Synechococcus* sp. PCC 7942.

SEQ ID NOs:22-26 show examples 22-26 for another set of designer-ethanol-production-pathway-enzyme DNA constructs using a *Synechococcus* sp. PCC 7002 rbcL promoter in combination with a nirA promoter. Briefly, SEQ ID NO: 22 presents example 22 for a designer rbcL-promoter-controlled Phosphoglycerate-Mutase DNA construct (2361 bp) that includes a PCR FD primer (sequence 1-20), a 621-bp rbcL promoter (21-641) selected/modified from *Synechococcus* sp. PCC 7002 gene rbcL promoter region (GenBank: D13971 region 345-962), a phosphoglycerate-mutase-encoding sequence (642-2177) selected/modified from the sequence of a thermophilic *Geobacillus stearothermophilus* phosphoglycerate mutase (GenBank: AF120091), a 164-bp *Synechococcus* sp. PCC 7002 gene rbcS terminator (2178-2341), and a PCR RE primer (2342-2361) at the 3' end.

SEQ ID NO: 23 presents example 23 for a designer rbcL-promoter-controlled Enolase DNA construct (2124 bp) that includes a PCR FD primer (sequence 1-20), a 621-bp *Synechococcus* sp. PCC 7002 rbcL promoter (21-641), a Enolase-encoding sequence (642-1940) selected/modified from the sequence of a thermophilic *Aeropyrum pernix* K1 enolase (GenBank: BAA81473), a 164-bp *Synechococcus* sp. PCC 7002 gene rbcS terminator (1941-2104), and a PCR RE primer (2105-2124) at the 3' end.

SEQ ID NO: 24 presents example 24 for a designer rbcL-promoter-controlled Pyruvate-Kinase DNA construct (2577 bp) that includes a PCR FD primer (sequence 1-20), a 621-bp *Synechococcus* sp. PCC 7002 rhcL promoter (21-641), a Pyruvate-Kinase-encoding sequence (642-2393) selected/modified from a thermophilic *Caldicellulosiruptor saccharolyticus* DSM 8903 pyruvate-kinase sequence (GenBank: ABP67416), a 164-bp *Synechococcus* sp. PCC 7002 gene rbcS terminator (2394-2557), and a PCR RE primer (2558-2577).

SEQ ID NO: 25 presents example 25 for a designer nirA-promoter-controlled Pyruvate-Decarboxylase DNA construct (2083 bp) that includes a PCR FD primer (sequence 1-20), a 88-bp nirA promoter (21-108) of *Plectonema boryanum*, a Pyruvate-Decarboxylase-encoding sequence (109-1899) selected/modified from a *Pichia stipitis* CBS 6054 pyruvate-decarboxylase sequence (GenBank: XM_001387532), a 164-bp *Synechococcus* sp. PCC 7002 gene rbcS terminator (1900-2063), and a PCR RE primer (2064-2083).

SEQ ID NO: 26 presents example 26 for a designer rbcL-promoter-controlled NAD(P)H-dependent Alcohol-Dehydrogenase DNA construct (1950 bp) that includes a PCR FD primer (sequence 1-20), a 621-bp *Synechococcus* sp. PCC 7002 rbcL promoter (21-641), a NAD(P)H-dependent Alcohol-Dehydrogenase-encoding sequence (642-1766) selected/modified from a *Kluyveromyces lactis* NRRL Y-1140 NAD (P)H-dependent alcohol-dehydrogenase sequence (GenBank: XM_451932), a 164-bp *Synechococcus* PCC 7002 gene rbcS terminator (1767-1930), and a PCR RE primer (1931-1950).

Since SEQ ID NOs:22-26 represent a set of rbcL- and nirA-promoter-controlled designer ethanol-production-pathway genes that can be used in a cyanobacteria host such as *Synechococcus* sp. PCC 7002, they also constitute an example of a designer ethanol-production pathway(s) such as the 3-phosphoglycerate-branched pathway (numerically labeled as 03-07 in FIG. 1) in a designer oxyphotobacterium such as a photosynthetic ethanol-producing designer *Synechococcus* in one of the various embodiments for photobiological ethanol production.

SEQ ID NOs:27-33 show examples 27-33 for yet another set of designer-ethanol-production-pathway-enzyme DNA constructs using a 137-bp *Synechocystis* sp. PCC 6803 groE promoter in combination with a nirA promoter. Since this set of *Synechocystis* sp. PCC 6803 groE- and nirA-promoter-controlled designer genes can be used in a *Synechocystis* host such as *Synechocystis* sp. PCC 6803, they also constitute an example of a designer ethanol-production pathway(s) such as the glyceraldehyde-3-phosphate-branched ethanol-production pathway (numerically labeled 01-07 in FIG. 1) in yet another designer cyanobacterium, for example, a designer *Synechocystis* in one of the various embodiments. Briefly, SEQ ID NO: 27 presents example 27 for a *Synechocystis* sp. PCC 6803 groE-promoter-controlled designer NAD-dependent Glyceraldehyde-3-Phosphate-Dehydrogenase DNA construct (1521 bp) that includes a PCR FD primer (sequence 1-20), a 137-bp *Synechocystis* sp. PCC 6803 heat- and light-responsive groE promoter (21-157), an NAD-dependent Glyceraldehyde-3-Phosphate-Dehydrogenase-encoding sequence (158-1092) selected and modified from a *Blastochloris viridis* NAD-dependent glyceraldehyde-3-phosphate-dehydrogenase sequence (GenBank accession number: CAC80993), a 409-bp *Synechocystis* sp. PCC 6803 rbcS terminator (1093-1501), and a PCR RE primer (1502-1521).

SEQ ID NO: 28 presents example 28 for a designer groE-promoter-controlled Phosphoglycerate-Kinase DNA construct (1768 bp) that includes a PCR FD primer (sequence 1-20), a 137-bp *Synechocystis* sp. PCC 6803 heat- and light-responsive groE promoter (21-157), a Phosphoglycerate-Kinase-encoding sequence (158-1339) selected and modified from a *Pelotomaculum thermopropionicum* SI phosphoglycerate-kinase sequence (GenBank: BAF60903), a 409-bp *Synechocystis* sp. PCC 6803 rbcS terminator (1340-1748), and a PCR RE primer (1749-1768).

SEQ ID NO: 29 presents example 29 for a designer groE-promoter-controlled Phosphoglycerate-Mutase DNA construct (1225 bp) that includes a PCR FD primer (sequence 1-20), a 137-bp *Synechocystis* sp. PCC 6803 groE promoter (21-157), a Phosphoglycerate-Mutase-encoding sequence (158-796) selected from a *Geobacillus kaustophilus* HTA426 phosphoglycerate-mutase sequence (GenBank: BAD75751), a 409-bp *Synechocystis* sp. PCC 6803 rbcS terminator (797-1205), and a PCR RE primer (1206-1225).

SEQ ID NO: 30 presents example 30 for a designer groE-promoter-controlled Enolase DNA construct (1885 bp) that includes a PCR FD primer (sequence 1-20), a 137-bp *Synechocystis* sp. PCC 6803 groE promoter (21-157), an Enolase-encoding sequence (158-1456) selected from a *Aeropyrum pernix* K1 enolase sequence (GenBank: BAA81473), a 409-bp *Synechocystis* sp. PCC 6803 rbcS terminator (1457-1865), and a PCR RE primer (1866-1885).

SEQ ID NO: 31 presents example 31 for a designer groE-promoter-controlled Pyruvate-Kinase DNA construct (2350 bp) that includes a PCR FD primer (sequence 1-20), a 137-bp *Synechocystis* sp. PCC 6803 groE promoter (21-157), a Pyruvate-Kinase-encoding sequence (158-1921) selected from a *Geobacillus kaustophilus* HTA426 pyruvate-kinase sequence (GenBank: BAD77024), a 409-bp *Synechocystis* sp. PCC 6803 rbcS terminator (1922-2330), and a PCR RE primer (2331-2350).

SEQ ID NO: 32 presents example 32 for a designer groE-promoter-controlled Pyruvate-Decarboxylase DNA construct (2245 bp) that includes a PCR FD primer (sequence 1-20), a 137-bp *Synechocystis* sp. PCC 6803 groE promoter (21-157), a Pyruvate Decarboxylase-encoding sequence (158-1816) selected from a *Sarcina ventriculi* pyruvate-decarboxylase sequence (GenBank: AAL18557), a 409-bp *Synechocystis* sp. PCC 6803 rbcS terminator (1817-2225), and a PCR RE primer (2226-2245).

SEQ ID NO: 33 presents example 33 for a designer nirA-promoter-controlled NAD(P)H-dependent Alcohol-Dehydrogenase DNA construct (1594 bp) that includes a PCR FD primer (sequence 1-20), a 89-bp *Synechocystis* sp. strain PCC 6803 nitrite-reductase nirA promoter (21-109), a NAD(P)H-dependent Alcohol-Dehydrogenase-encoding sequence (110-1165) selected from a *Kluyveromyces lactic* NAD(P)H-dependent alcohol-dehydrogenase sequence (GenBank: X62767), a 409-bp *Syneehocystis* sp. PCC 6803 rbcS terminator (1166-1574), and a PCR RE primer (1575-1594).

SEQ ID NOs:34-38 present examples 34-38 for a set of designer thermotolerant-enzyme DNA constructs using thermophilic host *Thermosynechococcus elongatus* BP-1 groE promoter and rbcS terminator. Briefly, SEQ ID NO: 34 presents example 34 for a designer groE-promoter-controlled thermotolerant Phosphoglycerate-Mutase DNA construct (2212 bp) that includes a PCR FD primer (sequence 1-20), a 134-bp light- and heat-responsive *Thermosynechococcus elongatus* BP-1 groE promoter (21-154), a thermotolerant phosphoglycerate-mutase-encoding sequence (155-1792) selected from the sequence of a *Pelotomaculum thermopropionicum* SI phosphoglycerate mutase (GenBank: YP_001213270), a 400-bp *Thermosynechococcus elongatus* BP-1 rbcS terminator (1793-2192), and a PCR RE primer (2193-2212) at the 3' end.

SEQ ID NO: 35 presents example 35 for a designer groE-promoter-controlled Enolase DNA construct (1882 bp) that includes a PCR FD primer (sequence 1-20), a 134-bp lightand heat-responsive *Thermosynechococcus elongatus* BP-1 groE promoter (21-154), a thermotolerant pyruvate-kinase-encoding sequence (155-1462) selected/modified from the sequence of a thermophilic *Caldicellulosiruptor saccharolyticus* DSM 8903 pyruvate kinase (GenBank: ABP67535), a 400-bp *Thermosynechococcus elongatus* BP-1 rbcS terminator (1463-1862), and a PCR RE primer (1863-1882).

SEQ ID NO: 36 presents example 36 for a designer groE-promoter-controlled thermotolerant Pyruvate-Kinase DNA construct (1918 bp) that includes a PCR FD primer (sequence 1-20), a 134-bp light- and heat-responsive *Thermosynechococcus elongatus* BP-1 groE promoter (21-154), a thermotolerant pyruvate-kinase-encoding sequence (155-1498) selected/modified from the sequence of a *Thermoproteus tenax* pyruvate kinase (GenBank: AF065890), a 400-bp *Thermosynechococcus elongatus* BP-1 rbcS terminator (1499-1898), and a PCR RE primer (1899-1918) at the 3' end.

SEQ ID NO: 37 presents example 37 for a designer groE-promoter-controlled thermotolerant Pyruvate-Decarboxylase DNA construct (2281 bp) that includes a PCR FD primer (sequence 1-20), a 134-bp light- and heat-responsive *Thermosynechococcus elongatus* BP-1 groE promoter (21-154), a thermotolerant pyruvate-decarboxylase-encoding sequence (155-1861) selected/modified from the sequence of a thermotolerant *Zymomonas mobilis* pyruvate decarboxylase (GenBank: BAF76067), a 400-bp *Thermosynechococcus elongatus* BP-1 rbcS terminator (1862-2261), and a PCR RE primer (2262-2281) at the 3' end.

SEQ ID NO: 38 presents example 38 for a designer groE-promoter-controlled thermotolerant and NADP(H)-dependent Alcohol-Dehydrogenase DNA construct (1795 bp) that includes a PCR FD primer (sequence 1-20), a 134-bp light- and heat-responsive *Thermosynechococcus elongatus* BP-1 groE promoter (21-154), an NADPH-dependent Alcohol-Dehydrogenase-encoding sequence (155-1375) selected/modified from the sequence of a *Thermococcus* sp. NADP(H)-dependent alcohol dehydrogenase (GenBank: U72646), a 400-bp *Thermosynechococcus elongatus* BP-1 rbcS terminator (1376-1775), and a PCR RE primer (1776-1795) at the 3' end.

Since SEQ ID NOs: 34-38 represent a set of *Thermosynechococcus elongatus* BP-1 groE promoter-controlled and nirA-promoter-controlled ethanol-production-pathway genes that can be used in a host *Thermosynechococcus elongatus* BP-1 and related thermophilic cyanobacterial species, they also constitute an example of a designer ethanol-production pathway(s) such as the 3-phosphoglycerate-branched pathway (03-07 as labeled in FIG. 1) in photosynthetic ethanol-producing designer thermophilic oxyphotobacteria including designer cyanobacteria such as a designer *Thermosynechococcus* in one of the various embodiments for photobiological ethanol production.

The nucleic acid constructs, such as those presented in the examples above, may include additional appropriate sequences, for example, a selection marker gene, and an optional biomolecular tag sequence (such as the Lumio tag described in example 4, SEQ ID NO: 4). Selectable markers that can be selected for use in the constructs include markers conferring resistances to kanamycin, neomycin, hygromycin, spectinomycin, streptomycin, bleomycin, erythromycin, sulfonyl urea, among others, all of which have been cloned and are available to those skilled in the art. Alternatively, the selective marker is a nutrition marker gene that can complement a deficiency in the host oxyphotobacterium.

Nucleic acid constructs carrying designer genes can be delivered into a host oxyphotobacterium such as a cyanobacterial cell using the available gene-transformation techniques, such as electroporation, PEG induced uptake, and ballistic delivery of DNA, conjugation and natural transformation. For the purpose of delivering a designer construct into the host organism cells, the techniques of electroporation, glass bead, and biolistic genegun can be selected for use as preferred methods. Transformants can be identified and tested based on routine techniques.

The various designer genes can be introduced into host cells sequentially in a step-wise manner, or simultaneously using one construct or in one transformation. For example, the five DNA constructs shown in SEQ ID NO: 12-16 for the five-enzyme ethanol-production pathway (that consists of alcohol dehydrogenase 07, pyruvate decarboxylase 06, pyruvate kinase 05, enolase 04, and phosphoglycerate mutase 03, as shown with the numerical labels in FIG. 1) can be placed into one genetic vector such as pCER20, pPT6803-1, pECAN8, and pMA4. Therefore, by use of a plasmid in this manner, it is possible to deliver all the five DNA constructs (designer genes) into an oxyphotobacterium host in one transformation for expression of the 3-phosphoglycerate-branched ethanol-production pathway (03-07 as labeled in FIG. 1). When necessary, a transformant containing the five DNA constructs can be further transformed to get more designer genes into its genomic DNA with an additional selection marker such as streptomycin. By using combinations of various designer-enzymes DNA constructs such as those presented in SEQ ID NO: 1-38 in gene transformation with appropriate host oxyphotobacteria, various ethanol-production pathways can be constructed in various host oxyphotobacteria including both cyanobacteria (such as *Synechococcus* sp. PCC 7942, *Synechococcus elongatus* PCC 6301, *Nostoc* sp. strain PCC 7120, *Synechococcus* sp. PCC 7002 *Synechocystis* sp. PCC 6803, and *Thermosynechococcus elongatus* BP-1) and oxychlorobacteria (such as *Prochlorococcus marinus* MED4 and *Prochlorococcus marinus* MIT9313). As mentioned before, the designer DNA constructs of SEQ ID NO: 1-7 (or 8) can be selected for construction of the glyceraldehydes-3-phosphate-branched ethanol-production pathway (01-07 as labeled in FIG. 1); The designer DNA constructs of SEQ ID NOs: 1-10 can be selected for construction of the fructose-1,6-diphosphate-branched ethanol-production pathway (15-23 in FIG. 1); and the designer DNA constructs of SEQ ID NOs: 1-11 can be selected for construction of the fructose-6-phosphate-branched ethanol-production pathway (14-23 in FIG. 1).

Additional Host Modifications to Enhance Photobiological Ethanol Production

A Designer Oxyphotobacterial NADPH/NADH Conversion Mechanism

According to the photosynthetic ethanol production pathway(s) illustrated in FIG. 1, to produce one molecule of ethanol from $2CO_2$ and $3H_2O$ is likely to require 8 ATP and 6 NADPH, both of which are generated by photosynthetic water splitting and photophosphorylation across the oxyphotobacterial thylakoid membrane. In order for the 3-phosphoglycerate-branched ethanol-production pathway (03-07 in FIG. 1) to operate, it is a preferred practice to use an alcohol dehydrogenase 07 that can use NADPH that is generated by the photo-driven electron transport process. The NADP(H)-dependent alcohol dehydrogenases (NCBI GenBank accession numbers: XM_001384263, ABN66271, EAZ62840, XM_001386628, U72646, M88600, Q04894 and P25377) are examples of an alcohol dehydrogenase that can use NADPH. The *Kluyveromyces lactis* mitochondrial K1ADH III enzyme (GenBank accession number: XM_451932) is an example of an alcohol dehydrogenase that is capable of accepting either NADP(H) or NAD(H). Such an alcohol dehydrogenase that can use both NADPH and NADH (i.e., NAD(P)H) can also be selected for use in this 3-phosphoglycerate-branched ethanol-production pathway (03-07 in FIG. 1) and any of the other designer ethanol-production pathway(s) (such as 01-07 and/or 15-07 in FIG. 1) as well. The use of NADPH-dependent and/or NAD(P)H-dependent alcohol dehydrogenases enables the designer ethanol-production pathway(s) to utilize the reducing power NADPH that can be generated directly by the photosynthetic water-oxidizing/oxygen-evolving electron-transport process.

When an alcohol dehydrogenase that can only use NADH is employed, it may require an NADPH/NADH conversion mechanism in order for the 3-phosphoglycerate-branched ethanol-production pathway (03-07 in FIG. 1) to operate efficiently. The reason is that the photosynthetic water-splitting electron-transport system can produce only NADPH but not NADH. If an NADH-requiring alcohol dehydrogenase (such as the *Saccharomyces cerevisiae* NADH-dependent alcohol dehydrogenase 1 (GenBank: CAA99098), the *Entamoeba histolytica* NADH-dependent alcohol dehydrogenase (GenBank: D49910), or the *Zymomonas mobilis* alcohol dehydrogenase II (GenBank: M15394, NADH-dependent)) is used, the 3-phosphoglycerate-branched ethanol-production pathway would not be able to use the reducing power NADPH that the photosynthetic water-oxidizing/oxygen-evolving electron-transport process can directly supply. Depending on the genetic backgrounds of a host oxyphotobacterium, there may or may not be any effective mechanism for conversion between NADPH and NADH during photosynthesis. Although their fermentative metabolism could generate some NADH from organic reserves, wild-type oxyphotobacteria including both cyanobacteria and oxychlorobacteria usually possess no known mechanism to convert photosynthetically-generated NADPH into NADH during photosynthesis. The wild-type fermentative metabolism is often slow and suppressed during oxygenic photosynthesis. Therefore, according to the understanding of this embodiment, one could predict that if a NADH-requiring alcohol dehydrogenase such as *Zymomonas mobilis* alcohol dehydrogenase II is used, a 3-phosphoglycerate-branched ethanol-production pathway (03-07 in FIG. 1) would either not be able to work or be able to function only with very slow rate because of the limited NADH supply. This prediction has recently been experimentally demonstrated in some extent. Using a shuttle vector (pCB4) containing the coding sequences of pyruvate decarboxylase and alcohol dehydrogenase II from *Zymomonas mobilis*, the two *Zymomonas* enzymes were expressed in *Synechococcus* sp. strain PCC 7942 at high level (Deng and Coleman (1999) "Ethanol synthesis by genetic engineering in cyanobacteria," *Applied and Environmental Microbiology*, 65(2):523-528); however, as expected, the ethanol-production rate of the genetically modified cyanobacteria having the *Zymomonas mobilis* pyruvate decarboxylase and alcohol dehydrogenase II is indeed quite limited (about 1.7 µmol ethanol per mg of chlorophyll per hour, see U.S. Pat. No. 6,699,696 B2). This type of genetically-modified cyanobacteria with *Zymomonas mobilis* pyruvate decarboxylase and alcohol dehydrogenase II could accumulate ethanol, after a 5-day fermentation, to a concentration level of about 10 mM (0.047% ethanol weight) in the culture medium (PCT publication number: WO07084477), which is significantly lower than the maximum concentration of 1% (w/w) ethanol that certain wild-type green-alga culture could reach (Hirano, Ueda, Hirayama, and Ogushi (1997) "$CO_2$ fixation and ethanol production with microalgal photosynthesis and intracellular anaerobic fermentation" *Energy* 22(2/3):137-142).

Consequently, in order for a 3-phosphoglycerate-branched ethanol-production pathway (03-07 in FIG. 1) to work efficiently, it may be crucial to use either an NADPH-to-NADH conversion mechanism or an alcohol dehydrogenase that can use NADPH. In one of the embodiments, therefore, an effective NADPH/NADH conversion mechanism is provided by using a pair of glyceraldehyde-3-phosphate dehydrogenases: one NADPH-dependent and the other NAD-dependent. The NADPH-dependent glyceraldehyde-3-phosphate dehydrogenase catalyzes the following reaction that uses NADPH in reducing 1,3-Diphosphoglycerate (1,3-DiPGA) to 3-Phosphoglyaldehyde (3-PGAld) and inorganic phosphate (Pi):

$$1,3\text{-DiPGA} + NADPH + H^+ \rightarrow 3\text{-PGAld} + NADP^+ + Pi \quad [3]$$

The NAD-dependent glyceraldehyde-3-phosphate dehydrogenase catalyzes the oxidation of 3-PGAld by $NAD^+$ back to 1,3-DiPGA:

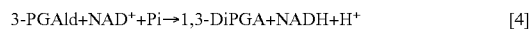
$$3\text{-PGAld} + NAD^+ + Pi \rightarrow 1,3\text{-DiPGA} + NADH + H^+ \quad [4]$$

Figure 2B:
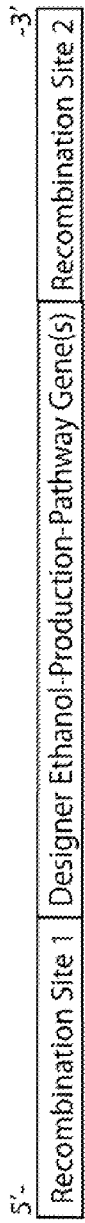
FIG. 2B presents a DNA construct for a designer oxyphotobacterial ethanol-production-pathway gene(s) with two recombination sites for integrative transformation in oxyphotobacteria such as cyanobacteria.
Figure 2C:
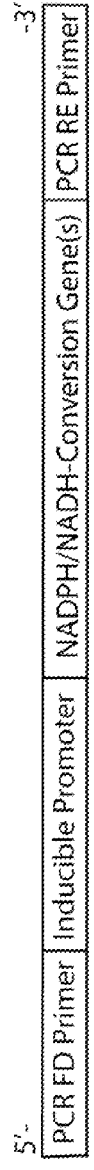
FIG. 2C presents a DNA construct for oxyphotobacterial NADPH/NADH-conversion designer gene(s) for NADPH/NADH inter-conversion.

The net result of the enzymatic reactions [3] and [4] is the conversion of NADPH to NADH. That is, the use of this pair of NADPH-dependent vs. NAD-dependent glyceraldehyde-3-phosphate dehydrogenases in the oxyphotobacterial cytoplasm constitutes a cyclic "transhydrogenase" redox-shuttle function that can effectively convert NADPH to NADH, which the NADH-requiring alcohol dehydrogenases such as the *Zymomonas mobilis* alcohol dehydrogenase II can use in reducing acetaldehyde to ethanol. Therefore, in one of the various embodiments, the NADPH/NADH-conversion designer genes in the DNA construct of FIG. 2B are a designer NADPH-dependent glyceraldehyde-3-phosphate-dehydrogenase gene and a designer NAD-dependent glyceraldehyde-3-phosphate-dehydrogenase gene for expression in host oxyphotobacteria to confer this NADPH/NADH-conversion mechanism for enhanced ethanol production.

When this designer cyclic NADPH/NADH redox-shuttle mechanism is employed, the 3-phosphoglycerate-branched ethanol-production pathway (03-07 in FIG. 1) can now use an NADH-requiring alcohol dehydrogenase such as the *Zymomonas mobilis* alcohol dehydrogenase as well. In this case, the 3-phosphoglycerate-branched ethanol-production pathway can now comprise the following seven enzymes: an NADPH-dependent glyceraldehyde-3-phosphate-dehydrogenase, an NAD-dependent glyceraldehyde-3-phosphate-dehydrogenase, a phosphoglycerate mutase, an enolase, a pyruvate kinase, a pyruvate decarboxylase, and an NADH-dependent alcohol dehydrogenase. As explained in reactions [3] and [4], the NADPH-dependent glyceraldehyde-3-phosphate-dehydrogenase and the NAD-dependent glyceraldehyde-3-phosphate-dehydrogenase together serve as the cyclic "transdehydrogenase" redox-shuttle mechanism to convert NADPH to NADH which an NADH-specific alcohol dehydrogenase such as the *Zymomonas mobilis* alcohol dehydrogenase can use in the 3-phosphoglycerate-branched ethanol-production pathway (03-07 in FIG. 1) for photobiological ethanol production. Note, a designer phosphoglycerate kinase is not required here. Therefore, this cyclic NADPH/NADH redox-shuttle-coupled 3-phosphoglycerate-branched ethanol-production pathway (03-07 in FIG. 1) differs from the glyceraldehyde-3-phosphate-branched ethanol-production pathway (01-07 in FIG. 1) that includes a designer phosphoglycerate kinase.

In certain host oxyphotobacteria, the native NADPH-dependent glyceraldehyde-3-phosphate-dehydrogenase activity which functions as part of the Calvin cycle is expressed naturally at such a sufficiently high level that an additional designer NADPH-dependent glyceraldehyde-3-phosphate dehydrogenase may or may not be necessary. Consequently, use of a designer NAD-dependent glyceraldehyde-3-phosphate dehydrogenase with the native NADPH-dependent glyceraldehyde-3-phosphate dehydrogenase in certain host oxyphotobacterium can also confer the needed designer cyclic NADPH/NADH conversion redox-shuttle mechanism. Therefore, in one of the various embodiments, a cyclic NADPH/NADH redox-shuttle-coupled 3-phosphoglycerate-branched ethanol-production pathway can now be encoded by six designer genes for the following six designer enzymes: NAD-dependent dependent glyceraldehyde-3-phosphate-dehydrogenase, phosphoglycerate mutase, enolase, pyruvate kinase, pyruvate decarboxylase, and NADH-dependent alcohol dehydrogenase. The novelty of this embodiment is the use of an exogenous designer NAD-dependent glyceraldehyde-3-phosphate-dehydrogenase 01 working with an endogenous native NADPH-dependent glyceraldehyde-3-phosphate dehydrogenase to confer and couple the needed designer cyclic NADPH/NADH conversion redox-shuttle mechanism with the 3-phosphoglycerate-branched ethanol-production pathway (03-07 in FIG. 1) for enhanced photobiological ethanol production.

Since the native NADPH-dependent glyceraldehyde-3-phosphate dehydrogenase which functions as part of the Calvin cycle in host oxyphotobacteria is often sufficient in most cases, the key is to include a designer NAD-dependent glyceraldehyde-3-phosphate-dehydrogenases gene to pair up with the native NADPH-dependent glyceraldehyde-3-phosphate dehydrogenase to provide the NADPH/NADH-conversion mechanism for enhanced photobiological ethanol production. This requirement can be satisfied also by properly selecting an appropriate branching point at the Calvin cycle for a designer ethanol-production pathway to branch from. To confer this NADPH/NADH conversion mechanism by pathway design according to this embodiment, it is a preferred practice to branch a designer ethanol-production pathway at or after the point of glyceraldehydes-3-phosphate of the Calvin cycle as shown in FIG. 1. In these pathway designs, the NADPH/NADH conversion is achieved essentially by a two-step mechanism: 1) Use of the step with the Calvin-cycle's NADPH-dependent glyceraldehyde-3-phosphate dehydrogenase, which uses NADPH in reducing 1,3-diphosphoglycerate to glyceraldehydes-3-phosphate; and 2) use of the step with the designer pathway's $NAD^+$-dependent glyceraldehyde-3-phosphate dehydrogenase, which produces NADH from $NAD^+$ in oxidizing glyceraldehyde-3-phosphate to 1,3-diphosphoglycerate. The net result of the two steps as shown in reactions [3] and [4] above is the conversion of NADPH to NADH, which can supply the needed reducing power in the form of NADH for the designer ethanol-production pathway(s) to use. For the function of step 1), the use of the Calvin-cycle's glyceraldehyde-3-phosphate dehydrogenase naturally in the host organism is usually sufficient. To confer this two-step NADPH/NADH conversion mechanism, it is important to use a $NAD^+$-dependent glyceraldehyde-3-phosphate dehydrogenase in the designer ethanol-production pathway(s). Therefore, in one of the various embodiments, it is a preferred practice to use a $NAD^+$-dependent glyceraldehyde-3-phosphate dehydrogenase, its isozymes, functional derivatives, analogs, designer modified enzymes and/or combinations thereof in the designer ethanol-production pathway(s) as illustrated in FIG. 1.

SEQ ID NOs:39 and 40 show examples 39 and 40 for a pair of designer NADPH/NADH-conversion-enzyme DNA-constructs (FIG. 2B) consisting of a designer NADP-dependent Glyceraldehyde-3-Phosphate Dehydrogenase DNA construct (SEQ ID NO: 39) and a designer NAD-dependent Glyceraldehyde-3-Phosphate Dehydrogenase DNA construct (SEQ ID NO: 40). Briefly, SEQ ID NO: 39 presents example 39 for a designer nirA-promoter-controlled NADP-dependent Glyceraldehyde-3-Phosphate Dehydrogenase DNA construct (1983 bp) that includes a PCR FD primer (sequence 1-20), a 400-bp *Thermosynechococcus elongatus* BP-1 nirA promoter (21-420), an NADP-dependent glyceraldehyde-3-phosphate-dehydrogenase-encoding sequence (421-1563) selected/modified from the sequence of a *Synechococcus elongatus* PCC 7942 NADP-dependent glyceraldehyde-3-phosphate dehydrogenase (GenBank: D61379), a 400-bp *Thermosynechococcus elongatus* BP-1 rbcS terminator (1564-1963), and a PCR RE primer (1964-1983). SEQ ID NO: 40 presents example 40 for a designer nirA-promoter-controlled NAD-dependent Glyceraldehyde-3-Phosphate Dehydrogenase DNA construct (1793 bp) that includes a PCR FD primer (sequence 1-20), a 400-bp *Thermosynechococcus elongatus* BP-1 nirA promoter (21-420), an NAD-dependent glyceraldehyde-3-phosphate-dehydrogenase-encoding sequence (421-1373) selected/modified from the sequence of a *Heliobacterium chlorum* NAD-dependent glyceraldehyde-3-phosphate dehydrogenase (NCBI accession numbers: AJ252110, CAC80992), a 400-bp *Thermosynechococcus elongatus* BP-1 rbcS terminator (1374-1773), and a PCR RE primer (1774-1793).

With the designer NADPH/NADH-conversion-enzyme DNA-constructs (FIG. 2B) such as those shown in examples 39 and 40 (SEQ ID NOs:39 and 40), an NADH-dependent alcohol-dehydrogenase DNA construct such as that shown in example 41 (SEQ ID NO:41) can now also be used in construction of a 3-phosphoglycerate-branched ethanol-production pathway (03-07 in FIG. 1). Briefly, SEQ ID NO:41 presents example 41 for a designer nirA-promoter-controlled thermotolerant and NADH-dependent Alcohol-Dehydrogenase DNA construct (1992 bp) that includes a PCR FD primer (sequence 1-20), a 400-bp *Thermosynechococcus elongatus* BP-1 nirA promoter (21-420), an NADH-dependent Alcohol-Dehydrogenase-encoding sequence (421-1572) selected/modified from the sequence of a *Zymomonas mobilis* NADH-dependent alcohol dehydrogenase (GenBank: M15394), a 400-bp *Thermosynechococcus elongatus* BP-1 rbcS terminator (1573-1972), and a PCR RE primer (1973-1992) at the 3' end.

SEQ ID NOs:42-47 show examples 42-47 for a set of DNA constructs encoding a *Prochlorococcus marinus* MED4 groE-promoter-controlled designer 3-phosphoglycerate-branched ethanol-production pathway (03-07 in FIG. 1; designer DNA-construct examples 42-47) and a designer NAD-dependent Glyceraldehyde-3-Phosphate-Dehydrogenase DNA construct (SEQ ID NO 46: example 46). The use of designer NAD-dependent Glyceraldehyde-3-Phosphate-Dehydrogenase (SEQ ID NO 46: DNA-construct example 46) with the native NADPH-dependent Glyceraldehyde-3-Phosphate-Dehydrogenase in host *Prochlorococcus marinus* MED4 cell essentially confers a designer cyclic "transdehydrogenase" redox-shuttle mechanism to convert NADPH into NADH, which enables the 3-phosphoglycerate-branched ethanol-production pathway (FIG. 2C; designer DNA-construct examples 42-45 and 47) to operate with a designer NADH-dependent alcohol dehydrogenase (DNA-construct example 46) as well.

Briefly, SEQ ID NO:42 presents example 42 for a designer groE-promoter-controlled Phosphoglycerate-Mutase DNA construct (1265 bp) that includes a PCR FD primer (sequence 1-20), a 138-bp *Prochlorococcus marinus* MED4 (sea-surface oxychlorobacterial strain) heat- and light-responsive groE promoter (21-158), a Phosphoglycerate-Mutase-encoding sequence (159-845) selected from a *Zymomonas mobilis* phosphoglycerate-mutase sequence (GenBank: L09651), a 400-bp *Prochlorococcus marinus* MED4 rbcS terminator (846-1245), and a PCR RE primer (1246-1265).

SEQ ID NO:43 presents example 43 for a designer groE-promoter-controlled Enolase DNA construct (1877 bp) that includes a PCR FD primer (sequence 1-20), a 138-bp *Prochlorococcus marinus* MED4 heat- and light-responsive groE promoter (21-158), an Enolase-encoding sequence (159-1457) selected from an *Aeropyrum pernix* K1 enolase sequence (GenBank: NP_148623), a 400-bp *Prochlorococcus marinus* MED4 rbcS terminator (1458-1857), and a PCR RE primer (1858-1877).

SEQ ID NO:44 presents example 44 for a designer groE-promoter-controlled Pyruvate-Kinase DNA construct (2093 bp) that includes a PCR FD primer (sequence 1-20), a 138-bp *Prochlorococcus marinus* MED4 heat- and light-responsive groE promoter (21-158), a Pyruvate-Kinase-encoding sequence (159-1673) selected from a *Pichia stipitis* CBS 6054 pyruvate-kinase sequence (GenBank: XM_001384591), a 400-bp *Prochlorococcus marinus* MED4 rbcS terminator (1674-2073), and a PCR RE primer (2074-2093).

SEQ ID NO:45 presents example 45 for a designer groE-promoter-controlled Pyruvate-Decarboxylase DNA construct (2369 bp) that includes a PCR FD primer (sequence 1-20), a 138-bp *Prochlorococcus marinus* MED4 heat- and light-responsive groE promoter (21-158), a Pyruvate-Decarboxylase-encoding sequence (159-1949) selected from a *Pichia stipitis* pyruvate-decarboxylase sequence (GenBank: U75310), a 400-bp *Prochlorococcus marinus* MED4 rbcS terminator (1950-2349), and a PCR RE primer (2350-2369).

SEQ ID NO:46 presents example 46 for a designer groE-promoter-controlled NAD-dependent Glyceraldehyde-3-Phosphate-Dehydrogenase DNA construct (1586 bp) that includes a PCR FD primer (sequence 1-20), a 138-bp *Prochlorococcus marinus* MED4 heat- and light-responsive groE promoter (21-158), an NAD-dependent Glyceraldehyde-3-Phosphate-Dehydrogenase-encoding sequence (159-1166) selected from a *Pinus sylvestris* glyceraldehyde-3-phosphate-dehydrogenase sequence (GenBank: L32560), a 400-bp *Prochlorococcus marinus* MED4 rbcS terminator (1167-1566), and a PCR RE primer (1567-1586).

SEQ ID NO:47 presents example 47 for a designer groE-promoter-controlled NADH-dependent Alcohol-Dehydrogenase DNA construct (1730 bp) that includes a PCR FD primer (sequence 1-20), a 138-bp *Prochlorococcus marinus* MED4 heat- and light-responsive groE promoter (21-158), an NADH-dependent Alcohol-Dehydrogenase-encoding sequence (159-1310) selected from a *Zymomonas mobilis* alcohol-dehydrogenase sequence (GenBank: M15394), a 400-bp *Prochlorococcus marinus* MED4 rbcS terminator (1311-1710), and a PCR RE primer (1711-1730).

Since SEQ ID NOs:42-47 represent a set of *Prochlorococcus marinus* MED4 groE promoter-controlled designer ethanol-production-pathway genes that can be used in a marine oxychlorobacterium host such as *Prochlorococcus marinus* MED4, they also constitute an example of a designer ethanol-production pathway(s) in a designer oxychlorobacterium, such as a photosynthetic ethanol-producing designer marine *Prochlorococcus*, in one of the various embodiments for photobiological ethanol production using seawater.

Using *Prochlorococcus marinus* MIT9313 groE and nirA promoters, SEQ ID NOs:48-53 show examples 48-53 for another set of DNA constructs encoding a designer 3-phosphoglycerate-branched ethanol-production pathway (03-07 in FIG. 1; designer DNA-construct examples 48-52) and a designer NAD-dependent Glyceraldehyde-3-Phosphate-Dehydrogenase DNA construct (example 53). The use of designer NAD-dependent Glyceraldehyde-3-Phosphate-Dehydrogenase DNA construct (example 53) with the endogenous (native) NADPH-dependent Glyceraldehyde-3-Phosphate-Dehydrogenase in a host *Prochlorococcus marinus* MIT9313 cell also forms a beneficial NADPH-to-NADH redox-shuttle mechanism for the 3-phosphoglycerate-branched ethanol-production pathway (03-07 in FIG. 1).

Briefly, SEQ ID NO:48 presents example 48 for a designer groE-promoter-controlled NADH-dependent Alcohol-Dehydrogenase DNA construct (1630 bp) that includes a PCR FD primer (sequence 1-20), a 137-bp *Prochlorococcus marinus* MIT9313 heat- and light-responsive groE promoter (21-157), an NADH-dependent Alcohol-Dehydrogenase-encoding sequence (158-1210) selected from a *Kluyveromyces lactics* alcohol-dehydrogenase sequence (GenBank: X62766), a 400-bp *Prochlorococcus marinus* MIT9313 rbcS terminator (1211-1610), and a PCR RE primer (1611-1630).

SEQ ID NO:49 presents example 49 for a designer groE-promoter-controlled Pyruvate-Decarboxylase DNA construct (2272 bp) that includes a PCR FD primer (sequence 1-20), a 137-bp *Prochlorococcus marinus* MIT9313 heat- and light-responsive groE promoter (21-157), a Pyruvate-Decarboxylase-encoding sequence (158-1852) selected from a *Saccharomyces kluyveri* pyruvate-decarboxylase sequence (GenBank: AY245517), a 400-bp *Prochlorococcus marinus* MIT9313 rbcS terminator (1853-2252), and a PCR RE primer (2253-2272).

SEQ ID NO:50 presents example 50 for a designer groE-promoter-controlled Pyruvate-Kinase DNA construct (2092 bp) that includes a PCR FD primer (sequence 1-20), a 137-bp *Prochlorococcus marinus* MIT9313 heat- and light-responsive groE promoter (21-157), a Pyruvate-Kinase-encoding sequence (158-1672) selected from a *Lodderomyces elongisporus* NRRL YB-4239 pyruvate-kinase sequence (GenBank: XM_001528210), a 400-bp *Prochlorococcus marinus* MIT9313 rbcS terminator (1673-2072), and a PCR RE primer (2073-2092).

SEQ ID NO:51 presents example 51 for a designer groE-promoter-controlled Enolase DNA construct (1897 bp) that includes a PCR FD primer (sequence 1-20), a 137-bp *Prochlorococcus marinus* MIT9313 heat- and light-responsive groE promoter (21-157), an Enolase-encoding sequence (158-1477) selected from a *Lodderomyces elongisporus* NRRL YB-4239 enolase sequence (GenBank: XM_001528071), a 400-bp *Prochlorococcus marinus* MIT9313 rbcS terminator (1478-1877), and a PCR RE primer (1878-1897).

SEQ ID NO:52 presents example 52 for a designer groE-promoter-controlled Phosphoglycerate-Mutase DNA construct (2113 bp) that includes a PCR FD primer (sequence 1-20), a 137-bp *Prochlorococcus marinus* MIT9313 heat- and light-responsive groE promoter (21-157), a Phosphoglycerate-Mutase-encoding sequence (158-1693) selected from a *Bacillus megaterium* phosphoglycerate-mutase sequence (GenBank: AF120090), a 400-bp *Prochlorococcus marinus* MIT9313 rbcS terminator (1694-2093), and a PCR RE primer (2094-2113).

SEQ ID NO:53 presents example 53 for a designer nirA-promoter-controlled NAD-dependent Glyceraldehyde-3-Phosphate-Dehydrogenase DNA construct (1776 bp) that includes a PCR FD primer (sequence 1-20), a 400-bp *Prochlorococcus marinus* MIT9313 nirA promoter (21-420), an NAD-dependent Glyceraldehyde-3-Phosphate-Dehydrogenase-encoding sequence (421-1356) selected from a *Scenedesmus vacuolatus* NAD-dependent cytosolic glyceraldehyde-3-phosphate-dehydrogenase sequence (GenBank: CAC81012, AJ252209), a 400-bp *Prochlorococcus marinus* MIT9313 rbcS terminator (1357-1756), and a PCR RE primer (1757-1776).

Since SEQ ID NOs: 48-53 also represent a set of *Prochlorococcus marinus* MIT9313 groE- and nirA-promoter-controlled designer ethanol-production-pathway genes that can be used in another host oxychlorobacteria such as *Prochlorococcus marinus* MIT9313 and related oxychlorobacterial species, they also constitute an example of a designer ethanol-production pathway(s) in still another photosynthetic ethanol-producing designer oxychlorobacterium such as a designer *Prochlorococcus marinus* MIT9313, in one of the various embodiments for photobiological ethanol production using seawater.

Furthermore, the pyridine-nucleotide cofactors NADP and NAD both play an essential role in some of the designer oxyphotobacteria where an NADH-requiring alcohol dehydrogenase is used. It is beneficial to ensure that both NADP and NAD are made available to function with the designer pathway(s) for photobiological ethanol production. It is known that NADP could be converted to NAD by a NADP-phosphatase activity (Pattanayak and Chatterjee (1998) "Nicotinamide adenine dinucleotide phosphate phosphatase facilitates dark reduction of nitrate: regulation by nitrate and ammonia," *Biologia Plantarium* 41(1):75-84) and that NAD can be converted to NADP by a NAD kinase activity (Muto, Miyachi, Usuda, Edwards and Bassham (1981) "Light-induced conversion of nicotinamide adenine dinucleotide to nicotinamide adenine dinucleotide phosphate in higher plant leaves," *Plant Physiology* 68(2):324-328; Matsumura-Kadota, Muto, Miyachi (1982) "Light-induced conversion of $NAD^+$ to $NADP^+$ in *Chlorella* cells," *Biochimica Biophysica Acta* 679(2):300-300). Therefore, when enhanced NADPH/NADH conversion is desirable, the host may be genetically modified to enhance the NADPH phosphatase and/or NAD kinase activities. Thus, in one of the various embodiments, the photosynthetic ethanol-producing designer oxyphotobacteria further contain additional designer transgenes (FIG. 2B) to inducibly express one or more enzymes to facilitate the NADPH/NADH inter-conversion, such as the NADPH phosphatase and NAD kinase (GenBank: P83576, P83575, A59480XM,_001609395, ZP_00519346, EAM47569, ZP_01632610, XM_001324239).

iRNA Techniques to Further Tame Oxyphotobacterial Regulation Mechanism

In another embodiment of the present invention, the host oxyphotobacterium or oxyphotobacterial cell is further modified to tame the Calvin cycle so that the host can directly produce liquid fuel ethanol instead of synthesizing glycogen (starch), celluloses and other cellular materials that are often inefficient and hard for the biorefinery industry to use. According to the present invention, inactivation of glycogen-synthesis activity is achieved by suppressing the expression of any of the key enzymes, such as, glycogen synthase 11, glucose-1-phosphate (G-1-P) adenylyltransferase 10, phosphoglucomutase 09, and hexose-phosphate-isomerase 08 of the glycogen-synthesis pathway which connects with the Calvin cycle as illustrated in FIG. 1.

Figure 2D:
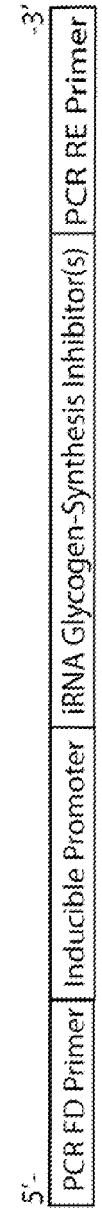
FIG. 2D presents a DNA construct for a designer iRNA glycogen-synthesis inhibitor gene.
Figure 2E:
FIG. 2E presents a DNA construct for a designer oxyphotobacterial glycogen-synthase iRNA gene.
Figure 2F:
FIG. 2F presents a DNA construct for a designer oxyphotobacterial glycogen-degradation-glycolysis gene(s).

Introduction of a genetically transmittable factor that can inhibit the glycogen-synthesis activity that is in competition with designer ethanol-production pathway(s) for the Calvin-cycle products can further enhance photosynthetic ethanol production. In a specific embodiment, a genetically encodedable inhibitor (FIG. 2C) to the competitive glycogen-synthesis pathway is an interfering RNA (iRNA) molecule that specifically inhibits the synthesis of a glycogen-synthesis-pathway enzyme, for example, glycogen synthase 11, glucose-1-phosphate (G-1-P) adenylyltransferase 10, phosphoglucomutase 09, and/or hexose-phosphate-isomerase 08. FIGS. 2D and 2E depict examples of a designer iRNA gene. The DNA sequences encoding glycogen synthase iRNA, glucose-1-phosphate (G-1-P) adenylyltransferase iRNA, a phosphoglucomutase iRNA and/or a hexose-phosphate-isomerase iRNA, respectively, can be designed and synthesized based on RNA interference techniques known to those skilled in the art (Liszewski (Jun. 1, 2003) Progress in RNA interference, *Genetic Engineering News*, Vol. 23, number 11, pp. 1-59). Generally speaking, an interfering RNA (iRNA) molecule is anti-sense but complementary to a normal mRNA of a particular protein (gene) so that such iRNA molecule can specifically bind with the normal mRNA of the particular gene, thus inhibiting (blocking) the translation of the gene-specific mRNA to protein (Fire, Xu, Montgomery, Kostas, Driver, Mello (1998) "Potent and specific genetic interference by double-stranded RNA in *Caenorhabditis elegans*". *Nature* 391(6669):806-11; Dykxhoorn, Novina, Sharp (2003) "Killing the messenger: short RNAs that silence gene expression", *Nat Rev Mol Cell Biol.* 4(6):457-67).

Examples of a designer glycogen-synthesis iRNA DNA construct (FIG. 2E) are shown in SEQ ID NOs: 54 and 55 listed. Briefly, SEQ ID NO: 54 presents example 54 for a designer nirA-promoter-controlled Glycogen-Synthase iRNA DNA construct (934 bp) that includes a PCR FD primer (sequence 1-20), a 88-bp *Synechococcus* sp. strain PCC 7942 (freshwater cyanobacterium) nitrite-reductase nirA promoter (21-108), a Glycogen-Synthase iRNA sequence (109-606) designed using the reverse complement of two unique sequence fragments of a *Synechococcus elongatus* PCC 7942 glycogen-synthase CDS sequence (GenBank: NC_007604), a 308-bp *Synechococcus* sp. strain PCC 7942 rbcS terminator (607-914), and a PCR RE primer (915-934). Because of the use of a nirA promoter (21-108), this designer glycogen-synthesis iRNA gene is designed to be expressed only when needed to enhance photobiological ethanol production in the presence of its specific inducer, nitrate ($NO_3^-$), which can be added into the culture medium as a fertilizer for induction of the designer oxyphotobacteria. The Glycogen-Synthase iRNA sequence (109-606) is designed to bind with the normal mRNA of the glycogen synthase gene, thus blocking its translation into a functional glycogen synthase. The inhibition of the glycogen synthase activity in this manner is to channel more photosynthetic products of the Calvin cycle into the ethanol-production pathway(s) such as the glyceraldehyde-3-phosphate-branched pathway (01-07) as shown in FIG. 1.

SEQ ID NO: 55 presents example 55 for a designer groE-promoter-controlled Glycogen-Synthase-iRNA DNA construct (1408 bp) that includes a PCR FD primer (sequence 1-20), a 137-bp light- and heat-responsive *Thermosynechococcus elongatus* BP-1 groE promoter (21-157), a Glycogen-Synthase iRNA sequence (158-988) consisting of a 300-bp sense mRNA fragment (158-457), a 231-bp designer intron-like loop (458-688), and a 300-bp antisense complement fragment (689-988) designed according to the first 300-bp unique sequence of a *Thermosynechococcus elongatus* BP-1 glycogen-synthase sequence (GenBank: BA000039 Region: 789655.791079), a 400-bp *Thermosynechococcus elongatus* BP-1 rbcS terminator (989-1388), and a PCR RE primer (1389-1408). This designer Glycogen-Synthase-iRNA sequence (158-988) is designed to inhibit the synthesis of glycogen synthase by the following two mechanisms. First, the 300-bp antisense complement iRNA sequence (corresponding to DNA sequence 689-988) binds with the normal mRNA of the glycogen synthase gene, thus blocking its translation into a functional glycogen synthase. Second, the 300-bp antisense complement iRNA sequence (corresponding to DNA sequence 689-988) can also bind with the 300-bp sense counterpart (corresponding to DNA sequence 158-457) in the same designer iRNA molecule, forming a hairpin-like double-stranded RNA structure with the 231-bp designer intron-like sequence (458-688) as a loop. Experimental studies have shown that this type of hairpin-like double-stranded RNA can also trigger post-transcriptional gene silencing (Fuhrmann, Stahlberg, Govorunova, Rank and Hegemann (2001) *Journal of Cell Science* 114:3857-3863). Because of the use of a groE promoter (21-157), this designer glycogen-synthesis-iRNA gene is designed to be expressed only in the presence of light and/or heat when needed to enhance photobiological ethanol production by channeling more photosynthetic products of the Calvin cycle into the ethanol-production pathway(s) (such as 01-07, 03-07, and/or 15-23 as labeled in FIG. 1).

Designer Glycogen-Degradation and Glycolysis Genes

In yet another embodiment of the present invention, the photobiological ethanol production is enhanced by incorporating an additional set of designer genes (FIG. 2F) that can facilitate glycogen (starch) degradation and glycolysis in combination with the designer ethanol-production gene(s) (FIG. 2A) in the cytoplasm. Such additional designer genes for glycogen degradation include, for example, genes coding for glycogen degradation enzymes 12: amylase, 4-alpha-glucotransferase, glycogen phosphorylase, glucokinase, and phosphoglucomutase. The designer glycolysis genes encode glycolysis enzymes: glucose-6-phosphate isomerase 13, phosphofructose kinase 14, fructose-diphosphate aldolase 15, triose phosphate isomerase 16, glyceraldehyde-3-phosphate dehydrogenase 17, phosphoglycerate kinase 18, phosphoglyccrate mutase 19, enolase 20, and pyruvate kinase 21. The designer glycogen-degradation and glycolysis genes in combination with any of the ethanol-production pathways (01-07, 03-07, and/or 15-23) can form additional pathway(s) from glycogen (starch) to ethanol such as 12-23 shown in FIG. 1. Consequently, co-expression of the designer glycogen-degradation and glycolysis genes with the ethanol-production-pathway genes can enhance photobiological production of ethanol as well. Therefore, this embodiment represents another approach to tame the Calvin cycle for enhanced photobiological production of ethanol. In this case, some of the Calvin-cycle products flow through the glycogen synthesis pathway (08-11 in FIG. 1) followed by the glycogen-to-ethanol pathway (12-23 in FIG. 1). In this case, glycogen acts as a transient storage pool of the Calvin-cycle products before they can be converted to ethanol. This mechanism can be quite useful in maximizing the ethanol-production yield in certain cases. For example, at high sunlight intensity such as around noon, the rate of Calvin-cycle photosynthetic $CO_2$ fixation can be so high that may exceed the maximal rate capacity of an ethanol-production pathway(s); use of the glycogen-synthesis mechanism allows temporary storage of the excess photosynthetic products to be used later for ethanol production as well.

FIG. 1 also illustrates the use of a designer glycogen-to-ethanol pathway (12-23) in combination with a Calvin-cycle-branched designer ethanol-production pathway(s) such as the glyceraldehyde-3-phosphate-branched pathway (01-07) for enhanced photobiological ethanol production. Similar to the benefits of using the Calvin-cycle-branched designer ethanol-production pathways (01-07, 03-07, 15-23, and 14-23 in FIG. 1), the use of the designer glycogen-to-ethanol pathway (12-23 in FIG. 1) can also help to convert the photosynthetic products to ethanol before the sugars could be converted into other more-complicated biomolecular materials which cannot be readily used by the biorefinery industries. Therefore, appropriate use of the Calvin-cycle-branched designer ethanol-production pathway(s) (01-07, 03-07, 15-23, and 14-23) and/or the designer glycogen-to-ethanol pathway (12-23) may represent revolutionary inter alia technologies that can effectively bypass the bottleneck problems of the current biomass technology.

Another feature is that a Calvin-cycle-branched designer ethanol-production pathway activity (01-07, 03-07, 15-23, and/or 14-23) can occur predominantly during the days when there is light because it uses an intermediate product of the Calvin cycle which requires supplies of reducing power (NADPH) and energy (ATP) generated by the photosynthetic water splitting and the light-driven proton-translocation-coupled electron transport process through the thylakoid membrane system. The designer glycogen-to-ethanol pathway (12-23) which can use the surplus sugar that has been stored as glycogen during photosynthesis, can operate not only during the days, but also at nights. Consequently, the use of a Calvin-cycle-branched designer ethanol-production pathway(s) (01-07, 03-07, 15-23, and/or 14-23) together with a designer glycogen-to-ethanol pathway (12-23) enables production of ethanol both during the days and at nights.

Because the expression for both the designer glycogen-to-ethanol pathway(s) and the Calvin-cycle-branched designer ethanol-production pathway(s) is controlled by the use of an inducible promoter such as an anaerobic hox promoter [or a nirA promoter], this type of designer oxyphotobacterial cells is also able to grow photoautotrophically under aerobic (normal) conditions. When the designer oxyphotobacterial cells are grown and ready for photobiological ethanol production, the cells are then placed under the specific inducing conditions such as under anaerobic conditions [or an ammonium-to-nitrate fertilizer use shift, if designer nirA-promoter-controlled ethanol-production pathway(s) is used] for enhanced ethanol production (FIG. 3).

Examples of designer glycogen-degradation genes are shown in SEQ ID NO: 56-61 listed. Briefly, SEQ ID NO:56 presents example 56 for a designer Amylase DNA construct (2470 bp) that includes a PCR FD primer (sequence 1-20), a 88-bp *Synechococcus elongatus* PCC 6301 nirA promoter (21-108), an Amylase-encoding sequence (109-2142) selected from a *Prochlorococcus marinus* isoamylase sequence (GenBank: YP_001091732), a 308-bp *Synechococcus elongatus* PCC 6301 rbcS terminator (2143-2450), and a PCR RE primer (2451-2470).

SEQ ID NO: 57 presents example 57 for a designer 4-alpha-Glucanotransferase DNA construct (1993 bp) that includes a PCR FD primer (sequence 1-20), a 88-bp *Synechococcus elongatus* PCC 6301 nirA promoter (21-108), a 4-alpha Glucanotransferase-encoding sequence (109-1665) selected from a *Thermosynechococcus elongatus* BP-1 4-alpha-Glucanotransferase sequence (GenBank: BAC08259), a 308-bp *Synechococcus elongatus* PCC 6301 rbcS terminator (1666-1973), and a PCR RE primer (1974-1993).

SEQ ID NO: 58 presents example 58 for a designer Glycogen-Phosphorylase DNA construct (2965 bp) that includes a PCR FD primer (sequence 1-20), a 88-bp *Synechococcus elongatus* PCC 6301 nirA promoter (21-108), a Glycogen-Phosphorylase-encoding sequence (109-2637) selected from a *Thermosynechococcus elongatus* BP-1 glycogen-phosphorylase sequence (GenBank: BAC09631), a 308-bp *Synechococcus elongatus* PCC 6301 rbcS terminator (2638-2945), and a PCR RE primer (2946-2965).

SEQ ID NO: 59 presents example 59 for a designer Phosphoglucomutase DNA construct (2119 bp) that includes a PCR FD primer (sequence 1-20), a 88-bp *Synechococcus elongatus* PCC 6301 nirA promoter (21-108), a Phosphoglucomutase-encoding sequence (109-1791) selected from a *Pichia stipitis* CBS 6054 phosphoglucomutase sequence (GenBank: XM_001383281), a 308-bp *Synechococcus elongatus* PCC 6301 rbcS terminator (1792-2099), and a PCR RE primer (2100-2119).

SEQ ID NO: 60 presents example 60 for a designer Glucokinase DNA construct (1852 bp) that includes a PCR FD primer (sequence 1-20), a 88-bp *Synechococcus elongatus* PCC 6301 nirA promoter (21-108), a Glucokinase-encoding sequence (109-1524) selected from a *Pichia stipitis* CBS 6054 glucokinase sequence (GenBank: XM_001386035), a 308-bp *Synechococcus elongatus* PCC 6301 rbcS terminator (1525-1832), and a PCR RE primer (1833-1852).

SEQ ID NO: 61 presents example 61 for a designer Glucose-6-Phosphate-Isomerase DNA construct (2101 bp) that includes a PCR FD primer (sequence 1-20), a 88-bp *Synechococcus elongatus* PCC 6301 nirA promoter (21-108), a Glucose-6-Phosphate-Isomerase-encoding sequence (109-1773) selected from a *Saccharomyces cerevisiae* glucose-6-phosphate-isomerase sequence (GenBank: M21696), a 308-bp *Synechococcus elongatus* PCC 6301 rbcS terminator (1774-2081), and a PCR RE primer (2082-2101).

The designer glycogen-degradation genes such as those shown in SEQ ID NO: 56-61 can be selected for use in combination with various designer ethanol-production-pathway genes for construction of various designer glycogen-degradation ethanol-production pathways such as the pathways shown in FIG. 1. For example, the designer genes shown in SEQ ID NOs: 1-11 and 56-61 can be selected for construction of a nirA-promoter-controlled glycogen-to-ethanol production pathway (12-23 in FIG. 1) that comprises of the following designer enzymes: amylase, 4-alpha-glucanotransferase, glycogen phosphorylase, glucokinase, phosphoglucomutase, glucose-6-phosphate isomerase, phosphofructose kinase, fructose diphosphate aldolase, triose phosphate isomerase, glyceraldehyde-3-phosphate dehydrogenase, phosphoglycerate kinase, phosphoglycerate mutase, enolase, pyruvate kinase, pyruvate decarboxylase, and alcohol dehydrogenase. This glycogen-to-ethanol pathway (12-23 in FIG. 1) may be used alone and/or in combinations with other ethanol-production pathway(s) such as the 3-phosphoglycerate-branched ethanol-production pathway (03-07 in FIG. 1).

Use of Photobiological Ethanol-Producing Designer Oxyphotobacteria with Photobioreactor-Ethanol-Harvesting Processes The various embodiments further teach how the designer oxyphotobacteria (FIG. 3) may be used with a photobioreactor and an ethanol-separation-harvesting system for photosynthetic production of ethanol ($CH_3CH_2OH$) and $O_2$ directly from $CO_2$ and $H_2O$ using sunlight. There are a number of embodiments on how the designer oxyphotobacteria may be used for photobiological ethanol production. One of the preferred embodiments is to use the designer transgenic oxyphotobacteria for direct photosynthetic ethanol production from $CO_2$ and $H_2O$ with a photobiological reactor and ethanol-harvesting (distillation) process, which includes a specific operational process described as a series of the following steps: a) Growing a designer transgenic oxyphotobacterium photoautotrophically in minimal (such as BG-11) culture medium using air $CO_2$ as the carbon source under aerobic (normal) conditions before inducing the expression of the designer ethanol-production-pathway genes; b) When the designer oxyphotobacterial cell culture is grown and ready for ethanol production, sealing or placing the culture into a specific condition, such as an anaerobic condition that can be generated by removal of $O_2$ from the photobiological reactor, to induce the expression of designer ethanol-production-pathway genes; c) When the designer ethanol-production-pathway enzymes are expressed in the designer organism's cytoplasm, supplying visible light energy such as sunlight for the designer-genes-expressed cells to work as the catalysts for photosynthetic ethanol production from $CO_2$ and $H_2O$; d) Harvesting the ethanol product by any method known to those skilled in the art. For example, harvesting the ethanol product from the photobiological reactor by a combination of membrane filtration and ethanol-distillation techniques and flexibly collecting the 0, gas product from the reactor.

The above process to use the designer oxyphotobacteria for photosynthetic $CH_3CH_2OH$ and $O_2$ production from $CO_2$ and $H_2O$ with a biological reactor and ethanol-harvesting (distillation) and gas product separation and collection system can be repeated for a plurality of operational cycles to achieve more desirable results. Any of the steps a) through d) of this process described above can also be adjusted in accordance of the invention to suit for certain specific conditions. In practice, any of the steps a) through d) of the process can be applied in full or in part, and/or in any adjusted combination as well for enhanced photobiological ethanol production in accordance of this invention.

The sources of $CO_2$ that can be used in this process include, but not limited to, industrial $CO_2$, (bi)carbonates, and atmospheric $CO_2$. For an example, flue-gas $CO_2$ from fossil fuel-fired and/or biomass-fired industrial facilities can be fed through a pipeline into a photobiological reactor in this process. The industrial facilities that can generate $CO_2$ supplies for the designer photosynthetic ethanol-production process include (but not limited to): coal-fired power plants, iron and steelmaking industries, cement-manufacturing plants, petroleum refinery facilities, chemical fertilizer production factories, biomass-fired and/or fossil fuel-fired ethanol distillation/separation facilities, biomass-pyrolysis processes, smokestacks, fermentation bioreactors, biofuel-refinery facilities, and combinations thereof.

Alternatively, this designer photobiological ethanol-production process can also use the $CO_2$ in the environment and from the atmosphere as well. Gaseous $CO_2$, dissolved $CO_2$, bicarbonate, and carbonates can all be used by the designer-oxyphotobacteria photobiological ethanol production technology.

This embodiment is illustrated in more details here using designer cyanobacteria as an example. As described above, designer oxyphotobacteria of the present invention, such as the designer cyanobacterium that contains a set of designer hox-promoter-controlled designer ethanol-production-pathway genes (for examples, the DNA constructs of SEQ ID NOs: 12-16), can grow normally under aerobic conditions by autotrophic photosynthesis using air $CO_2$ as the carbon source in a manner similar to that of a wild-type cyanobacterium. The designer oxyphotobacteria such as designer cyanobacteria can grow also photoheterotrophically using an organic substrate as well.

In a preferred embodiment, a designer oxyphotobacterium is grown photoautotrophically using air $CO_2$ as the carbon source under the aerobic conditions in a minimal (BG-11) medium that contains the essential mineral (inorganic) nutrients. No organic substrate such as glucose or acetate is required to grow a designer oxyphotobacterium under the normal conditions before the designer ethanol-production-pathway genes are expressed. Most of the oxyphotobacteria can grow rapidly in water through autotrophic photosynthesis using air $CO_2$ as long as there are sufficient mineral nutrients. The nutrient elements that are commonly required for oxyphotobacterial growth are: N, P, and K at the concentrations of about 1-10 mM, and Mg, Ca, S, and Cl at the concentrations of about 0.5 to 1.0 mM, plus some trace elements Mn, Fe, Cu, Zn, B, Co, Mo among others at μM concentration levels. All of the mineral nutrients can be supplied in an aqueous minimal medium such as the BG-11 medium that can be made with well-established recipes of oxyphotobacterial culture media using water (freshwater for designer freshwater oxyphotobacteria; seawater for designer marine oxyphotobacteria) and relatively small of inexpensive fertilizers and mineral salts such as ammonium bicarbonate ($NH_4HCO_3$) (or ammonium nitrate, urea, ammonium chloride), potassium phosphates ($K_2HPO_4$ and $KH_2PO_4$), magnesium sulfate heptahydrate ($MgSO_4.7H_2O$), calcium chloride ($CaCl_2$), zinc sulfate heptahydrate ($ZnSO_4.7H_2O$), iron (II) sulfate heptahydrate ($FeSO_4.7H_2O$), and boric acid ($H_3BO_3$), among others. That is, large amounts of designer oxyphotobacteria cells can be inexpensively grown in a short period of time because, under aerobic conditions such as in an open pond, the designer oxyphotobacteria can photoautotrophically grow by themselves using air $CO_2$ as rapidly as their wild-type parental strains. This is a significant feature (benefit) of the invention that could provide a cost-effective solution in generation of photoactive biocatalysts (the designer photosynthetic ethanol-producing oxyphotobacteria) for renewable solar energy production.

When the oxyphotobacterial culture is grown and ready for ethanol production, the grown oxyphotobacterial culture is sealed or placed into certain specific conditions, such as anaerobic conditions that can be generated by removal of $O_2$ from the sealed photobiological reactor (FIG. 4), to induce the expression of designer hox-promoter-controlled photosynthetic ethanol-production-pathway genes (for examples, the DNA constructs of SEQ ID NOs: 12-16). When the designer ethanol-production-pathway enzymes are expressed, visible light energy such as sunlight is supplied for the designer-genes-expressing oxyphotobacterial cells to work as the catalysts for photosynthetic ethanol production from $CO_2$ and $H_2O$. When the designer genes are expressed, the oxyphotobacterial cells can essentially become efficient and robust "blue-green machines" that are perfect for photosynthetic production of ethanol ($CH_3CH_2OH$) and $O_2$ from $CO_2$ and $H_2O$. The ethanol product from the oxyphotobacterial photobiological rector can be harvested by a combination of membrane filtration and ethanol-distillation techniques.

Photosynthetic production of $CH_3CH_2OH$ and $O_2$ directly from $CO_2$ and $H_2O$ in accordance with the present invention can, in principle, have high quantum yield. Theoretically, it requires only 24 photons to produce a $CH_3CH_2OH$ and $3O_2$ from water and carbon dioxide by this mechanism. The maximal theoretical sunlight-to-ethanol energy efficiency by the process of direct photosynthetic ethanol production from $CO_2$ and $H_2O$ is about 10%, which is the highest possible among all the biological approaches. Consequently, this approach has great potential when implemented properly with an oxyphotobacterial reactor and ethanol-oxygen-harvesting process.

The above process to use the designer oxyphotobacteria for photosynthetic production of $CH_3CH_2OH$ and $O_2$ from $CO_2$ and $H_2O$ with an oxyphotobacterial reactor and an ethanol-harvesting (distillation) and gas product separation and collection process can be repeated for a plurality of operational cycles to achieve more desirable results.

Another feature is that the designer switchable ethanol-production oxyphotobacterium (FIG. 3) such as a designer cyanobacterium provides the capability for repeated cycles of photoautotrophic culture growth under normal aerobic conditions with a manner similar to that of a wild type and efficient photobiological production of ethanol when the designer ethanol-production pathway is switched on by an inducible promoter (such as the hox promoter) at certain specific inducing conditions (such as under anaerobic conditions) in a bioreactor. For example, the switchable designer oxyphotobacterium with designer hox-promoter-controlled ethanol-production-pathway genes contains normal respiratory mechanism, which uses the reducing power (NADH) from organic reserves (and/or exogenous substrates, such as glucose or acetate) to power the cell immediately after its return to aerobic conditions. Therefore, when the oxyphotobacterial culture is returned to aerobic conditions after its use under anaerobic conditions for production of ethanol, the culture will stop producing ethanol-production-pathway enzymes and start to restore its normal photoautotrophic capability by synthesizing normal functional Calvin-cycle enzymes and producing new and functional cells. Consequently, it is possible to use this type of genetically transformed organism for repeated cycles of photoautotrophic culture growth under normal aerobic conditions and efficient production of ethanol under anaerobic conditions in an anaerobic reactor. That is, this photobiological ethanol-production technology can be operated for a plurality of operational cycles by rejuvenating the used culture under aerobic conditions and recyclably using the rejuvenated oxyphotobacterial culture under ethanol-producing conditions to achieve more desirable results. Optionally, this photobiological ethanol-production technology is operated continuously by circulating rejuvenated oxyphotobacterial culture from an aerobic reactor into the anaerobic reactor while circulating the used oxyphotobacterial culture from the anaerobic reactor (after its use for ethanol production) into the aerobic reactor for rejuvenation by synthesizing normal functional Calvin-cycle enzymes and producing new cells through photosynthetic $CO_2$ fixation and photoautotrophic growth.

Some of the designer oxyphotobacteria could grow photoautotrophically even with the ethanol-production pathway(s) switched on. Whether or how fast a designer oxyphotobacterium could grow under the ethanol-producing conditions may depend on its genetic background and how much of the Calvin cycle products are still available for cell growth after use by the designer ethanol-production pathway(s). Designer oxyphotobacteria that can, under the ethanol-producing conditions, maintain essential cellular functions with an appropriate growth rate can also be used for continuous photobiological production of $CH_3CH_2OH$ and $O_2$ from $CO_2$ and $H_2O$ with a bioreactor and an ethanol-harvesting (distillation) process.

There are additional ways that the switchable designer oxyphotobacteria can be used. For example, the used designer oxyphotobacterial culture from a photobiological ethanol-production reactor does not have to be circulated back to a culture-growth reactor. Instead, the used oxyphotobacterial culture is taken out to be used as fertilizers or biomass feed stocks for other processing because the photoautotrophic growth of the switchable designer oxyphotobacterium in a culture-growth reactor is capable of continuously supplying oxyphotobacterial cells to a photobiological ethanol-production reactor for the biofuel production. This embodiment is, especially, helpful to using some of the designer oxyphotobacteria that can grow photoautotrophically only before (but not after) the ethanol-production-pathway(s) is switched on. For example, by keeping a continuously growing culture of a designer oxyphotobacterium (that can grow photoautotrophically only before the ethanol-production-pathway(s) is switched on) in a culture-growth reactor, it can provide continuous supplies of grown oxyphotobacterial cells for use in a photobiological ethanol-production reactor. This approach makes it possible to use those designer oxyphotobacteria that can grow only before the ethanol-production-pathway(s) is switched on for photobiological ethanol production as well.

Because of various reasons, some of the designer ethanol-production oxyphotobacteria could grow only photohetrotrophically or photomixotrophically but not photoautotrophically. Use of a culture-growth reactor can also grow this type of designer ethanol-production oxyphotobacteria photohetrotrophically or photomixotrophically using organic substrates including, but not limited to, glucose, fructose, sucrose, acetate, ethanol, methanol, propanol, butanol, acetone, starch, hemicellulose, cellulose, lipids, proteins, organic acids, biomass materials and combination thereof. The so-grown culture can also be supplied to a photobiological ethanol-production reactor for induction of the designer pathways for ethanol production. This modified embodiment on culture growth makes it possible to use those designer oxyphotobacteria that can grow only photohetrotrophically, or photomixotrophically also for photobiological ethanol production as well.

For certain specific designer oxyphotobacteria with designer nitrite-reductase (nirA) promoter-controlled ethanol-production-pathway genes, the above photobiological reactor process may be further adjusted to achieve more beneficial results. For example, a designer oxyphotobacterium that contains nirA-promoter-controlled ethanol-production-pathway genes such as the ones shown in DNA sequence design examples 1-7 (SEQ ID NO: 1-7), can grow normally in a culture medium with ammonium (but no nitrate) by autotrophic photosynthesis using air $CO_2$ in a manner similar to that of a wild-type oxyphotobacterium. This is because the expression of the ethanol-production-pathway genes in this designer oxyphotobacterium will be turned on only in the presence of nitrate as desired owning to the use of nitrite reductase (nirA) promoter in controlling the designer pathway expression. A significant feature of the designer oxyphotobacteria with nirA-promoter-controlled ethanol-production-pathway genes is that the expression of the designer ethanol-production pathways can be induced by manipulating the concentration levels of nitrate ($NO_3^-$) relative to that of ammonium ($NH_4^+$) in the culture medium without requiring any anaerobic conditions. That is, the expression of the designer ethanol-production pathway(s) can be induced under both aerobic and anaerobic conditions. This enables the designer photobiological ethanol-production process to operate even under aerobic conditions using atmospheric $CO_2$. Likewise, this type of designer oxyphotobacteria with nirA-promoter-controlled ethanol-production-pathway genes can grow photoautotrophically both under aerobic and anaerobic conditions as well. Therefore, as a further embodiment, the operational process of using designer oxyphotobacteria with nitrite reductase (nirA) promoter-controlled ethanol-production-pathway genes is adjusted to the following: a) Growing a designer transgenic oxyphotobacterium photoautotrophically in minimal (such as BG-11) culture medium in the presence of ammonium ($NH_4^+$) but no nitrate ($NO_3^-$) before inducing the expression of the designer ethanol-production-pathway genes; b) When the designer oxyphotobacterial culture is grown and ready for ethanol production, adding nitrate ($NO_3^-$) fertilizer into the culture medium to raise the concentration of nitrate ($NO_3^-$) relative to that of ammonium ($NH_4^+$) to induce the expression of designer ethanol-production-pathway genes; c) When the designer ethanol-production-pathway enzymes are expressed, supplying visible light energy such as sunlight for the designer-genes-expressed cells to work as the catalysts for photosynthetic ethanol production from $CO_2$ and $H_2O$; d) Harvesting the ethanol product from the photobiological reactor by a combination of membrane filtration and ethanol-distillation techniques.

For certain specific designer oxyphotobacteria with designer groE-promoter-controlled ethanol-production-pathway genes (for examples, SEQ ID NO: 17-21), their ethanol-production-pathway activities can be controlled by the light and/or temperature conditions. For example, when the designer oxyphotobacteria are used in a sealed transparent plastic reactor, the designer groE-promoter-controlled ethanol-production-pathway genes can be induced by sunlight and the associated rising temperature (heat) because of the plastic reactor's greenhouse effect upon solar illumination. For some designer oxyphotobacteria with designer rbcL-promoter-controlled ethanol-production-pathway genes (for examples, SEQ ID NOs: 22-24 and 26), their ethanol-production-pathway activities are expressed simultaneously with the Rubisco operon expression typically when the light is on.

Depending on the season and geographic location, the temperature in a sealed plastic bioreactor could get as high as about 30-70° C. The designer thermophilic oxyphotobacteria created from a thermophilic host oxyphotobacterium such as *Thermosynechococcus elongatus* BP-1 with groE-promoter-controlled thermotolerant designer ethanol-pathway genes (for examples, SEQ ID NOs: 34-38) are especially suitable for photobiological ethanol production at this type of hot temperature range (30-70° C.).

In addition to ethanol production, it is also possible to use a designer oxyphotobacterium or part of its designer ethanol-production pathway(s) to produce certain intermediate products including: acetaldehyde, pyruvate, phosphoenolpyruvate, 2-phosphoglycerate, 1,3-diphosphoglycerate, glyceraldehye-3-phosphate, dihydroxyacetone phosphate, fructose-1,6-diphosphate, fructose-6-phosphate, glucose-6-phosphate, and glucose-1-phosphate. Therefore, a further embodiment comprises an additional step of harvesting the intermediate products that can be produced also from induced transgenic designer oxyphotobacteria. The production of an intermediate product can be selectively enhanced by switching off a designer-enzyme activity that catalyzes its consumption in the designer pathways. The production of a said intermediate product can be enhanced also by using a designer oxyphotobacterium with one or some of designer enzymes omitted from the designer ethanol-production pathways. For instance, a designer oxyphotobacterium with the alcohol dehydrogenase or pyruvate decarboxylase omitted (or switched off) from the designer pathways (FIG. 1) may be used to produce acetaldehyde or pyruvate, respectively. For examples, in the designer oxyphotobacteria created from host *Synechocystis* sp. strain PCC 6803 with the DNA constructs of SEQ ID NO: 27-33, when the nirA-promoter-controlled Alcohol-Dehydrogenase gene (SEQ ID NO: 33) is either omitted or switched off in the presence of ammonium fertilizer, the groE-promoter-controlled designer genes (SEQ ID NOs: 27-32) can be induced by sunlight (and its associated heat) to produce certain intermediate products such as pyruvate.

Photobiological Ethanol-Production and Harvesting with Greenhouse Distillations

The present invention also provides an integrated photobiological ethanol production and harvesting technology using a special solar-greenhouse-distillation system (FIGS. 4-8) combined with the use of special ethanol-producing designer photosynthetic organisms such as designer transgenic oxyphotobacteria as illustrated in FIG. 1.

Figure 4A:
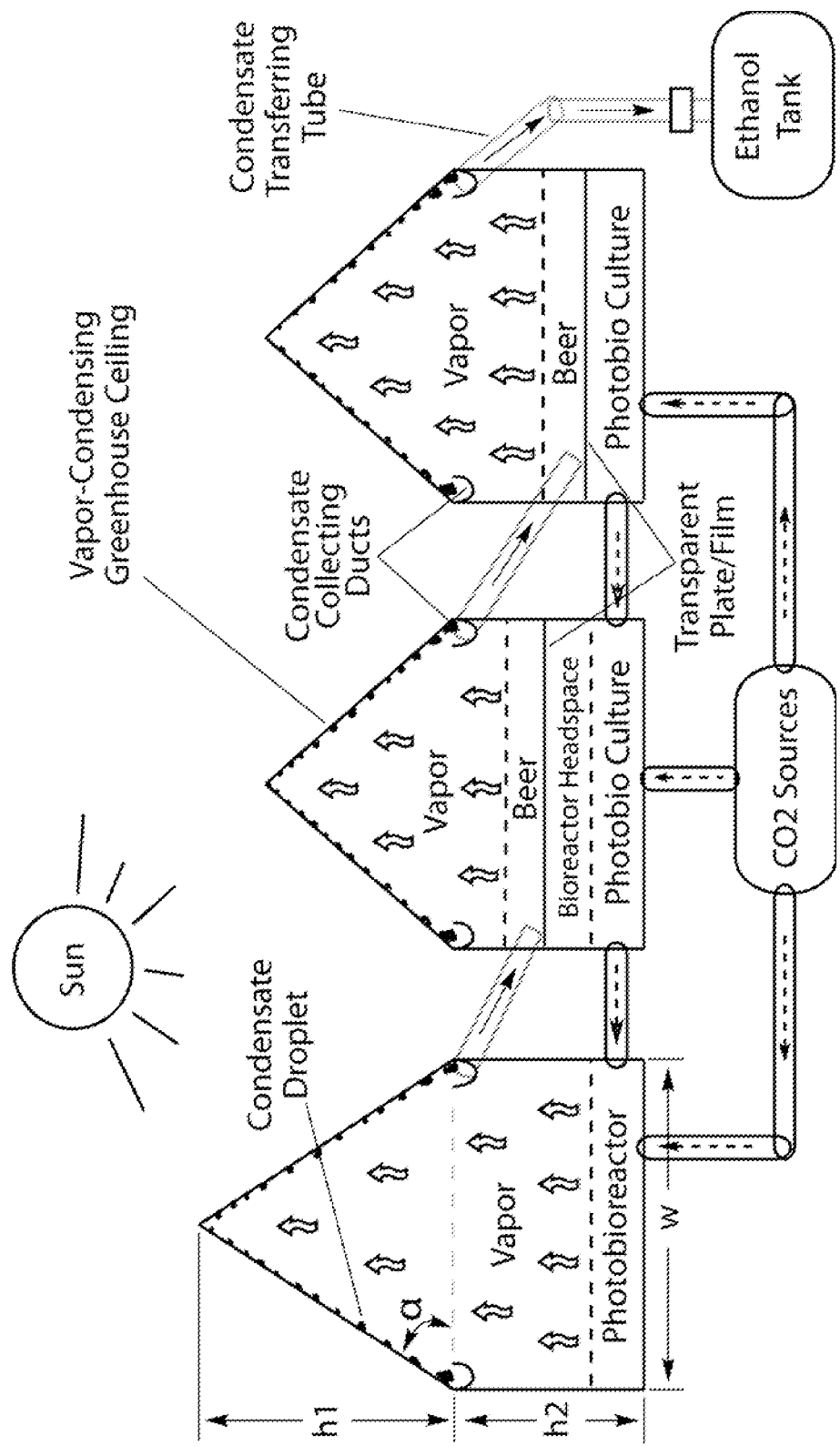
FIG. 4A presents the front view of an integrated photobiological ethanol-production and solar-heat-driven distillation greenhouse system which comprises multiple greenhouses and multistage distillation components.
Figure 4B:
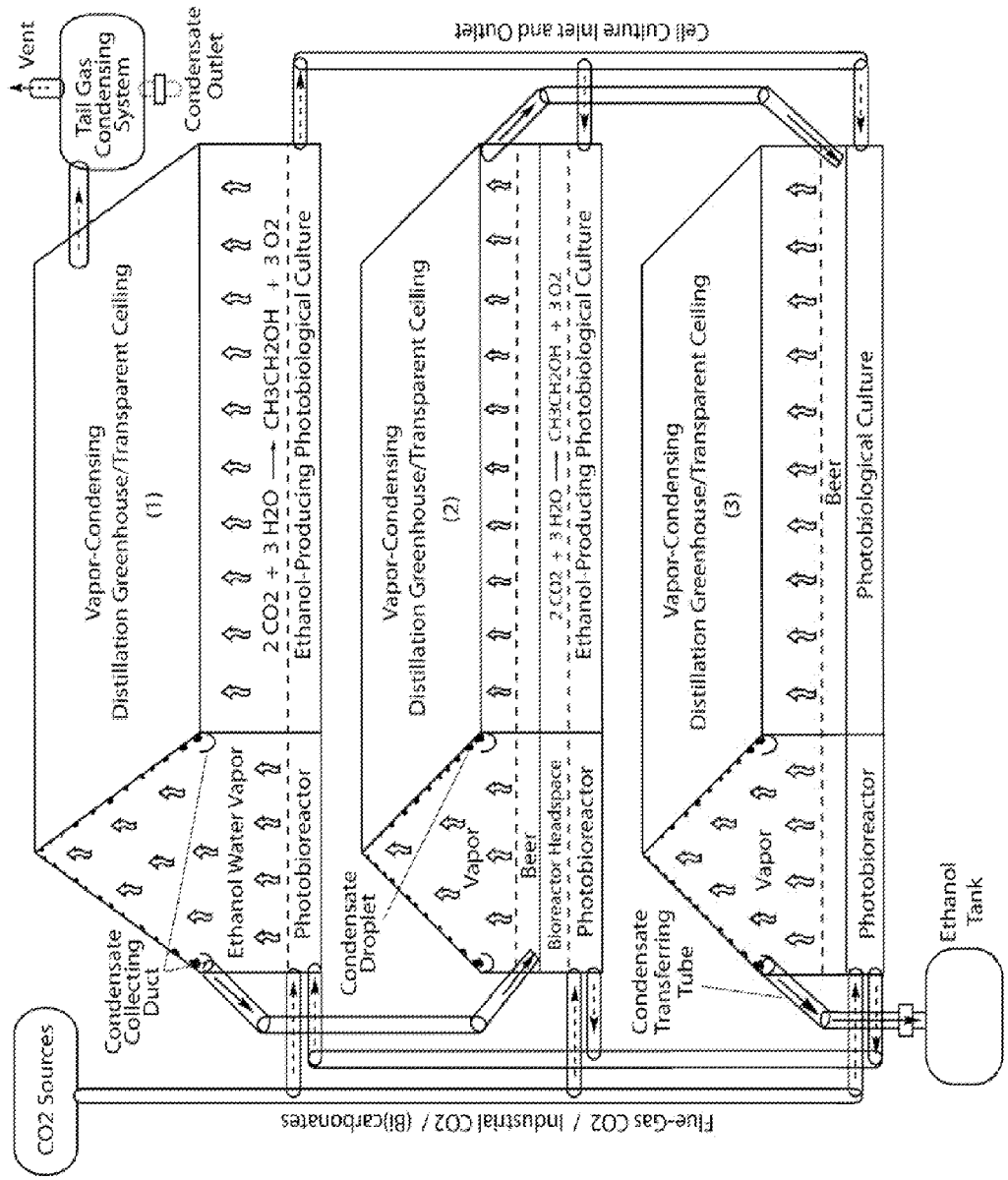
FIG. 4B presents an integrated photobiological ethanol-production and solar-heat-driven distillation greenhouse system which comprises multiple greenhouses and multistage distillation components.

The integrated solar-greenhouse-distillation system (FIGS. 4A and 4B) comprises a series of various distillation greenhouses and ethanol-harvesting units (FIGS. 5A-5D) working together in series and/or in parallel for photobiological culture growth, ethanol production, and ethanol harvesting with efficient utilization of sunlight energy. In various embodiments, sunlight is used to drive photobiological ethanol production and, at the same time, generate heat in the culture medium (FIG. 4A). With a theoretical maximum of about 10% photosynthetic solar energy conversion efficiency, nearly 90% of the solar energy goes to heat during the photobiological process. In various embodiments, the waste solar heat associated with the photobiological process is utilized in vaporizing the product ethanol (and water) for harvesting by fractional greenhouse distillation and redistillation (FIG. 4). Consequently, a fundamental feature of the present photobiological ethanol production and harvesting methodology is to use solar energy to drive both photosynthesis and ethanol harvesting through greenhouse distillation with higher sunlight utilization efficiency and minimal cost.

In the fundamental photobiological (photosynthetic) process, the photosynthetically active radiation (wavelength 400-700 nm) of sunlight (photons) can be absorbed by photosynthetic pigments such as chlorophylls in photosynthetic organisms (e.g., algae and oxyphotobacteria). Photosynthesis, in general, is the fundamental biological process that converts the electromagnetic energy of sunlight into stored chemical energy that supports essentially all life on Earth. Briefly, the absorption of photons creates excited states (excitations) of photosynthetic pigments (such as Chlorophylls) and the excitation energy is then captured by a vectorial photochemical charge separation at a reaction center pigment such as P680 and P700. The light energy captured by the photosynthetic reaction carters is stored predominately by reduction of $CO_2$, using water as the source of electrons. The key components of the photosynthetic apparatus involved light absorption and energy conversion are embedded in thylakoid membranes. They are two chlorophyll (Chl)-protein complexes: photosystem I (PSI) with a reaction center, P700, and photosystem II (PSII) with another distinct reaction center, P680. PSII can split water and reduce the plastoquinone (PQ) pool, the cytochrome (Cyt) b/f complex, and plastocyanin (PC), while PSI can reduce ferredoxin (Fd)/nicotinamide adenine dinucleotide phosphate ($NADP^+$) and oxidize PC, the Cyt b/f complex and the PQ pool. As a result, the electrons derived from water splitting are transferred to $Fd/NADP^+$, which provides the reducing power for reduction of $CO_2$ to carbohydrate (in the case of wild-type photosynthesis) at the stroma region by a series of enzymatic reactions collectively called the Calvin cycle. Electron transport in the membrane is coupled with proton transport from the stroma into the lumen, generating a proton gradient across the thylakoid membrane. The proton gradient drives phosphorylation through the coupling factor CFo-CF1 to make essential ATP for the reduction of $CO_2$. This is a brief description of wild-type oxygenic photosynthesis.

In a designer transgenic photosynthetic ethanol-producing organism such as a designer alga or designer oxyphotobacterium, the Calvin cycle is tamed typically with a designer ethanol-production pathway(s) so that the products from the Calvin cycle is converted into ethanol (FIG. 1). Theoretically, it requires only 24 photons to produce a $CH_3CH_2OH$ and $3O_2$ from water and carbon dioxide by this mechanism. The maximal theoretical sunlight-to-ethanol energy efficiency by the process of photosynthetic ethanol production directly from $CO_2$ and $H_2O$ is about 10%, which is the highest possible among all the biological approaches.

Note, the theoretical maximum 10% sunlight-to-ethanol energy efficiency also implies that nearly 90% of sunlight energy is dissipated as heat energy (molecular vibrations and thermo infra-red radiation) during the photobiological process. That is, heat generation/dissipation is an intrinsic part of the photobiological process that involves photon absorption, excitation transfer, photochemical charge separation, electron transfer, proton transport, and enzymatic reactions. In addition, certain non-visible portion of the solar radiation such as the infra-red light could also be absorbed by a liquid culture medium generating heat. Consequently, in a photobiological culture medium as shown in FIG. 4A, sunlight drives photosynthesis and, at the same time, generates significant amounts of heat. In fact, the majority (nearly 90%) of the sunlight energy goes to heat during the photobiological process. In the present invention, this waste solar heat energy is utilized in situ with a special greenhouse distillation system to drive a distillation process for harvesting product ethanol from the photobiological culture medium (of designer transgenic organisms).

Figure 5A:
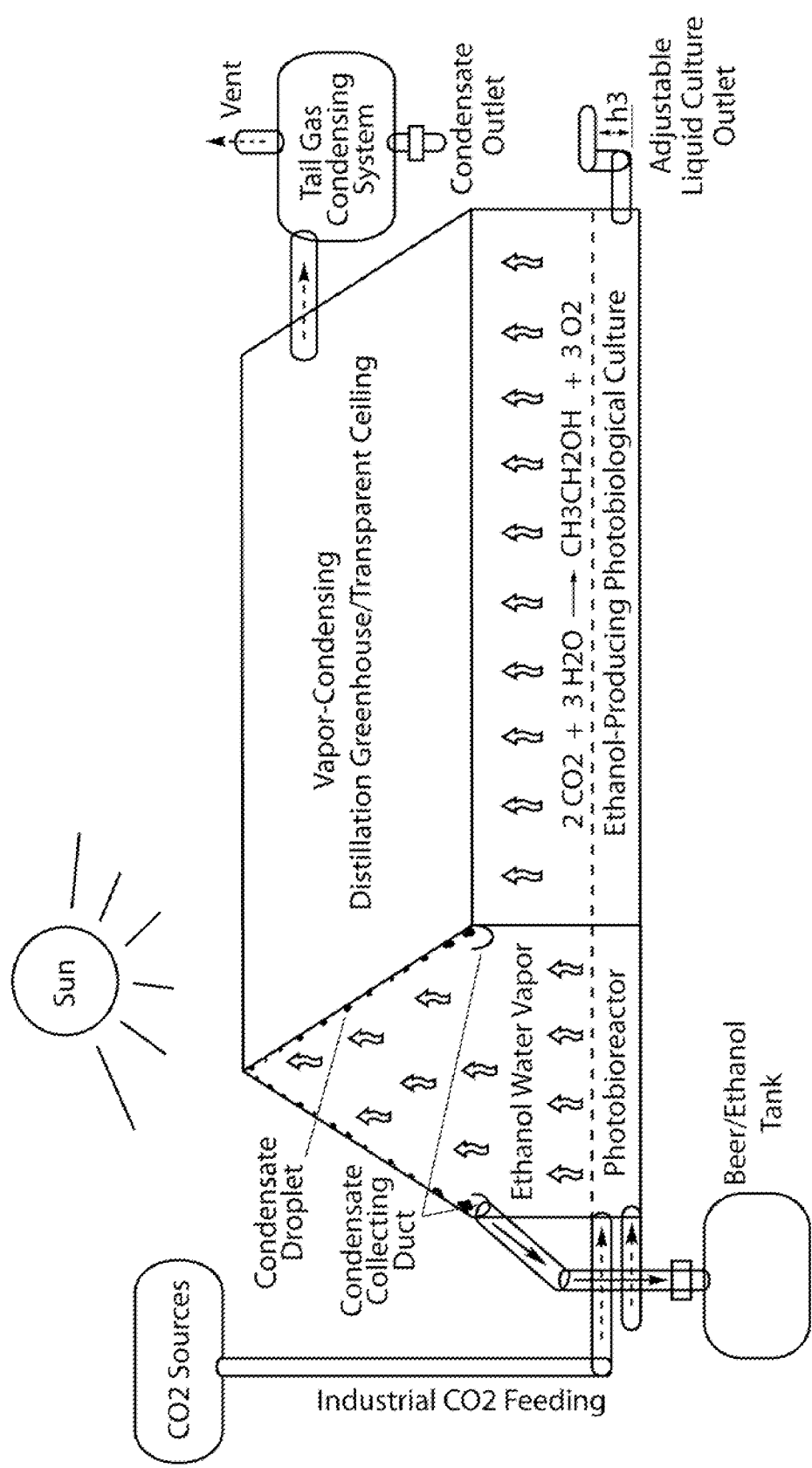
FIG. 5A presents an example of a photobiological ethanol-production reactor coupled with a distillation greenhouse system for harvesting ethanol using the associated waste solar heat.

In one of the various embodiments, as illustrated in FIG. 5A, a distillation greenhouse comprises a photobiological ethanol-production culture reactor in a sealed greenhouse with a tilted vapor-condensing transparent ceiling and condensate-collecting ducts around the greenhouse walls below the ceiling level. The distillation greenhouse can be built from a number of materials including glass, plastics and polymer materials. A distillation greenhouse can also be in various forms and/or shapes including (but not limited to) in a form of photobiological growth chambers and/or growth bags that can be made from various synthetic materials such as certain ethanol-tolerant plastic and/or polymer materials. As the use of sunlight driving photosynthesis and generating heat in the photobiological ethanol-production liquid culture medium, the associated solar heat vaporizes the product ethanol (with water) from the reactor medium. The ethanol-richer vapor condenses onto the vapor-condensing transparent ceiling that is cooled by air, winds, and thermo infra-red radiation to the outer space. The vapor-condensing transparent ceiling can also be cooled flexibly by running cold water over the ceiling as well.

As shown in FIG. 4A, the tilted-ceiling angle $\alpha$ should be properly chosen to ensure that the condensate droplets be able to slide downwards along the inner surface of the tilted ceiling and flow into the collecting ducts around the walls. Depending on the surface property of the ceiling surface material interacting with condensate droplets, the tilted-ceiling angle $\alpha$ should be at least above 5 degrees, preferably 15-30 degrees, and more preferably 30-70 degrees at all inner surface areas of the ceiling to prevent condensate droplets from free falling from the ceiling surface back into the culture medium below. In this way, as the vapor condenses, the condensate droplets can slide downwards along the inner surface of the tilted ceiling and finally flow into the collecting ducts around the greenhouse walls by use of the surface tension (ceiling surface-condensate droplets interaction) and the Earth gravity pulling force. The collected condensate which is richer in ethanol content is then transported through a condensate-transferring tube by use of gravity as well to a storage tank or into the next distillation greenhouse for redistillation until achieving the desired ethanol concentration in the final distillate(s).

FIG. 4A also illustrates how the condensate collected by the ducts in the first greenhouse can be transferred with a condensate-transporting tube into the next greenhouse for re-distillation. According to one of the various embodiments, it is a preferred practice to place the condensate collecting ducts in the first greenhouse high enough so that the condensate collected by the ducts there can flow through a condensate-transporting tube into the next greenhouse by use of gravity without requiring any pumping. As shown in FIG. 4A, the outlet of the condensate-transporting tube should be immersed in the liquid of the next greenhouse so that any undesirable exchange of vapor between the greenhouses is properly blocked by the liquid.

The second greenhouse shown in FIG. 4A (middle) is an example where the photobiological culture is placed into the lower bioreactor chamber. The condensate from the first greenhouse (on the left, FIG. 4A) is transported through a tube into the upper distillation chamber of the second greenhouse (middle, FIG. 4A) for redistillation. The upper distillation chamber and lower bioreactor chamber of the second greenhouse (middle, FIG. 4A) are separated by a transparent and impermeable plate and/or film (or membrane) that allows only sunlight to go through. Use of sunlight drives photosynthesis and generates heat in the photosynthetic cell culture at the lower chamber. The waste solar heat is used for re-evaporation of the ethanol-containing liquid (beer) at the upper distillation chamber above the photobiological culture reactor. The vapor is then re-condensed onto the inner surface of the ceiling in the second greenhouse as well. The condensate of the second distillation greenhouse is collected in a manner similar to that in the first distillation greenhouse by using a tilted ceiling surface and a system of condensate-collecting ducts around the greenhouse walls below the ceiling. The ethanol concentration in the condensate collected from the second distillation greenhouse (FIG. 4A, middle) is now higher (typically in a range about 1-70% ethanol depending on the source beer and operating conditions) than that (about 0.5-40% ethanol) in the condensate collected at the first distillation greenhouse (FIG. 4A, left). Higher and higher ethanol concentration can be achieved with further re-distillations using the third (FIG. 4A, left) and/or more distillation greenhouses. Therefore, this is also an example where sunlight energy (both the photosynthetically active photons and the associated waste solar heat) can be effectively used simultaneously for both photosynthesis and distillation for harvesting of ethanol.

Figure 5B:
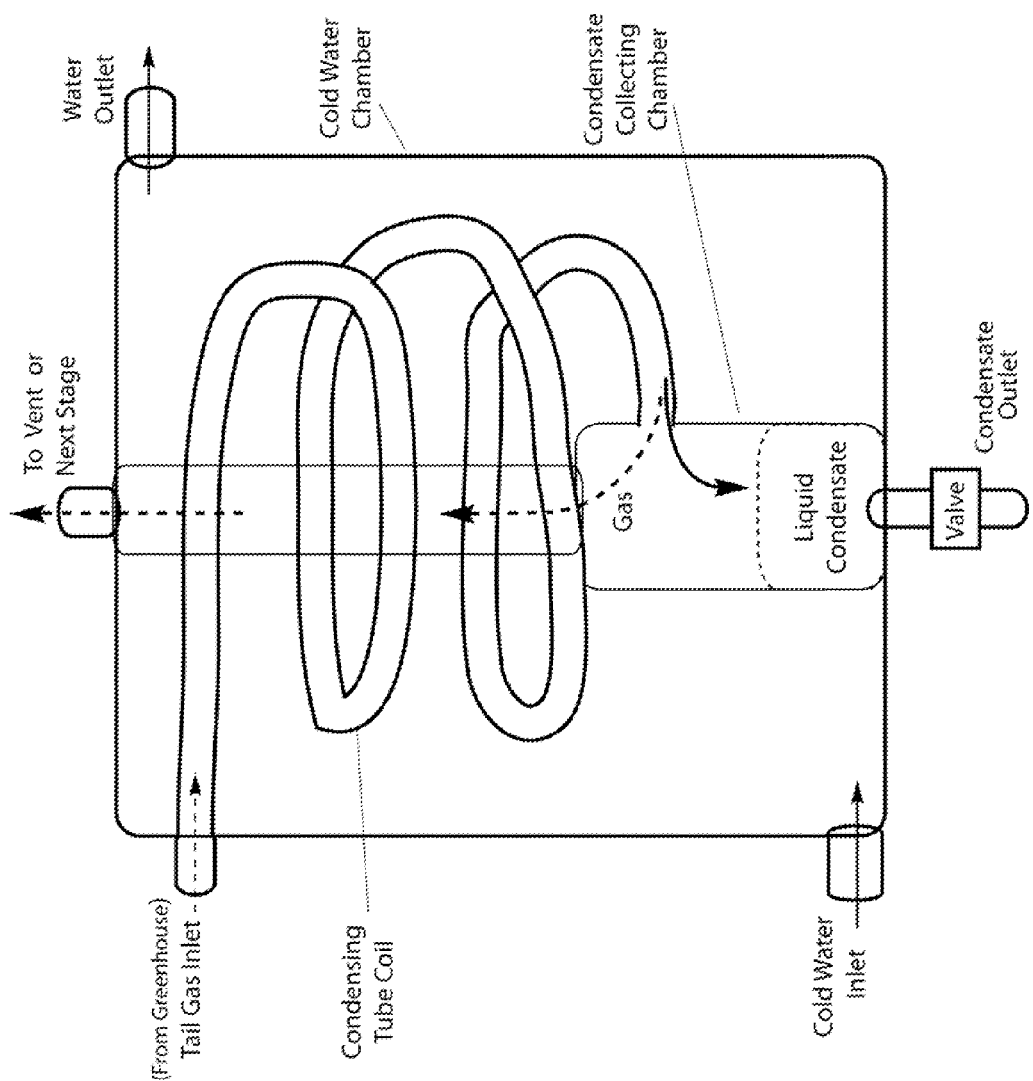
FIG. 5B illustrates a tail-gas condensing and venting unit that comprises a cold-water-bath chamber cooling a tail-gas condensing tube coil, a gas/vapor-condensate chamber, and a vertical venting tube.

FIG. 5B illustrates a tail-gas condensing and venting unit that comprises a cold-water-bath chamber, a tail-gas condensing tube coil, a gas-condensate chamber, and a vertical venting tube. During the operation, the tail-gas condensing tube coil, gas-condensate chamber, and vertical venting tube are all cooled by running cold water through the cold-water-bath chamber so that the vapor in the tail gas will condense along the condensing tube coil which is connected with gas-condensate chamber before venting through the vertical venting tube. This unit is useful in processing the tail gas from a photobiological ethanol-producing greenhouse. "Tail gas" is certain residual gas such as $O_2$ and $N_2$ that is accumulated during a photobiological process and needs to be removed from the reactor in order for photobiological process to continue. As shown in FIG. 5A, when industrial $CO_2$ such as flue-gas $CO_2$ (which typically contains about 15% $CO_2$, 6% $O_2$ and 79% $N_2$) is fed into a photobiological reactor, the photobiological process converts $CO_2$ and water to ethanol and oxygen ($O_2$). What remains in the gas phase will finally be mostly $N_2$ and $O_2$ (plus some ethanol vapor)—tail gas. In order for the photobiological process to continue, the tail gas needs to be removed so that more flue-gas $CO_2$ can be fed into the reactor. Because the tail gas contains ethanol vapor, direct venting without treatment would result in undesirable emission of ethanol vapor along with the tail gas into the atmosphere. Use of the tail-gas condensing and venting system (FIG. 5B) can solve this problem. When tail gas (from a greenhouse) flows through the condensing tube coil which is cooled by the cold water bath, its vapor (including ethanol vapor) will condense and flow along the condensing tube into the gas-condensate chamber where the condensate will accumulate in the bottom of the condensate collecting chamber while the vapor-removed tail gas can then be vented through a vertical venting tube connected with the upper part of the gas-condensate chamber. The condensate (containing ethanol and water) can be collected through use of the condensate outlet (FIG. 5B).

Therefore, according to one of the various embodiments, product ethanol and fresh water can also be harvested from the tail gas through use of a tail-gas condensing and venting unit or a number of tail-gas condensing and venting units in series and/or in parallel.

FIG. 5A also represents an example for a photobiological ethanol production reactor coupled with a distillation system for harvesting ethanol using the associated waste solar heat. In this example, industrial $CO_2$ and/or bicarbonates are used as a source of $CO_2$ for the photobiological ethanol-production process. During the photobiological process, nearly 90% of the sunlight energy is usually dissipated as heat. The waste solar heat can raise the temperature of a culture medium to as high as about 30-70° C., depending on the geographic location and the season. This heat (temperature) is sufficient to vaporize the product ethanol (with water) from the culture medium (typically containing 0.1-6% ethanol). The vapor is then condensed onto the inner surface of the distillation greenhouse's ceiling which is transparent and can be cooled by the surrounding air, winds, and/or by its thermo infra-red radiation to the outer space. As the vapor condenses, the condensate grows into small droplets that can slide downwards along the inner surface of a tilted ceiling and finally flow into the collecting ducts around the greenhouse walls by use of the surface tension (ceiling surface-condensate droplet interaction) and the Earth gravity pulling force. The ethanol concentration in the condensate is significantly higher than that in the culture medium (typically 0.1-6% ethanol), because the ethanol-to-water ratio in the vapor is usually greater than that in the liquid culture medium. Therefore, use of this technology enables harvesting of ethanol from photobiological liquid culture medium using waste solar heat with minimal cost.

As mentioned before, the solar heat can raise the temperature of a culture medium to as high as about 30-70° C., depending on the geographic location and the season. Therefore, according to one of the various embodiments, it is a preferred practice to use thermophilic designer organisms (such as the designer thermophilic cyanobacteria, which can tolerate this type of heat) for photobiological ethanol production and harvesting.

In another embodiment, a distillation greenhouse comprises a photobiological reactor with a series of culture tubes, adjustable culture inlets and outlets, and/or baffles to guide the flow of the liquid culture medium for enhanced photobiological ethanol production and harvesting efficiency. For example, as the culture is used for photobiological ethanol production coupled with the solar-heat-utilizing greenhouse distillation for ethanol harvesting, the guided flow of the designer-organism culture can facilitate the removal of used culture and enhance proper circulation of the culture medium so that the process can operate continuously with high efficiency. This feature is beneficial, especially, in the integrated multi-greenhouse photobiological ethanol production and harvesting operation where guided circulation of culture medium is essential (FIGS. 4 and 6).

Figure 5C:
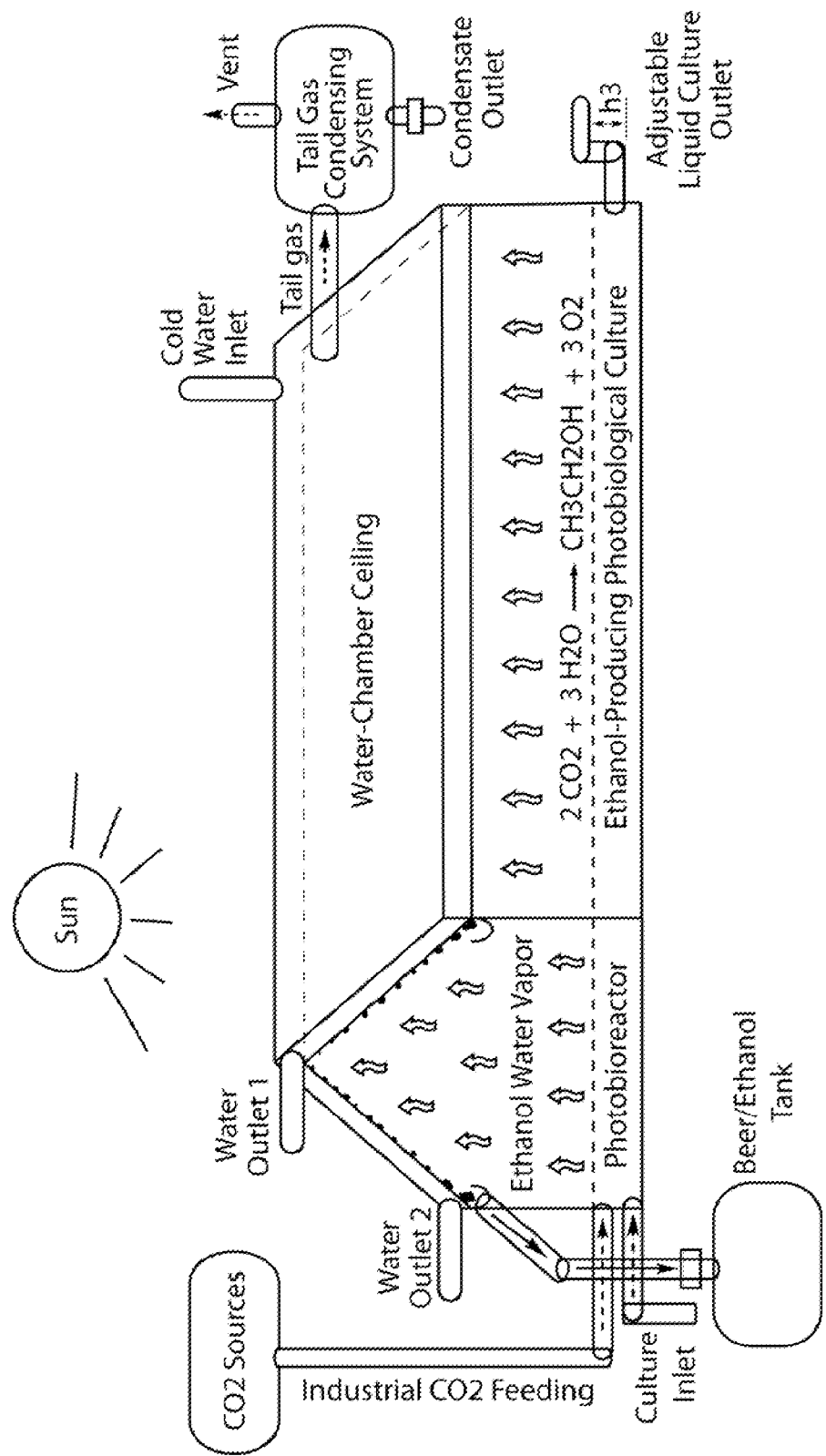
FIG. 5C presents another example for a photobiological ethanol-production reactor coupled with a solar-heat-driven distillation greenhouse system for harvesting ethanol using a water-chamber ceiling system.

In another embodiment, a distillation greenhouse comprises a photobiological reactor with a water-chamber transparent ceiling (FIG. 5C) that can be cooled by running cold water through the chamber over the ceiling to enhance the distillation process. The use of a water-cooled ceiling system can also moderate the greenhouse temperature so that not only thermophilic but also mesophilic designer organisms can be used with the greenhouse distillation system for photobiological ethanol production and harvesting. FIG. 5C presents an example for a photobiological ethanol-production reactor coupled with a solar-heat-driven distillation system for harvesting ethanol, where the vapor-condensing ceiling is a transparent water-chambered ceiling that can be cooled by running cold water through the chamber over the ceiling. Use of a water-cooled ceiling system enhances the distillation process by increasing the rate of vapor condensation at the inner surface of the cooled ceiling. As sunlight driving photobiological ethanol production with heat generation, the vapor that arises from the culture medium carries heat energy to the water-cooled ceiling as it condenses there. Therefore, use of a water-cooled ceiling system can, in some extent, reduce the temperature of the culture medium to a moderate level, which is favorable for use of a designer mesophilic organism (which may have less tolerance to heat) for photobiological ethanol production as well.

Figure 5D:
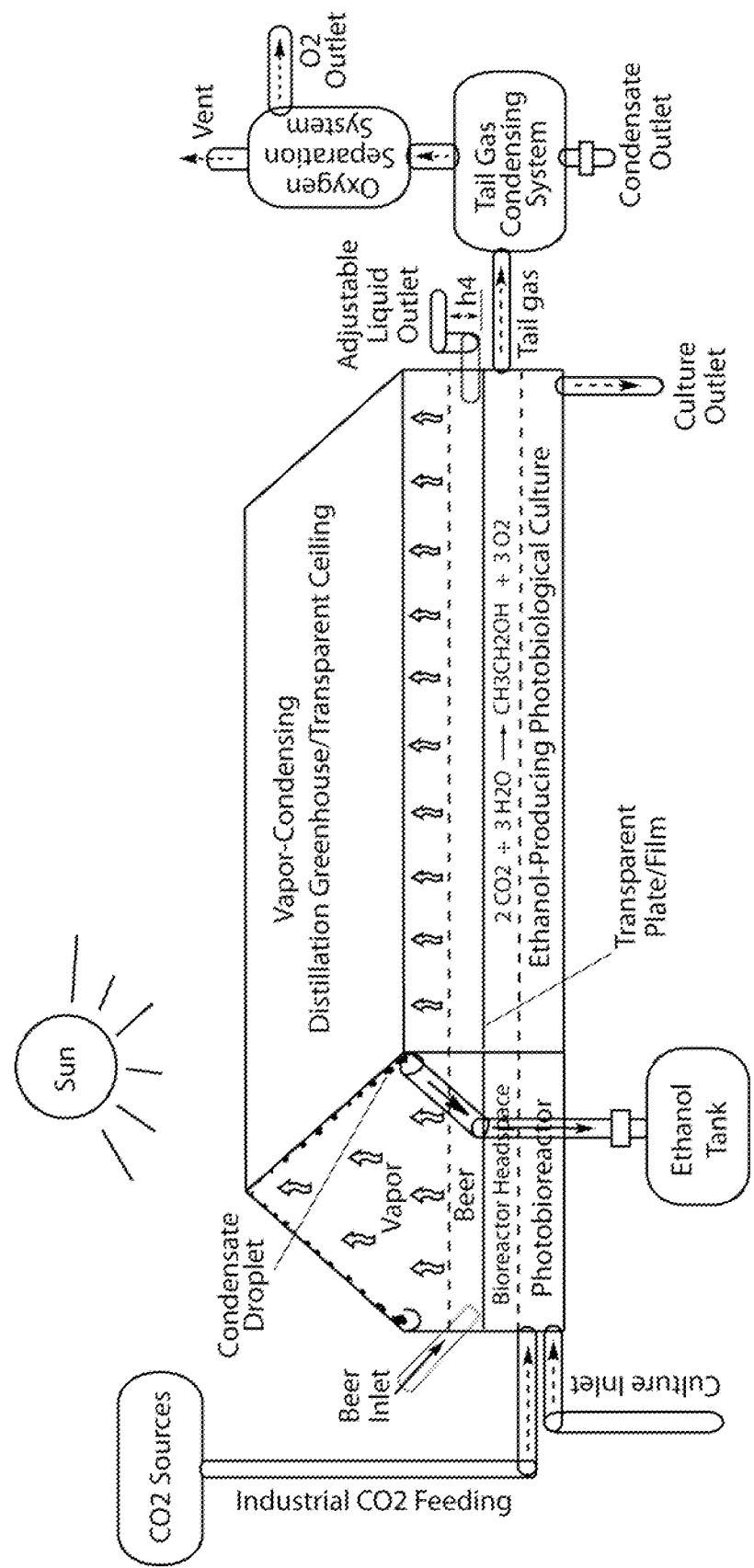
FIG. 5D presents another example for a photobiological ethanol-production and solar-heat-driven distillation greenhouse system, which comprises a lower reactor chamber for photobiological culture growth and an upper chamber space for beer distillation.

In yet another embodiment, as illustrated in FIG. 5D, a distillation greenhouse comprises a lower bioreactor chamber for photobiological culture growth and an upper chamber for beer distillation. The upper distillation chamber and lower bioreactor chamber are separated by a transparent ethanol-impermeable plate and/or film (or membrane) that allows only sunlight to go through. Sunlight drives photosynthesis and generates heat in the photosynthetic cell culture at the lower bioreactor chamber. The solar waste heat is used for evaporation of the ethanol-containing beer liquid at the upper distillation chamber above the photobiological culture reactor (FIG. 5D). The vapor is then condensed onto the inner surface of the ceiling as mentioned previously. This distillation system can be operated both in a batch and/or in a continuous mode. When it is operated in a batch mode of solar heat-driven distillation, the residual liquid of the beer in the upper distillation chamber will gradually become pure water (containing no or very little ethanol) that can then be harvested as freshwater.

Figure 6:
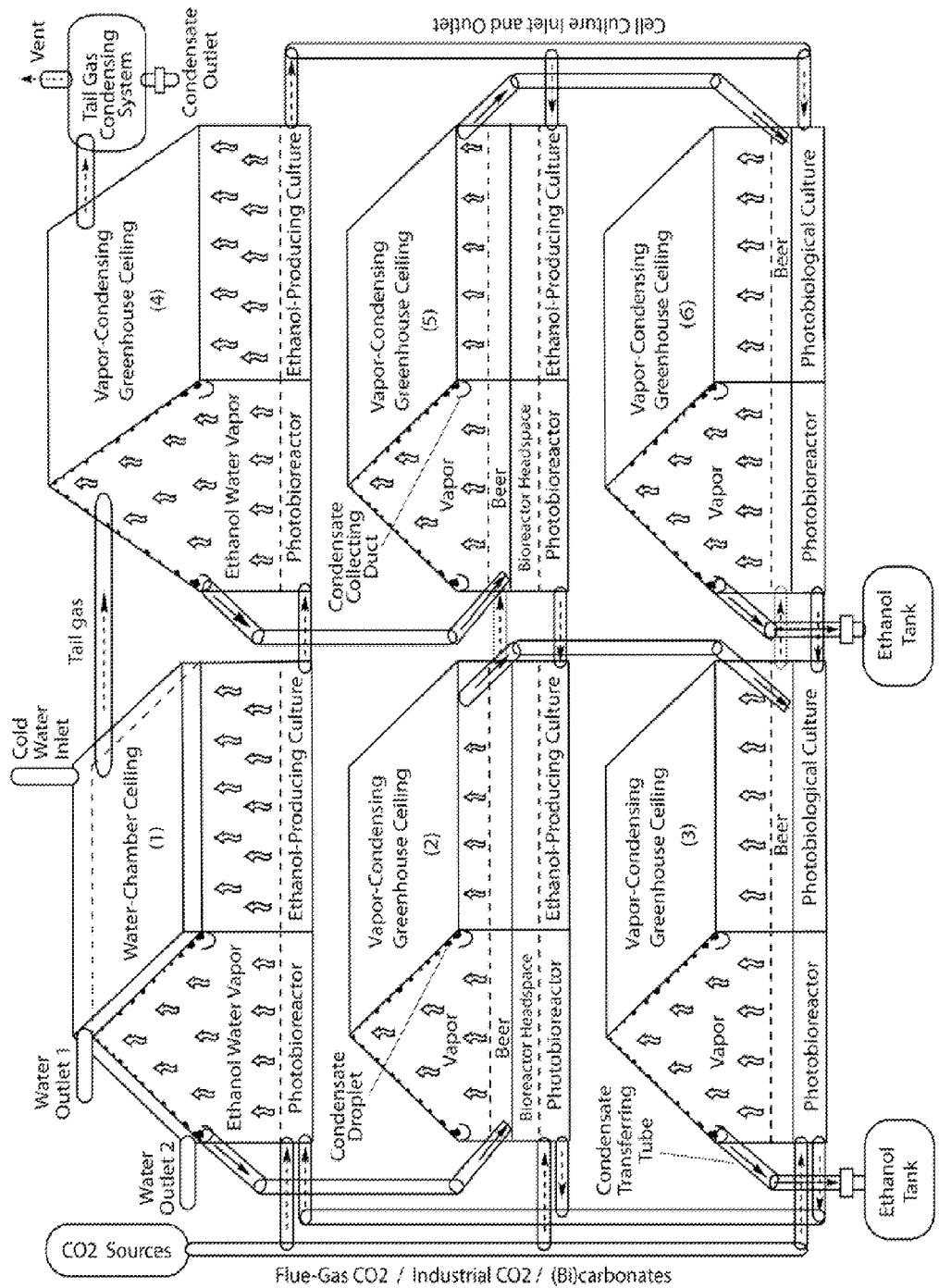
FIG. 6 presents another example for an integrated photobiological ethanol-production and solar-heat-driven distillation greenhouse system using multiple and multistage distillation greenhouses operating in series and in parallel.
Figure 7:
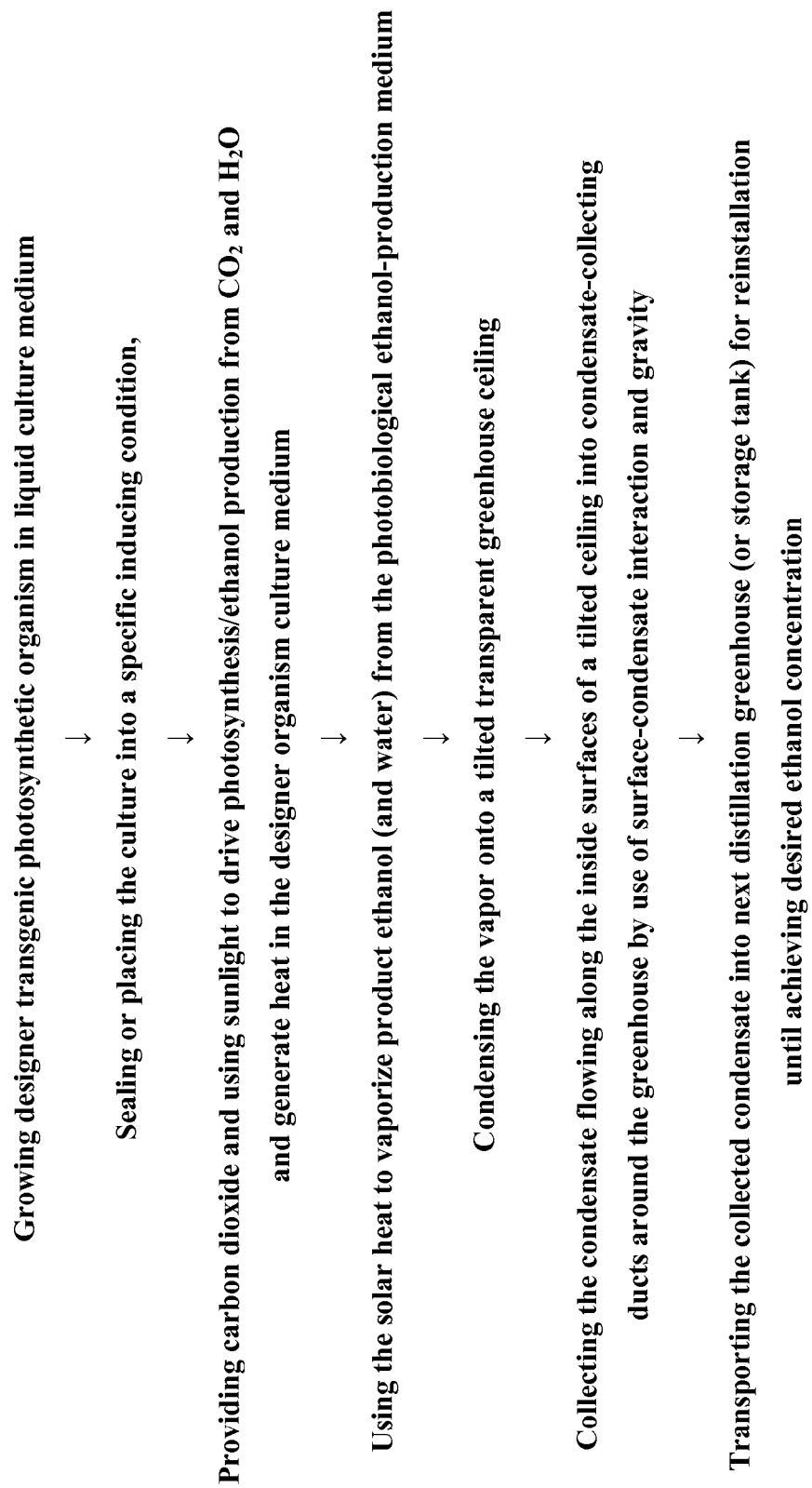
FIG. 7 presents a process of photobiological ethanol production and harvesting with distillation greenhouse systems.

The distillation chamber can also be compartmentalized (or use a number of distillation greenhouses in series and/or in parallel as shown in FIGS. 4 and 6) so that the vapor in one compartment (or greenhouse) is separated from those of other compartments (or greenhouses) while only the beer liquid can gradually flow from one compartment to the next in series through the flow-guiding tubes, adjustable inlets/outlets, baffles and/or a liquid channel or hole at the lower part (immersed in the beer liquid) of an inter compartment wall. In this way, as the beer gradually passes through the distillation compartments (or greenhouses) in series, its ethanol content is removed by distillation. By "beer liquid" is meant a liquid mixture of mainly water and ethanol that is yet to be distilled to make more-concentrated ethanol. Depending on the need and processing conditions, any number of distillation compartments (such as 2, 3, 4, 5, 6, 7, 8, 9, 10, 11, 12, and etc) can be used in series. Therefore, as a beer liquid passes through the distillation compartments in series, the ethanol content in the beer liquid can be reduced to a minimal level so that the residual liquid exiting from the last re-distillation compartment is largely pure freshwater that may be recycled for making culture media and/or for other use as a byproduct. On the other hand, the distillate collected from the first distillation compartment usually has higher ethanol content than that from the successive distillation compartments.

In still another embodiment, as illustrated in FIG. 5D, a photobiological ethanol-production and solar-heat-driven greenhouse distillation system comprises a bioreactor (for photobiological culture with headspace), distillation chamber compartments above the bioreactor, a tail gas condensing system and an oxygen-gas harvesting system. The headspace in the bioreactor allows convenient gas exchange for $CO_2$ feeding and flexible $O_2$ harvesting. Both industrial $CO_2$ and/or atmospheric $CO_2$ from the environment can be fed through a pipeline into the bioreactor for use in the oxygenic photobiological ethanol-production process. The oxygen-gas harvesting system comprises an $O_2$-separation membrane system, an oxygen-gas pump, and an $O_2$ storage tank. Use of this oxygen-gas harvesting system connected through a pipeline can flexibly harvest the photosynthetically produced $O_2$ from the headspace of the bioreactor According to one of the various embodiments, any number of various distillation greenhouses (such as 1, 2, 3, 4, 5, 6, 7, 8, 9, 10, 11, 12, and etc) may be used in series and/or in parallel (FIGS. 4 and 6). As the number of redistillations increase, the resulting ethanol concentration in the condensates (distillates) usually increases. The maximum achievable ethanol concentration through this type of fractional greenhouse distillation is 96% ethanol, which is sufficiently high in quality that can be used directly as a fuel to run ethanol-powered and/or flexible-fuel vehicles. Therefore, this process technology is designed to maximally utilize solar (both its visible and infra-red radiation) energy for both photobiological production of ethanol from $CO_2$ and $H_2O$ and harvesting of the product ethanol through a series of greenhouse distillations with high efficiency and minimal cost.

Note, sometimes, the product ethanol concentration in a large volume of the photobiological liquid culture medium could be as low as below 0.1% ethanol. It would be impractical to use the conventional ethanol-separation technologies such as the boiler-distillation-column-based ethanol-separation technologies to harvest ethanol from such a low concentration in such a large volume of the liquid live culture medium. However, with the use of the greenhouse distillation technology (FIGS. 4-8), it is possible to harvest and/or enrich from a very dilute ethanol concentration (which sometimes could be as low as below 0.1% ethanol) of a photobiological liquid culture medium to first produce a beer liquid (condensate) that contains more than 3% ethanol so that can then be further processed with certain conventional ethanol-separation technologies including the boiler-distillation-column-based ethanol-separation technologies. In this case, the greenhouse distillation technology (FIGS. 4-8) can also be used in combination with the existing ethanol-separation technologies including the boiler-distillation-column-based ethanol-separation technologies. In addition to photobiological production and harvesting of product ethanol, use of the technology can also produce freshwater, oxygen gas, and used biomass culture as byproducts. Therefore, the photobiological ethanol production and harvesting technology of the present invention is expected to have multiple applications with a higher solar-to-ethanol energy-conversion efficiency than the current technology.

FIG. 4B presents an example of an integrated photobiological ethanol-production and solar-heat-driven distillation system which comprises multiple distillation greenhouses. In this example, the designer-organism culture in the first distillation-greenhouse bioreactor (FIG. 4B, upper) photobiologically produces ethanol from water and $CO_2$. The product ethanol is harvested from the photobiological culture by the solar-heat-driven distillation. The condensate collected from this distillation greenhouse (FIG. 4B, upper) is transported to the next greenhouse (FIG. 4B, middle) where the condensate is re-distillated with a series of distillation compartments. According to one of various embodiments, any number of distillation compartments (such as 2, 3, 4, 5, 6, 7, 8, 9, 10, 11, 12, and etc) can be used in series and/or in parallel. As mentioned before, when the beer liquid passes through the distillation compartments (or distillation greenhouse) in series, the ethanol content in the beer liquid can be removed so that the residual liquid exiting from the last re-distillation compartment (distillation greenhouse) becomes largely pure freshwater that may be recycled for making culture media and/or for other use. That is, use of this photobiological ethanol-production process technology can also produce freshwater as a byproduct.

The condensates from the re-distillation are transferred to the third greenhouse (FIG. 4B, bottom), which can also comprises multiple distillation compartments for re-distillation. The final distillates from the third distillation greenhouse typically contain 10-90% ethanol, largely depending on the ethanol content of the source beers. Higher ethanol concentration can be achieved with further re-distillation. According to one of the various embodiments, any number of distillation compartments and/or greenhouses (such as 2, 3, 4, 5, 6, 7, 8, 9, 10, 11, 12, and etc) can be used in series and/or in parallel. As the number of re-distillations increase, the resulting ethanol concentration in the condensates increases. The maximum achievable ethanol concentration through this type of fractional distillation is 96% ethanol with 4% water, because, at this concentration (96% ethanol, which is also known as an azeotropic mixture), the ethanol in the vapor is no longer more concentrated than that in the liquid phase and consequently the fractional distillation reaches its limit.

FIG. 6 presents another example of an integrated photobiological ethanol-production and solar-heat-driven distillation system which comprises multiple distillation greenhouses in series and in parallel operation for enhanced total process efficiency. This system is similar to the example of FIG. 4B, except that comprises 6 distillation greenhouses with the first distillation greenhouse employs a water-chambered ceiling that can be cooled by running cold water through the ceiling chamber. As mentioned before, use of cooling water can not only increase the distillation efficiency, but also enables the use of less-heat-tolerant designer organisms for photobiological ethanol production. Furthermore, when the vapor condenses on the water-chambered ceiling, it releases its heat to the cooling water and thus gradually raises the temperature of the cooling water. As a result, the water exiting from outlet 1 (or outlet 2) of the chamber ceiling is relatively warm and may be used for other processes for heat recovery. The other operations are similar to the example of FIG. 4B. Briefly, use of sunlight drives photobiological production of ethanol from water and $CO_2$ and generates heat. The produced ethanol is harvested from the photobiological culture medium by the solar-heat-driven distillation (FIG. 6, upper left). The distillate from the first distillation greenhouse is transported to the second distillation greenhouse (FIG. 6, left middle) where the condensate is re-distillated with a series of distillation compartments. The condensates from the second distillation greenhouse are transferred to the third distillation greenhouse (FIG. 6, bottom right) again for re-distillation. The condensates from the third distillation greenhouse typically contain 10-90% ethanol, depending on the ethanol content of the source beer. Higher ethanol concentration can be achieved with further re-distillation with a maximum achievable ethanol concentration of about 96%, which can be used to run an ethanol-powered and/or flexible-fuel vehicles. When necessary, the 96% ethanol can also be used to produce 100% ethanol (200 proof) by removing its residual 4% water with separation techniques of azeotropic distillation and/or molecular sieve.

Furthermore, as mentioned before, use of this photobiological ethanol-production process technology (FIG. 6) can also produce freshwater as a byproduct. When seawater is used in the culture medium, this photobiological ethanol-production process technology can effectively produce freshwater as a byproduct from seawater as well. Therefore, in one of the various embodiments, a designer salt-tolerant photosynthetic organism made from marine photosynthetic organism is preferably used in this integrated photobiological ethanol-production and solar-heat-driven greenhouse distillation system (FIG. 6). The use of a designer salt-tolerant photosynthetic organism with this greenhouse distillation technology (FIGS. 4-6) can produce both ethanol and freshwater from seawater with minimal cost.

As mentioned previously, the temperature in a sealed plastic photobioreactor and/or distillation greenhouse could get as high as about 30-70° C. depending on the season and geographic location. Certain designer thermophilic organisms such as designer oxyphotobacteria created from a thermophilic host oxyphotobacterium such as *Thermosynechococcus elongatus* BP-1 with inducible-promoter-controlled thermotolerant designer ethanol-pathway genes are especially suitable for use in this invention for integrated photobiological ethanol production and ethanol harvesting with solar-heat driven greenhouse distillation at this type of hot temperature range (30-70° C.).

The various embodiments further teach how the designer photosynthetic organisms such as designer oxyphotobacteria including transgenic cyanobacteria may be used with the integrated photobiological ethanol-production and solar-heat-driven greenhouse distillation systems (FIGS. 4-6). There are a number of embodiments on how the designer photosynthetic organisms such as designer algae and designer cyanobacteria may be used for photobiological ethanol production with greenhouse distillation systems (FIGS. 4B and 6). Here, designer oxyphotobacteria such as designer cyanobacteria are used as an example showing how to use the integrated photobiological ethanol-production and solar-heat-driven greenhouse distillation systems with the designer photosynthetic organisms. One of the preferred embodiments is to use the designer transgenic oxyphotobacteria for direct photosynthetic ethanol production from $CO_2$ and $H_2O$ with a combined system of photobiological reactors and ethanol-harvesting distillation greenhouses (FIGS. 4 and 6), which includes a specific operational process (FIG. 7) described as a series of the following steps: a) Growing a designer transgenic oxyphotobacterium photoautotrophically in minimal (such as BG-11) culture medium using air $CO_2$ as the carbon source under aerobic (normal) conditions before inducing the expression of the designer ethanol-production-pathway genes; b) When the designer oxyphotobacterial cell culture is grown and ready for ethanol production, sealing or placing the culture into a specific inducing condition, such as an anaerobic condition that can be generated by removal of $O_2$ from the photobiological reactor, to induce the expression of designer ethanol-production-pathway genes; c) When the designer ethanol-production-pathway enzymes are expressed in the designer organism, providing carbon dioxide and using sunlight to drive photosynthesis/ethanol production from $CO_2$ and $H_2O$ and generate heat with the designer organism culture medium; (d) Using the waste solar heat to vaporize product ethanol (and water) from the designer-organism photobiological ethanol-production reactor medium; (e) Condensing the vapor onto a tilted transparent ceiling; (f) Collecting the condensate flowing along the inside surfaces of the tilted ceiling system into condensate-collecting ducts around the walls of the greenhouse by use of surface-condensate interaction and gravity; and (g) Transporting the collected condensate into the next distillation greenhouse (or a storage tank) for reinstallation until achieving the desired ethanol concentration.

The above process to use the designer oxyphotobacteria for photosynthetic $CH_3CH_2OH$ and $O_2$ production from $CO_2$ and $H_2O$ with a combined system of photobiological reactors and ethanol-harvesting distillation greenhouses (FIGS. 4 and 6) can be repeated for a plurality of operational cycles to achieve more desirable results. Any of the steps a) through g) of this process described above can also be adjusted in accordance of the invention to suit for certain specific conditions. For example, when a distillation greenhouse with a water-cooled vapor-condensing ceiling system (FIG. 5C) is used as illustrated in FIG. 6 for a combined system of photobiological reactors and ethanol-harvesting distillation greenhouses, the step e) of vapor condensing can be enhanced by running cold water through the water-chamber ceiling system at the top of the distillation greenhouse. In practice, any of the steps a) through g) of the process can be applied in full or in part, and/or in any adjusted combination as well for enhanced photobiological ethanol production and harvesting in accordance of this invention.

The sources of $CO_2$ that can be used in this process include, but not limited to, industrial $CO_2$, (bi)carbonates, and atmospheric $CO_2$. For an example, flue-gas $CO_2$ from fossil fuel-fired and/or biomass-fired industrial facilities can be fed through a pipeline into a photobiological reactor in this process as illustrated in FIGS. 4 and 6. The industrial facilities that can generate $CO_2$ supplies for the designer photobiological ethanol-production and harvesting process include (but not limited to): coal-fired power plants, iron and steelmaking industries, cement-manufacturing plants, petroleum refinery facilities, chemical fertilizer production factories, biomass-fired and/or fossil fuel-fired ethanol distillation/separation facilities, biomass-pyrolysis processes, smokestacks, fermentation bioreactors, biofuel-refinery facilities, and combinations thereof. Alternatively, this designer photobiological ethanol-production-harvesting process can also use the $CO_2$ in the environment and from the atmosphere as well. Gaseous $CO_2$, dissolved $CO_2$, bicarbonate, and carbonates can all be used by the integrated designer photobiological ethanol-production-harvesting technology (FIGS. 4-8).

As mentioned previously, certain inducible designer photosynthetic organisms such as the designer cyanobacterium that contain a set of designer hox-promoter-controlled designer ethanol-production-pathway genes can grow normally under aerobic conditions by autotrophic photosynthesis using air $CO_2$ in a manner similar to that of a wild-type cyanobacterium. The designer cyanobacterium can grow also photoheterotrophically using an organic substrate as well.

In a preferred embodiment, an inducible designer photosynthetic organism such as a designer oxyphotobacterium is grown photoautotrophically using air $CO_2$ as the carbon source under the aerobic conditions in a minimal (BG-11) medium that contains the essential mineral (inorganic) nutrients. No organic substrate such as glucose or acetate is required to grow a designer oxyphotobacterium under the normal conditions before the designer photosynthetic ethanol-production genes are expressed. Most of the oxyphotobacteria including cyanobacteria can grow rapidly in water through autotrophic photosynthesis using air $CO_2$ as long as there are sufficient mineral nutrients. The nutrient elements that are commonly required for oxyphotobacterial growth are: N, P, and K at the concentrations of about 1-10 mM, and Mg, Ca, S, and Cl at the concentrations of about 0.5 to 1.0 mM, plus some trace elements Mn, Fe, Cu, Zn, B, Co, Mo among others at μM concentration levels. All of the mineral nutrients can be supplied in an aqueous minimal medium such as the BG-11 medium that can be made with well-established recipes of oxyphotobacterial culture media using water (freshwater for designer freshwater oxyphotobacteria; seawater for designer marine oxyphotobacteria) and relatively small of inexpensive fertilizers and mineral salts such as ammonium bicarbonate ($NH_4HCO_3$) (or ammonium nitrate, urea, ammonium chloride), potassium phosphates ($K_2HPO_4$ and $KH_2PO_4$), magnesium sulfate heptahydrate ($MgSO_4.7H_2O$), calcium chloride ($CaCl_2$), zinc sulfate heptahydrate ($ZnSO_4.7H_2O$), iron (II) sulfate heptahydrate ($FeSO_4.7H_2O$), and boric acid ($H_3BO_3$), among others. That is, large amounts of designer oxyphotobacteria cells can be inexpensively grown in a short period of time because, under aerobic conditions such as in an open pond, the designer oxyphotobacteria can photoautotrophically grow by themselves using air $CO_2$ as rapidly as their wild-type parental strains. This is a significant feature (benefit) that could provide a cost-effective solution in generation of photoactive biocatalysts (the designer photosynthetic ethanol-producing oxyphotobacteria) for renewable solar energy production. Use of the integrated designer photobiological ethanol-production-harvesting technology (FIGS. 4-8) reported in this invention can maximize the benefit.

For example, the photobiological culture reactors in the second and/or third distillation greenhouses (FIG. 4B, middle and/or bottom) can be used to grow an inducible designer photosynthetic organism such as an inducible designer oxyphotobacterium photoautotrophilcally using $CO_2$ as the carbon source. As shown in FIG. 4A, the waste solar heat generated during photosynthesis is used to drive the vaporization of the beer liquid in the distillation chambers above the photobiological culture reactors so that the sunlight energy is utilized for both photosynthesis and ethanol-harvesting greenhouse distillation with high energy efficiency. When the oxyphotobacterial culture is grown and ready for ethanol production, the grown oxyphotobacterial culture is placed into certain specific inducing conditions, such as anaerobic conditions that can be generated by removal of $O_2$ from the sealed photobiological reactor using a flexible oxygen-gas harvesting system (FIG. 5D), to induce the expression of, for an example, designer anaerobic-hox-promoter-controlled photosynthetic ethanol-production-pathway genes. When the designer ethanol-production-pathway enzymes are induced, the induced designer oxyphotobacterial cells can be sent to the first distillation-greenhouse photobiological reactor (FIG. 4B, upper) to work as the catalysts for photosynthetic ethanol production from $CO_2$ and $H_2O$. The waste solar heat generated during photosynthetic ethanol production is also utilized to vaporize the ethanol product from the oxyphotobacterial photobiological rector medium for harvesting ethanol by the greenhouse distillation process. The vapor arising from the oxyphotobacterial photobiological rector medium condenses onto the vapor-condensing-ceiling system that is cooled by air/winds (FIG. 4B) and/or by running cold water over the ceiling (FIGS. 5C and 6). As mentioned previously, the condensate from the first distillation greenhouse (FIG. 4B, upper) is transferred automatically with use of gravity through a condensate-transporting tube into the beer liquid reactor of the second distillation greenhouse (FIG. 4B, middle) for re-distillation to increase ethanol concentration in the distillate.

The distillate (condensate) from the second distillation greenhouse is transported also automatically with use of gravity through a condensate-transporting tube into the beer liquid reactor of the third distillation greenhouse (FIG. 4B, bottom) for redistillation again to raise the ethanol concentration to a desired level in the final distillates.

When necessary, the distillates from the third distillation greenhouse (FIG. 4B, bottom) can be transported into the fourth, the fifth, the sixth, and more distillation greenhouses for redistillations until achieving desired higher ethanol in the final distillates. According to one of the various embodiments, any number of distillation greenhouses (such as 1, 2, 3, 4, 5, 6, 7, 8, 9, 10, 11, 12, and etc) can be used in series and/or in parallel. As the number of redistillations increase, the resulting ethanol concentration in the condensates (distillates) increases. The maximum achievable ethanol concentration through the fractional greenhouse distillation is about 96% ethanol, which is sufficiently good and can be used directly as a fuel to run ethanol-powered and/or flexible-fuel vehicles. Therefore, this process technology (FIGS. 4-8) is designed to maximally utilize sunlight (both its visible and infra-red radiation) energy for both photobiological production of ethanol from $CO_2$ and $H_2O$ and harvesting of the product ethanol through greenhouse distillation with high efficiency and minimal cost.

The above process to use the designer photosynthetic organisms for photobiological production of $CH_3CH_2OH$ and $O_2$ from $CO_2$ and $H_2O$ and harvesting of product ethanol with integrated greenhouse distillation systems (FIGS. 4 and 6) can be repeated for a plurality of operational cycles to achieve more desirable results. In addition to ethanol product, use of the process technology can also produce freshwater as a byproduct since the residual liquid from a beer liquid (condensate) after removal of ethanol through re-distillation is mostly pure water. This feature is also beneficial, especially, when seawater is the source of culture medium and when production of freshwater from seawater is desirable.

Figure 8:
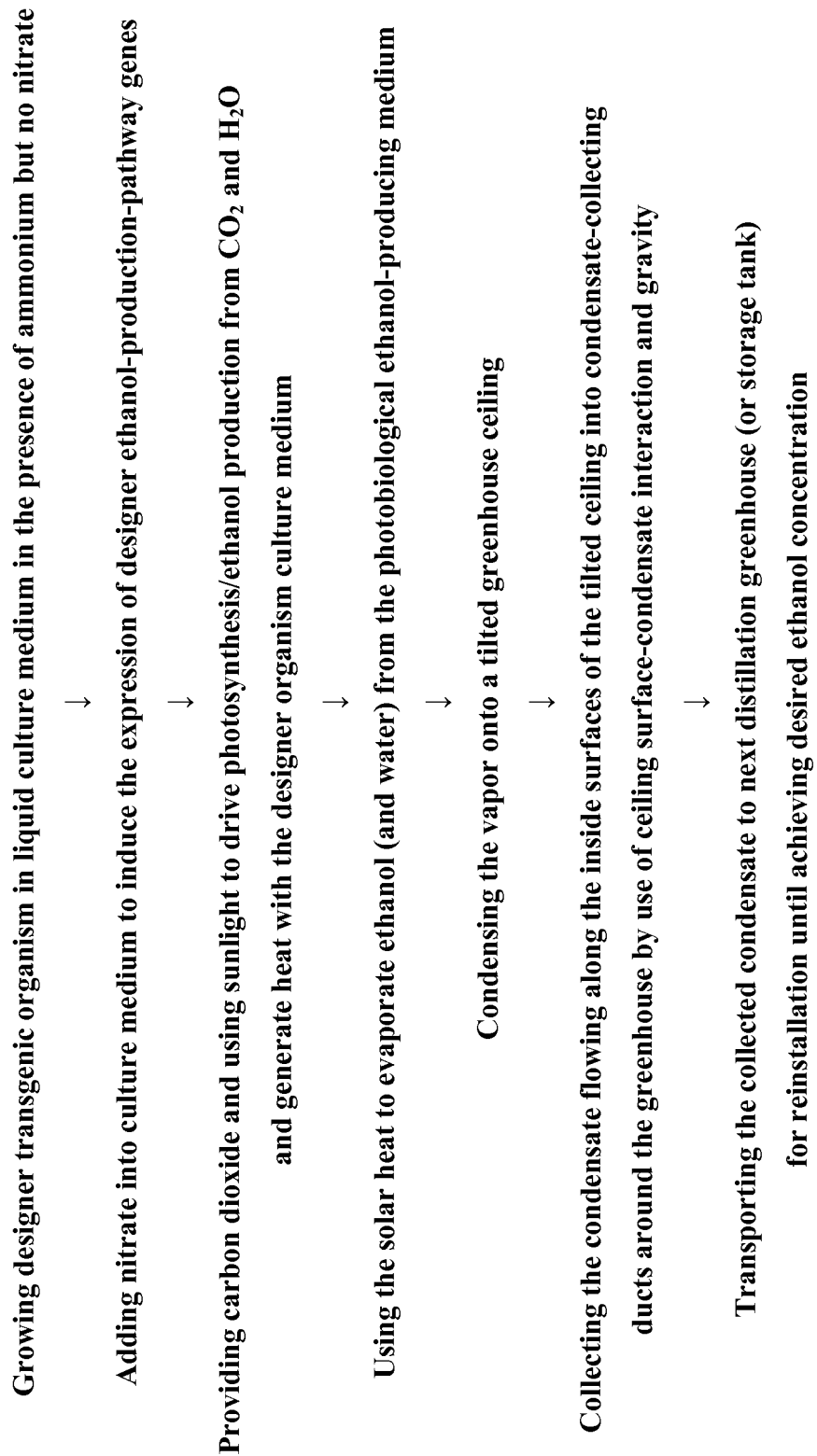
FIG. 8 presents another process of photobiological ethanol production and harvesting with distillation greenhouse systems using ammonium vs. nitrate-inducible designer organisms.

For certain specific designer oxyphotobacteria with designer nitrite-reductase (nirA) promoter-controlled ethanol-production-pathway genes, the above photobiological reactor process may be further adjusted to achieve more beneficial results. For example, a designer oxyphotobacterium that contains nirA-promoter-controlled ethanol-production-pathway genes can grow normally in a culture medium with ammonium (but no nitrate) by autotrophic photosynthesis using air $CO_2$ in a manner similar to that of a wild-type oxyphotobacterium. This is because the expression of the ethanol-production-pathway genes in this designer oxyphotobacterium will be turned on only in the presence of nitrate as desired owing to the use of nitrite reductase (nirA) promoter in controlling the designer pathway expression. As mentioned previously, a significant feature of the designer oxyphotobacteria with nirA-promoter-controlled ethanol-production-pathway genes is that the expression of the designer ethanol-production pathways can be induced by manipulating the concentration levels of nitrate ($NO_3^-$) relative to that of ammonium ($NH_4^+$) in the culture medium without requiring any anaerobic conditions. That is, the expression of the designer ethanol-production pathway(s) can be induced under both aerobic and anaerobic conditions in a photobiological reactor such as the one in the first distillation greenhouse (FIG. 4B, upper). This enables the designer photobiological ethanol-production process to operate even under aerobic conditions using atmospheric $CO_2$. Likewise, use of a photobiological culture reactor such as the ones in the second and/or the third distillation greenhouses (FIG. 4B, middle and/or bottom) with an ammonium (but no nitrate) containing culture medium can also grow this type of designer oxyphotobacteria with nirA-promoter-controlled ethanol-production-pathway genes photoautotrophically using $CO_2$ as the source of carbon under both aerobic and anaerobic conditions as well. Therefore, as a further embodiment, the operational process of using designer oxyphotobacteria with nitrite reductase (nirA) promoter-controlled ethanol-production-pathway genes is adjusted as shown in FIG. 8 to the following: a) Growing a designer transgenic oxyphotobacterium photoautotrophically in minimal (such as BG-11) culture medium in the presence of ammonium ($NH_4^+$) but no nitrate ($NO_3^-$) before inducing the expression of the designer ethanol-production-pathway genes; b) When the designer oxyphotobacterial culture is grown and ready for ethanol production, adding nitrate ($NO_3^-$) fertilizer into the culture medium to raise the concentration of nitrate ($NO_3^-$) relative to that of ammonium ($NH_4^+$) to induce the expression of designer ethanol-production-pathway genes; c) When the designer ethanol-production-pathway enzymes are expressed, providing carbon dioxide ($CO_2$) and using sunlight to drive photosynthesis/ethanol production from $CO_2$ and $H_2O$ and generate heat with the designer organism culture medium; (d) Using the waste solar heat to evaporate ethanol (and water) from the designer-organism photobiological ethanol-producing reactor medium; (e) Condensing the vapor onto a transparent tilted ceiling; (f) Collecting the condensate flowing along the inside surfaces of the tilted ceiling system into condensate-collecting ducts around the walls of distillation greenhouse by use of ceiling surface-condensate interaction and gravity; and (g) Transporting the collected condensate to the next distillation greenhouse (or a storage tank) for reinstallation until achieving the desired ethanol concentration.

In one of the various embodiments, the process further comprises the steps of: h) harvesting the ethanol from the environment by a combination of greenhouse distillation and re-distillation techniques; i) harvesting the residual beer liquid (mostly pure freshwater) after harvesting the product ethanol from the beer liquid; j) harvesting the ethanol and fresh water from the tail gas by using of the tail-gas condensing and venting unit; k) harvesting the used transgenic designer organism that is converted from the induced transgenic organism; and l) repeating steps a) through k) for a continuous photobiological ethanol production and harvesting.

Another feature is that the designer switchable ethanol-production oxyphotobacterium such as a designer cyanobacterium provides the capability for repeated cycles of photoautotrophic culture growth under normal aerobic conditions with a manner similar to that of a wild type and efficient photobiological production of ethanol (FIGS. 1 and 3) when the designer ethanol-production pathway is switched on by an inducible promoter (such as the nirA promoter) in presence of nitrate in a bioreactor such as the photobiological reactor in the first distillation greenhouse (FIG. 4B, upper). For example, the switchable designer oxyphotobacterium with designer nirA-promoter-controlled ethanol-production genes contains normal respiratory mechanism, which uses the reducing power (NADH) from organic reserves (and/or exogenous substrates, such as glucose or acetate) to power the cell immediately after its return to normal aerobic conditions in presence of ammonium (but no nitrate). Therefore, when the oxyphotobacterial culture is returned to aerobic normal conditions in presence of ammonium (but no nitrate) after its use in a nitrate-containing medium for production of ethanol, the culture will stop producing ethanol-production-pathway enzymes and start to restore its normal photoautotrophic capability by synthesizing normal functional Calvin-cycle enzymes and producing new and functional cells. Consequently, it is possible to use this type of genetically transformed organism for repeated cycles of photoautotrophic culture growth in an ammonium-containing medium under normal aerobic conditions and efficient production of ethanol in a nitrate-containing medium (FIG. 3). That is, this photobiological ethanol-production technology can be operated for a plurality of operational cycles by rejuvenating the used culture in an ammonium-containing medium under aerobic conditions and recyclably using the rejuvenated oxyphotobacterial culture under ethanol-producing conditions to achieve more desirable results. Optionally, this photobiological ethanol-production technology is operated continuously by circulating rejuvenated oxyphotobacterial culture from a rejuvenating culture reactor such as the one in the second distillation greenhouse (FIG. 4B, middle) into the photobiological ethanol-producing reactor as the one in the first distillation greenhouse (FIG. 4B, upper) while circulating the used oxyphotobacterial culture from the ethanol-producing bioreactor (after its use for ethanol production) into a photobiological culture reactor (FIG. 4B, middle or bottom) in the presence of ammonium under aerobic conditions for rejuvenation by synthesizing normal functional Calvin-cycle enzymes and producing new cells through photosynthetic $CO_2$ fixation and photoautotrophic growth.

Some of the designer oxyphotobacteria could grow photoautotrophically even with the ethanol-production pathway(s) switched on. Whether or how fast a designer oxyphotobacterium could grow under the ethanol-producing conditions may depend on its genetic background and how much of the Calvin cycle products are still available for cell growth after use by the designer ethanol-production pathway(s). Designer oxyphotobacteria that can, under the ethanol-producing conditions, maintain essential cellular functions with an appropriate growth rate can also be used for continuous photobiological production of $CH_3CH_2OH$ and $O_2$ from $CO_2$ and $H_2O$ and harvesting of product ethanol with greenhouse distillation systems (FIGS. 4-6).

There are additional ways that the switchable designer oxyphotobacteria can be used. For example, the used designer oxyphotobacterial culture from a photobiological ethanol-production reactor (FIG. 4B, upper) does not have to be circulated back to a culture-growth reactor (FIG. 4B, middle). Instead, the used oxyphotobacterial culture is taken out to be used as fertilizers or biomass feed stocks for other processing because the photoautotrophic growth of the switchable designer oxyphotobacterium in a culture-growth reactor (FIG. 4B, middle) is capable of continuously supplying oxyphotobacterial cells to a photobiological ethanol-production reactor for biofuel production (FIG. 4B, upper). This embodiment is, especially, helpful to using some of the designer oxyphotobacteria that can grow photoautotrophically only before (but not after) the ethanol-production-pathway(s) is switched on. For example, by keeping a continuously growing culture of a designer oxyphotobacterium (that can grow photoautotrophically only before the ethanol-production-pathway(s) is switched on) in a culture-growth reactor (FIG. 4B, middle and/or bottom), it can provide continuous supplies of grown oxyphotobacterial cells for use in a photobiological ethanol-production reactor (FIG. 4B, upper). This approach makes it possible to use those designer organisms that can grow only before the ethanol-production-pathway(s) is switched on for photobiological ethanol production and harvesting with greenhouse distillation as well.

Because of various reasons, some of the designer ethanol-production oxyphotobacteria could grow only photohetrotrophically or photomixotrophically but not photoautotrophically. Use of a culture-growth reactor (FIG. 4B, middle or bottom) can also grow this type of designer ethanol-production oxyphotobacteria photohetrotrophically or photomixotrophically using organic substrates including, but not limited to, glucose, fructose, sucrose, acetate, ethanol, methanol, propanol, butanol, acetone, starch, hemicellulose, cellulose, lipids, proteins, organic acids, biomass materials and combination thereof. The so-grown culture can also be supplied to a photobiological ethanol-production reactor (FIG. 4B, upper) for induction of the designer pathways for ethanol production. This modified embodiment on culture growth makes it possible to use those designer organisms that can grow only photohetrotrophically, or photomixotrophically also for photobiological ethanol production and harvesting with greenhouse distillation as well. This greenhouse distillation methodology (FIGS. 4-8) can be useful to photobiological ethanol production and harvesting with a number of designer organisms including designer transgenic oxyphotobacteria, algae, plants, or plant cells.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. A method for photobiological production and harvesting of ethanol comprising growing a transgenic oxyphotobacterium or oxyphotobacterial cells in a liquid medium, wherein the oxyphotobacterium or oxyphotobacterial cells are genetically engineered with a set of DNA constructs to express a set of enzymes consisting of NAD-dependent glyceraldehyde-3-phosphate dehydrogenase comprising SEQ ID NO: 40 or 53, pyruvate decarboxylase, and NAD(P)H-using alcohol dehydrogenase comprising SEQ ID NO: 7 or 17 that act on an intermediate product of the Calvin cycle and convert the intermediate product into ethanol using photosynthetic reducing power NADPH; and recovering ethanol from said liquid medium with a special greenhouse distillation system.

2. The method according to claim 1, wherein said oxyphotobacterium is selected from the group consisting of following oxyphotobacteria (cyanobacteria and oxychlorobacteria): *Thermosynechococcus elongatus* BP-1, *Nostoc* sp. PCC 7120, *Synechococcus elongatus* PCC 6301, *Syncechococcus* sp. strain PCC 7942, *Syncechococcus* sp. strain PCC 7002, *Synechococcus elongates*, *Synechococcus* (MC-A), *Synechococcus* WH7803, *Synechococcus* WH8102, *Syncechococcus* sp. strain PCC 7943, *Synechococcus bigranulatus*, thermophilic *Synechococcus bigranulatus*, *Synechococcus lividus*, *Synechococcus vulcanus*, *Synechococcus* sp. strain MA4, and *Synechococcus* sp. strain MA19.

3. The method of claim 2, wherein said oxyphotobacterium comprises heat-tolerant oxyphotobacterial strains selected from the group consisting of *Thermosynechococcus elongatus* BP-1, thermophilic *Mastigocladus laminosus*, thermophilic *Synechococcus bigranulatus*, and *Thermosynechococcus elongatus*.

4. The method of claim 1, wherein the set of enzymes further consists of NAD-dependent glyceraldehyde-3-phosphate dehydrogenase comprising SEQ ID NO:27, NADPH-dependent glyceraldehyde-3-phosphate dehydrogenase comprising SEQ ID NO:39, phosphoglycerate mutase comprising SEQ ID NO:16, enolase comprising SEQ ID NO:4, pyruvate kinase comprising SEQ ID NO:5, pyruvate decarboxylase comprising SEQ ID NO:6, and NAD(P)H-using alcohol dehydrogenase comprising SEQ ID NO:26.

5. The method of claim 1, wherein said DNA construct comprising from 5' to 3', an inducible promoter and a nucleotide sequence coding for an NAD-dependent glyceraldehyde-3-phosphate dehydrogenase comprising SEQ ID NO:1 to function with a native NADPH-dependent glyceraldehyde-3-phosphate dehydrogenase in forming a cyclic transhydrogenase redox-shuttle mechanism to convert NADPH to NADH for enhanced photobiological ethanol production.

6. The method of claim 5, wherein said cyclic transhydrogenase redox-shuttle mechanism for NADPH/NADH conversion is achieved by a two-step mechanism:
 1) step with said NADPH-dependent glyceraldehyde-3-phosphate dehydrogenase comprising SEQ ID NO:39, which uses NADPH in reducing 1,3-diphosphoglycerate to glyceraldehydes-3-phosphate; and
 2 step with said $NAD^+$-dependent glyceraldehyde-3-phosphate dehydrogenase comprising SEQ ID NO:40, which produces NADH in oxidizing glyceraldehyde-3-phosphate to 1,3-diphosphoglycerate.

7. The construct according to claim 5, wherein said promoter is selected from the group consisting of the nitrite-reductase-gene (nirA) promoters, the bidirectional-hydrogenase-gene hox promoters, the light- and heat-responsive groE promoters, the Rubisco-operon rbcL promoters, the metal (zinc)-inducible smt promoter, the iron-responsive idiA promoter, the redox-responsive crhR promoter, the heat-shock-gene hsp16.6 promoter, the small heat-shock protein (Hsp) promoter, the $CO_2$-responsive carbonic-anhydrase-gene promoters, the green/red light responsive cpcB2A2 promoter, the UV-light responsive lexA promoters, the nitrate-reductase-gene (narB) promoters, and combinations thereof.

8. The method of claim 1, wherein said DNA construct comprises from 5' to 3', an inducible promoter and a nucleotide sequence coding for an interfering RNA molecule that inhibits the expression of a glycogen-synthesis enzyme, consists of glycogen-synthase iRNA.

9. The method of claim 1, wherein said DNA construct comprising from 5' to 3', an inducible promoter and a nucleotide sequence coding for an enzyme that facilitates glycogen degradation and glycolysis, and is selected from the group consisting of amylase comprising SEQ ID NO:56, 4-alpha-glucotransferase, glycogen phosphorylase comprising SEQ ID NO:57, glucokinase comprising SEQ ID NO:60, phosphoglucomutase comprising SEQ ID NO:59, glucose-6-phosphate isomerase comprising SEQ ID NO:61, phosphofructose kinase comprising SEQ ID NO:9, fructose diphosphate aldolase comprising SEQ ID NO:10, triose phosphate isomerase comprising SEQ ID NO:11, NAD-dependent glyceraldehyde-3-phosphate dehydrogenase comprising SEQ ID NO:53, NADPH-dependent glyceraldehyde-3-phosphate dehydrogenase comprising SEQ ID NO:39, phosphoglycerate kinase comprising SEQ ID NO:28, phosphoglycerate mutase comprising SEQ ID NO:29, enolase comprising SEQ ID NO:30, pyruvate kinase comprising SEQ ID NO:31, and combinations thereof.

10. The method of claim 1, wherein said transgenic oxyphotobacterium or oxyphotobacterial cell inducibly expresses at least one of genes encoding the following enzymes: amylase comprising SEQ ID NO:56, glycogen phosphorylase comprising SEQ ID NO:58, 4-alpha-glucanotransferase comprising SEQ ID NO:57, glucokinase comprising SEQ ID NO:60, phosphoglucomutase comprising SEQ ID NO:59, glucose-6-phosphate isomerase comprising SEQ ID NO:61, phosphofructose kinase comprising SEQ ID NO:9, fructose diphosphate aldolase comprising SEQ ID NO:10, triose phosphate isomerase comprising SEQ ID NO:11, NAD-dependent glyceraldehyde-3-phosphate dehydrogenase comprising SEQ ID NO:1, phosphoglycerate kinase comprising SEQ ID NO:13, phosphoglycerate mutase comprising SEQ ID NO:52, enolase comprising SEQ ID NO:51, pyruvate kinase comprising SEQ ID NO:50, pyruvate decarboxylase comprising SEQ ID NO:49, NAD(P)H-using alcohol dehydrogenase comprising SEQ ID NO:48, NADPH-dependent glyceraldehyde-3-phosphate dehydrogenase comprising SEQ ID NO:39; an interfering RNA molecule that inhibits the expression of glycogen synthase comprising SEQ ID NO:54 or 55; or the set of enzymes in part or in full that facilitates starch degradation and glycolysis consisting of amylase comprising SEQ ID NO:56, 4-alpha-glucotransferase, glycogen phosphorylase comprising SEQ ID NO:57, glucokinase comprising SEQ ID NO:60, phosphoglucomutase comprising SEQ ID NO:59, glucose-6-phosphate isomerase comprising SEQ ID NO:61, phosphofructose kinase comprising SEQ ID NO:9, fructose diphosphate aldolase comprising SEQ ID NO:10, triose phosphate isomerase comprising SEQ ID NO:11, NAD-dependent glyceraldehyde-3-phosphate dehydrogenase comprising SEQ ID NO:53, NADPH-dependent glyceraldehyde-3-phosphate dehydrogenase comprising SEQ ID NO:39, phosphoglycerate kinase comprising SEQ ID NO:13, phosphoglycerate mutase comprising SEQ ID NO:21, enolase comprising SEQ ID NO:43, pyruvate kinase comprising SEQ ID NO:44, and combinations thereof.

11. The method according to claim 1, wherein said greenhouse distillation system comprises a photobiological reactor connected with a $CO_2$ source, a cell culture inlet, and outlet; a tilted vapor-condensing transparent ceiling; a tail-gas condensing and venting unit; and condensate-collecting ducts around the distillation greenhouse walls below the ceiling level.

12. The method according to claim 11, wherein use of sunlight driving photobiological production of ethanol ($CH_3CH_2OH$) and oxygen ($O_2$) from carbon dioxide ($CO_2$) and water ($H_2O$) and generating heat to vaporize the produced ethanol in said photobiological reactor wherein the vapor condensing onto the vapor-condensing transparent tilted ceiling that is cooled by air and/or radiation to outer space.

13. The method according to claim 12, wherein as the vapor condenses, the condensate grows into small droplets that can slide downwards along the inner surface of a tilted ceiling and finally flow into the collecting ducts around the greenhouse walls by use of the surface-condensate interactions and the Earth gravity pulling force, and wherein the collected condensate is transported from the collecting ducts through a condensate-transporting tube into a storage tank or next distillation greenhouse by use of gravity.

14. The method according to claim 11, wherein vapor-condensing transparent ceiling is water-chamber ceiling with pipeline inlet and outlets 1 and 2 at the top and the bottom of water chamber.

15. The method according to claim 11, wherein said tail-gas condensing and venting unit comprises a cold-water-bath chamber, a tail-gas condensing tube coil, a gas-condensate chamber, and a vertical venting tube; and wherein said tail-gas condensing tube coil, gas-condensate chamber, and vertical venting tube are cooled by running cold water through the cold-water-bath chamber so that the vapor in the tail gas will condense along the condensing tube coil which is connected with gas-condensate chamber before venting through the vertical venting tube.

16. The method according to claim 1, wherein said greenhouse distillation system comprises an upper multiple-compartmentalized distillation chamber with inter compartment liquid tube, adjustable inlet, adjustable outlet, hole and/or baffles to guide beer liquid flow from beer inlet to liquid outlet, and a lower photobiological culture reactor located below the distillation chamber and connected with a $CO_2$ source.

17. The method according to claim 16, wherein said upper multiple-compartmentalized distillation chamber and said lower photobiological culture reactor are separated by a transparent film or plate that allows only sunlight to go through; and wherein use of sunlight driving photosynthesis and generating heat in said lower photobiological culture reactor while said upper compartmentalized distillation chamber using solar heat for distillation of a beer liquid to generate a distillate in each of the distillation compartments.

18. The method according to claim 17, wherein said distillate in each of the distillation compartments are collected by use of collecting ducts around the inside walls of the distillation compartments and transported to storage tanks through condensate-transporting tubes by use of gravity; and wherein said lower photobiological culture reactor contains a headspace to facilitate $CO_2$ feeding and the flexible removal of $O_2$ gas.

19. The method according to claim 1, wherein said greenhouse distillation system comprises multiple distillation greenhouses working in series and/or in parallel for enhanced photobiological ethanol production and harvesting, and wherein photobiologically produced ethanol is harvested by use of the waste solar heat to distill ethanol from the photobiological ethanol-producing culture medium and followed by a series of successive sequences of re-distillations (re-evaporation, condensation, re-evaporation and re-condensation) of the condensates (distillates) using a number of distillation greenhouses and/or multiple distillation compartments until achieving the desired ethanol concentration in the final distillates.

* * * * *